United States Patent
Armani et al.

(10) Patent No.: US 9,265,768 B2
(45) Date of Patent: Feb. 23, 2016

(54) DERIVATIVES OF 1-PHENYL-2-PYRIDINYL ALKYL ALCOHOLS AS PHOSPHODIESTERASE INHIBITORS

(71) Applicant: Chiesi Farmaceutici S.p.A., Parma (IT)

(72) Inventors: Elisabetta Armani, Parma (IT); Gabriele Amari, Parma (IT); Carmelida Capaldi, Parma (IT); Oriana Esposito, Parma (IT); Ilaria Peretto, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 14/164,527

(22) Filed: Jan. 27, 2014

(65) Prior Publication Data

US 2014/0142074 A1  May 22, 2014

Related U.S. Application Data

(63) Continuation of application No. 13/627,221, filed on Sep. 26, 2012, now abandoned.

(30) Foreign Application Priority Data

Sep. 26, 2011 (EP) .................................. 11182814

(51) Int. Cl.
| | |
|---|---|
| *C07D 211/82* | (2006.01) |
| *A61K 31/435* | (2006.01) |
| *A61K 31/5377* | (2006.01) |
| *C07D 213/89* | (2006.01) |
| *C07D 213/69* | (2006.01) |
| *A61K 31/44* | (2006.01) |
| *A61K 31/4439* | (2006.01) |
| *A61K 31/496* | (2006.01) |
| *A61M 15/00* | (2006.01) |
| *A61M 16/14* | (2006.01) |
| *C07D 213/55* | (2006.01) |
| *C07D 213/56* | (2006.01) |
| *C07D 401/12* | (2006.01) |
| *C07D 413/12* | (2006.01) |
| *C07D 417/12* | (2006.01) |

(52) U.S. Cl.
CPC ............ *A61K 31/5377* (2013.01); *A61K 31/44* (2013.01); *A61K 31/4439* (2013.01); *A61K 31/496* (2013.01); *A61M 15/009* (2013.01); *A61M 15/0045* (2013.01); *A61M 16/14* (2013.01); *C07D 213/55* (2013.01); *C07D 213/56* (2013.01); *C07D 213/69* (2013.01); *C07D 213/89* (2013.01); *C07D 401/12* (2013.01); *C07D 413/12* (2013.01); *C07D 417/12* (2013.01)

(58) Field of Classification Search
USPC .......................... 546/301, 339; 514/345, 277
See application file for complete search history.

(56) References Cited

U.S. PATENT DOCUMENTS

| | | | |
|---|---|---|---|
| 7,671,066 B2 | 3/2010 | Amari et al. | |
| 7,820,698 B2 | 10/2010 | Rizzi et al. | |
| 7,923,565 B2* | 4/2011 | Delcanale ............ | C07D 213/61 546/301 |
| 7,968,724 B2 | 6/2011 | Armani et al. | |
| 8,203,000 B2 | 6/2012 | Delcanale et al. | |
| 8,440,834 B2* | 5/2013 | Amari ................... | C07D 213/61 546/339 |
| 8,648,204 B2 | 2/2014 | Amari et al. | |
| 2009/0048220 A1* | 2/2009 | Delcanale ............ | C07D 213/61 514/171 |
| 2010/0204256 A1 | 8/2010 | Amari et al. | |
| 2011/0144075 A1 | 6/2011 | Delcanale et al. | |
| 2012/0116091 A1 | 5/2012 | Delcanale et al. | |
| 2013/0005716 A1 | 1/2013 | Armani et al. | |
| 2013/0012487 A1 | 1/2013 | Amari et al. | |
| 2013/0102576 A1 | 4/2013 | Armani et al. | |
| 2013/0137648 A1 | 5/2013 | Delcanale et al. | |
| 2013/0324501 A1 | 12/2013 | Armani et al. | |
| 2014/0057882 A1 | 2/2014 | Armani et al. | |

FOREIGN PATENT DOCUMENTS

| | | |
|---|---|---|
| WO | 2008/006509 | 1/2008 |
| WO | 2009/018909 | 2/2009 |
| WO | 2010/089107 | 8/2010 |

OTHER PUBLICATIONS

U.S. Appl. No. 14/161,285, filed Jan. 22, 2014, Delcanale, et al.
U.S. Appl. No. 14/097,693, filed Dec. 5, 2013, Armani, et al.
U.S. Appl. No. 14/097,397, filed Dec. 5, 2013, Armani, et al.
U.S. Appl. No. 14/097,586, filed Dec. 5, 2013, Armani, et al.
U.S. Appl. No. 14/097,445, filed Dec. 5, 2013, Armani, et al.
U.S. Appl. No. 14/108,731, filed Dec. 17, 2013, Amari, et al.
European Search Reort issued in Application No. 111828141.1 on Feb. 9, 2012.
U.S. Appl. No. 14/482,287, filed Sep. 10, 2014, Amari, et al.

* cited by examiner

*Primary Examiner* — Paul Zarek
*Assistant Examiner* — George W Kosturko
(74) *Attorney, Agent, or Firm* — Oblon, McClelland, Maier & Neustadt, L.L.P.

(57) ABSTRACT

The invention relates to inhibitors of the phosphodiesterase 4 (PDE4) enzyme. More particularly, the invention relates to compounds that are derivatives of 1-phenyl-2-pyridinyl alkyl alcohols, methods of preparing such compounds, compositions containing them and therapeutic use thereof.

9 Claims, No Drawings

DERIVATIVES OF 1-PHENYL-2-PYRIDINYL ALKYL ALCOHOLS AS PHOSPHODIESTERASE INHIBITORS

CROSS REFERENCES TO RELATED APPLICATIONS

This application claims priority to European Patent Application No. 11182814.1, filed on Sep. 26, 2011, which is incorporated herein by reference in its entirety.

BACKGROUND OF THE INVENTION

1. Field of the Invention

The present invention relates to inhibitors of the phosphodiesterase 4 (PDE4) enzyme. More particularly, the present invention relates to derivatives of 1-phenyl-2-pyridinyl alkyl alcohols, methods of preparing such compounds, compositions containing them and therapeutic use thereof.

2. Discussion of the Background

Airway obstruction characterizes a number of severe respiratory diseases including asthma and chronic obstructive pulmonary disease (COPD). Events leading to airway obstruction include oedema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, reducing systemic side-effects, thus resulting in a more rapid clinical response and a higher therapeutic ratio.

Inhaled corticosteroids are the current maintenance therapy of choice for asthma and together with bronchodilator $beta_2$-agonists for acute symptom relief, they form the mainstay of current therapy for the disease. The current management of COPD is largely symptomatic by means of bronchodilating therapy with inhaled anticholinergics and inhaled $beta_2$-adrenoceptor agonists. However, corticosteroids do not reduce the inflammatory response in COPD as they do in asthma.

Another class of therapeutic agents which has been widely investigated in view of its anti-inflammatory effects for the treatment of inflammatory respiratory diseases such as asthma and COPD is represented by the inhibitors of the enzymes phosphodiesterases (PDEs), in particular of the phosphodiesterase type 4 (hereinafter referred to as PDE4).

Various compounds acting as PDE4 inhibitors have been disclosed in the prior art. However, the usefulness of several PDE4 inhibitors of the first-generation such as rolipram and piclamilast has been limited due to their undesirable side effects. Said effects include nausea and emesis due to their action on PDE4 in the central nervous system and gastric acid secretion due to the action on PDE4 in parietal cells in the gut.

The cause of said side effects has been widely investigated. It has been found that PDE4 exists in two distinct forms representing different conformations, that were designated as high affinity rolipram binding site or HPDE4, especially present in the central nervous system and in parietal cells, and low affinity rolipram binding site or LPDE4 (see Jacobitz, S et al., Mol. Pharmacol., 1996, 50, 891-899, which is incorporated herein by reference in its entirety), which is found in the immune and inflammatory cells. While both forms appear to exhibit catalytic activity, they differ with respect to their sensitivity to inhibitors. In particular, compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as roflumilast. Nonetheless, roflumilast is under dosed in order to achieve an acceptable side effect profile.

Other classes of compounds acting as PDE4 inhibitors have been disclosed. For example, EP 1 634 606 discloses, among others, ketone derivatives like benzofuran or 1,3-benzodioxole derivatives.

WO 94/02465 discloses, among others, ketone derivatives of general formula

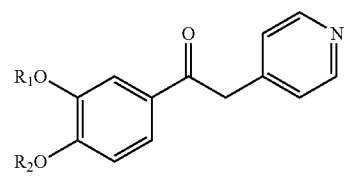

wherein $R_1$ is lower alkyl and $R_2$ may be alkyl, alkenyl, cycloalkyl, cycloalkyl, cycloalkenyl, cyclothioalkyl, or cyclothioalkenyl.

WO 95/35281 in the name of Celltech Therapeutics concerns tri-substituted phenyl derivatives.

WO 2009/018909 discloses derivatives of 1-phenyl-2-pyridinyl alkyl alcohols which have general formula below

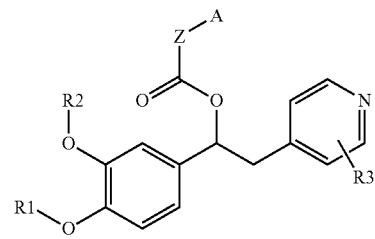

as inhibitors of phosphodiesterase 4 (PDE4) enzyme.

WO 2009/077068 discloses further derivatives of 1-phenyl-2-pyridinyl alkyl alcohols which have general formula below

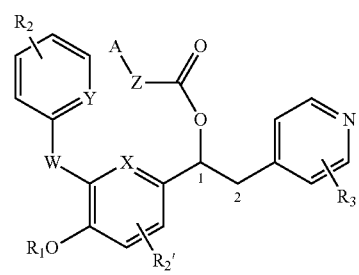

as inhibitors of phosphodiesterase 4 (PDE4) enzyme.

WO 2010/089107 discloses further derivatives of 1-phenyl-2-pyridinyl alkyl alcohols which have general formula below

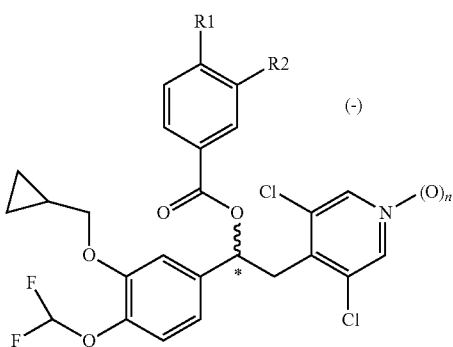

as inhibitors of phosphodiesterase 4 (PDE4) enzyme.

Although several PDE4 inhibitors have been disclosed so far as above reported, there is still a need for further PDE4 inhibitors. Particularly, there is still a need for further PDE4 inhibitors endowed with a high affinity for PDE4 enzyme and which would show an appropriate developability profile as an inhalation treatment for example in terms of reduced side effects.

Such reduction of side effects may be achieved, by way of example, through a low systemic exposure of the drug; an appropriate profile in terms of some pharmacokinetic characteristics, especially metabolic clearance, may be thus key to this goal.

SUMMARY OF THE INVENTION

Accordingly, it is one object of the present invention to provide novel compounds which act as inhibitors of the phosphodiesterase 4 (PDE4) enzyme.

It is another object of the present invention to provide novel methods of preparing said compound It is another object of the present invention to provide novel compositions which contain such a compound.

It is another object of the present invention to provide novel therapeutic uses of such a compound.

These and other objects, which will become apparent during the following detailed description, have been achieved by the inventors' discovery that the compounds of formula (I) are useful as PDE4 inhibitors.

Thus, the present invention is directed is directed to derivatives of 1-phenyl-2-pyridinyl alkyl alcohols of formula (I)

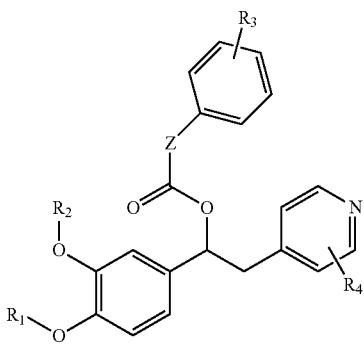

(I)

wherein:

$R_1$ and $R_2$ are different or the same and are independently selected from the group consisting of:

$(C_1-C_6)$alkyl, optionally substituted by $(C_3-C_7)$cycloalkyl;
$(C_1-C_6)$haloalkyl;
$(C_3-C_7)$cycloalkyl;
$R_4$ is one or more substituents independently selected from the group consisting of H, CN, $NO_2$, $CF_3$ and halogen atoms;
Z is a group selected in the list consisting of:
[3]-$CH_2$—X-[4];
[3]-Y-[4];
[3]-$CH_2CH_2$—K-[4];
[3]-$CHR_{26}$—$NR_{27}$—$SO_2$-[4];
[3]-$C(CH_3)(R_5)$—O—(CO)-[4];
[3]-$CHR_6$—$CH_2$-[4];
[3]-$CHR_7$—NH—(CO)-J-[4]; and
[3]-C(OH)(OH)-[4];
wherein [3] and [4] indicate the points of attachment for group Z with, respectively, carboxylic group and phenyl group;
$R_{27}$ is hydrogen, $(C_1-C_4)$alkyl;
$R_{26}$ is selected in the group consisting of:
a group —$C(CH_3)(CH_3)$—S—(CO)$CH_3$;
a group —$CH_2$—$CH_2$—$CH_2$—O—(CO)$CH_3$;
a group $(C_1-C_4)$alkyl; and
a group $(C_1-C_4)$alkylthio$(C_1-C_4)$alkyl group;
$R_5$ is hydrogen, $(C_1-C_4)$alkyl or a phenyl group;
$R_6$ is hydrogen or a group —$NHR_{10}$;
$R_7$ is a $(C_1-C_4)$alkylthio$(C_1-C_4)$alkyl group;
X is selected in the group consisting of:
a group [5]-O—(CH2)$_n$-[4];
a group —$SO_2$—;
a group [5]-O—(CO)—(CH$_2$)$_n$-[4];
a group [5]-(CO)—NH-[4];
a group [5]-(CO)—O—(CH$_2$)$_n$-[4];
a group [5]-NH—(CO)-[4];
a group [5]-$NR_8$—$SO_2$—(CH$_2$)$_n$-[4];
a group [5]-O—$SO_2$-[4];
a group [5]-$SO_2$—NH-[4];
a group [5]-NH—(CO)—(CO)-[4];
a group [5]-NH—(CO)—NH-[4];
a group [5]-S—(CO)-[4];
a group [5]-$NR_9$—(CH$_2$)$_n$-[4];
wherein [5] and [4] indicate the points of attachment for group X with, respectively, methylene and phenyl groups;
n is 0 or 1;
$R_8$ is hydrogen, $(C_1-C_4)$alkyl or $(C_3-C_8)$heterocycloalkyl $(C_1-C_4)$alkyl;
$R_9$ is hydrogen, $(C_1-C_4)$alkyl or a group —$SO2(C_1-C_4)$alkyl;
Y is selected in the group consisting of:
a group [3]-O—(CH2)$_n$-[4];
a group [3]-$NR_9$—(CH2)$_n$-[4];
a group [3]-S—(CH2)$_n$-[4];
a group [3]-(CO)—NH-[4];
a group [3]-(CO)—S-[4];
a group [3]-(CO)-[4]; and
a group [3]-CH=CH—$SO_2$-[4];
K is selected in the group consisting of:
a group [6]-$SO_2$-[4];
a group [6]-NH—(CO)-[4]; and
a group [6]-O—(CO)-[4];
wherein [6] and [4] indicate the points of attachment for group K with, respectively, ethylene and phenyl groups;
$R_{10}$ is hydrogen or a group —$SO_2$—$(C_1-C_4)$alkyl;
J is a bond or a group [7]-CH($NH_2$)-[4];
wherein [7] and [4] indicate the points of attachment for group J with, respectively, aminocarbonyl and phenyl groups;

$R_3$ are one or more optional substituents which may be the same or different, and are independently selected from the group consisting of:
- $(C_1-C_6)$alkyl optionally substituted by one or more $(C_3-C_7)$ cycloalkyl;
- $(C_1-C_6)$haloalkyl;
- $(C_3-C_7)$heterocycloalkyl;
- $(C_3-C_7)$heterocycloalkyl$(C_1-C_4)$alkyl;
- a group —$OR_{11}$ wherein $R_{11}$ is selected from the group consisting of:
  - H:
  - $(C_1-C_6)$haloalkyl;
  - a group —$SO_2R_{12}$, wherein $R_{12}$ is $(C_1-C_6)$alkyl;
  - a group —$C(O)R_{12}$ wherein $R_{12}$ is as above defined;
  - $(C_1-C_{10})$alkyl optionally substituted by one or more $(C_3-C_7)$cycloalkyl or by a group —$NR_{13}R_{14}$ as below defined; and
  - $(C_3-C_7)$cycloalkyl;
- a group —$SR_{25}$ wherein $R_{25}$ is selected from the group consisting of:
  - H:
  - $(C_1-C_6)$haloalkyl;
  - a group —$C(O)R_{12}$;
  - $(C_1-C_{10})$alkyl optionally substituted by one or more $(C_3-C_7)$cycloalkyl or by a group —$NR_{13}R_{14}$; and
  - $(C_3-C_7)$cycloalkyl;
- halogen atoms;
- CN;
- $NO_2$;
- $NR_{13}R_{14}$ wherein $R_{13}$ and $R_{14}$ are different or the same and are independently selected from the group consisting of:
  - H;
  - $(C_1-C_4)$alkyl-$NR_{15}R_{16}$ wherein $R_{15}$ and $R_{16}$ are different or the same and are independently selected from the group consisting of: H and $(C_1-C_6)$ alkyl, which is optionally substituted with $(C_3-C_7)$cycloalkyl or $(C_3-C_7)$ heterocycloalkyl; or they form with the nitrogen atom to which they are linked a $(C_3-C_y)$heterocycloalkyl which is optionally substituted by $(C_1-C_6)$ alkyl;
  - linear or branched $(C_1-C_6)$alkyl, optionally substituted with $(C_3-C_7)$ cycloalkyl, $(C_3-C_7)$heterocycloalkyl, a group —OH, $(C_1-C_6)$alkoxyl or by an aminocarbonyl group;
  - a group —$SO_2R_{17}$, wherein $R_{17}$ is selected in the group consisting of: $(C_1-C_6)$alkyl optionally substituted by $(C_3-C_7)$cycloalkyl or $(C_3-C_7)$ heterocycloalkyl; $(C_3-C_7)$heterocycloalkyl; and phenyl optionally substituted by one or more $(C_1-C_6)$alkyl, halogen or —OH;
  - a group —$C(O)R_{18}$, wherein $R_{18}$ is selected in the group consisting of: $(C_1-C_6)$ alkyl optionally substituted by $(C_3-C_7)$cycloalkyl; $(C_1-C_6)$ alkylcarboxyl; and phenyl optionally substituted by one or more $(C_1-C_6)$ alkyl, halogen or hydroxyl; and a group —$NR_{20}R_{21}$; wherein $R_{20}$ and $R_{21}$ are different or the same and are independently selected from the group consisting of: H and $(C_1-C_6)$alkyl, which is optionally substituted with $(C_1-C_6)$ alkoxy;
  - a group —$C(O)OR_{19}$, wherein $R_{19}$ is selected in the group consisting of: $(C_1-C_6)$alkyl optionally substituted by $(C_3-C_7)$cycloalkyl; and phenyl optionally substituted by one or more $(C_1-C_6)$alkyl, halogen or —OH; or they form with the nitrogen atom to which they are linked a saturated or partially saturated heterocyclic ring, which is optionally substituted by $(C_1-C_6)$alkyl;
  - $(C_1-C_4)$alkyl-$NR_{13}R_{14}$;
  - $COR_{22}$ wherein $R_{22}$ is phenyl, heterocycloalkyl or $(C_1-C_6)$ alkyl;
  - —$SO_2R_{23}$ wherein $R_{23}$ is $(C_1-C_4)$alkyl, —OH or $NR_{28}R_{29}$ wherein $R_{28}$ and $R_{29}$ are each independently H or $(C_1-C_4)$alkyl;
  - —$COOR_{24}$ wherein $R_{24}$ is H or $(C_1-C_4)$alkyl or $(C_1-C_4)$ alkyl-$NR_{13}R_{14}$; and
  - —$CONR_{13}R_{14}$ wherein $R_{13}$ and $R_{14}$ are as defined above;

wherein groups $R_3$, $R_4$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{28}$ and $R_{29}$ may assume the same or different meanings at each occurrence, if present in more than one group;

N-oxides on the pyridine ring, and pharmaceutically acceptable salts, or solvates thereof.

In a second aspect, the present invention is directed to compounds of formula (ID)

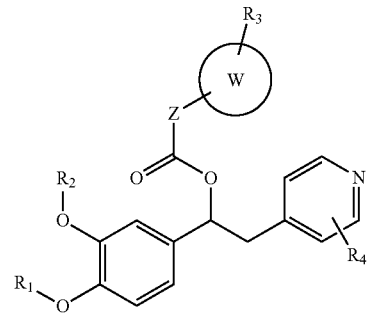

(ID)

wherein:

$R_1$ and $R_2$ are different or the same and are independently selected from the group consisting of:
- $(C_1-C_6)$alkyl, optionally substituted by $(C_3-C_7)$cycloalkyl;
- $(C_1-C_6)$haloalkyl;
- $(C_3-C_7)$cycloalkyl;

$R_4$ is one or more substituents independently selected from the group consisting of H, CN, $NO_2$, $CF_3$ and halogen atoms;

Z is a group [3]-$CH_2$—X-[4]; wherein [3] and [4] indicate the points of attachment for group Z with, respectively, carboxylic group and group W;

X is a group [5]-O—(CO)—$(CH_2)_n$-[4]; wherein [5] and [4] indicate the points of attachment for group X with, respectively, methylene and W groups;

n is 0;

W is a monocyclic or bicyclic heteroaryl ring;

$R_3$ are one or more optional substituents which may be the same or different, and are independently selected from the group consisting of:
- $(C_1-C_6)$alkyl optionally substituted by one or more $(C_3-C_7)$ cycloalkyl;
- $(C_1-C_6)$haloalkyl;
- $(C_3-C_7)$heterocycloalkyl;
- $(C_3-C_7)$heterocycloalkyl$(C_1-C_4)$alkyl;
- a group —$OR_{11}$ wherein $R_{11}$ is selected from the group consisting of:
  - H:
  - $(C_1-C_6)$haloalkyl;
  - a group —$SO_2R_{12}$, wherein $R_{12}$ is $(C_1-C_6)$alkyl;
  - a group —$C(O)R_{12}$ wherein $R_{12}$ is as above defined;
  - $(C_1-C_{10})$alkyl optionally substituted by one or more $(C_3-C_7)$cycloalkyl or by a group —$NR_{13}R_{14}$ as below defined; and
  - $(C_3-C_7)$cycloalkyl;

a group —$SR_{25}$ wherein $R_{25}$ is selected from the group consisting of:
  H:
  ($C_1$-$C_6$)haloalkyl;
  a group —$C(O)R_{12}$;
  ($C_1$-$C_{10}$)alkyl optionally substituted by one or more ($C_3$-$C_7$)cycloalkyl or by a group —$NR_{13}R_{14}$; and
  ($C_3$-$C_7$)cycloalkyl;
halogen atoms;
CN;
$NO_2$;
$NR_{13}R_{14}$ wherein $R_{13}$ and $R_{14}$ are different or the same and are independently selected from the group consisting of:
  H;
  ($C_1$-$C_4$)alkyl-$NR_{15}R_{16}$ wherein $R_{15}$ and $R_{16}$ are different or the same and are independently selected from the group consisting of: H and ($C_1$-$C_6$) alkyl, which is optionally substituted with ($C_3$-$C_7$)cycloalkyl or ($C_3$-$C_7$) heterocycloalkyl; or they form with the nitrogen atom to which they are linked a ($C_3$-$C_y$)heterocycloalkyl which is optionally substituted by ($C_1$-$C_6$) alkyl;
  linear or branched ($C_1$-$C_6$)alkyl, optionally substituted with ($C_3$-$C_7$) cycloalkyl, ($C_3$-$C_7$)heterocycloalkyl, a group —OH, ($C_1$-$C_6$)alkoxyl or by an aminocarbonyl group;
  a group —$SO_2R_{17}$, wherein $R_{17}$ is selected in the group consisting of: ($C_1$-$C_6$)alkyl optionally substituted by ($C_3$-$C_7$)cycloalkyl or ($C_3$-$C_7$) heterocycloalkyl; ($C_3$-$C_7$)heterocycloalkyl; and phenyl optionally substituted by one or more ($C_1$-$C_6$)alkyl, halogen or —OH;
  a group —$C(O)R_{18}$, wherein $R_{18}$ is selected in the group consisting of: ($C_1$-$C_6$)alkyl optionally substituted by ($C_3$-$C_7$)cycloalkyl; ($C_1$-$C_6$) alkylcarboxyl; and phenyl optionally substituted by one or more ($C_1$-$C_6$) alkyl, halogen or hydroxyl; and a group —$NR_2OR_{21}$; wherein $R_{20}$ and $R_{21}$ are different or the same and are independently selected from the group consisting of: H and ($C_1$-$C_6$)alkyl, which is optionally substituted with ($C_1$-$C_6$)alkoxy;
  a group —$C(O)OR_{19}$, wherein $R_{19}$ is selected in the group consisting of: ($C_1$-$C_6$)alkyl optionally substituted by ($C_3$-$C_7$)cycloalkyl; and phenyl optionally substituted by one or more ($C_1$-$C_6$)alkyl, halogen or —OH; or they form with the nitrogen atom to which they are linked a saturated or partially saturated heterocyclic ring, which is optionally substituted by ($C_1$-$C_6$)alkyl;
($C_1$-$C_4$)alkyl-$NR_{13}R_{14}$;
$COR_{22}$ wherein $R_{22}$ is phenyl, heterocycloalkyl or ($C_1$-$C_6$) alkyl;
—$SO_2R_{23}$ wherein $R_{23}$ is ($C_1$-$C_4$)alkyl, —OH or $NR_{28}R_{29}$ wherein $R_{28}$ and $R_{29}$ are each independently H or ($C_1$-$C_4$)alkyl;
—$COOR_{24}$ wherein $R_{24}$ is H or ($C_1$-$C_4$)alkyl or ($C_1$-$C_4$)alkyl-$NR_{13}R_{14}$; and
—$CONR_{13}R_{14}$ wherein $R_{13}$ and $R_{14}$ are as defined above;
wherein groups $R_3$, $R_4$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{28}$, $R_{29}$ and $R_{25}$ may assume the same or different meanings at each occurrence, if present in more than one group;
N-oxides on the pyridine ring, and pharmaceutically acceptable salts, or solvates thereof.

The present invention also encompasses the pharmaceutically acceptable salts and/or solvates of compounds of formula (I) and (ID).

The invention further comprises the corresponding N-oxides on the pyridine ring of compounds of formula (I) and (ID).

Hereinafter, compounds of formula (I), compounds of formula (ID), their N-oxides on the pyridine ring, embodiments thereof and their pharmaceutically acceptable salts and solvates, defined in any aspect of the invention (except intermediate compounds described in the chemical processes) are referred to as "compounds of the invention".

The present invention further comprises a process for the preparation of compounds of the invention.

The present invention also provides pharmaceutical compositions of compounds of the invention either alone or in combination, in admixture with one or more pharmaceutically acceptable carriers.

In a further aspect the present invention provides the use of the compounds of the invention as a medicament.

In one aspect, the present invention provides the use of the compounds of the invention for the manufacture of a medicament.

In particular, the present invention provides the use of the compounds of the invention for the prevention and/or treatment of any disease characterized by phosphodiesterase 4 (PDE4) overactivity and/or wherein an inhibition of PDE4 activity is desirable.

In particular, the compounds of the invention alone or combined with other active ingredients may be administered for the prevention and/or treatment of a disease of the respiratory tract characterized by airway obstruction such as asthma and COPD.

In a further aspect, the present invention provides the use of compounds of the invention for the preparation of a medicament for the prevention and/or treatment of any disease characterized by phosphodiesterase 4 (PDE4) overactivity and/or wherein an inhibition of PDE4 activity is desirable.

Moreover, the present invention provides a method for prevention and/or treatment of any disease wherein PDE4 inhibition is desirable, said method comprises administering to a patient in need of such treatment a therapeutically effective amount of a compound of the invention.

DETAILED DESCRIPTION OF THE PREFERRED EMBODIMENTS

The term "halogen atoms" as used herein includes fluorine, chlorine, bromine, and iodine, preferably chlorine.

The term "($C_1$-$C_x$) alkyl" where x is an integer greater than 1, refers to straight-chained and branched alkyl groups wherein the number of constituent carbon atoms is in the range 1 to x. Particular alkyl groups are methyl, ethyl, n-propyl, isopropyl and t-butyl.

The term "($C_1$-$C_x$) alkoxyl" where x is an integer greater than 1, refers to straight-chained and branched alkoxy groups wherein the number of constituent carbon atoms is in the range 1 to x. Particular alkyl groups are methoxyl, ethoxyl, n-propoxyl, isopropoxyl and t-butoxyl.

The expressions "($C_1$-$C_6$)haloalkyl" refer to the above defined "($C_1$-$C_6$)alkyl" groups wherein one or more hydrogen atoms are replaced by one or more halogen atoms, which can be the same or different from each other. Examples of said ($C_1$-$C_6$)haloalkyl groups may thus include halogenated, polyhalogenated and fully halogenated alkyl groups wherein all of the hydrogen atoms are replaced by halogen atoms, e.g. trifluoromethyl or difluoro methyl groups.

The expressions "($C_1$-$C_x$)alkyl$N_jN_w$" refer to the above defined "($C_1$-$C_x$)alkyl" groups wherein one hydrogen atom is replaced by one a group —$N_jN_w$.

The term "($C_1$-$C_x$)alkylthio" where x is an integer greater than 1, refers to straight-chained and branched alkylthio groups wherein the number of constituent carbon atoms is in the range 1 to x and which is linked to other groups via sulfur. Particular alkylthio groups are methylthio, ethylthio, and so on.

The term "($C_1$-$C_x$)alkylthio($C_1$-$C_x$)alkyl" refer to the above "($C_1$-$C_x$)alkyl" group wherein one or more hydrogen atoms are replaced by one "($C_1$-$C_x$)alkylthio" group.

The term "($C_3$-$C_y$) cycloalkyl", where y is an integer greater than or equal to 3, refers to saturated cyclic hydrocarbon groups containing from 3 to y ring carbon atoms. Examples include cyclopropyl, cyclobutyl, cyclopentyl, cyclohexyl and cycloheptyl.

The expression "($C_3$-$C_y$)heterocycloalkyl" refers to monocyclic ($C_3$-$C_y$)cycloalkyl groups, in which at least one ring carbon atom is replaced by a heteroatom (e.g. N, NH, S or O). Examples of ($C_3$-$C_y$)heterocycloalkyl include pyrrolidinyl, thiazolidinyl, piperazinyl, piperidinyl, morpholinyl, and thiomorpholinyl.

The term "aminocarbonyl" refers to a radical of formula —$CONH_2$.

The expression "($C_1$-$C_x$)alkylcarboxyl" refers to ($C_1$-$C_x$)alkylCOO— groups wherein the group "($C_1$-$C_x$)cycloalkyl" has the meaning above defined.

By analogy, the term "($C_3$-$C_y$)heterocycloalkylene", refers to a divalent ($C_3$-$C_x$)heterocycloalkyl radical, wherein ($C_3$-$C_y$)heterocycloalkyl is as above defined.

The term "($C_3$-$C_y$)heterocycloalkyl($C_1$-$C_x$) alkyl" refers to the above "($C_1$-$C_x$)alkyl" group wherein one or more hydrogen atoms are replaced by one or more "($C_3$-$C_y$)heterocycloalkyl" groups.

The expression "aryl" refers to mono or bi-cyclic ring systems which have 6 to 10 ring atoms, wherein at least one ring is aromatic.

The expression "heteroaryl" refers to mono or bi-cyclic ring systems with 5 to 11 ring atoms, in which at least one ring is aromatic and in which at least one ring atom is a heteroatom (e.g. N, NH, S or O).

Examples of suitable monocyclic aryl or heteroaryl systems include, for instance, phenyl, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals, and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepin, benzo oxazin radicals, and the like.

Thus, the present invention is directed to a class of compounds acting as inhibitors of the phosphodiesterase 4 (PDE4) enzyme. Said class of compounds inhibits the conversion of cyclic nucleotides, in particular cyclic adenosine monophosphate (cAMP), into their inactive 5'-mononucleotide forms. In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-1, IL-3 and tumor necrosis factor-alpha (TNF-$\alpha$)$^-$. It also leads to an airway smooth muscle relaxation and a decrease in oedema.

The present invention relates to derivatives of 1-phenyl-2-pyridinyl alkyl alcohols of general formula (I), pharmaceutically acceptable salts and N-oxides on the pyridine ring thereof,

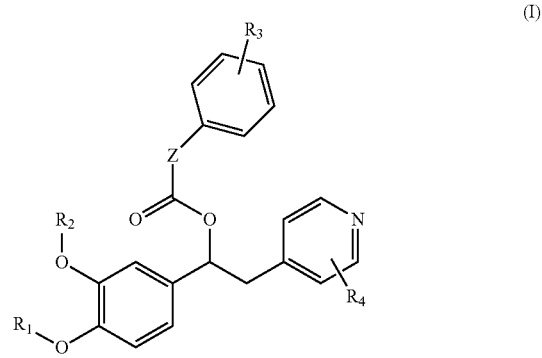

(I)

wherein $R_1$, $R_2$, $R_3$, $R_4$, Z and A are as above defined.

The present invention also relates to derivatives of 1-phenyl-2-pyridinyl alkyl alcohols of general formula (ID), pharmaceutically acceptable salts and N-oxides on the pyridine ring thereof,

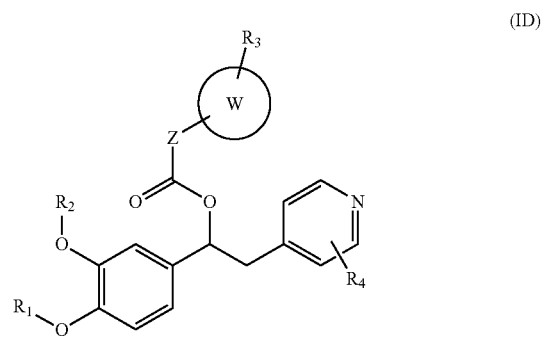

(ID)

wherein $R_1$, $R_2$, $R_3$, $R_4$, Z and W are as above defined.

The term "pharmaceutically acceptable salts" refers to derivatives of compounds of formula (I) or (ID) wherein the parent compound is suitably modified by converting any of the free acid or basic groups, if present, into the corresponding addition salt with any base or acid conventionally intended as being pharmaceutically acceptable. Suitable examples of said salts may thus include mineral or organic acid addition salts of basic residues such as amino groups, as well as mineral or organic basic residues such as carboxylic groups.

Cations of inorganic bases which can be suitably used to prepare used to prepare salts within the invention comprise ions of alkali or alkaline earth metals such as potassium, sodium, calcium, or magnesium.

Those obtained by reacting the main compound, functioning as a base, with an inorganic or organic acid to form a salt comprise, for example, salts of hydrochloric acid, sulfuric acid, phosphoric acid, methane sulfonic acid, camphor sulfonic acid, oxalic acid, maleic acid, succinic acid, and citric acid.

It will be apparent to those skilled in the art that compounds of general formula (I) contain at least one stereogenic center, namely represented by the carbon atom (1) with an asterisk below, and therefore exist as optical stereoisomers.

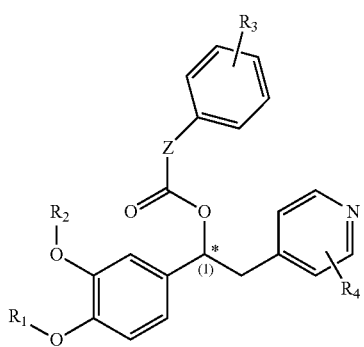

(I)

It will also be apparent to those skilled in the art that the compounds of general formula (ID) contain at least one stereogenic center, namely represented by the carbon atom (1) with an asterisk below, and therefore exist as optical stereoisomers.

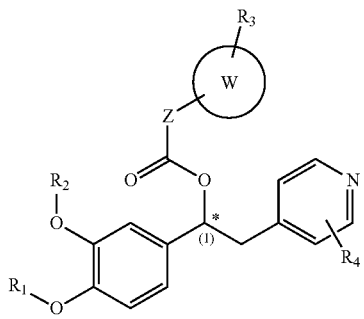

When the compounds according to the invention have at least one stereogenic center, they will exist as enantiomers. When the compounds according to the invention possess two or more stereogenic centers, they may additionally exist as diastereoisomers. It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is shown herebelow:

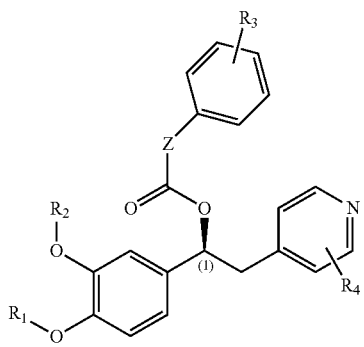

(I)'

In a preferred embodiment, the present invention is directed to compounds of formula (ID)', which are compounds of formula (ID) as above defined where the absolute configuration of carbon (1) is shown herebelow:

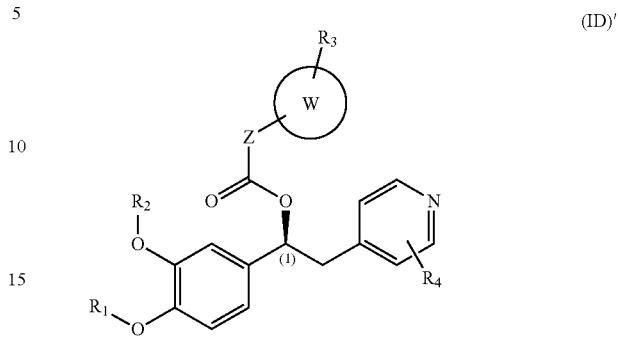

(ID)'

The absolute configuration for carbon (1) is assigned on the basis of Cahn-Ingold-Prelog nomenclature based on groups' priorities.

In one preferred embodiment, for compounds of formula (I), the absolute configuration at carbon (1) is (S).

It is to be understood that all preferred groups or embodiments described herebelow for compounds of formula (I) and (ID) may be combined among each other and, where applicable, apply to compounds of formula (I)', (IA), (IB), (IC) and to compounds of formula (ID) and (ID)' as well mutatis mutandis.

In a preferred embodiment, compounds of the invention are N-oxides derivatives of the pyridine ring.

In another preferred embodiment, the 4-pyridinyl ring has two $R_4$ substituents which are halogen atom (for example 3,5-dichloro).

In another preferred embodiment, $R_1$ is $(C_1$-$C_6)$haloalkyl (for example difluoromethyl) and $R_2$ is $(C_1$-$C_6)$alkyl which is substituted by $(C_3$-$C_7)$cycloalkyl (for example cyclopropyl methyl).

A preferred group of compounds of general formula (I) is that wherein the 4-pyridinyl ring is substituted in 3 and 5 with two atoms of chlorine, according to the general formula (IA)

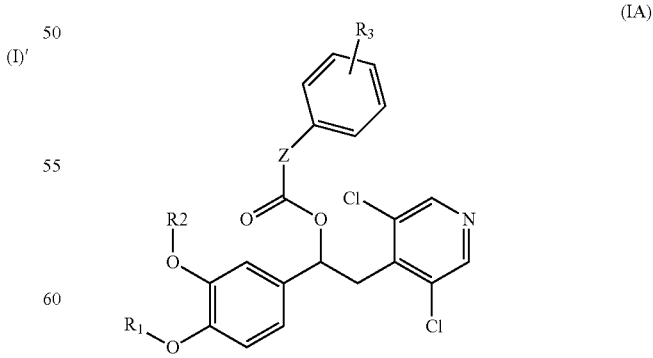

(IA)

wherein $R_1$, $R_2$, $R_3$ and z are as defined above.

Another preferred group of compounds of formula (I) is that shown below according to general formula (IB):

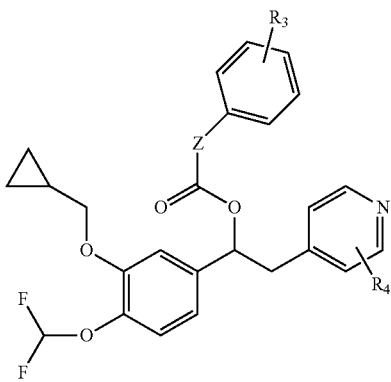

(IB)

wherein $R_4$, Z and $R_3$ are as defined above, and their.

A further preferred group of compounds of formula (I) is that shown below according to general formula (IC):

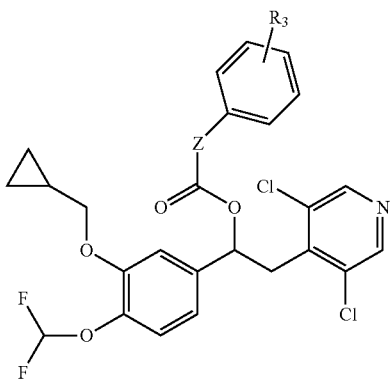

(IC)

wherein Z and $R_3$ are as defined above.

In one preferred embodiment, Z is selected from the group consisting of:

[3]-$CH_2$—X-[4] wherein X is a group [5]-NH—(CO)-[4];
[3]-$CH_2$—X-[4], wherein X is a group [5]-O—(CH2)n-[4];
[3]-$CH_2$—X-[4], wherein X is a group a group —SO2-;
[3]-$CH_2$—X-[4] wherein X is a group [5]-(CO)—O—(CH2)n[4];
[3]-$CH_2$—X-[4] wherein X is a group [5]-(CO)—NH-[4];
[3]-$CH_2$—X-[4] wherein X is a group [5]-$NR_9$—(CH2)n-[4];
[3]-$CH_2$—X-[4] wherein X is a group [5]-$SO_2$—NH-[4];
[3]-$CH_2$—X-[4] wherein X is a group [5]-NH—(CO)—(CO)-[4];
[3]-$CH_2$—X-[4] wherein X is a group [5]-O—(CO)—$(CH_2)_n$-[4];
[3]-$CH_2$—X-[4] wherein X is a group [5]-S—(CO)-[4];
[3]-$CH_2$—X-[4] wherein X is a group [5]-$NR_9$—$(CH_2)_n$-[4];
[3]-$CH_2$—X-[4] wherein X is a group [5]-$NR_8$—$SO_2$—$(CH_2)_n$-[4];
[3]-$CH_2$—X-[4] wherein X is a group [5]-O—$SO_2$-[4];
[3]-$CH_2$—X-[4] wherein X is a group [5]-NH—(CO)—NH-[4];
[3]-$CHR_7$—NH—(CO)-J-[4];
[3]-$CH_2CH_2$—K-[4] wherein K is a group [6]—NH—(CO)-[4];
[3]-$CH_2CH_2$—K-[4] wherein K is a group [6]-$SO_2$-[4];
[3]-$CH_2CH_2$—K-[4] wherein K is a group a group [6]-O—(CO)-[4];
[3]-Y-[4] wherein Y is a group [3]-(CO)-[4];
[3]-Y-[4], wherein Y is a group [3]-$NR_9$—(CH2) n -[4];
[3]-Y-[4], wherein Y is a group [3]-S—(CH2)n-[4];
[3]-Y-[4] wherein Y is a group [3]-(CO)—NH-[4];
[3]-Y-[4] wherein Y is [3]-O—(CH2)n-[4];
[3]-Y-[4] wherein Y is [3]-CH=CH—$SO_2$-[4];
[3]-$CHR_{26}$—$NR_{27}$—$SO_2$-[4];
[3]-$CHR_6$—$CH_2$-[4];
[3]-C(OH)(OH)-[4]; and
[3]-C($CH_3$)($R_5$)—O—(CO)-[4].

In a further preferred embodiment, Z is selected from the group consisting of:

[3]-$CH_2$—X-[4] wherein X is a group [5]—NH—(CO)-[4]:
[3]-$CHR_7$—NH—(CO)-J-[4], wherein J is a bond and $R_7$ is a group ($C_1$-$C_4$) alkylthio($C_1$-$C_4$)alkyl:
[3]-$CH_2CH_2$—K-[4] wherein K is a group [6]- NH—(CO)-[4];
[3]-$CH_2CH_2$—K-[4] wherein K is a group [6]-$SO_2$-[4];
[3]-$CH_2$—X-[4], wherein X is a group [5]-O—(CH2)n-[4] and n is;
[3]-$CH_2$—X-[4], wherein X is a group [5]-O—(CH2)n-[4] and n is 0;
[3]-$CH_2$—X-[4], wherein X is a group a group —SO2-;
[3]-Y-[4] wherein Y is a group [3]-(CO)-[4];
[3]-$CHR_6$—$CH_2$-[4] and $R_6$ is hydrogen;
[3]-Y-[4], wherein Y is a group [3]-$NR_9$—(CH2)n-[4], n is 1 and $R_9$ is hydrogen or ($C_1$-$C_4$)alkyl;
[3]-Y-[4], wherein Y is a group [3]-S—(CH2)n-[4] and n is 0 or 1;
[3]-$CHR_{26}$—NH—$SO_2$-[4] wherein $R_{26}$ is a group —CH2-CH2-CH2-O—(CO)CH3;
[3]-$CH_2$—X-[4] wherein X is a group [5]-(CO)—O—(CH2)n[4] and n is 0 or 1;
[3]-$CH_2$—X-[4] wherein X is a group [5]-(CO)—NH-[4];
[3]-$CH_2$—X-[4] wherein X is a group [5]-$NR_9$—(CH2)n-[4], n is 1 and $R_9$ is hydrogen or a group —$SO_2$($C_1$-$C_4$) alkyl;
[3]-$CH_2$—X-[4] wherein X is a group [5]-$NR_9$—(CH2)n-[4] and n is 1 and $R_9$ is ($C_1$-$C_4$)alkyl;
[3]-$CH_2$—X-[4] wherein X is a group [5]-$SO_2$—NH-[4];
[3]-$CH_2$—X-[4] wherein X is a group [5]-O—(CO)—$(CH_2)_n$-[4] and n is 0;
[3]-C($CH_3$)($R_5$)—O—(CO)-[4] wherein $R_5$ is hydrogen, ($C_1$-$C_4$)alkyl or a phenyl group;
[3]-$CH_2CH_2$—K-[4] wherein K is a group a group [6]-O—(CO)-[4];
[3]-$CH_2$—X-[4] wherein X is a group [5]—NH—(CO)—(CO)-[4];
[3]-$CH_2$—X-[4] wherein X is a group [[5]-O—(CO)—$(CH_2)_n$-[4] and n is 0 or 1;
[3]-$CHR_{26}$—$NR_{27}$—$SO_2$-[4] wherein $R_{26}$ is a group —C(CH3)(CH3)-S—(CO)CH3;
[3]-$CHR_{26}$—$NR_{27}$—$SO_2$-[4] wherein $R_{26}$ is hydrogen or ($C_1$-$C_4$)alkyl;
[3]-Y-[4] wherein Y is [3]-O—$(CH2)_n$-[4] and n is 0;
[3]-$CH_2$—X-[4] wherein X is a group [5]-S—(CO)-[4];
[3]-$CH_2$—X-[4] wherein X is a group [5]-$NR_9$—$(CH_2)_n$-[4], n is 0 or 1, and $R_9$ is —$SO_2$($C_1$-$C_4$)alkyl;
[3]-$CHR_6$—$CH_2$-[4] wherein $R_6$ is a group —$NHR_{10}$ and $R_{10}$ is hydrogen;
[3]-$CH_2$—X-[4] wherein X is a group [5]-$NR_8$—$SO_2$—$(CH_2)_n$-[4], n is 0, and $R_8$ is hydrogen, ($C_1$-$C_4$)alkyl or alkyl(heterocycloalkyl);

[3]-CH$_2$—X-[4] wherein X is a group [5]-NR$_8$—SO$_2$—(CH$_2$)$_n$-[4], n is 0 or 1, and R$_8$ is hydrogen;
[3]-Y-[4] wherein Y is a group [3]-(CO)—NH-[4];
[3]-C(OH)(OH)-[4]:
[3]-CH$_2$—X-[4], wherein X is a group [5]-O—SO$_2$-[4];
[3]-CH$_2$—X-[4], wherein X is a group [5]-NH—(CO)—NH-[4];
[3]-Y-[4] wherein Y is a group [3]-NR$_9$—(CH2)n-[4], n is 0 and R$_9$ is (C$_1$-C$_4$)alkyl;
[3]-Y-[4] wherein Y is [3]-O—(CH$_2$)n-[4] and n is 0 or 1;
[3]-Y-[4] wherein Y is [3]-CH=CH—SO$_2$-[4]; and
[3]-C(CH$_3$)(R$_5$)—O—(CO)-[4] wherein R$_5$ is (C$_1$-C$_4$)alkyl.

In a further preferred embodiment, Z is [3]-CH$_2$—X-[4] wherein X is selected from the group consisting of:
a group [5]-O—(CO)—(CH$_2$)$_n$-[4] wherein n is 0;
a group [5]-S—(CO)-[4];
a group [5]-NH—(CO)-[4];
a group [5]-NR$_8$—SO$_2$—(CH$_2$)$_n$-[4], n is 0, and R$_8$ is hydrogen, (C$_1$-C$_4$)alkyl or alkyl(heterocycloalkyl); and
a group [5]-NR$_9$—(CH$_2$)$_n$-[4], R$_9$ is hydrogen, (C$_1$-C$_4$)alkyl or —SO$_2$(C$_1$-C$_4$)alkyl and n is 1.

In a still preferred embodiment, Z is [3]-CH$_2$—X-[4] wherein X is selected from the group consisting of:
a group [5]-O—(CO)—(CH$_2$)$_n$-[4] wherein n is 0;
is a group [5]-S—(CO)-[4];
a group [5]-NR$_8$—SO$_2$—(CH$_2$)$_n$-[4], n is 0, and R$_8$ is hydrogen, (C$_1$-C$_4$)alkyl or alkyl(heterocycloalkyl); and
a group [5]-NR$_9$—(CH$_2$)$_n$-[4], R$_9$ is hydrogen, (C$_1$-C$_4$)alkyl or —SO$_2$(C$_1$-C$_4$)alkyl and n is 1.

In another preferred embodiment, Z is [3]-Y-[4], wherein Y is selected from the group consisting of:
a group [3]-NR$_9$—(CH2)n-[4];
a group [3]-S—(CH2)n-[4];
a group [3]-(CO)—NH-[4]; and
a group [3]-O—(CH$_2$)n-[4].

In further preferred embodiment, Z is [3]-Y-[4], wherein Y is a group [3]-NR$_9$—(CH2)n-[4].

In another preferred embodiment, Z is a group [3]-CHR$_{26}$—NR$_{27}$—SO$_2$-[4].

In one embodiment, for compounds of formula (IC), Z is selected from the group consisting of:
[3]-CH$_2$—X-[4] wherein X is a group [5]-NH—(CO)-[4];
[3]-CH$_2$—X-[4], wherein X is a group [5]-O—(CH2)n-[4];
[3]-CH$_2$—X-[4], wherein X is a group a group —SO2-;
[3]-CH$_2$—X-[4] wherein X is a group [5]-(CO)—O—(CH2)n[4];
[3]-CH$_2$—X-[4] wherein X is a group [5]-(CO)—NH-[4];
[3]-CH$_2$—X-[4] wherein X is a group [5]-NR$_9$—(CH2)n-[4];
[3]-CH$_2$—X-[4] wherein X is a group [5]-SO$_2$—NH-[4];
[3]-CH$_2$—X-[4] wherein X is a group [5]-NH—(CO)—(CO)-[4];
[3]-CH$_2$—X-[4] wherein X is a group [5]-O—(CO)—(CH$_2$)$_n$-[4];
[3]-CH$_2$—X-[4] wherein X is a group [5]-S—(CO)-[4];
[3]-CH$_2$—X-[4] wherein X is a group [5]-NR$_9$—(CH$_2$)$_n$-[4];
[3]-CH$_2$—X-[4] wherein X is a group [5]-NR$_8$—SO$_2$—(CH$_2$)$_n$-[4];
[3]-CH$_2$—X-[4], wherein X is a group [5]-O—SO$_2$-[4];
[3]-CH$_2$—X-[4], wherein X is a group [5]-NH—(CO)—NH-[4];
[3]-CHR$_7$—NH—(CO)-J-[4];
[3]-CH$_2$CH$_2$—K-[4] wherein K is a group [6]- NH—(CO)-[4];
[3]-CH$_2$CH$_2$—K-[4] wherein K is a group [6]-SO$_2$-[4];
[3]-CH$_2$CH$_2$—K-[4] wherein K is a group a group [6]-O—(CO)-[4];
[3]-Y-[4] wherein Y is a group [3]-(CO)-[4];
[3]-Y-[4], wherein Y is a group [3]-NR$_9$—(CH2)n-[4];
[3]-Y-[4], wherein Y is a group [3]-S—(CH2)n-[4];
[3]-Y-[4] wherein Y is a group [3]-(CO)—NH-[4];
[3]-Y-[4] wherein Y is [3]-O—(CH$_2$)n-[4];
[3]-Y-[4] wherein Y is [3]-CH=CH—SO$_2$-[4];
[3]-CHR$_{26}$—NR$_{27}$—SO$_2$-[4];
[3]-CHR$_6$—CH$_2$-[4];
[3]-C(OH)(OH)-[4]; and
[3]-C(CH$_3$)(R$_5$)—O—(CO)-[4].

According to a preferred embodiment, a compound of formula (I) is selected in the group consisting of:
(S)-3,5-dichloro-4-(2-(3-(cyclopropylmethoxy)-4-(difluoromethoxy)phenyl)-2-(2-(3,4-dimethoxyphenoxy)acetoxy)ethyl)pyridine 1-oxide;
(S)-3,5-dichloro-4-(2-(3-(cyclopropylmethoxy)-4-(difluoromethoxy)phenyl)-2-(2-(3,4-dimethoxyphenylsulfonyl)acetoxy)ethyl)pyridine 1-oxide;
(S)-3,5-dichloro-4-(2-(3-(cyclopropylmethoxy)-4-(difluoromethoxy)phenyl)-2-(3,4-dimethoxyphenylcarbamoyloxy)ethyl)pyridine 1-oxide;
(S)-4-(2-(benzyloxycarbonyloxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)phenyl)-2-((4-methoxyphenoxy)carbonyloxy)ethyl)pyridine 1-oxide;
(S)-3,5-dichloro-4-(2-(3-(cyclopropylmethoxy)-4-(difluoromethoxy)phenyl)-2-((3,4-dimethoxybenzyloxy)carbonyloxy)ethyl)pyridine 1-oxide;
(S)-3,5-dichloro-4-(2-(3-(cyclopropylmethoxy)-4-(difluoromethoxy)phenyl)-2-(2-((3,4-dimethoxybenzyl)(methyl)amino)acetoxy)ethyl)pyridine 1-oxide;
3,5-dichloro-4-((S)-2-(3-(cyclopropylmethoxy)-4-(difluoromethoxy)phenyl)-2-((S)-2-(3-(cyclopropylmethoxy)-4-(methylsulfonamido)benzoyloxy)-propanoyloxy)ethyl)pyridine 1-oxide;
(S)-3,5-dichloro-4-(2-(3-(cyclopropylmethoxy)-4-(difluoromethoxy)phenyl)-2-(2-(3,4-dimethoxybenzylamino)acetoxy)ethyl)pyridine 1-oxide;
(S)-3,5-dichloro-4-(2-(3-(cyclopropylmethoxy)-4-(difluoromethoxy)phenyl)-2-(3,4-dimethoxybenzylcarbamoyloxy)ethyl)pyridine 1-oxide;
(S)-3,5-dichloro-4-(2-((3-(cyclopropylmethoxy)-4-(difluoromethoxy)-benzyloxy)carbonyloxy)-2-(3-(cyclopropylmethoxy)-4-(difluoromethoxy)phenyl)-ethyl)pyridine 1-oxide;
(S)-3,5-dichloro-4-(2-(3-(cyclopropylmethoxy)-4-(difluoromethoxy)phenyl)-2-(2-(3-(cyclopropylmethoxy)-4-(methylsulfonamido)benzoyloxy)acetoxy)-ethyl)pyridine 1-oxide;
4-((S)-2-((R)-2-amino-3-phenylpropanoyloxy)-2-(3-(cyclopropylmethoxy)-4-(difluoromethoxy)phenyl)ethyl)-3,5-dichloropyridine 1-oxide;
4-((S)-2-((S)-2-amino-3-(4-(methylsulfonyloxy)phenyl)propanoyloxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)phenyl)-2-((3,4-dimethoxyphenylthio)carbonyloxy)ethyl)pyridine 1-oxide;
(S)-3,5-dichloro-4-(2-(3-(cyclopropylmethoxy)-4-(difluoromethoxy)phenyl)-2-((4-(methylsulfonamido)phenoxy)carbonyloxy)ethyl)pyridine 1-oxide;

(S)-3,5-dichloro-4-(2-(3-(cyclopropylmethoxy)-4-(difluoromethoxy)phenyl)-2-((3,4-dimethoxybenzylthio)carbonyloxy)ethyl)pyridine 1-oxide;

(S)-3,5-dichloro-4-(2-(3-(cyclopropylmethoxy)-4-(difluoromethoxy)phenyl)-2-((3-(cyclopropylmethoxy)-4-(methylsulfonamido)benzyloxy)carbonyloxy)-ethyl)pyridine 1-oxide;

(S)-3,5-dichloro-4-(2-(3-(cyclopropylmethoxy)-4-(difluoromethoxy)phenyl)-2-((3,4-dimethoxybenzyl)(methyl)carbamoyloxy)ethyl)pyridine 1-oxide;

(S)-3,5-dichloro-4-(2-(3-(cyclopropylmethoxy)-4-(difluoromethoxy)phenyl)-2-((3,4-dimethoxyphenyl)(methylcarbamoyloxy)ethyl)pyridine 1-oxide;

(S)-3,5-dichloro-4-(2-(3-(cyclopropylmethoxy)-4-(difluoromethoxy)phenyl)-2-(4-(methylsulfonamido)benzylcarbamoyloxy)ethyl)pyridine 1-oxide;

(S)-4-(2-((4-aminobenzyl)(methylcarbamoyloxy)-2-(3-(cyclopropyl-methoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(methyl(4-(methylsulfonamido)benzyl)carbamoyloxy)ethyl)pyridine 1-oxide;

(S)-3,5-dichloro-4-(2-(3-(cyclopropylmethoxy)-4-(difluoromethoxy)phenyl)-2-(methyl(4-nitrobenzyl)carbamoyloxy)ethyl)pyridine 1-oxide;

3,5-dichloro-4-((S)-2-(3-(cyclopropylmethoxy)-4-(difluoromethoxy)phenyl)-2-((S)-2-(methylsulfonamido)-3-(4-(methylsulfonyloxy)phenyl)propanoyloxy)-ethyl)pyridine 1-oxide;

(S)-3,5-dichloro-4-(2-(3-(cyclopropylmethoxy)-4-(difluoromethoxy)phenyl)-2-(3-(3-(cyclopropylmethoxy)-4-(methylsulfonamido)benzyloxy)-3-oxopropanoyloxy)ethyl)pyridine 1-oxide;

(S)-3,5-dichloro-4-(2-(3-(cyclopropylmethoxy)-4-(difluoromethoxy)phenyl)-2-(2-(N-(2-(methoxycarbonyl)phenyl)methylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(3-(cyclopropylmethoxy)-4-(methylsulfonamido)benzamido)acetoxy)-ethyl)pyridine 1-oxide;

3,5-dichloro-4-((S)-2-(3-(cyclopropylmethoxy)-4-(difluoromethoxy)phenyl)-2-((S)-2-(3-(cyclopropylmethoxy)-4-(methylsulfonamido)benzamido)-4-(methylthio)butanoyloxy)ethyl)pyridine 1-oxide;

(S)-3,5-dichloro-4-(2-(3-(cyclopropylmethoxy)-4-(difluoromethoxy)phenyl)-2-((3-methoxy-4-(2-morpholinoethoxy)benzyl)(methyl)carbamoyloxy)ethyl)pyridine 1-oxide;

(S)-3,5-dichloro-4-(2-(3-(cyclopropylmethoxy)-4-(difluoromethoxy)phenyl)-2-((4-methoxy-3-(methylsulfonamido)benzyl)(methyl)carbamoyloxy)ethyl)pyridine 1-oxide;

(S)-3,5-dichloro-4-(2-(3-(cyclopropylmethoxy)-4-(difluoromethoxy)phenyl)-2-((4-methoxy-3-(N-(2-morpholinoethyl)methylsulfonamido)benzyl)(methyl)-carbamoyloxy)ethyl)pyridine 1-oxide;

(S)-3,5-dichloro-4-(2-(3-(cyclopropylmethoxy)-4-(difluoromethoxy)phenyl)-2-((4-methoxy-3-(N-(2-morpholinoethyl)methylsulfonamido)phenoxy)carbonyloxy)-ethyl)pyridine 1-oxide;

(S)-3,5-dichloro-4-(2-(3-(cyclopropylmethoxy)-4-(difluoromethoxy)phenyl)-2-(2-(methyl(4-(methylsulfonamido)benzyl)amino)acetoxy)ethyl)pyridine 1-oxide;

(S)-3,5-dichloro-4-(2-(3-(cyclopropylmethoxy)-4-(difluoromethoxy)phenyl)-2-(2-(2-(methoxycarbonyl)phenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(2-(methylsulfonyl)benzamido)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(N-(2-morpholinoethyl)methylsulfonamido)benzoyloxy)-acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(methylsulfonyloxy)benzamido)acetoxy)ethyl)pyridine 1-oxide;

(S)-3,5-dichloro-4-(2-(3-(cyclopropylmethoxy)-4-(difluoromethoxy)phenyl)-2-(2-(4-(methylsulfonyloxy)benzamido)acetoxy)ethyl)pyridine 1-oxide;

(S)-4-(2-(2-benzamidoacetoxy)-2-(3-(cyclopropylmethoxy)-4-(difluoromethoxy)phenyl)ethyl)-3,5-dichloropyridine 1-oxide;

(S)-4-(2-(2-(4-carbamoylbenzamido)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(4-methoxy-3-(N-(2-morpholinoethyl)methylsulfonamido)benzamido)-acetoxy)ethyl)pyridine 1-oxide;

(S)-4-(2-(2-(3-acetamido-4-methoxyphenylsulfonamido)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(3,4-dimethoxybenzoyloxy)acetoxy)ethyl)pyridine 1-oxide;

(S)-3,5-dichloro-4-(2-(3-(cyclopropylmethoxy)-4-(difluoromethoxy)phenyl)-2-(2-(4-(N-methylsulfamoyl)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(N-(4-(methoxycarbonyl)benzyl)methylsulfonamido)acetoxy)ethyl)pyridine 1-oxide;

(S)-4-(2-(2-(3-(N-(2-amino-2-oxoethyl)methylsulfonamido)-4-methoxy-benzamido)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(3,4-dimethoxybenzamido)acetoxy)ethyl)pyridine 1-oxide;

(S)-3,5-dichloro-4-(2-(3-(cyclopropylmethoxy)-4-(difluoromethoxy)phenyl)-2-(2-(2-methoxy-4-(methylsulfonyloxy)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(4-(methylsulfonamidomethyl)benzoyloxy)acetoxy)ethyl)pyridine 1-oxide;

(S)-4-(2-(2-(3-(N-(2-amino-2-oxoethyl)methylsulfonamido)-4-methoxy-benzoyloxy)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(N-(3,4-dimethoxyphenyl)sulfamoyl)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(methyl sulfonyloxy)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(N-(3,4-dimethoxyphenyl)sulfamoyl)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(methylsulfonyloxy)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(methylsulfonamido)benzoyloxy)acetoxy)ethyl)pyridine 1-oxide;

(S)-4-(2-(3-(4-acetamidophenyl)propanoyloxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(3-(4-(methylsulfonamido)phenyl)propanoyloxy)ethyl)pyridine 1-oxide;

(S)-3,5-dichloro-4-(2-(3-(cyclopropylmethoxy)-4-(difluoromethoxy)phenyl)-2-(2-(3,4-dimethoxyphenylsulfonamido)acetoxy)ethyl)pyridine 1-oxide;

(S)-3,5-dichloro-4-(2-(3-(cyclopropylmethoxy)-4-(difluoromethoxy)phenyl)-2-(3-(3-(cyclopropylmethoxy)-4-(methylsulfonamido)benzamido)propanoyloxy)-ethyl)pyridine 1-oxide;

(S)-3,5-dichloro-4-(2-(2-(4-(cyclopropylmethoxy)-3-(methyl sulfonyloxy)-benzoyloxy)acetoxy)-2-(3-(cyclopropylmethoxy)-4-(difluoromethoxy)phenyl)ethyl)-pyridine 1-oxide;

(S)-3,5-dichloro-4-(2-(3-(cyclopropylmethoxy)-4-(difluoromethoxy)phenyl)-2-(2-(5-(N-(cyclopropylmethyl)methylsulfonamido)-2-hydroxybenzoyloxy)acetoxy)-ethyl)pyridine 1-oxide;

(S)-3,5-dichloro-4-(2-(3-(cyclopropylmethoxy)-4-(difluoromethoxy)phenyl)-2-(2-(2-oxo-2-phenylacetamido)acetoxy)ethyl)pyridine 1-oxide;

(S)-3,5-dichloro-4-(2-(3-(cyclopropylmethoxy)-4-(difluoromethoxy)phenyl)-2-(2-(N-(3,4-dimethoxybenzyl)methylsulfonamido)acetoxy)ethyl)pyridine 1-oxide;

(S)-4-(2-(2-(benzyloxy)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(3-(4-(methylthio)phenylamino)-3-oxopropanoyloxy)ethyl)pyridine 1-oxide;

(S)-3,5-dichloro-4-(2-(3-(cyclopropylmethoxy)-4-(difluoromethoxy)phenyl)-2-(3-(3,4-dimethoxyphenylamino)-3-oxopropanoyloxy)ethyl)pyridine 1-oxide;

(S)-3,5-dichloro-4-(2-(3-(cyclopropylmethoxy)-4-(difluoromethoxy)phenyl)-2-(3-(3,4-dimethoxyphenoxy)-3-oxopropanoyloxy)ethyl)pyridine 1-oxide;

3,5-dichloro-4-((S)-2-(3-(cyclopropylmethoxy)-4-(difluoromethoxy)phenyl)-2-((R)-2-(3,4-dimethoxyphenylsulfonamido)-4-(methylthio)butanoyloxy)ethyl)-pyridine 1-oxide;

(S)-3,5-dichloro-4-(2-(3-(cyclopropylmethoxy)-4-(difluoromethoxy)phenyl)-2-(2-(3,4-dimethoxy-N-methylphenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(N-(4-(methylthio)phenyl)methylsulfonamido)acetoxy)ethyl)pyridine I-oxide;

(S)-3,5-dichloro-4-(2-(3-(cyclopropylmethoxy)-4-(difluoromethoxy)phenyl)-2-(2-(N-(3,4-dimethoxyphenyl)methylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(4-(morpholine-4-carbonyl)phenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(3,4-dimethoxy-N-(2-morpholinoethyl)phenylsulfonamido)acetoxy)ethyl)-pyridine 1-oxide;

(S)-3,5-dichloro-4-(2-(3-(cyclopropylmethoxy)-4-(difluoromethoxy)phenyl)-2-((4-methoxyphenylthio)carbonyloxy)ethyl)pyridine 1-oxide;

(S)-3,5-dichloro-4-(2-(3-(cyclopropylmethoxy)-4-(difluoromethoxy)phenyl)-2-((3-methoxyphenylthio)carbonyloxy)ethyl)pyridine 1-oxide;

(S)-3,5-dichloro-4-(2-(3-(cyclopropylmethoxy)-4-(difluoromethoxy)phenyl)-2-((2-methoxyphenylthio)carbonyloxy)ethyl)pyridine 1-oxide;

(S)-3,5-dichloro-4-(2-(3-(cyclopropylmethoxy)-4-(difluoromethoxy)phenyl)-2-(phenylthiocarbonyloxy)ethyl)pyridine 1-oxide;

(S)-3,5-dichloro-4-(2-(3-(cyclopropylmethoxy)-4-(difluoromethoxy)phenyl)-2-((3-(dimethylamino)phenylthio)carbonyloxy)ethyl)pyridine 1-oxide;

(S)-3,5-dichloro-4-(2-((2-chlorophenylthio)carbonyloxy)-2-(3-(cyclopropylmethoxy)-4-(difluoromethoxy)phenyl)ethyl)pyridine 1-oxide;

(S)-3,5-dichloro-4-(2-((4-chlorophenylthio)carbonyloxy)-2-(3-(cyclopropylmethoxy)-4-(difluoromethoxy)phenyl)ethyl)pyridine 1-oxide;

(S)-3,5-dichloro-4-(2-(2-(3-(cyclopropylmethoxy)-4-(N-(2-(4-methylpiperazin-1-yl)ethyl)methylsulfonamido)benzoyloxy)acetoxy)-2-(3-(cyclopropylmethoxy)-4-(difluoromethoxy)phenyl)ethyl)pyridine 1-oxide;

(S)-3,5-dichloro-4-(2-(3-(cyclopropylmethoxy)-4-(difluoromethoxy)phenyl)-2-((2-fluorophenylthio)carbonyloxy)ethyl)pyridine 1-oxide;

(S)-3,5-dichloro-4-(2-(3-(cyclopropylmethoxy)-4-(difluoromethoxy)phenyl)-2-((3-fluorophenylthio)carbonyloxy)ethyl)pyridine 1-oxide;

(S)-3,5-dichloro-4-(2-(3-(cyclopropylmethoxy)-4-(difluoromethoxy)phenyl)-2-((5-fluoro-2-methoxyphenylthio)carbonyloxy)ethyl)pyridine 1-oxide;

(S)-3,5-dichloro-4-(2-(3-(cyclopropylmethoxy)-4-(difluoromethoxy)phenyl)-2-((4-(trifluoromethyl)phenylthio)carbonyloxy)ethyl)pyridine 1-oxide;

(S)-3,5-dichloro-4-(2-(3-(cyclopropylmethoxy)-4-(difluoromethoxy)phenyl)-2-((3-(trifluoromethyl)phenylthio)carbonyloxy)ethyl)pyridine 1-oxide;

(S)-3,5-dichloro-4-(2-(3-(cyclopropylmethoxy)-4-(difluoromethoxy)phenyl)-2-((2-(trifluoromethyl)phenylthio)carbonyloxy)ethyl)pyridine 1-oxide;

(S)-3,5-dichloro-4-(2-(3-(cyclopropylmethoxy)-4-(difluoromethoxy)phenyl)-2-(2-(4-(methylsulfonamido)phenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(3,4-dimethoxyphenylsulfonyloxy)acetoxy)ethyl)pyridine 1-oxide;

(S)-3,5-dichloro-4-(2-(3-(cyclopropylmethoxy)-4-(difluoromethoxy)phenyl)-2-(2,2-dihydroxy-2-(4-nitrophenyl)acetoxy)ethyl)pyridine 1-oxide;

(S)-3,5-dichloro-4-(2-(3-(cyclopropylmethoxy)-4-(difluoromethoxy)phenyl)-2-((4-fluorophenylthio)carbonyloxy)ethyl)pyridine 1-oxide;

(S)-3,5-dichloro-4-(2-(3-(cyclopropylmethoxy)-4-(difluoromethoxy)phenyl)-2-(2-(3-(cyclopropylmethoxy)-4-(methylsulfonamido)benzoyloxy)-2-methylpropanoyloxy)ethyl)pyridine 1-oxide;

(S)-3,5-dichloro-4-(2-(3-(cyclopropylmethoxy)-4-(difluoromethoxy)phenyl)-2-((3-(methylsulfonamido)phenylthio)carbonyloxy)ethyl)pyridine 1-oxide;

(S)-3,5-dichloro-4-(2-(3-(cyclopropylmethoxy)-4-(difluoromethoxy)phenyl)-2-(2-(4-(dimethylamino)phenyl)-2-oxoacetoxy)ethyl)pyridine 1-oxide;

(S)-3,5-dichloro-4-(2-(3-(cyclopropylmethoxy)-4-(difluoromethoxy)phenyl)-2-(2-(4-(N-methylsulfamoyl)phenylsulfonamido)acetoxy)ethyl)pyridine 1-oxide;

(S)-3,5-di chloro-4-(2-(3-(cyclopropylmethoxy)-4-(difluoromethoxy)phenyl)-2-(2-(2,5-dimethoxyphenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(4-(methylsulfonyl)phenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(4-(methylthio)phenylamino)-2-oxoacetoxy)ethyl)pyridine 1-oxide;

(S)-3,5-dichloro-4-(2-(3-(cyclopropylmethoxy)-4-(difluoromethoxy)phenyl)-2-((2,5-dimethoxyphenylthio)carbonyloxy)ethyl)pyridine 1-oxide;

(S)-3,5-dichloro-4-(2-(3-(cyclopropylmethoxy)-4-(difluoromethoxy)phenyl)-2-(2-(3-(3,4-dimethoxyphenyl)ureido)acetoxy)ethyl)pyridine 1-oxide;

(S)-3,5-dichloro-4-(2-(3-(cyclopropylmethoxy)-4-(difluoromethoxy)phenyl)-2-(2-(4-ethoxy-3-(3-(2-methoxyethyl)ureido)phenylsulfonamido)acetoxy)-ethyl)pyridine 1-oxide;

(S)-3,5-dichloro-4-(2-(3-(cyclopropylmethoxy)-4-(difluoromethoxy)phenyl)-2-((4-(methylsulfonamido)phenyl)methylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(2-methoxy-4-nitrophenylamino)-2-oxoacetoxy)ethyl)pyridine 1-oxide;

(S)-3,5-dichloro-4-(2-(3-(cyclopropylmethoxy)-4-(difluoromethoxy)phenyl)-2-(3-(3-(cyclopropylmethoxy)-4-(methylsulfonamido)benzoyloxy)propanoyloxy)-ethyl)pyridine 1-oxide;

(S)-3,5-dichloro-4-(2-(3-(cyclopropylmethoxy)-4-(difluoromethoxy)phenyl)-2-((4-(methylsulfonamido)phenylthio)carbonyloxy)ethyl)pyridine 1-oxide;

(S)-3,5-dichloro-4-(2-((3-chlorophenylthio)carbonyloxy)-2-(3-(cyclopropylmethoxy)-4-(difluoromethoxy)phenyl)ethyl)pyridine 1-oxide;

(S)-3,5-dichloro-4-(2-(3-(cyclopropylmethoxy)-4-(difluoromethoxy)phenyl)-2-((3-(cyclopropylmethoxy)-4-(methylsulfonamido)phenylthio)carbonyloxy)-ethyl)pyridine 1-oxide;

(S)-3,5-dichloro-4-(2-(3-(cyclopropylmethoxy)-4-(difluoromethoxy)phenyl)-2-(2-(4-nitrophenylsulfonyl)acetoxy)ethyl)pyridine 1-oxide;

(S)-3,5-dichloro-4-(2-(3-(cyclopropylmethoxy)-4-(difluoromethoxy)phenyl)-2-(3-(3,5-dimethoxyphenoxy)-3-oxopropanoyloxy)ethyl)pyridine 1-oxide;

(S)-3,5-dichloro-4-(2-(3-(cyclopropylmethoxy)-4-(difluoromethoxy)phenyl)-2-((2,4-dimethoxyphenylthio)carbonyloxy)ethyl)pyridine 1-oxide;

(S)-3,5-dichloro-4-(2-(3-(cyclopropylmethoxy)-4-(difluoromethoxy)phenyl)-2-((3-(N-(2-morpholinoethyl)methylsulfonamido)phenylthio)carbonyloxy)-ethyl)pyridine 1-oxide;

(S)-3,5-dichloro-4-(2-(3-(cyclopropylmethoxy)-4-(difluoromethoxy)phenyl)-2-(phenoxycarbonyloxy)ethyl)pyridine 1-oxide;

(S)-4-(2-(2-(benzoyloxy)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(3-(methylsulfonamido)benzoyloxy)acetoxy)ethyl)pyridine 1-oxide;

(S)-4-(2-(2-(benzoyloxy)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(3-(methylsulfonamido)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(3-(cyclopropylmethoxy)-4-(methylsulfonamido)benzoylthio)acetoxy)ethyl)-pyridine 1-oxide;

(S)-3,5-dichloro-4-(2-(3-(cyclopropylmethoxy)-4-(difluoromethoxy)phenyl)-2-(2-(4-methoxy-3-(methylsulfonamido)benzoylthio)acetoxy)ethyl)pyridine 1-oxide;

(S)-3,5-dichloro-4-(2-(3-(cyclopropylmethoxy)-4-(difluoromethoxy)phenyl)-2-(3-oxo-3-phenoxypropanoyloxy)ethyl)pyridine 1-oxide;

(S)-3,5-dichloro-4-(2-(3-(cyclopropylmethoxy)-4-(difluoromethoxy)phenyl)-2-(2-(4-(methylsulfonamido)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(3-(N-methylsulfamoyl)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(methylsulfonamido)phenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(2-(4-methoxy-3-(methylsulfonamido)phenyl)acetoxy)acetoxy)ethyl)pyridine 1-oxide;

(S)-3,5-dichloro-4-(2-(2-(2-(4-(cyclopropylmethoxy)-3-(methylsulfonamido)-phenylacetoxy)acetoxy)-2-(3-(cyclopropylmethoxy)-4-(difluoromethoxy)phenyl)-ethyl)pyridine 1-oxide;

(S)-3,5-dichloro-4-(2-(3-(cyclopropylmethoxy)-4-(difluoromethoxy)phenyl)-2-(2-(2-(2-(methylsulfonamido)phenyl)acetoxy)acetoxy)ethyl)pyridine 1-oxide;

4-((S)-2-((R)-5-acetoxy-2-(3,4-dimethoxyphenylsulfonamido)pentanoyloxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(2-(methylsulfonamido)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(2-(4-(methylsulfonamido)phenyl)acetoxy)acetoxy)ethyl)pyridine 1-oxide;

(S)-3,5-dichloro-4-(2-(3-(cyclopropylmethoxy)-4-(difluoromethoxy)phenyl)-2-(2-(3-methoxy-5-(methylsulfonamido)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(2-(3-(methylsulfonamido)phenyl)acetoxy)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(methylsulfonyloxy)benzoylthio)acetoxy)ethyl)pyridine 1-oxide;

(S)-3,5-dichloro-4-(2-(3-(cyclopropylmethoxy)-4-(difluoromethoxy)phenyl)-2-(2-(3-(methylsulfonamido)-5-(trifluoromethyl)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(N-(2-morpholinoethyl)methylsulfonamido)benzoylthio)-acetoxy)ethyl)pyridine 1-oxide;

(S)-3,5-dichloro-4-(2-(2-(4-(cyclopropylmethoxy)-3-(morpholinomethyl)-benzoyloxy)acetoxy)-2-(3-(cyclopropylmethoxy)-4-(difluoromethoxy)phenyl)ethyl)-pyridine 1-oxide;

(S)-3,5-dichloro-4-(2-(3-(cyclopropylmethoxy)-4-(difluoromethoxy)phenyl)-2-(2-(3-(dimethylcarbamoyl)phenylsulfonamido)acetoxy)ethyl)pyridine 1-oxide;

3,5-dichloro-4-((S)-2-(3-(cyclopropylmethoxy)-4-(difluoromethoxy)phenyl)-2-((S)-2-(3-(dimethylcarbamoyl)phenylsulfonamido)-3-methylbutanoyloxy)ethyl)-pyridine 1-oxide;

(S)-3,5-dichloro-4-(2-(3-(cyclopropylmethoxy)-4-(difluoromethoxy)phenyl)-2-(2-(3-(dimethylcarbamoyl)-4-methoxyphenylsulfonamido)acetoxy)ethyl)pyridine 1-oxide;

4-((2S)-2-(3-(acetylthio)-3-methyl-2-(phenylsulfonamido)butanoyloxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(3-(phenylsulfonyl)propanoyloxy)ethyl)pyridine 1-oxide;

3,5-dichloro-4-((S)-2-(3-(cyclopropylmethoxy)-4-(difluoromethoxy)phenyl)-2-((R)-2-(N-methylphenylsulfonamido)propanoyloxy)ethyl)pyridine 1-oxide;

(S,Z)-3,5-dichloro-4-(2-(3-(cyclopropylmethoxy)-4-(difluoromethoxy)-phenyl)-2-(3-(phenylsulfonyl)acryloyloxy)ethyl)pyridine 1-oxide;

(S,E)-3,5-dichloro-4-(2-(3-(cyclopropylmethoxy)-4-(difluoromethoxy)-phenyl)-2-(3-(phenylsulfonyl)acryloyloxy)ethyl)pyridine 1-oxide;

3,5-dichloro-4(S)-2-(3-(cyclopropylmethoxy)-4-(difluoromethoxy)phenyl)-2-((S)-2-(N-methylphenylsulfonamido)propanoyloxy)ethyl)pyridine 1-oxide;

3,5-dichloro-4-((S)-2-(3-(cyclopropylmethoxy)-4-(difluoromethoxy)phenyl)-2-((R)-2-(3-(dimethylcarbamoyl)-N-methylphenylsulfonamido)propanoyloxy)ethyl)pyridine 1-oxide;

3,5-dichloro-4-((S)-2-(3-(cyclopropylmethoxy)-4-(difluoromethoxy)phenyl)-2-((S)-2-(3-(dimethylcarbamoyl)-N-methylphenylsulfonamido)propanoyloxy)ethyl)pyridine 1-oxide;

3,5-dichloro-4-((R)-2-(3-(cyclopropylmethoxy)-4-(difluoromethoxy)phenyl)-2-((S)-2-(N-methylphenylsulfonamido)propanoyloxy)ethyl)pyridine 1-oxide;

3,5-dichloro-4-((R)-2-(3-(cyclopropylmethoxy)-4-(difluoromethoxy)phenyl)-2-((R)-2-(N-methylphenylsulfonamido)propanoyloxy)ethyl)pyridine 1-oxide;

3,5-dichloro-4-((R)-2-(3-(cyclopropylmethoxy)-4-(difluoromethoxy)phenyl)-2-((R)-2-(3-(dimethylcarbamoyl)-N-methylphenylsulfonamido)propanoyloxy)ethyl)pyridine 1-oxide;

3,5-dichloro-4-((R)-2-(3-(cyclopropylmethoxy)-4-(difluoromethoxy)phenyl)-2-((S)-2-(3-(dimethylcarbamoyl)-N-methylphenylsulfonamido)propanoyloxy)ethyl)pyridine 1-oxide;

and pharmaceutically acceptable salts or solvates thereof.

According to another preferred embodiment, a compound of formula (ID) is selected in the group consisting of:

(S)-3,5-dichloro-4-(2-(3-(cyclopropylmethoxy)-4-(difluoromethoxy)phenyl)-2-(2-(thiophene-2-carbonyloxy)acetoxy)ethyl)pyridine 1-oxide;

(S)-3,5-dichloro-4-(2-(3-(cyclopropylmethoxy)-4-(difluoromethoxy)phenyl)-2-(2-(6-(dimethylamino)nicotinoyloxy)acetoxy)ethyl)pyridine 1-oxide;

(S)-3,5-dichloro-4-(2-(3-(cyclopropylmethoxy)-4-(difluoromethoxy)phenyl)-2-(2-(thiazole-5-carbonyloxy)acetoxy)ethyl)pyridine 1-oxide;

(S)-3,5-dichloro-4-(2-(3-(cyclopropylmethoxy)-4-(difluoromethoxy)phenyl)-2-(2-(1-methyl-1H-pyrrole-2-carbonyloxy)acetoxy)ethyl)pyridine 1-oxide;

(S)-4-(2-(2-(benzo[b]thiophene-2-carbonyloxy)acetoxy)-2-(3-(cyclopropylmethoxy)-4-(difluoromethoxy)phenyl)ethyl)-3,5-dichloropyridine 1-oxide;

(S)-4-(2-(2-(1H-indole-2-carbonyloxy)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(oxazole-4-carbonyloxy)acetoxy)ethyl)pyridine 1-oxide;

(S)-4-(2-(2-(1H-indole-3-carbonyloxy)acetoxy)-2-(3-(cyclopropylmethoxy)-4-(difluoromethoxy)phenyl)ethyl)-3,5-dichloropyridine 1-oxide;

(S)-4-(2-(2-(1H-pyrrole-2-carbonyloxy)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(2-(methylsulfonamido)pyrimidine-5-carbonyloxy)acetoxy)ethyl)pyridine 1-oxide;

(S)-3,5-dichloro-4-(2-(3-(cyclopropylmethoxy)-4-(difluoromethoxy)phenyl)-2-(2-(2-(methylsulfonamido)isonicotinoyloxy)acetoxy)ethyl)pyridine 1-oxide;

and pharmaceutically acceptable salts or solvates thereof.

In one aspect of the present invention, a process for the preparation of compounds of the invention is provided, according to general synthetic routes summarized in Table A herebelow, where reference is made to specific synthetic schemes which are better detailed in the experimental section.

The skilled person may introduce, where appropriate, suitable variations to the conditions specifically described in the Examples in order to adapt the synthetic routes to the provision of further compounds of the invention. Such variations may include, but are not limited to, use of appropriate starting materials to generate different compounds, changes in the solvent and temperature of reactions, replacements of reactants with analogous chemical role, introduction or removal of protection/deprotection stages of functional groups sensitive to reaction conditions and reagents, as well as introduction or removal of specific synthetic steps oriented to further functionalization of the chemical scaffold.

Processes which can be used and are described and reported in the Examples and Schemes, should not be viewed as limiting the scope of the synthetic methods available for the preparation of the compounds of the invention.

The N-oxides on the 4-pyridinyl ring of the compounds of general formula (I) may be prepared according to methods available in the literature and well known to the skilled person. For instance, they may be prepared by dissolving the compound of general formula (I) in $CH_2Cl_2$ or $CHCl_3$, then adding an oxidizing agent such as m-chloro perbenzoic acid (mCPBA) to the resulting solution. Other oxidizing agents which may be used are hydrogen peroxide, perbenzoic acid and peracetic acid.

Alternatively, in particular for those compounds where a functional group sensitive to oxidation is present, the corresponding N-oxides are prepared by carrying out the oxidation step before further functional groups are introduced, for example on compounds of formula (II), thus generating compounds of formula (III).

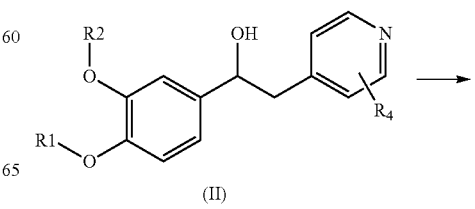

(II)

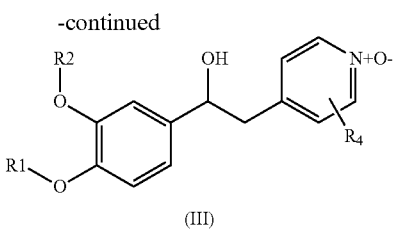

(III)

In a preferred embodiment, the process for preparation of compounds of formula (I) is performed starting from an N-oxide compound of formula (III) on the pyridine ring, thus allowing the preparation of compound of formula (I) in the form of N-oxides on the pyridine ring.

Compounds used as starting materials or intermediates may be commercially available, their preparation may be specifically described in the literature or they may be prepared according to methods available in the literature and well known to the person skilled in the art.

Compounds of formula (II) and (III) may also be prepared as described in International Patent Application WO 2009/018909, which is incorporated herein by reference in its entirety.

The process described is particularly advantageous as it is susceptible of being properly modulated, through any proper variant known to the skilled person, so as to obtained any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981) which is incorporated herein by reference in its entirety).

Likewise, selective protection and deprotection of any of the said groups, for instance including carbonyl, hydroxyl or amino groups, may be accomplished according to very well known methods commonly employed in organic synthetic chemistry.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear that the above processes, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

TABLE A

Starting from compounds of formula (II) shown below and by using procedures described in the referenced Examples and Schemes (or appropriate variations thereof), subgroups of compounds of formula (I) as below reported may be obtained (II)

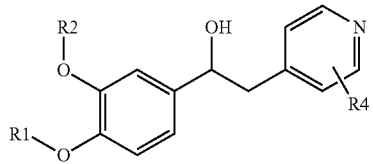

| Example (Synthetic Scheme) | Compounds |
| --- | --- |
| 1 | (Ia), (Ib), (Ic) |
| 20, 26 | (Ia) |
| 2 | (Id), (Ie), (If), (Ig), (Ih), (Ii) |
| 3, 52, 53 | (Ik), (Ij) |
| 4 | (Ika) |
| 5, 6, 7 | (Ija) |
| 8 | (Il) |
| 9 | (Im) |
| 10, 11 | (In) |
| 12 | (Io) |
| 13 | (Ip) |
| 14 | (Iq) |
| 15, 17, 18, 19, 22, 23, 25, 27 | (Ir), (Is) |
| 16 | (It) |
| 20 | (Iu) |
| 21 | (Iv) |
| 24 | (Iw) |
| 28, 45, 45bis, 47 | (Iy) |
| 29, 30, 31, 32 | (Iz) |
| 33, 34 | (Iα) |
| 35, 48 | (Iβ) |
| 44 | (Iδ) |
| 36 | (Iε) |
| 37 | (Iφ) |
| 38 | (Iγ) |
| 39 | (Iλ) |
| 40 | (Iμ) |
| 41 | (Iπ) |
| 42 | (Iθ) |
| 43 | (Iσ) |
| 45, 46 | (Iτ) |
| 49 | (Iυ) |
| 50 | (Iwa) |
| 54 | (Iω) |
| 55 | |
| 56 | |
| 57 | |
| 58 | |

Compounds of formula (Ia), i.e. compounds of formula (I) wherein Z is a group [3]-$CH_2$—X-[4] and X is a group [5]-NH—(CO)-[4], or compounds of formula (Ib), i.e. compounds of formula (I) wherein Z is a group [3]-$CHR_7$—NH—(CO)-J-[4], J is a bond and $R_7$ is a group ($C_1$-$C_4$)alkylthio($C_1$-$C_4$)alkyl, or compounds of formula (Ic), i.e. compounds of formula (I) wherein Z is a group [3]-$CH_2CH_2$—K-[4] and K is a group [6]-NH—(CO)-[4], may be prepared according to the procedures described in Example 1 (Scheme 1) of the Examples section or by appropriate variations thereof contemplated by the skilled person as above described.

Alternatively, compounds of formula (Ia), as above defined, may be prepared according to the procedures described in Example 20 (Scheme 20) or Example 26 (Scheme 26) of the Examples section or by appropriate variations thereof contemplated by the skilled person as above described.

Compounds of formula (Id), i.e. compounds of formula (I) wherein Z is a group [3]-CH$_2$CH$_2$—K-[4] and K is a group [6]-SO$_2$-[4], or compounds of formula (Ie), i.e. compounds of formula (I) wherein Z is a group [3]-CH$_2$—X-[4], X is a group [5]-O—(CH2)n-[4] and n is 1, or compounds of formula (If), i.e. compounds of formula (I) wherein Z is a group [3]-CH$_2$—X-[4], X is a group [5]-O—(CH2)n-[4] and n is 0, or compounds of formula (Ig), i.e. compounds of formula (I) wherein Z is a group [3]-CH$_2$—X-[4], X is a group a group —SO2-, or compounds of formula (Ih), i.e. compounds of formula (I) wherein Z is a group [3]-Y-[4] and Y is a group [3]-(CO)-[4], or compounds of formula (Ii), i.e. compounds of formula (I) wherein Z is a group [[3]-CHR$_6$—CH$_2$-[4] and R$_6$ is hydrogen, may be prepared according to the procedures described in Example 2 (Scheme 2) of the Examples section or by appropriate variations thereof contemplated by the skilled person as above described.

Compounds of formula (Ik), i.e. compounds of formula (I) wherein Z is a group [3]-Y-[4], Y is a group [3]-NR$_9$—(CH2)n-[4], n is 1 and R$_9$ is hydrogen or (C$_1$-C$_4$)alkyl, or compounds of formula (Ij), i.e. compounds of formula (I) wherein Z is a group [3]-Y-[4], Y is a group [3]-S—(CH2)n-[4] and n is 0 or 1, may be prepared according to the procedures described in Example 3 (Scheme 3), Example 53 (Scheme 53) or Example 52 (Scheme 52) of the Examples section or by appropriate variations thereof contemplated by the skilled person as above described.

Alternatively, compounds of formula (Ika), i.e. compounds of formula (Ik) as above defined wherein R$_9$ is (C$_1$-C$_4$)alkyl, may be prepared according to the procedures described in Example 4 (Scheme 4) of the Examples section or by appropriate variations thereof contemplated by the skilled person as above described.

Alternatively, compounds of formula (Ija), i.e. compounds of formula (Ij) as above defined wherein n is 0, may be prepared according to the procedures described in Example 5 (Scheme 5), Example 6 (Scheme 6) or Example 7 (Scheme 7) of the Examples section, or by appropriate variations thereof contemplated by the skilled person as above described.

Compounds of formula (Il), i.e. compounds of formula (I) wherein Z is a group [3]-CHR$_{26}$—NH—SO$_2$-[4] and R$_{26}$ is a group —CH2-CH2-CH2-O—(CO)CH3, may be prepared according to the procedures described in Example 8 (Scheme 8) of the Examples section or by appropriate variations thereof contemplated by the skilled person as above described.

Compounds of formula (Im), i.e. compounds of formula (I) wherein Z is a group [3]-CH$_2$—X-[4] and X is a group [5]-(CO)—O—(CH2)n[4] wherein n is 0 or 1, may be prepared according to the procedures described in Example 9 (Scheme 9) of the Examples section or by appropriate variations thereof contemplated by the skilled person as above described.

Compounds of formula (In), i.e. compounds of formula (I) wherein Z is a group [3]-CH$_2$—X-[4] and X is a group [5]-(CO)—NH-[4], may be prepared according to the procedures described in Example 10 (Scheme 10) or Example 11 (Scheme 11) of the Examples section, or by appropriate variations thereof contemplated by the skilled person as above described.

Compounds of formula (Io), i.e. compounds of formula (I) wherein Z is a group [3]-CH$_2$—X-[4] and X is a group [5]-NR$_9$—(CH2)n-[4] wherein n is 1 and R$_9$ is hydrogen or a group —SO$_2$(C$_1$-C$_4$)alkyl, may be prepared according to the procedures described in Example 12 (Scheme 12) of the Examples section, or by appropriate variations thereof contemplated by the skilled person as above described.

Compounds of formula (Ip), i.e. compounds of formula (I) wherein Z is a group [3]-CH$_2$—X-[4] and X is a group [5]-NR$_9$—(CH2)n-[4] wherein n is 1 and R$_9$ is (C$_1$-C$_4$) alkyl, may be prepared according to the procedures described in Example 13 (Scheme 13) of the Examples section, or by appropriate variations thereof contemplated by the skilled person as above described.

Compounds of formula (Iq), i.e. compounds of formula (I) wherein Z is a group [3]-CH$_2$—X-[4] and X is a group a group [5]-SO$_2$—NH-[4], may be prepared according to the procedures described in Example 14 (Scheme 14) of the Examples section, or by appropriate variations thereof contemplated by the skilled person as above described.

Compounds of formula (Ir), i.e. compounds of formula (I) wherein Z is a group [3]-CH$_2$—X-[4] and X is a group [[5]-O—(CO)—(CH$_2$)$_n$-[4] wherein n is 0, or compounds of formula (Is), i.e. compounds of formula (I) wherein Z is a group [3]-C(CH$_3$)(R$_5$)—O—(CO)-[4] and R$_5$ is a group R$_5$ is hydrogen, (C$_1$-C$_4$)alkyl or a phenyl group, may be prepared according to the procedures described in Example 15 (Scheme 15), Example 17 (Scheme 17), Example 18 (Scheme 18), Example 19 (Scheme 19), Example 22 (Scheme 22), Example 23 (Scheme 23), Example 25 (Scheme 25), Example 27 (Scheme 27) of the Examples section, or by appropriate variations thereof contemplated by the skilled person as above described.

Compounds of formula (It), i.e. compounds of formula (I) wherein Z is a group [3]-CH$_2$CH$_2$—K-[4] and K is a group a group [6]-O—(CO)-[4], may be prepared according to the procedures described in Example 16 (Scheme 16) of the Examples section, or by appropriate variations thereof contemplated by the skilled person as above described.

Compounds of formula (Iu), i.e. compounds of formula (I) wherein Z is a group [3]-CH$_2$—X-[4] and X is a group [5]-NH—(CO)—(CO)-[4] may be prepared according to the procedures described in Example 20 (Scheme 20) of the Examples section, or by appropriate variations thereof contemplated by the skilled person as above described.

Compounds of formula (Iv), i.e. compounds of formula (I) wherein Z is a group [3]-CH$_2$—X-[4] and X is a group [[5]-O—(CO)—(CH$_2$)$_n$-[4] wherein n is 0 or 1, may be prepared according to the procedures described in Example 21 (Scheme 21) of the Examples section, or by appropriate variations thereof contemplated by the skilled person as above described.

Compounds of formula (Iw), i.e. compounds of formula (I) wherein Z is a group [3]-CHR$_{26}$—NR$_{27}$—SO$_2$-[4] and R$_{26}$ is a group a group —C(CH3)(CH3)-S—(CO)CH3, may be prepared according to the procedures described in Example 24 (Scheme 24) of the Examples section or by appropriate variations thereof contemplated by the skilled person as above described.

Compounds of formula (Iwa), i.e. compounds of formula (I) wherein Z is a group [3]-CHR$_{26}$—NR$_{27}$—SO$_2$-[4] and R$_{26}$ is hydrogen or (C$_1$-C$_4$)alkyl, may be prepared according to the procedures described in Example 51 (Scheme 51) of the Examples section or by appropriate variations thereof contemplated by the skilled person as above described.

Compounds of formula (Iy), i.e. compounds of formula (I) wherein Z is a group [3]-Y-[4], Y is [3]-O—(CH2)$_n$-[4] and n is 0, may be prepared according to the procedures described in Example 28 (Scheme 28), Example 45 (Scheme 45), Example 45bis (Scheme 45bis), or Example 47 (Scheme 47) of the Examples section, or by appropriate variations thereof contemplated by the skilled person as above described.

Compounds of formula (Iz), i.e. compounds of formula (I) wherein Z is a group [3]-CH$_2$—X-[4] and X is a group [5]-

S—(CO)-[4], may be prepared according to the procedures described in Example 29 (Scheme 20), Example 30 (Scheme 30), Example 31 (Scheme 31) or Example 32 (Scheme 32) of the Examples section, or to appropriate variations thereof contemplated by the skilled person as above described.

Compounds of formula (Iα), i.e. compounds of formula (I) wherein Z is a group [3]-CH$_2$—X-[4] and X is a group [5]-NR$_9$—(CH$_2$)$_n$-[4], n is 0 or 1, and R$_9$ is —SO$_2$(C$_1$-C$_4$) alkyl, may be prepared according to the procedures described in Example 33 (Scheme 33) or Example 34 (Scheme 34) of the Examples section, or by appropriate variations thereof contemplated by the skilled person as above described.

Compounds of formula (Iβ), i.e. compounds of formula (I) wherein Z is a group [3]-CHR$_6$—CH$_2$-[4], R$_6$ is a group —NHR$_{10}$ and R$_{10}$ is hydrogen, may be prepared according to the procedures described in Example 35 (Scheme 35) or Example 48 (Scheme 48) of the Examples section, or by appropriate variations thereof contemplated by the skilled person as above described.

Compounds of formula (Iδ), i.e. compounds of formula (I) wherein Z is a group [3]-CHR$_6$—CH$_2$-[4] and R$_6$ is hydrogen, may be prepared according to the procedures described in Example 44 (Scheme 44) of the Examples section, or by appropriate variations thereof contemplated by the skilled person as above described.

Compounds of formula (Iε), i.e. compounds of formula (I) wherein Z is a group [3]-CH$_2$—X-[4], X is a group [5]-NR$_8$—SO$_2$—(CH$_2$)$_n$-[4], n is 0, and R$_8$ is hydrogen, (C$_1$-C$_4$) alkyl or alkyl(heterocycloalkyl), may be prepared according to the procedures described in Example 36 (Scheme 36) of the Examples section, or by appropriate variations thereof contemplated by the skilled person as above described.

Alternatively, compounds of formula (Iϕ), i.e. compounds of formula (Iε) as above defined wherein R$_8$ is hydrogen, may be prepared according to the procedures described in Example 37 (Scheme 37) of the Examples section, or by appropriate variations thereof contemplated by the skilled person as above described.

Compounds of formula (Iγ)), i.e. compounds of formula (I) wherein Z is a group [3]-CH$_2$—X-[4], X is a group [5]-NR$_8$—SO$_2$—(CH$_2$)$_n$-[4], n is 0 or 1, and R$_8$ is hydrogen, may be prepared according to the procedures described in Example 38 (Scheme 38) of the Examples section, or by appropriate variations thereof contemplated by the skilled person as above described.

Compounds of formula (Iλ), i.e. compounds of formula (I) wherein Z is a group [3]-Y-[4], and Y is a group [3]-(CO)—NH-[4], may be prepared according to the procedures described in Example 39 (Scheme 39) of the Examples section, or by appropriate variations thereof contemplated by the skilled person as above described.

Compounds of formula (Iμ), i.e. compounds of formula (I) wherein Z is a group [3]-C(OH)(OH)-[4], may be prepared according to the procedures described in Example 40 (Scheme 40) of the Examples section, or by appropriate variations thereof contemplated by the skilled person as above described.

Compounds of formula (Iπ), i.e. compounds of formula (I) wherein Z is a group [3]-CH$_2$—X-[4], and X is a group [5]-O—SO$_2$-[4], may be prepared according to the procedures described in Example 41 (Scheme 41) of the Examples section, or by appropriate variations thereof contemplated by the skilled person as above described.

Compounds of formula (Iθ), i.e. compounds of formula (I) wherein Z is a group [3]-CH$_2$—X-[4], and X is a group [[5]-NH—(CO)—NH-[4], may be prepared according to the procedures described in Example 42 (Scheme 42) of the Examples section, or by appropriate variations thereof contemplated by the skilled person as above described.

Compounds of formula (Iσ), i.e. compounds of formula (I) wherein Z is a group [3]-Y-[4], Y is a group [3]-NR$_9$—(CH2)n-[4], n is 0 and R$_9$ is (C$_1$-C$_4$)alkyl, may be prepared according to the procedures described in Example 43 (Scheme 43) of the Examples section, or by appropriate variations thereof contemplated by the skilled person as above described.

Compounds of formula (Iι), i.e. compounds of formula (I) wherein Z is a group [3]-Y-[4], Y is [3]-O—(CH$_2$)n-[4] and n is 0 or 1, may be prepared according to the procedures described in Example 45 (Scheme 45), or Example 46 (Scheme 46), of the Examples section, or by appropriate variations thereof contemplated by the skilled person as above described.

Compounds of formula (Iv), i.e. compounds of formula (I) wherein Z is a group [3]-Y-[4] and Y is [3]-CH=CH—SO$_2$-[4], may be prepared according to the procedures described in Example 59 (Scheme 49) of the Examples section, or by appropriate variations thereof contemplated by the skilled person as above described.

Compounds of formula (Iω), i.e. compounds of formula (I) wherein Z is a group [3]-C(CH$_3$)(R$_5$)—O—(CO)-[4] and R$_5$ is (C$_1$-C$_4$)alkyl may be prepared according to the procedures described in Example 54 (Scheme 54) of the Examples section, or by appropriate variations thereof contemplated by the skilled person as above described.

Compounds of formula (ID), may be prepared according to the procedures described in Example 55 (Scheme 55), Example 56 (Scheme 56), Example 57 (Scheme 57) or Example 58 (Scheme 58) of the examples section, or by appropriate variations thereof contemplated by the skilled person as above described.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the present invention may be administered alone or combined with various known pharmaceutically acceptable carriers, diluents (such as sucrose, mannitol, lactose, starches) and excipients, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the present invention, including aqueous and non-aqueous solutions, emulsions, suspensions, syrups, and elixirs. Such dosage forms can also contain suitable inert diluents known in the art such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, known suitable carriers.

For topical administration, the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable preparations include inhalable powders, propellant-containing metering aerosols or propellant-free inhalable formulations.

For administration as a dry powder, known single- or multi-dose inhalers may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the present invention may be administered as the sole active agent or in combination with other pharmaceutical active ingredients including those currently used in the treatment of respiratory disorders, e.g. beta$_2$-agonists, corticosteroids and anticholinergic or antimuscarinic agents.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the invention may be administered for example, at a dosage of 0.001 to 1000 mg/day, preferably 0.1 to 500 mg/day.

When they are administered by inhalation route, the dosage of the compounds of the present invention is advantageously 0.01 to 20 mg/day, preferably 0.1 to 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

However the compounds of the present invention may be administered for the prevention and/or treatment of any disease wherein PDE4 inhibition is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia greata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases, and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Chemical Names of the compounds were generated with Structure To Name Enterprise 10.0 Cambridge Software.
Abbreviations
EDC=1-ethyl-3-(3-dimethylaminopropyl)carbodiimide);
DMAP=4-dimethylaminopyridine;
DMF=dimethylformamide;
EtOAc=ethyl acetate;
RT=room temperature;
THF=tetrahydrofuran;
DCM=dichloromethane;
Et2O=diethyl ether;
MeOH=methyl alcohol;
n-butOH=n-butyl alcohol;
EtOH=ethyl alcohol;
IprOH or IPA=isopropyl alcohol;
IprO2=diisopropylether;
TEA=triethylamine;
Py=pyridine;
MsCl=methanesulfonyl chloride;
TFA=trifluoroacetic acid;
CH3CN=acetonitrile;
(Boc)2O=ditertbutyl dicarbonate;
AcOH=acetic acid;
CDI=carbonyldiimidazole;
DMSO=dimethyl sulfoxide;
MW=microwave irradiation;
HATU=2-(1H-7-azabenzotriazol-1-yl)-1,1,3,3-tetramethyl uranium hexafluorophosphate Methanaminium.

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

NMR Characterization

NMR spectra recording was performed either with:

$^1$H-NMR spectra were recorded on a 400 MHz Varian AS400 spectrometer. Chemical shift are reported as S values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined):

or $^1$H-NMR spectra were recorded on a Bruker ARX300 Spectrometer at 300.13 MHz (1H) using deuterated solvents, such as deuterated dimethylsulfoxide (DMSO-d6) or deuterated chloroform (CDCl3). The instrument was equipped with a multinuclear inverse probe and temperature controller. Chemical shifts are expressed in parts per million (ppm) downfield of tetramethylsilane (d units). Multiplicity is indicated as follow: (s) singlet, (d) doublet, (dd) double doublet, (ddd) triple doublet, (t) triplet, (dt) double triplet, (q) quartet, (m) multiplet, (br s) broad signal. Coupling constants J are expressed in units of hertz (Hz).

LC/MS preparative method:
Waters Micromass ZQ/sample manager 2767
Photodiode array detector: 2996
Column: XTERRA Prep MS C18 10 um 19×300
Flow: 20 ml/min
Mobile phases: H$_2$O, 0.1% TFA (A); acetonitrile, 0.1% TFA (B)
Gradient:

| Time (min) | % A | % B |
|---|---|---|
| 0.00 | 90 | 10 |
| 2 | 90 | 10 |
| 23 | 0 | 100 |
| 30 | 0 | 100 |

Conditioning:

| Time (min) | % A | % B |
|---|---|---|
| 30.5 | 90 | 10 |
| 32 | 90 | 10 |

HPLC Preparative Method
Column: Waters Symmetry Prep C18 17 um 19×300
Flow: 20 ml/min
Mobile phase: 90% H$_2$O, 10% acetonitrile, 0.05% TFA (A), 10% H$_2$O, 90% acetonitrile, 0.05% TFA (B)
Gradient:

| Time (min) | % A | % B |
|---|---|---|
| 0.00 | 95 | 5 |
| 5 | 95 | 5 |
| 28 | 0 | 100 |
| 30 | 0 | 100 |

The same gradient without TFA in mobile phase was used for preparative HPLC under neutral conditions.

Preparative Reverse-phase HPLC Method
Waters Micromass ZQ; Sample manager 2767; Photodiode array detector 2996;
Column XTerra Prep MS C18 Column (5 μm, 19×150 mm, Waters); flow rate of 20 ml/min with MS detection or UV set at 254 nm.

Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Eluent
Solvent A (water:MeCN:HCOOH 95:5:0.05)
Solvent B (water:MeCN:HCOOH 5:95:0.05)

Optical Rotation (Activity) Determination
Specific rotations of compounds were measured with a Polarimeter Perkin Elmer model 341.
Temperature (° C.) 25
Path Length (dm)1
Wavelength Sodium D-line (589 nm)
The MS/ESI$^+$ [MH]$^+$ values reported in the text below may be obtained either by MS instrument Waters ZQ (or equivalent) or by UPLC Waters instrument:
MS Instrument: Waters ZQ (or Equivalent):
Polarity ES+
Capillary (kV)3.00
Cone (V) 20.00
Extractor (V) 3.00
RF Lens (V) 1.0
Polarity ES−
Capillary (kV) 3.00
Cone (V) 20.00
Extractor (V) 3.00
RF Lens (V) 1.0
Source Temperature (° C.) 110
Desolvation Temperature (° C.) 210
Cone Gas Flow (L/Hr) 150
Desolvation Gas Flow (L/Hr) 650
Mass range: 100 to 950
Scan time (sec): 0.32
Inter-Scan delay (sec): 0.03
LC instrument: Acquity Waters UPLC:
Instrument: UPLC Waters coupled with ZQ micromass and interfaced with 2996 PDA detector
Column: Acquity UPLC BEH C18 1.7 um 50×2.1 mm
Method: TFA long
Conditions: ESI+, 3.2 KV, 25V, 350° C.
Wavelength: PBI

| Time (sec) | % B | Flow (mL/min) | A | B |
|---|---|---|---|---|
| 0.00 | 5.0 | 0.6 | 95:5 H2O:ACN (0.1% TFA) | 5:95 H2O:ACN (0.1% TFA) |
| 0.50 | 5.0 | 0.6 | | |
| 6.00 | 100.0 | 0.6 | | |
| 7.00 | 100.0 | 0.6 | | |
| 7.10 | 5.0 | 0.6 | | |
| 8.50 | 5.0 | 0.6 | | |

Detailed synthetic pathways and procedures for specific examples are outlined in Schemes 1-54. The synthesis of compound I was described in WO 2010/089107, which is incorporated herein by reference in its entirety, (compound 7). The synthesis of compound (3,5-dichloro-4-(2-(3-(cyclopropylmethoxy)-4-(difluoromethoxy)phenyl)-2-hydroxyethyl)pyridine 1-oxide) (was described in WO 2009/18909, which is incorporated herein by reference in its entirety, (compound 18).

Example 1
Synthesis of (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzamido)acetoxy)ethyl)pyridine 1-oxide (5)
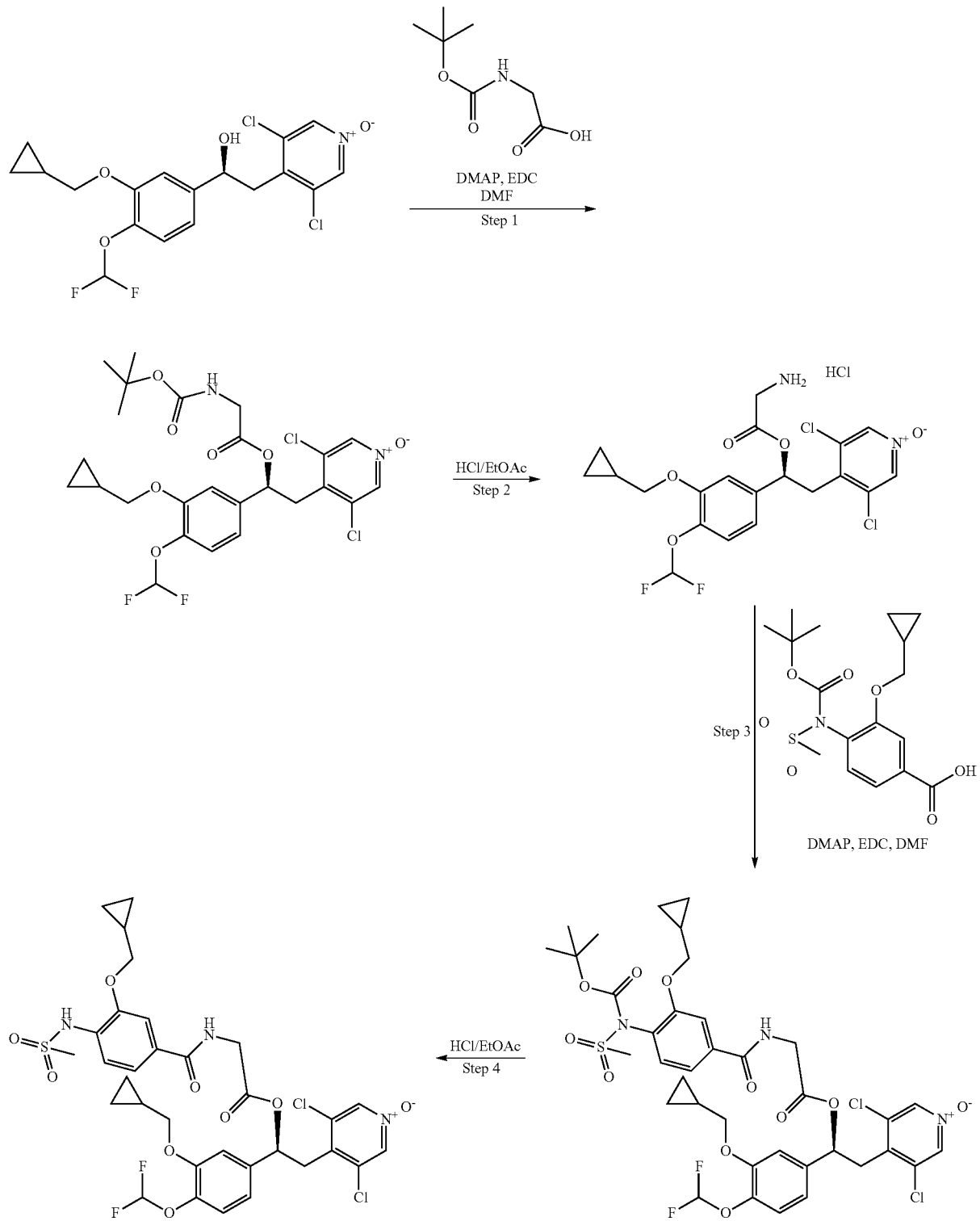
Scheme 1

Step 1: Synthesis of (S)-4-(2-(2-(tert-butoxycarbonylamino)acetoxy)-2-(3-(cyclopropylmethoxy)-4-(difluoromethoxy)phenyl)ethyl)-3,5-dichloropyridine 1-oxide (2)

(S)-3,5-dichloro-4-(2-(3-(cyclopropylmethoxy)-4-(difluoromethoxy)phenyl)-2-hydroxyethyl)pyridine 1-oxide (80 mg; 0.19 mmol) was dissolved in DMF (2 ml), then 2-(tert-butoxycarbonylamino)acetic acid (70 mg, 0.4 mmol), EDC (60 mg, 0.3 mmol), and DMAP (30 mg, 0.25 mmol) were added. The reaction was stirred at RT for 6 hours, then it was diluted with water and extracted with EtOAc. The organic phase was extracted with HCl 1M and with K2CO3 sat, dried over Na$_2$SO$_4$ and evaporated under vacuum to give 80 mg of the desired compound (Yield: 74%).

Step 2: Synthesis of (S)-4-(2-(2-aminoacetoxy)-2-(3(cyclopropylmethoxy)-4-(difluoromethoxy)phenyl)ethyl)-3,5-dichloropyridine 1-oxide hydrochloride (3)

(S)-4-(2-(2-(tert-butoxycarbonylamino)acetoxy)-2-(3-(cyclopropylmethoxy)-4-(difluoromethoxy)phenyl)ethyl)-3,5-dichloropyridine 1-oxide (80 mg, 0.17 mmol) was dissolved in HCl 4M in EtOAc (2 ml) and stirred at RT for 3 hours. The solvent was evaporated under vacuum, and the crude product was crystallized from EtOAc/Hexane to give 60 mg of the desired product (Yield: 69%).

Step 3: Synthesis of (S)-4-(2-(2-(4-(N-(tert-butoxycarbonyl)-methylsulfonamido)-3-(cyclopropylmethoxy)benzamido)-acetoxy)-2-(3-(cyclopropylmethoxy)-4-(difluoromethoxy)phenyl)ethyl)-3,5-dichloropyridine 1-oxide (4)

((S)-4-(2-(2-aminoacetoxy)-2-(3-(cyclopropylmethoxy)-4-(difluoromethoxy)-phenyl)ethyl)-3,5-dichloropyridine 1-oxide hydrochloride) (103 mg; 0.2 mmol) was dissolved in DMF (1.5 ml), then 3-(N-(tert-butoxycarbonyl)methylsulfonamido)-4-(cyclopropylmethoxy)benzoic acid (80 mg, 0.2 mmol), (for a reference procedure see Example 18, WO 2010/089107, which is incorporated herein by reference in its entirety), EDC (80 mg, 0.42 mmol), and DMAP (60 mg, 0.49 mmol) were added. The reaction was stirred at RT overnight, then was diluted with HCl 1M and extracted with EtOAc. The organic phase was washed with HCl 1M and with K2CO3 sat, dried over Na$_2$SO$_4$ and evaporated under vacuum to give 180 mg of the desired product (Yield: quantitative).

Step 4: Synthesis of (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzamido)acetoxy)ethyl)pyridine 1-oxide (5)

(S)-4-(2-(2-(4-(N-(tert-butoxycarbonyl)methylsulfonamido)-3-(cyclopropylmethoxy)benzamido)acetoxy)-2-(3-(cyclopropylmethoxy)-4-(difluoromethoxy)phenyl)ethyl)-3,5-dichloropyridine 1-oxide (180 mg, 0.2 mmol) was dissolved in HCl 4M in EtOAc and stirred overnight at 0° C. The solvent was evaporated under vacuum, and the crude product was purified by Preparative reverse-phase HPLC to give 12 mg of the final product (Yield: 8%).

MS/ESI$^+$ 744.587 [MH]$^+$ $^1$H NMR (400 MHz, acetone) δ ppm 8.17 (s, 3 H), 7.92-8.02 (bs, 1 H), 7.43-7.68 (m, 3 H), 7.15-7.25 (m, 2 H), 7.06 (d, J=1.76 Hz, 1 H), 6.92 (t, J=75.00 Hz, 1 H), 6.09-6.19 (m, 1 H), 4.06-4.20 (m, 2 H), 3.97-4.05 (m, 4 H), 3.47-3.60 (m, 1 H), 3.25-3.36 (m, 1 H), 3.08 (s, 3 H), 1.23-1.41 (m, 2 H), 0.56-0.68 (m, 4 H), 0.41 (t, J=4.85 Hz, 4 H).

The compounds listed in Table 1 were prepared with an analogous procedure to that described in Scheme 1, Step 1, 2 and 3 by reacting the appropriate precursors (commercially available or synthesized by a person skilled in the art) with suitable reagents, and where purification step has been performed as indicated in Table 1.

TABLE 1

| Structure | Cmp | $^1$H NMR | MS/ESI$^+$ [MH]$^+$ | Purification Method |
|---|---|---|---|---|
| 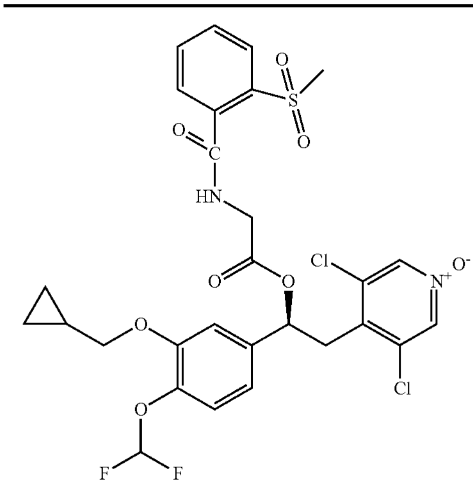 | 6 | 1H NMR (400 MHz, acetone) δ ppm 8.25 (s, 2 H), 8.04 (dd, J = 7.72, 1.10 Hz, 2 H), 7.75-7.83 (m, 1 H), 7.68-7.74 (m, 1 H), 7.65 (dd, J = 7.28, 1.10 Hz, 1 H), 7.25 (d, J = 1.76 Hz, 1 H), 7.19 (d, J = 8.38 Hz, 1 H), 7.04-7.13 (m, 1 H), 6.91 (t, 1 H, CHF2), 6.20 (dd, J = 8.82, 4.85 Hz, 1 H), 4.19 (d, J = 5.73 Hz, 2 H), 3.89-4.05 (m, 2 H), 3.62 (dd, J = 14.11, 8.82 Hz, 1 H), 3.28-3.44 (m, 4 H), 1.14-1.35 (m, 1 H), 0.48-0.66 (m, 2 H), 0.24-0.41 (m, 2 H). | 659.48 | Preparative reverse-phase HPLC |

TABLE 1-continued

| Structure | Cmp | ¹H NMR | MS/ESI⁺ [MH]⁺ | Purification Method |
|---|---|---|---|---|
| 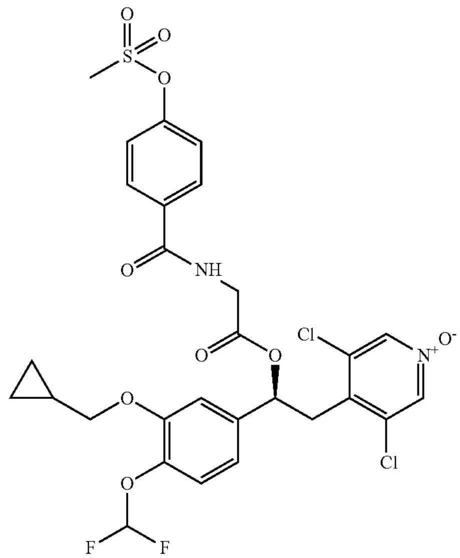 | 7 | 1H NMR (400 MHz, acetone) ☐ ppm 8.26 (br. s., 1 H), 8.19 (s, 2 H), 8.02 (d, J = 8.82 Hz, 2 H), 7.47 (d, J = 8.38 Hz, 2 H), 7.15-7.27 (m, 2 H), 7.05 (d, J = 7.94 Hz, 1 H), 6.92 (t, 1 H, CHF2), 6.14 (m, 1 H), 4.15 (dd, J = 11.25, 5.95 Hz, 2 H), 4.00 (dd, J = 6.62, 4.41 Hz, 2 H), 3.52 (d, J = 9.70 Hz, 1 H), 3.25-3.38 (m, 4 H), 1.29 (m, 1 H), 0.62 (d, J = 7.94 Hz, 2 H), 0.40 (d, J = 3.97 Hz, 2 H) | 675.48 | Trituration in Et2O |
| 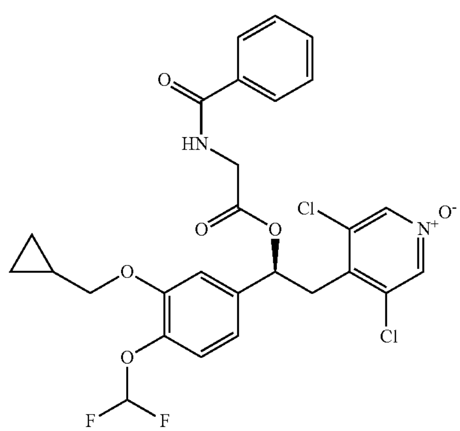 | 8 | 1H NMR (400 MHz, acetone) δ ppm 8.22 (s, 2 H), 8.15 (br. s., 1 H), 7.92 (d, J = 7.06 Hz, 2 H), 7.42-7.62 (m, 3 H), 7.15-7.28 (m, 2 H), 7.03-7.09 (m, 1 H), 6.92 (t, 1 H, CHF2), 6.14 (dd, J = 9.48, 4.63 Hz, 1 H), 4.15 (dd, J = 8.38, 5.73 Hz, 2 H), 4.00 (dd, J = 6.84, 5.07 Hz, 2 H), 3.54 (dd, J = 14.11, 9.70 Hz, 1 H), 3.33 (dd, J = 14.11, 4.41 Hz, 1 H), 1.17-1.36 (m, 1 H), 0.55-0.68 (m, 2 H), 0.40 (d, J = 4.41 Hz, 2 H) | 581.39 | Trituration in Et2O |
| 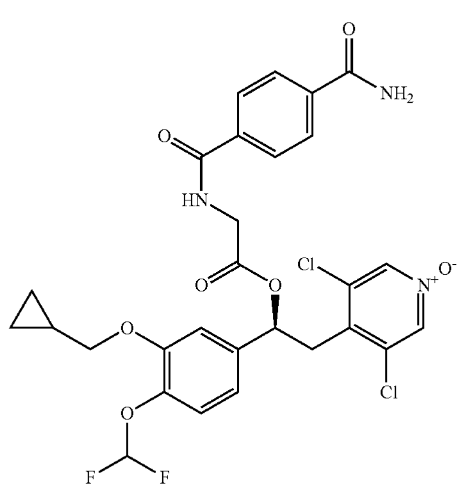 | 9 | 1H NMR (400 MHz, acetone) δ ppm 8.29 (t, 1 H), 8.22 (s, 2 H), 7.93-8.06 (m, 4 H), 7.48-7.62 (m, 1 H), 7.16-7.26 (m, 2 H), 7.05 (dd, J = 7.94, 1.76 Hz, 1 H), 6.93-6.74 (m, 2 H), 6.14 (dd, J = 9.48, 4.63 Hz, 1 H), 4.17 (dd, J = 11.03, 5.73 Hz, 2 H), 4.00 (dd, J = 6.62, 4.85 Hz, 2 H), 3.48-3.63 (m, 1 H), 3.33 (dd, J = 14.11, 4.85 Hz, 1 H), 1.29 (m, 1 H), 0.56-0.68 (m, 2 H), 0.40 (d, J = 4.41 Hz, 2 H) | 624.42 | Crystallization in EtOH |

TABLE 1-continued

| Structure | Cmp | ¹H NMR | MS/ESI⁺ [MH]⁺ | Purification Method |
|---|---|---|---|---|
| 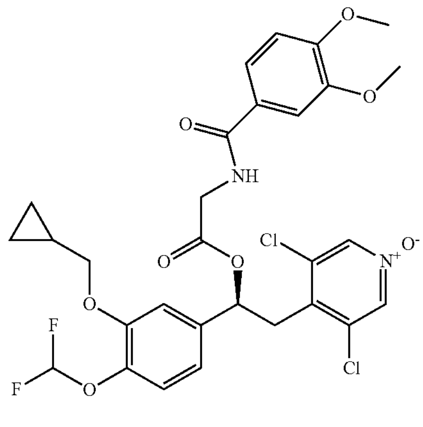 | 10 | 1H NMR (400 MHz, acetone) δ ppm 8.21 (s, 2 H), 8.04 (br. s., 1 H), 7.47-7.56 (m, 2 H), 7.16-7.26 (m, 2 H), 6.99-7.07 (m, 2 H), 6.92 (t, J = 75.00 Hz, 1 H), 6.13 (dd, J = 9.70, 4.41 Hz, 1 H), 4.10 (dd, J = 12.79, 5.73 Hz, 2 H), 3.94-4.05 (m, 2 H), 3.87 (s, 6 H), 3.53 (dd, J = 14.11, 9.70 Hz, 1 H), 3.31 (dd, J = 14.11, 4.41 Hz, 1 H), 1.28 (m, 1 H), 0.51-0.69 (m, 2 H), 0.31-0.47 (m, 2 H) | 641.44 | Preparative reverse-phase HPLC |

The compounds listed in Table 2 were prepared with an analogous procedure to that described in Scheme 1, Step 1-4 by reacting the appropriate precursors (commercially available or synthesized by a person skilled in the art) with suitable reagents, and where purification step has been performed as indicated in Table 2.

TABLE 2

| Structure | Cmp | ¹H NMR | MS/ESI⁺ [MH]⁺ [α$_D$] | Starting Material [And conditions, if different] | Purification Method |
|---|---|---|---|---|---|
| 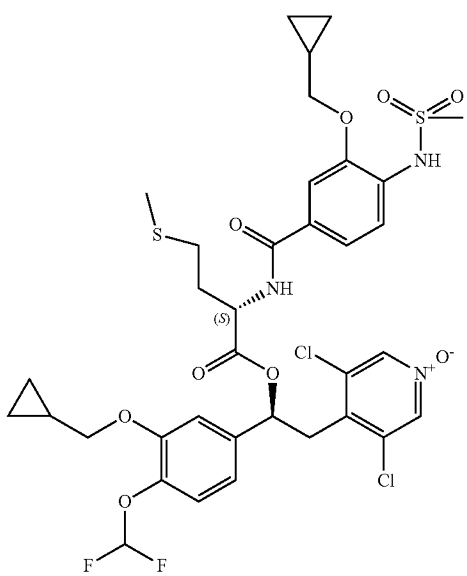 | 11 | ¹H NMR (400 MHz, acetone) δ ppm 8.14 (s, 2 H), 7.52 (m, 3 H), 7.21-7.25 (m, 1 H), 7.15-7.19 (m, 1 H), 7.03-7.11 (m, 1 H), 6.91 (t, J = 75.00 Hz, 1 H), 6.06-6.15 (m, 1 H), 4.66-4.73 (m, 1 H), 3.97-4.06 (m, 4 H), 3.51-3.62 (m, 1 H), 3.29-3.36 (m, 1 H), 3.08 (s, 3 H), 2.48-2.67 (m, 2 H), 2.08-2.14 (m, 5 H), 1.24-1.38 (m, 2 H), 0.55-0.68 (m, 4 H), 0.31-0.48 (m, 4 H) | 819.73 | | Evaporation of Ethyl Acetate |

TABLE 2-continued

| Structure | Cmp | ¹H NMR | MS/ESI⁺ [MH]⁺ [α_D] | Starting Material [And conditions, if different] | Purification Method |
|---|---|---|---|---|---|
| 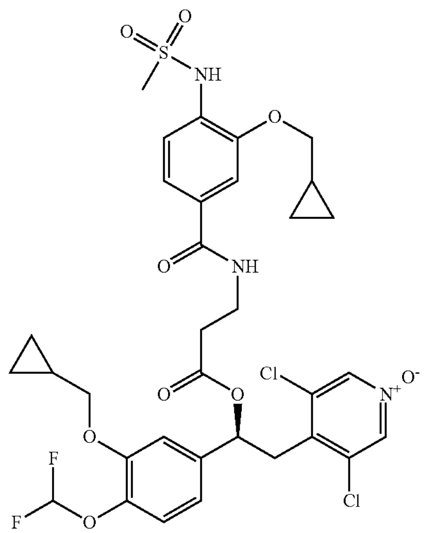 | 12 | ¹H NMR (300 MHz, DMSO-d₆) δ ppm 8.94 (s, 1 H), 8.47 (s, 2 H), 8.45 (t, 1 H), 7.42 (d, 1 H), 7.37 (dd, 1 H), 7.31 (d, 1 H), 7.13 (d, 1 H), 7.07 (d, 1 H), 6.95 (dd, 1 H), 7.04 (t, 1 H), 5.97 (dd, 1 H), 3.92 (d, 2 H), 3.89 (d, 2 H), 3.37-3.49 (m, 3 H), 3.20 (dd, 1 H), 3.07 (s, 3 H), 2.58-2.67 (m, 2 H), 1.03-1.49 (m, 2 H), 0.48-0.69 (m, 4 H), 0.19-0.46 (m, 4 H) | 757.94 [α_D] = −7.613 (c = 0.31, MeOH) | Step 1: DCM r.t. Step 2: HCl 4M in dioxane (22 eq), DCM, r.t. Step 3: DCM, r.t. Step 4: HCl 4M in dioxane (45 eq.), DCM, r.t. | Trituration with Et₂O followed by flash chromatography on silica gel (EtOAc then EtOAc/MeOH = 97/3) and preparative HPLC |

Example 2

Synthesis of (S)-3,5-dichloro-4-(2-(3-(cyclopropyl-methoxy)-4-(difluoromethoxy)phenyl)-2-(3-(phenyl-sulfonyl)propanoyloxy)ethyl)pyridine 1-oxide (13)

Scheme 2.

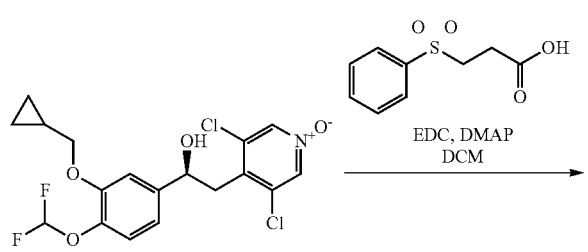

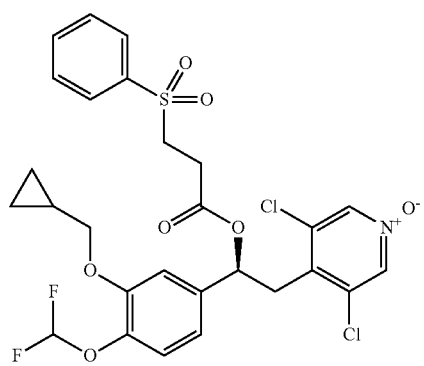

Synthesis of (S)-3,5-dichloro-4-(2-(3-(cyclopropyl-methoxy)-4-(difluoromethoxy)phenyl)-2-(3-(phenyl-sulfonyl)propanoyloxy)ethyl)pyridine 1-oxide (13)

((S)-3,5-dichloro-4-(2-(3-(cyclopropylmethoxy)-4-(difluoromethoxy)phenyl)-2-hydroxyethyl)pyridine 1-oxide) (150 mg, 0.357 mmol), EDC (103 mg, 0.535 mmol), 3-(phenylsulfonyl)propanoic acid (84 mg, 0.393 mmol), and DMAP (65.4 mg, 0.535 mmol) in DCM (30 ml) were stirred at RT for 4 hours. The reaction mixture was washed with HCl 1N (2×) and NaHCO₃ sat. sol. (2×); the organic layer was dried over Na₂SO₄ and evaporated to dryness. The residue was purified by trituration with iPr₂O (10 ml). Further triturations with petroleum ether (15 ml) and Et₂O (20 ml) were performed to afford (S)-3,5-dichloro-4-(2-(3-(cyclopropylmethoxy)-4-(difluoromethoxy)phenyl)-2-(3-(phenylsulfonyl)propanoyloxy)ethyl)pyridine 1-oxide (151 mg, 0.245 mmol, 68.6% yield, MS/ESI⁺ 616.08 [MH]⁺, [α_D]=−11.9, c=0.54, DCM ¹H NMR (300 MHz, DMSO-d₆) δ ppm 8.53 (s, 2 H), 7.81-7.89 (m, 2 H), 7.70-7.81 (m, 1 H), 7.58-7.70 (m, 2 H), 7.16 (d, 1 H), 7.08 (d, 1 H), 6.94 (dd, 1 H), 7.06 (t, 1 H), 5.88 (dd, 1 H), 3.91 (d, 2 H), 3.54 (t, 2 H), 3.42 (dd, 1 H), 3.19 (dd, 1 H), 2.55-2.69 (m, 2 H), 1.09-1.33 (m, 1 H), 0.43-0.71 (m, 2 H), 0.13-0.43 (m, 2 H).

The compounds listed in Table 3 were prepared with an analogous procedure to that described in Example 2 by reacting the appropriate precursors (commercially available or synthesized by a person skilled in the art) with suitable reagents, and where purification step has been performed as indicated in Table 3.

TABLE 3

| Structure | Cmp | ¹H NMR | MS/ESI⁺ [MH]⁺ [α$_D$] | Salt Name | Starting Material | Purification method |
|---|---|---|---|---|---|---|
| (structure 14) | 14 | ¹H NMR (400 MHz, acetone) δ ppm 8.28 (s, 2 H), 6.59-7.45 (m, 9 H), 6.19 (dd, J = 9.26, 4.85 Hz, 1 H), 4.43-4.59 (m, 2 H), 4.09-4.28 (m, 2 H), 3.95 (d, J = 6.62 Hz, 2 H), 3.58 (dd, J = 13.89, 9.04 Hz, 1 H), 3.34 (dd, J = 14.11, 4.85 Hz, 1 H), 1.13-1.37 (m, 1 H), 0.48-0.74 (m, 2 H), 0.24-0.43 (m, 2 H) | 568.182 | | (benzyloxyacetyl chloride) Condensation with DMAP and DCM | Evaporation of Ethyl Acetate |
| (structure 15) | 15 | 1H NMR (300 MHz, DMSO-d6) δ ppm 8.56 (s, 2 H), 7.17 (d, 1 H), 7.09 (d, 1 H), 6.96 (dd 1 H), 7.06 (t, 1 H), 6.78 (d, 1 H), 6.53 (d, 1 H), 6.19 (dd, 1 H), 6.07 (dd, 1 H), 4.79 (d, 1 H), 4.65 (d, 1 H), 3.89 (d, 2 H), 3.69 (s, 6 H), 3.47 (dd, 1 H), 3.25 (dd, 1 H), 1.10-1.33 (m, 1 H), 0.47-0.69 (m, 2 H), 0.17-0.47 (m, 2 H) | 614.05 [α$_D$] = −20.7° (c = 0.515 MeOH) | | (3,4-dimethoxyphenoxyacetic acid) | Flash chromatography on silica gel cartridge (DCM to DCM/EtOAc = 7/3) followed by trituration with EtOH |
| (structure 16) | 16 | ¹H NMR (300 MHz, DMSO-d$_6$) δ ppm 8.49 (s, 2 H), 7.37 (dd, 1 H), 7.28 (d, 1 H), 7.13 (d, 1 H), 7.10 (d, 1 H), 7.03 (d, 1 H), 7.06 (t, 1 H), 6.63-6.93 (m, 1 H), 5.89 (dd, 1 H), 4.58 (s, 2 H), 3.88 (d, 2 H), 3.84 (s, 3 H), 3.75 (s, 3 H), 3.35 (dd, 1 H), 3.18 (dd, 1 H), 1.09-1.35 (m, 1 H), 0.45-0.69 (m, 2 H), 0.19-0.45 (m, 2 H) | 661.97 [α$_D$] = −21.67 (c = 0.18, DCM) | | (3,4-dimethoxyphenylsulfonyl acetic acid) | Crystallization from iPrOH/H$_2$O = 98/2 |

TABLE 3-continued

| Structure | Cmp | ¹H NMR | MS/ESI⁺ [MH]⁺ [α_D] | Salt Name | Starting Material | Purification method |
|---|---|---|---|---|---|---|
| 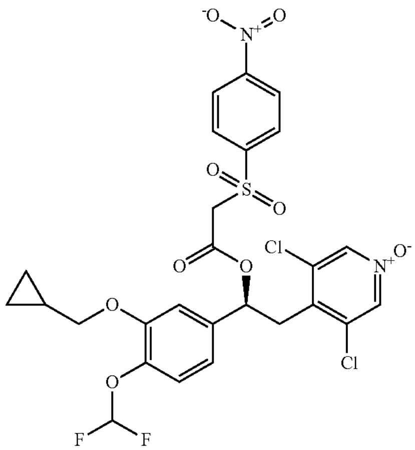 | 17 | ¹H NMR (400 MHz, acetone) δ ppm 8.41 (d, J = 8.82 Hz, 2 H), 8.21 (s, 2 H), 8.12 (d, J = 8.82 Hz, 2 H), 7.12-7.19 (m, 2 H), 6.94-7.00 (m, 1 H), 6.92 (t, J = 75.00 Hz, 1 H), 5.99-6.08 (m, 1 H), 4.52-4.72 (m, 2 H), 3.94 (d, J = 7.06 Hz, 2 H), 3.46-3.59 (m, 1 H), 3.19-3.35 (m, 1 H), 1.22-1.33 (m, 1 H), 0.58-0.61 (m, 2 H), 0.35-0.38 (m, 2 H). | 647.2 | | | Preparative reverse-phase HPLC |
| 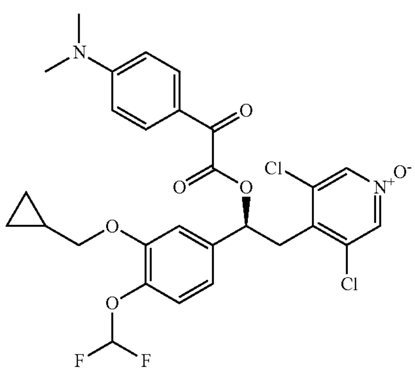 | 18 | ¹H NMR (400 MHz, acetone) δ ppm 8.27 (s, 2 H), 7.47 (d, J = 8.82 Hz, 2 H), 7.28 (d, J = 1.76 Hz, 1 H), 7.24 (d, J = 8.38 Hz, 1 H), 7.09-7.17 (m, 1 H), 6.95 (t, J = 75.00 Hz, 1 H), 6.69-6.78 (m, 2 H), 6.38 (dd, J = 10.14, 4.85 Hz, 1 H), 3.98 (dd, J = 6.84, 1.98 Hz, 2 H), 3.67 (dd, J = 14.33, 9.92 Hz, 1 H), 3.44 (dd, J = 14.33, 4.63 Hz, 1 H), 3.13 (s, 6 H), 1.29 (m, 1 H), 0.54-0.68 (m, 2 H), 0.32-0.46 (m, 2 H). | 595.1 | No Salt | | Crystallization in EtOH |
| 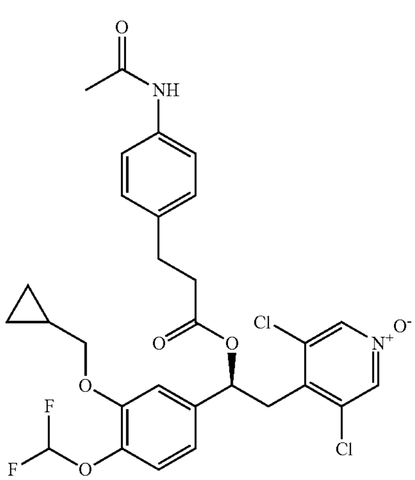 | 19 | ¹H NMR (400 MHz, acetone) δ ppm 8.95-9.12 (m, 1 H), 8.25 (s, 2 H), 7.48 (d, J = 8.44 Hz, 2 H), 7.13-7.21 (m, 2 H), 7.05 (d, J = 8.44 Hz, 2 H), 6.96-7.01 (m, 1 H), 6.91 (t, J = 75.00 Hz, 1 H), 5.99-6.08 (m, 1 H), 3.95 (d, J = 6.97 Hz, 2 H), 3.45-3.57 (m, 1 H), 3.16-3.30 (m, 1 H), 2.77 (s, 5 H), 2.63 (d, J = 6.97 Hz, 2 H), 1.20-1.33 (m, 1 H), 0.61 (dd, J = 8.13, 1.65 Hz, 2 H), 0.34-0.42 (m, 2 H) | 607.4 [M − H]− 643.3 [M + Cl]− | | | Preparative reverse-phase HPLC |

Example 3

Synthesis of (S)-3,5-dichloro-4-(2-(3-(cyclopropylmethoxy)-4-(difluoromethoxy)phenyl)-2-(4-(methylsulfonamido)benzylcarbamoyloxy)ethyl)pyridine 1-oxide (24)

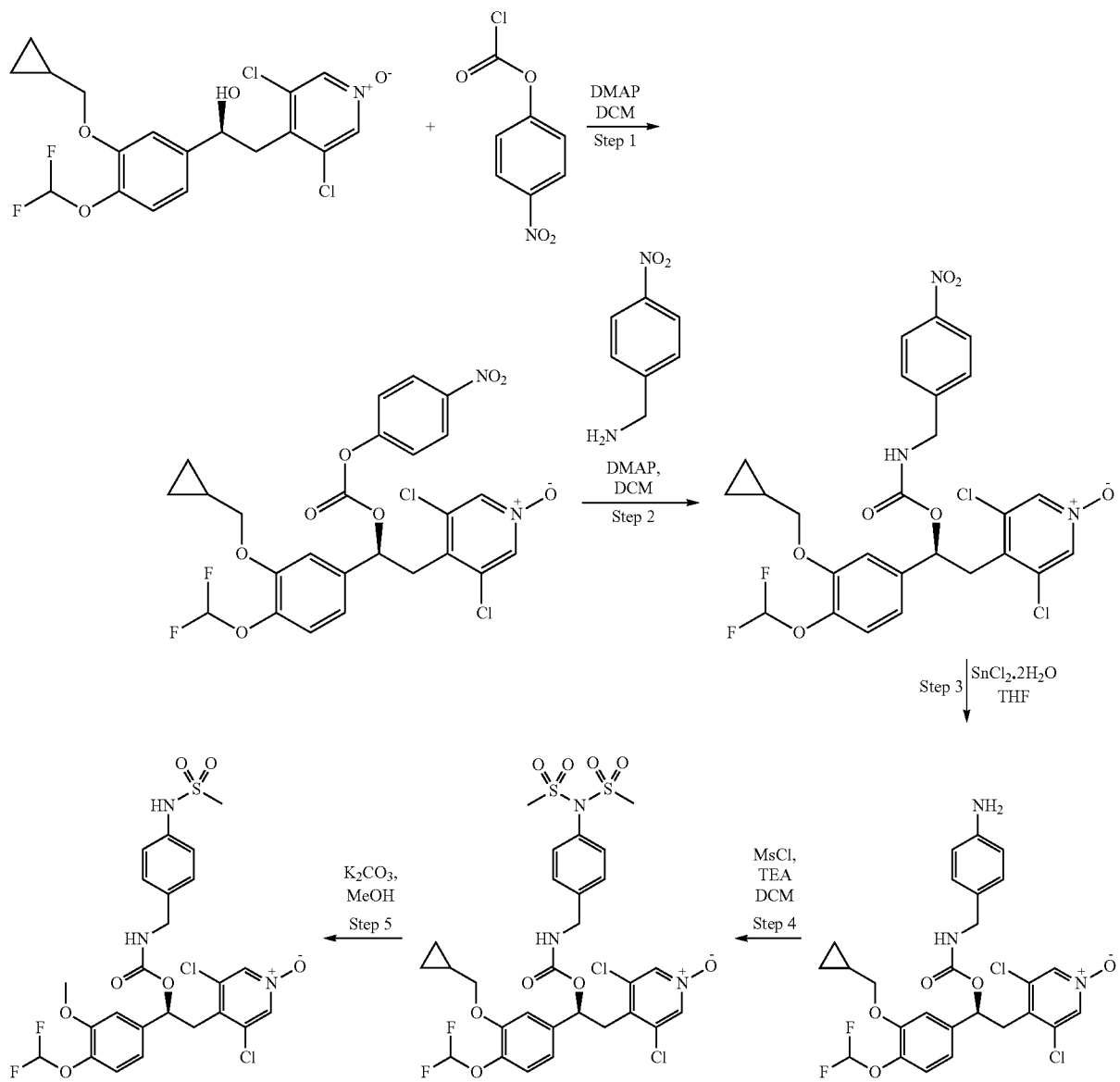

Step 1: Synthesis of (S)-3,5-dichloro-4-(2-(3-(cyclopropylmethoxy)-4-(difluoromethoxy)phenyl)-2-((4-nitrophenoxy)carbonyloxy)ethyl)pyridine 1-oxide (20)

(S)-3,5-dichloro-4-(2-(3-(cyclopropylmethoxy)-4-(difluoromethoxy)phenyl)-2-hydroxyethyl)pyridine 1-oxide (1.5 g, 3.57 mmol), and DMAP (0.436 g, 3.57 mmol) were dissolved in DCM (50 ml), and 4-nitrophenyl carbonochloridate (0.863 g, 4.28 mmol) was added portion wise. The mixture was stirred at RT overnight. After 18 hours, the solvent was evaporated and the crude purified by silica gel flash chromatography (petroleum ether:EtOAc 3:7) affording (S)-3,5-dichloro-4-(2-(3-(cyclopropylmethoxy)-4-(difluoromethoxy)phenyl)-2-((4-nitrophenoxy)carbonyloxy)ethyl)pyridine 1-oxide (1.609 g, 2.75 mmol, 77% yield, MS/ESI$^+$ 585 [MH]$^+$).

Step 2: Synthesis of (S)-3,5-dichloro-4-(2-(3-(cyclopropylmethoxy)-4-(difluoromethoxy)phenyl)-2-(4-nitrobenzylcarbamoyloxy)ethyl)pyridine 1-oxide (21)

To a stirred solution of compound (S)-3,5-dichloro-4-(2-(3-(cyclopropylmethoxy)-4-(difluoromethoxy)phenyl)-2-((4-nitrophenoxy)-carbonyloxy)ethyl)pyridine 1-oxide, (227 mg, 0.388 mmol) in DCM (10 ml), (4-nitrophenyl)methanamine hydrochloride (88 mg, 0.465 mmol), and DMAP (56.9 mg, 0.465 mmol) were added. The reaction mixture was stirred at RT overnight. After 20 hours, the mixture was diluted with DCM and washed with a solution of $K_2CO_3$. he organic layer was dried over $Na_2SO_4$, evaporated and the resulting crude was purified by flash chromatography on silica gel (DCM:MeOH 10:0.3) affording the desired product (200 mg, 0.334 mmol, 86% yield, MS/ESI$^+$ 598.3 [MH]$^+$).

Step 3: Synthesis of (S)-4-(2-(4-aminobenzylcarbamoyloxy)-2-(3-(cyclopropylmethoxy)-4-(difluoromethoxy)phenyl)ethyl)-3,5-dichloropyridine 1-oxide (22)

To a stirred solution of (S)-3,5-dichloro-4-(2-(3-(cyclopropylmethoxy)-4-(difluoromethoxy)phenyl)-2-(4-nitrobenzylcarbamoyloxy)ethyl)pyridine 1-oxide (200 mg, 0.334 mmol) in THF (10 ml), $SnCl_2$ dihydrate (603 mg, 2.67 mmol) was added, and the mixture was stirred at 60° C. for 5 hours, then the mixture was diluted with $NaHCO_3$ sat (pH=7) followed by the addition of EtOAc and filtered trough a celite pad. The inorganic phase was extracted with EtOAc. The combined organic layers were rinsed with brine, dried over $Na_2SO_4$ and evaporated affording the desired product (190 mg, 0.334 mmol, 100% yield, MS/ESI$^+$ 568.3 [MH]$^+$).

Step 4: Synthesis of (S)-3,5-dichloro-4-(2-(3-(cyclopropylmethoxy)-4-(difluoromethoxy)phenyl)-2-(4-(N-(methylsulfonyl)methylsulfonamido)benzylcarbamoyloxy)ethyl)pyridine 1-oxide (23)

A mixture of (S)-4-(2-(4-aminobenzylcarbamoyloxy)-2-(3-(cyclopropylmethoxy)-4-(difluoromethoxy)phenyl)ethyl)-3,5-dichloropyridine 1-oxide (190 mg, 0.334 mmol) and TEA (0.102 ml, 0.735 mmol) in DCM (7 ml) was cooled to 0° C., and methanesulfonyl chloride (0.051 ml, 0.669 mmol) was added. The cold bath was removed and the solution was stirred at RT for 5 hours. The reaction mixture was concentrated under reduced pressure and the resulting crude product (218 mg, 0.301 mmol, 90% yield, MS/ESI$^+$ 646.3 [MH]$^+$) was used in the next step without further purification.

Step 5: Synthesis of (S)-3,5-dichloro-4-(2-(3-(cyclopropylmethoxy)-4-(difluoromethoxy)phenyl)-2-(4-(methylsulfonamido)benzylcarbamoyloxy)ethyl)pyridine 1-oxide (24)

(S)-3,5-dichloro-4-(2-(3-(cyclopropylmethoxy)-4-(difluoromethoxy)phenyl)-2-(4-(N-(methylsulfonyl)methylsulfonamido)benzylcarbamoyloxy)ethyl)pyridine 1-oxide (218 mg, 0.301 mmol) was dissolved in MeOH (10 ml), and potassium carbonate (125 mg, 0.903 mmol) was added. The mixture was stirred at 60° C. for 1 hour. The solvent was removed under vacuum, and the crude material was portioned between water and EtOAc. The organic layer was dried over $Na_2SO_4$, and the solvent was evaporated affording a crude material that was purified by flash chromatography on silica gel (DCM:MeOH 100:0.2) affording the desired product (90 mg, 0.139 mmol, 46.3% yield, MS/ESI$^+$ 645.85 [MH]$^+$ [$\alpha_D$]=−32.16, c 0.523, DCM).

$^1$H NMR (300 MHz, DMSO-d6) δ ppm 9.62 (s, 1 H), 8.51 (s, 2 H), 7.77 (t, 1 H), 6.93 (dd, 1 H), 6.75-7.36 (m, 7 H), 5.91 (dd, 1 H), 4.09 (dd, 1 H), 4.02 (dd, 1 H), 3.81-3.95 (m, 2 H), 3.40 (dd, 1 H), 3.20 (dd, 1 H), 2.96 (s, 3 H), 1.06-1.34 (m, 1 H), 0.50-0.67 (m, 2 H), 0.26-0.43 (m, 2 H).

The compounds listed in Table 4 were prepared with an analogous procedure to that described in Example 3, Step 1 and 2, by reacting the appropriate precursors (Es: Amines or Thiols, commercially available or synthesized by a person skilled in the art) with suitable reagents, and where purification step has been performed as indicated in Table 4.

TABLE 4

| Structure | Cmp | $^1$H NMR | MS/ESI$^+$ [MH]$^+$ [$\alpha_D$] | Starting Material | Purification method |
|---|---|---|---|---|---|
| (structure shown) | 314 | 1H NMR (300 MHz, DMSO-d6 353K) δ ppm 8.38 (s, 2 H) 7.24-7.42 (m, 1 H) 7.15 (d, 1 H) 7.06 (d, 1 H) 6.94 (dd, 1 H) 6.87 (d, 1 H) 6.81 (d, 1 H) 6.97 (t, 1 H) 6.68 (dd, 1 H) 5.96 (dd, 1 H) 4.05-4.13 (m, 2 H) 3.85-3.94 (m, 2 H) 3.76 (s, 3 H) 3.72 (s, 3 H) 3.43 (dd, 1 H) 3.24 (dd, 1 H) 1.12-1.26 (m, 1 H) 0.53-0.63 (m, 2 H) 0.30-0.39 (m, 2 H) | 612.97 [$\alpha_D$] = −15.38 (c = 0.429, DCM) | Intermediate of Step 2 | Flash chromatography on silica gel (DCM/MeOH = 100/4) followed by flash chromatography on silica gel (DCM/acetone = 10/1) |

TABLE 4-continued

| Structure | Cmp | ¹H NMR | MS/ESI⁺ [MH]⁺ [$\alpha_D$] | Starting Material | Purification method |
|---|---|---|---|---|---|
| 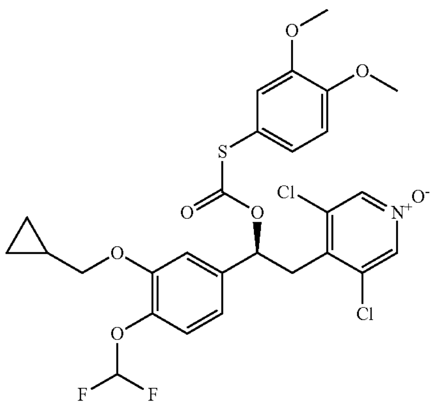 | 315 | 1H NMR (300 MHz, DMSO-d6) δ ppm 8.60 (s, 2 H), 7.21 (d, 1 H), 7.06-7.10 (m, 1 H), 6.94-7.01 (m, 4 H), 7.08 (t, 1 H), 6.08 (dd, 1 H), 3.90 (d, 2 H), 3.78 (s, 3 H), 3.73 (s, 3 H), 3.50 (dd, 1 H), 3.24 (d, 1 H), 1.08-1.33 (m, 1 H), 0.48-0.66 (m, 2 H), 0.27-0.44 (m, 2 H) | 615.76 [$\alpha_D$] = −56.55 (c = 0.458, DCM) | Intermediate of Step 2 | Flash chromatography on silica gel (DCM/EtOAc = 2/1) followed by dissolution in DCM and washing with aqueous $K_2CO_3$ |
| 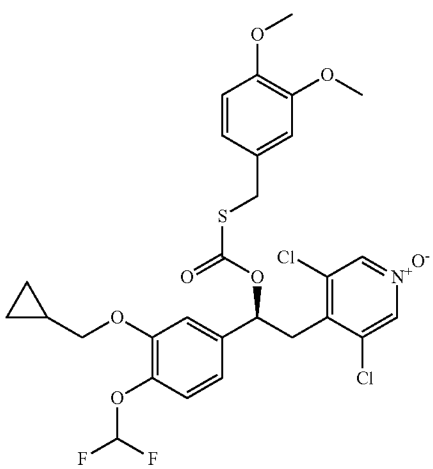 | 316 | 1H NMR (300 MHz, DMSO-d6) δ ppm 8.56 (s, 2 H), 7.20 (d, 1 H), 7.11 (d, 1 H), 6.97 (dd, 1 H), 6.87 (d, 1 H), 6.86 (d, 1 H), 7.07 (t, 1 H), 6.76 (dd, 1 H), 6.09 (dd, 1 H), 4.04 (d, 1 H), 3.99 (d, 1 H), 3.91 (dd, 1 H), 3.87 (dd, 1 H), 3.73 (s, 3 H), 3.68 (s, 3 H), 3.50 (dd, 1 H), 3.27 (dd, 1 H), 1.06-1.31 (m, 1 H), 0.45-0.63 (m, 2 H), 0.23-0.42 (m, 2 H) | 629.81 [$\alpha_D$] = −44.43 (c = 0.370, DCM) | Intermediate of Step 2 | Flash chromatography on silica gel (DCM/MeOH = 100/4) |
| 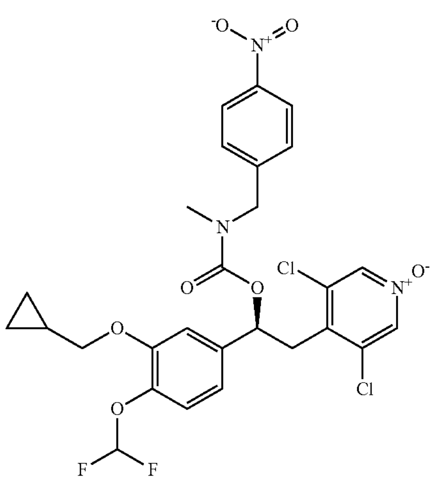 | 25 | 1H NMR (300 MHz, DMSO-d6) ppm 8.38 (and 8.61 (s, 2 H), 8.09-8.26 (m, 2 H), 6.75-7.44 (m, 6 H), 5.82-5.93 and 6.00-6.10 (m, 1 H), 4.56 and 4.75 (d, 1 H), 4.34 and 4.65 (d, 1 H), 3.70-4.03 (m, 2 H), 3.34-3.55 (m, 1 H), 3.05-3.23 (m, 1 H), 2.77 and 2.94 (s, 3 H), 0.90-1.46 (m, 1 H), 0.48-0.68 (m, 2 H), 0.09-0.46 (m, 2 H) | 611.92 [$\alpha_D$] = −13.7 (c = 0.4, DCM) | Intermediate of Step 2 | Flash chromatography on silica gel (DCM to DCM/EtOAc = 70/30) followed by trituration with $Et_2O$ |

TABLE 4-continued

| Structure | Cmp | ¹H NMR | MS/ESI⁺ [MH]⁺ [α_D] | Starting Material | Purification method |
|---|---|---|---|---|---|
| 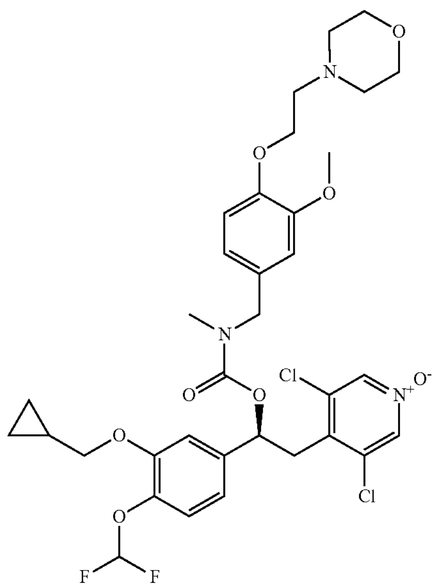 | 26 | 1H NMR (300 MHz, DMSO-d6) δ ppm 8.49 and 8.59 (s, 2 H), 6.78-7.43 (m, 5 H), 6.70 (br. s., 1 H), 6.41-6.57 (m, 1 H), 5.82-6.04 (m, 1 H), 4.12-4.65 (m, 2 H), 3.99-4.11 (m, 2 H), 3.75-3.95 (m, 2 H), 3.65 (s, 3 H), 3.54-3.60 (m, 4 H), 3.38-3.50 (m, 1 H), 3.10-3.25 (m, 1 H), 2.68 and 2.86 (s, 3 H), 2.65-2.71 (m, 2 H), 2.44-2.48 (m, 4 H), 1.11-1.24 (m, 1 H), 0.45-0.63 (m, 2 H), 0.27-0.44 (m, 2 H) | 726.09 [α_D] = −15.32 (c = 0.47, DCM) | Intermediate of Step 2 | Flash chromatography on silica gel (DCM/acetone = 8/2 to 1/1) followed by dissolution in EtOAc and washing with 1 N HCl and aq. NaHCO₃; then treatment with iPrOH, evaporation and trituration with Et₂O |
| 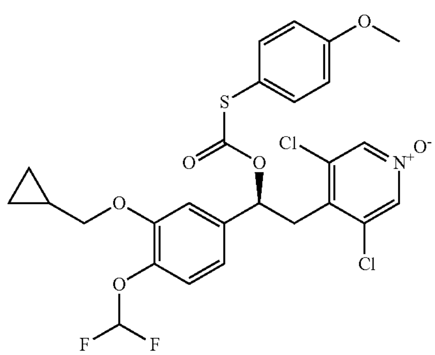 | 27 | 1H NMR (300 MHz, DMSO-d6) δ ppm 8.59 (s, 2 H) 7.34-7.41 (m, 2 H) 7.20 (d, 1 H) 7.07 (d, 1 H) 6.98 (m, 2 H) 6.95 (dd, 1 H) 7.08 (t, 1 H) 6.06 (dd, 1 H) 3.90 (d, 2 H) 3.79 (s, 3 H) 3.49 (dd, 1 H) 3.27 (dd, 1 H) 1.12-1.32 (m, 1 H) 0.51-0.66 (m, 2 H) 0.29-0.45 (m, 2 H) | 586.04 [α_D] = −60.71 (c = 0.479 DCM) | Intermediate of Step 2 | Crystallization from EtOH |
| 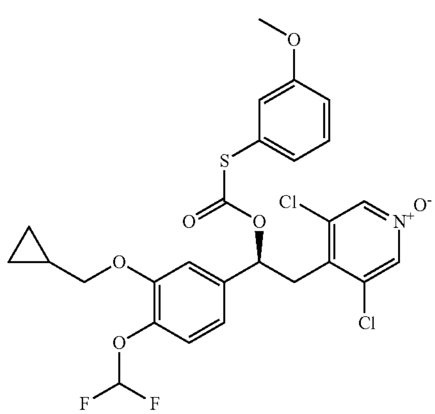 | 28 | 1H NMR (300 MHz, DMSO-d6) δ ppm 8.59 (s, 2 H) 7.28-7.41 (m, 1 H) 7.21 (d, 1 H) 6.99-7.12 (m, 4 H) 6.97 (dd, 1 H) 7.08 (t, 1 H) 6.08 (dd, 1 H) 3.90 (d, 2 H) 3.76 (s, 3 H) 3.51 (dd, 1 H) 3.23-3.28 (m, 1 H) 1.13-1.29 (m, 1 H) 0.49-0.66 (m, 2 H) 0.26-0.45 (m, 2 H) | 586.04 [α_D] = −72.40 (c = 0.450 DCM) | Intermediate of Step 2 | Crystallization from EtOH |

TABLE 4-continued

| Structure | Cmp | ¹H NMR | MS/ESI+ [MH]+ [α_D] | Starting Material | Purification method |
|---|---|---|---|---|---|
| (structure) | 29 | 1H NMR (300 MHz, DMSO-d6) δ ppm 8.59 (s, 2 H) 7.48 (ddd, 1 H) 7.40 (dd, 1 H) 7.21 (d, 1 H) 7.11 (dd, 1 H) 7.08 (d, 1 H) 6.97 (td, 1 H) 6.94 (dd, 1 H) 7.08 (t, 1 H) 6.06 (dd, 1 H) 3.90 (d, 2 H) 3.72 (s, 3 H) 3.48 (dd, 1 H) 3.26 (dd, 1 H) 1.03-1.43 (m, 1 H) 0.50-0.69 (m, 2 H) 0.26-0.45 (m, 2 H) | 586.04 [α_D] = −45.18 (c = 0.463 DCM) | Intermediate of Step 2 | Crystallization from EtOH |
| (structure) | 30 | ¹H NMR (300 MHz, DMSO-d₆) δ ppm 8.59 (s, 2 H) 7.37-7.57 (m, 5 H) 7.20 (d, 1 H) 7.05-7.11 (m, 1 H) 6.96 (dd, 1 H) 7.08 (t, 1 H) 6.07 (dd, 1 H) 3.90 (d, 2 H) 3.51 (dd, 1 H) 3.23-3.28 (m, 1 H) 1.08-1.33 (m, 1 H) 0.50-0.65 (m, 2 H) 0.26-0.46 (m, 2 H) | 556.03 [α_D] = −57.02 (c = 0.430 DCM) | Intermediate of Step 2 | Crystallization from EtOH |
| (structure) | 31 | 1H NMR (300 MHz, DMSO-d6) δ ppm 8.59 (s, 2 H) 7.16-7.27 (m, 2 H) 7.07-7.10 (m, 1 H) 6.97 (dd, 1 H) 7.08 (t, 1 H) 6.76-6.82 (m, 1 H) 6.64-6.73 (m, 2 H) 6.08 (dd, 1 H) 3.90 (d, 2 H) 3.50 (dd, 1 H) 3.21-3.27 (m, 1 H) 2.88 (s, 6 H) 1.13-1.24 (m, 1 H) 0.50-0.69 (m, 2 H) 0.28-0.45 (m, 2 H) | 599.11 [α_D] = −62.8 (c = 0.515, DCM) | Intermediate of Step 2 | Crystallization from EtOH |
| (structure) | 32 | 1H NMR (300 MHz, DMSO-d6) δ ppm 8.59 (s, 2 H) 7.66 (dd, 1 H) 7.63 (dd, 1 H) 7.53 (td, 1 H) 7.40 (td, 1 H) 7.22 (d 1 H) 7.12 (d, 1 H) 6.99 (dd, 1 H) 7.09 (t, 1 H) 6.12 (dd, 1 H) 3.92 (d, 2 H) 3.52 (dd, 1 H) 3.27-3.33 (m, 1 H) 1.15-1.23 (m, 1 H) 0.51-0.65 (m, 2 H) 0.28-0.43 (m, 2 H) | 590.00 [α_D] =−50.45 (c = 0.375, DCM) | Intermediate of Step 2 | Crystallization from EtOH |

TABLE 4-continued

| Structure | Cmp | 1H NMR | MS/ESI+ [MH]+ [α_D] | Starting Material | Purification method |
|---|---|---|---|---|---|
| (structure) | 33 | 1H NMR (300 MHz, DMSO-d6) δ ppm 8.59 (s, 2 H) 7.44-7.56 (m, 4 H) 7.21 (d, 1 H) 7.09 (d, 1 H) 6.96 (dd, 1 H) 7.08 (t, 1 H) 6.07 (dd, 1 H) 3.91 (d, 2 H) 3.52 (dd, 1 H) 3.22-3.28 (m, 1 H) 1.11-1.23 (m, 1 H) 0.48-0.68 (m, 2 H) 0.27-0.46 (m, 2 H) | 590.01 [α_D] = −56.4 (c = 0.39, DCM) | 4-chlorothiophenol; Intermediate of Step 2 | Flash chromatography on silica gel (hexane/EtOAc = 80/20) |
| (structure) | 34 | 1H NMR (300 MHz, DMSO-d6) δ ppm 8.58 (s, 2 H) 7.49-7.68 (m, 2 H) 7.32-7.40 (m, 1 H) 7.27 (td, 1 H) 7.21 (d, 1 H) 7.10 (d, 1 H) 6.97 (dd, 1 H) 7.09 (t, 1 H) 6.08 (dd, 1 H) 3.91 (d, 2 H) 3.51 (dd, 1 H) 3.28 (dd, 1 H) 1.09-1.34 (m, 1 H) 0.49-0.69 (m, 2 H) 0.26-0.43 (m, 2 H) | 573.99 [α_D] = −52.44 (c = 0.492 DCM) | 2-fluorothiophenol; Intermediate of Step 2 | Crystallization from EtOH |
| (structure) | 35 | 1H NMR (300 MHz, DMSO-d6) δ ppm 8.59 (s, 2 H) 7.49 (td, 1 H) 7.26-7.43 (m, 3 H) 7.21 (d, 1 H) 7.09 (d, 1 H) 6.97 (dd, 1 H) 7.08 (t, 1 H) 6.08 (dd, 1 H) 3.91 (d, 2 H) 3.52 (dd, 1 H) 3.28 (dd, 1 H) 1.11-1.33 (m, 1 H) 0.52-0.67 (m, 2 H) 0.29-0.42 (m, 2 H) | 574.04 [α_D] = −55.98 (c = 0.488 DCM) | 3-fluorothiophenol; Intermediate of Step 2 | Crystallization from EtOH |
| (structure) | 36 | 1H NMR (300 MHz, DMSO-d6) δ ppm 8.59 (s, 2 H) 7.28-7.40 (m, 2 H) 7.22 (d, 1 H) 7.12 (dd, 1 H) 7.07-7.09 (m, 1 H) 6.95 (dd, 1 H) 7.09 (t, 1 H) 6.06 (dd, 1 H) 3.91 (d, 2 H) 3.71 (s, 3 H) 3.50 (dd, 1 H) 3.26 (dd, 1 H) 1.15-1.33 (m, 1 H) 0.50-0.69 (m, 2 H) 0.24-0.47 (m, 2 H) | 604.05 [α_D] = −50.3 (c = 0.42, DCM) | 5-fluoro-2-methoxythiophenol; Intermediate of Step 2 | Flash Chromatography on silica gel (EtOAc/hexane = 70/30) |

TABLE 4-continued

| Structure | Cmp | $^1$H NMR | MS/ESI$^+$ [MH]$^+$ [$\alpha_D$] | Starting Material | Purification method |
|---|---|---|---|---|---|
| (structure 37) | 37 | $^1$H NMR (300 MHz, DMSO-d$_6$) ☐ ppm 8.59 (s, 2 H) 7.76-7.86 (m, 2 H) 7.65-7.76 (m, 2 H) 7.21 (d, 1 H) 7.12 (d, 1 H) 6.98 (dd, 1 H) 7.08 (t, 1 H) 6.08 (dd, 1 H) 3.91 (d, 2 H) 3.54 (dd, 1 H) 3.29 (dd, 1 H) 1.07-1.33 (m, 1 H) 0.48-0.67 (m, 2 H) 0.28-0.48 (m, 2 H) | 624.04 [$\alpha_D$] = −63.8 (c = 0.245, DCM) | 4-(trifluoromethyl)benzenethiol, Intermediate of Step 2 | Two crystallization from EtOH/H$_2$O (about 95/5) |
| (structure 38) | 38 | 1H NMR (300 MHz, DMSO-d6) δ ppm 8.58 (s, 2 H) 7.82-7.90 (m, 2 H) 7.75-7.82 (m, 1 H) 7.61-7.75 (m, 1 H) 7.20 (d, 1 H) 7.10 (d, 1 H) 6.96 (dd, 1 H) 7.08 (t, 1 H) 6.08 (dd, 1 H) 3.91 (d, 2 H) 3.53 (dd, 1 H) 3.28 (dd, 1 H) 1.10-1.30 (m, 1 H) 0.49-0.68 (m, 2 H) 0.25-0.48 (m, 2 H) | 624.04 [$\alpha_D$] = −56.1 (c = 0.38, DCM) | 3-(trifluoromethyl)benzenethiol, Intermediate of Step 2 | Crystallization from EtOH |
| (structure 39) | 39 | 1H NMR (300 MHz, DMSO-d6) δ ppm 8.57 (s, 2 H) 7.82-7.96 (m, 1 H) 7.68-7.80 (m, 3 H) 7.21 (d, 1 H) 7.09 (d, 1 H) 6.96 (dd, 1 H) 7.09 (t, 1 H) 6.08 (dd, 1 H) 3.93 (dd, 1 H) 3.89 (dd, 1 H) 3.51 (dd, 1 H) 3.26 (dd, 1 H) 1.14-1.34 (m, 1 H) 0.44-0.67 (m, 2 H) 0.24-0.49 (m, 2 H) | 624.04 [$\alpha_D$] = −48.98 (c = 0.265, DCM) | 2-(trifluoromethyl)benzenethiol, Intermediate of Step 2 | Two crystallization from EtOH/H$_2$O (about 95/5) |
| (structure 40) | 40 | $^1$H NMR (300 MHz, DMSO-d$_6$) δ ppm 8.59 (s, 2 H) 7.43-7.62 (m, 2 H) 7.25-7.32 (m, 2 H) 7.20 (d, 1 H) 7.08 (d, 1 H) 6.96 (dd, 1 H) 7.08 (t, 1 H) 6.06 (dd, 1 H) 3.90 (d, 2 H) 3.51 (dd, 1 H) 3.25 (m, 1 H) 1.11-1.35 (m, 1 H) 0.48-0.67 (m, 2 H) 0.27-0.44 (m, 2 H) | 574.05 [$\alpha_D$] = −52.91 (c = 0.282 DCM) | 4-fluorobenzenethiol, Intermediate of Step 2 | Flash chromatography on silica gel (DCM/MeOH = 100/2) followed by crystallization from EtOH |

TABLE 4-continued

| Structure | Cmp | ¹H NMR | MS/ESI⁺ [MH]⁺ [$\alpha_D$] | Starting Material | Purification method |
|---|---|---|---|---|---|
| 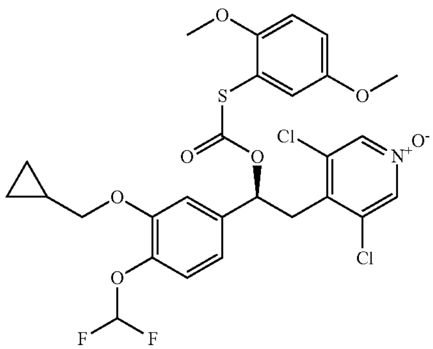 | 41 | 1H NMR (300 MHz, DMSO-d6) δ ppm 8.59 (s, 2 H) 7.21 (d, 1 H) 7.07-7.10 (m, 1 H) 6.97-7.06 (m, 3 H) 6.95 (dd, 1 H) 7.08 (t, 1 H) 6.07 (dd, 1 H) 3.91 (d, 2 H) 3.71 (s, 3 H) 3.66 (s, 3 H) 3.49 (dd, 1 H) 3.26 (dd, 1 H) 1.08-1.32 (m, 1 H) 0.49-0.67 (m, 2 H) 0.26-0.42 (m, 2 H) | 616.14 [$\alpha_D$] = −48.3 (c = 0.275, DCM) | Intermediate of Step 2 | Crystallization from EtOH |
| 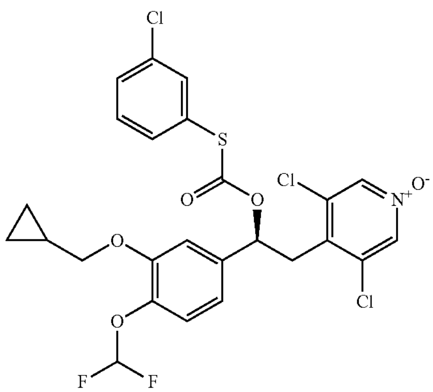 | 42 | 1H NMR (300 MHz, DMSO-d6) δ ppm 8.59 (s, 2 H) 7.56-7.60 (m, 1 H), 7.55 (t, 1 H), 7.42-7.50 (m, 2 H), 7.21 (d, 1 H) 7.09 (d, 1 H), 6.96 (dd, 1 H), 7.08 (t, 1 H), 6.07 (dd, 1 H), 3.91 (d, 2 H), 3.52 (dd, 1 H), 3.28 (dd, 1 H), 1.12-1.33 (m, 1 H), 0.50-0.68 (m, 2 H), 0.27-0.44 (m, 2 H) | 590.16 [$\alpha_D$] = −57.10 (c = 0.434 DCM) | Intermediate of Step 2 | Flash chromatography on silica gel (DCM/MeOH = 100/2) |
| 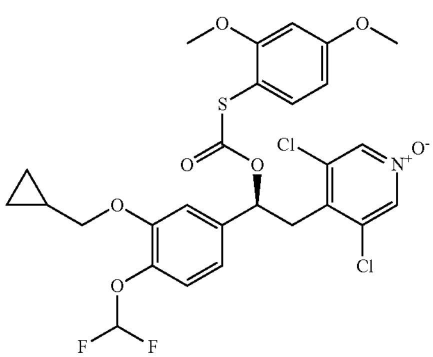 | 43 | ¹H NMR (300 MHz, DMSO-d₆) δ ppm 8.58 (s, 2 H), 7.28 (d, 1 H), 7.21 (d, 1 H), 7.07 (d, 1 H), 6.94 (dd, 1 H), 7.08 (t, 1 H), 6.63 (d, 1 H), 6.55 (dd, 1 H), 6.05 (dd, 1 H), 3.90 (d, 2 H), 3.81 (s, 3 H), 3.72 (s, 3 H), 3.47 (dd, 1 H), 3.25 (dd, 1 H), 1.22 (m, 1 H), 0.44-0.69 (m, 2 H), 0.25-0.44 (m, 2 H) | 616.20 [$\alpha_D$] = −52.49 (c = 0.506 DCM) | Intermediate of Step 2 | Flash chromatography on silica gel (DCM/MeOH = 100/2) |

The compounds listed in Table 6 were prepared with an analogous procedure to that described in Example 3, Step 1-3, by reacting the appropriate precursors (commercially available or synthesized by a person skilled in the art) with suitable reagents, and where purification step has been performed as indicated in Table 6.

TABLE 6

| Structure | Cmp | ¹H NMR | MS/ESI⁺ [MH]⁺ [α$_D$] | Starting Material (and conditions of Step 3) | Purification method |
|---|---|---|---|---|---|
| 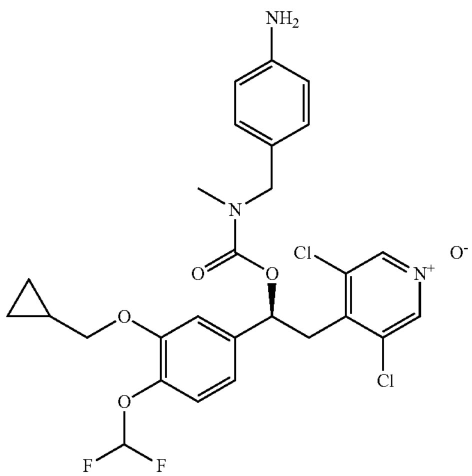 | 44 | 1H NMR (300 MHz, DMSO-d6) δ ppm 8.55 (s, 2 H), 7.11-7.23 (m, 1 H), 7.07-7.10 (m, 1 H), 6.88-7.02 (m, 1 H), 7.06 (t, 1 H), 6.64-6.80 (m, 2 H), 6.38-6.57 (m, 2 H), 5.70-6.10 (m, 1 H), 4.96 and 4.99 (s, 2 H), 3.71-4.57 (m, 4 H), 3.36-3.53 (m, 1 H), 3.11-3.25 (m, 1 H), 2.61 and 2.79 (s, 3 H), 1.09-1.29 (m, 1 H), 0.47-0.66 (m, 2 H), 0.29-0.44 (m, 2 H) | 581.98 [α$_D$] = −14.9 (c = 0.36 DCM) | Intermediate of Step 2 Step 3 Condition: THF, 45° C. | SCX cartridge |

Example 4

Synthesis of (S)-3,5-dichloro-4-(2-(3-(cyclopropylmethoxy)-4-(difluoromethoxy)phenyl)-2-((4-methoxy-3-(methylsulfonamido)benzyl)-(methyl)carbamoyloxy)ethyl)pyridine 1-oxide (51) and (S)-3,5-dichloro-4-(2-(3-(cyclopropylmethoxy)-4-(difluoromethoxy)phenyl)-2-((4-methoxy-3-(N-(2-morpholinoethyl)methylsulfonamido)benzyl)(methyl)carbamoyloxy)ethyl)pyridine 1-oxide (54)

Scheme 4.
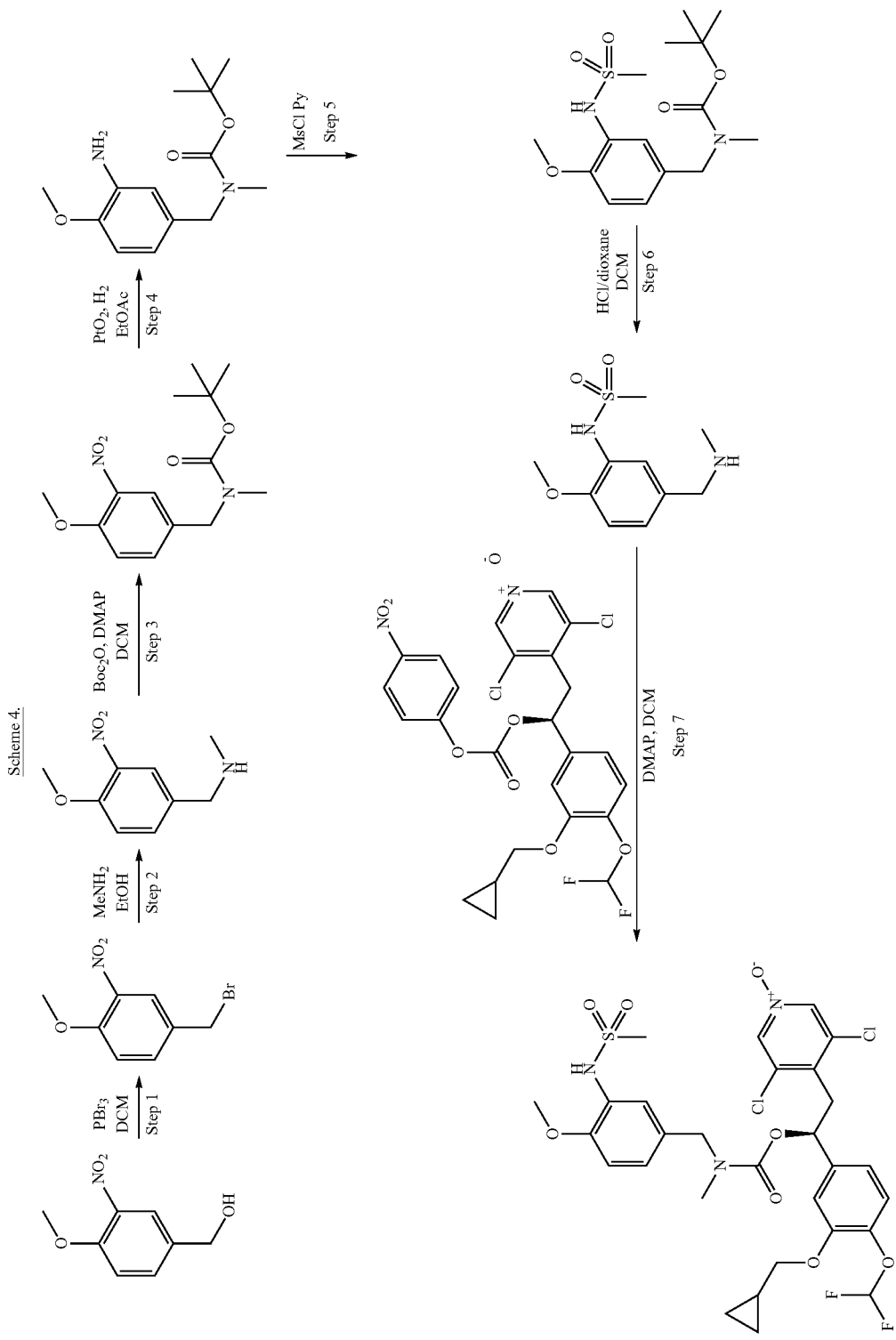

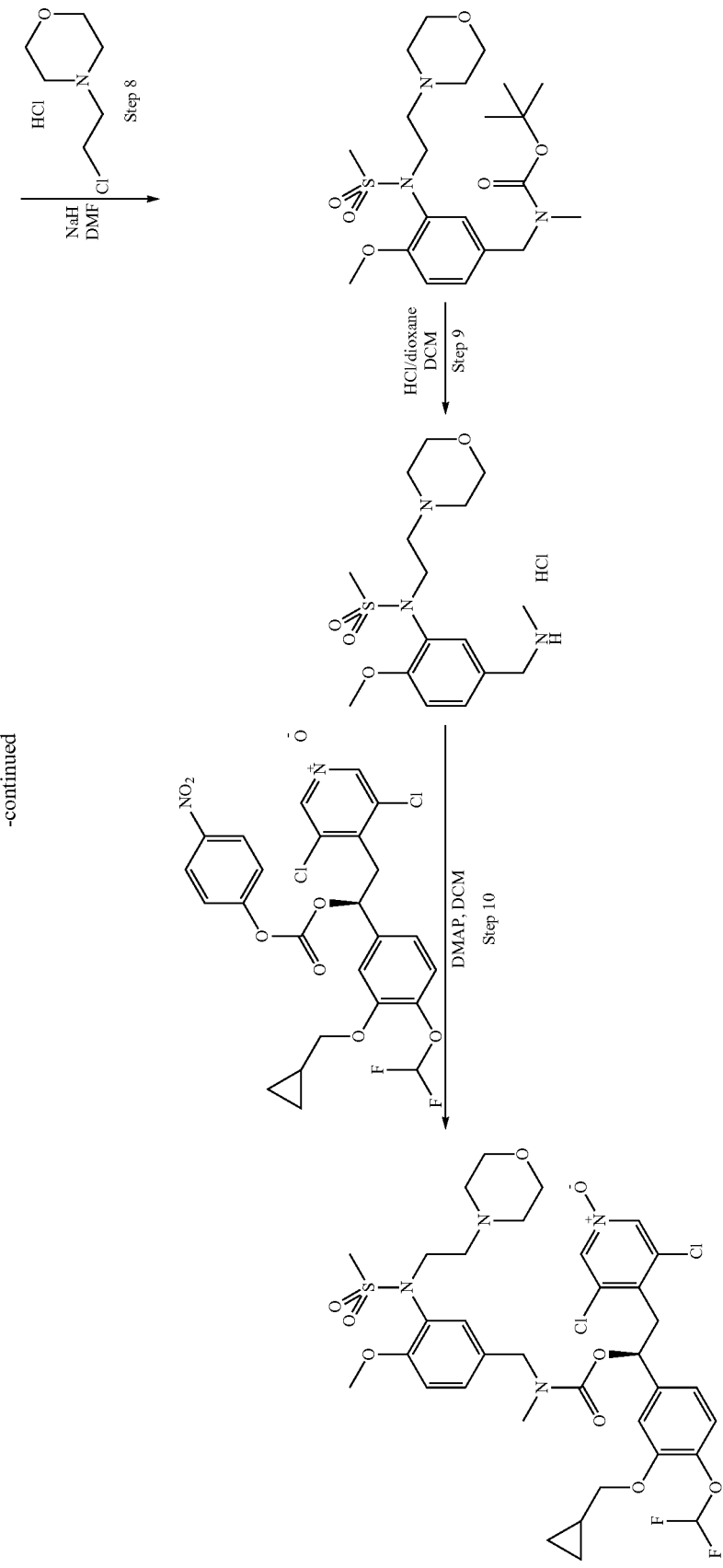

Step 1: Synthesis of 4-(bromomethyl)-1-methoxy-2-nitrobenzene 45)

(4-methoxy-3-nitrophenyl)methanol (215 mg, 1.174 mmol) was dissolved, under $N_2$ atmosphere, in dry DCM and cooled to 0° C. $PBr_3$ (55.4 µl, 0.587 mmol) was added, and the reaction was stirred RT for 1 hour. Ice and DCM were added to the reaction mixture. The mixture was diluted with WATER and brine and extracted twice with DCM. The organic layers were dried and evaporated to dryness to give 4-(bromomethyl)-1-methoxy-2-nitrobenzene (276 mg, 1.122 mmol, 96% yield) that was used in the next step without further purification.

Step 2: Synthesis of 1-(4-methoxy-3-nitrophenyl)-N-methylmethanamine (46)

4-(bromomethyl)-1-methoxy-2-nitrobenzene (276 mg, 1.122 mmol) was dissolved in methanamine in EtOH (33% w/w, 8 ml, 64.5 mmol) and stirred at RT for 1.5 hours. The mixture was evaporated to dryness and diluted with WATER/brine. The aqueous phase was extracted twice with EtOAc. $NaHCO_3$ sat. sol. was added until basic pH, and the aqueous phase was extracted twice with DCM. The combined organic layers were dried and evaporated under vacuum to give 1-(4-methoxy-3-nitrophenyl)-N-methylmethanamine (220 mg, 1.121 mmol, 100% yield, MS/ESI$^+$ 197.1 [MH]$^+$) that was used in the next step without further purification.

Step 3: Synthesis of tert-butyl 4-methoxy-3-nitrobenzyl(methyl)carbamate (47)

1-(4-methoxy-3-nitrophenyl)-N-methylmethanamine (220 mg, 1.121 mmol) was dissolved in DCM (8 ml), $Boc_2O$ (260 µl, 1.121 mmol), and DMAP (137 mg, 1.121 mmol) were added, and the reaction was stirred at RT for 2 hours. Additional $Boc_2O$ (390 µl, 1.683 mmol) and DMAP (68.5 mg, 0.561 mmol) were added over 48 hours with stirring at the same temperature. The mixture was diluted with DCM and washed with a solution of water and a few drops of 1N HCl until pH 6 and then with $NaHCO_3$ 5%. The organic phase was dried and evaporated under vacuum. This procedure was repeated twice, then the residue was dissolved in EtOAc and washed twice with HCl solution pH 5/6. tert-butyl 4-methoxy-3-nitrobenzyl(methyl)-carbamate was obtained (333 mg, 1.124 mmol, 100% yield, MS/ESI$^+$ 319.2 [MNa]$^+$) and used in the next step without further purification.

Step 4: Synthesis of tert-butyl 3-amino-4-methoxybenzyl(methyl)-carbamate (48)

Tert-Butyl 4-methoxy-3-nitrobenzyl(methyl)carbamate (333 mg, 1.124 mmol) was dissolved in EtOAc (20 ml), $Pt_2O$ (33 mg, 0.145 mmol) was added, and the mixture was hydrogenated in a Parr apparatus at 20 psi for 3 hours. The solution was filtered and evaporated to dryness to give tert-butyl 3-amino-4-methoxybenzyl(methyl)carbamate (265.3 mg, 0.996 mmol, 89% yield, MS/ESI$^+$ 289.2 [MNa]$^+$) that was used in the next step without further purification.

Step 5: Synthesis of tert-butyl 3-amino-4-methoxybenzyl(methyl)-carbamate (49)

tert-Butyl 3-amino-4-methoxybenzyl(methyl)carbamate (265.3 mg, 0.996 mmol) was dissolved in pyridine (3000 µl, 37.1 mmol) and cooled to 0° C. MsCl (93 µl, 1.195 mmol) was added dropwise, and the reaction was stirred at RT for 1 hour. The solution was diluted with $NH_4Cl$ sat. sol. and extracted twice with DCM. The organic layers were washed with brine, dried over $Na_2SO_4$ and evaporated under vacuum to give tert-butyl 4-methoxy-3-(methylsulfonamido)benzyl(methyl)-carbamate (249.5 mg, 0.724 mmol, 72.7% yield, MS/ESI$^+$ 367.2 [MNa]$^+$) that was used in the next step without further purification.

Step 6: Synthesis of N-(2-methoxy-5-((methylamino)methyl)phenyl)-methanesulfonamide (50)

tert-Butyl 4-methoxy-3-(methylsulfonamido)benzyl(methyl)carbamate (60.4 mg, 0.175 mmol) was dissolved in DCM (5 ml), HCl 4M in dioxane (250 µl, 1.000 mmol) was added, and the reaction was stirred at RT overnight. Additional HCl 4M in dioxane (500 µl, 2.00 mmol) was added over 30 hours with stirring at the same temperature. The solvent was evaporated under vacuum, and the solid so obtained was triturated in DCM and filtered to give N-(2-methoxy-5-((methylamino)methyl)-phenyl)methanesulfonamide as hydrochloride (42.8 mg, 0.175 mmol, 100% yield, MS/ESI$^+$ 245.3 [MH]$^+$) that was used in the next step without further purification.

Step 7: Synthesis of (S)-3,5-dichloro-4-(2-(3-(cyclopropylmethoxy)-4-(difluoromethoxy)phenyl)-2-(4-methoxy-3-(methylsulfonamido)benzyl)-(methyl) carbamoyloxy)ethyl)pyridine 1-oxide (51)

(S)-3,5-dichloro-4-(2-(3-(cyclopropylmethoxy)-4-(difluoromethoxy)phenyl)-2-((4-nitrophenoxy)carbonyloxy) ethyl)pyridine 1-oxide (prepared with an analogous procedure to that described in Scheme 3, Step 1) (103 mg, 0.176 mmol), N-(2-methoxy-5-((methylamino)methyl)phenyl) methanesulfonamide (43.0 mg, 0.176 mol), and DMAP (43.0 mg, 0.352 mmol) were suspended in DCM (10 ml) and stirred at RT for 24 hours. The reaction mixture was loaded on a silica gel cartridge and eluted with DCM to DCM/EtOAc 4:6. A further purification by preparative HPLC was necessary in order to obtain a pure product. By treatment with $Et_2O$/Hexane 1:1 the desired product was obtained (29 mg, 0.042 mmol, 24% yield, MS/ESI$^+$ 690.23 [MH]$^+$, [□$_D$]=−7.44, c=0.277 in DCM).

1 H NMR (300 MHz, DMSO-d6) δ ppm 8.83 (br. s., 1 H), 8.57 (s, 1H), 8.43 (s, 1H), 6.56-7.42 (m, 7 H), 5.58-6.11 (m, 1 H), 4.09-4.55 (m, 2 H), 3.74-3.97 (m, 5 H), 3.36-3.51 (m, 1 H), 3.10-3.24 (m, 1 H), 2.91 and 2.95 (s, 3H), 2.69 and 2.85 (s, 3H), 1.14-1.22 (m, 1 H), 0.45-0.67 (m, 2 H), 0.30-0.44 (m, 2 H)

Step 8: Synthesis of tert-butyl 4-methoxy-3-(N-(2-morpholinoethyl)-methylsulfonamido)benzyl(methyl)carbamate (52)

tert-Butyl 4-methoxy-3-(methylsulfonamido)benzyl(methyl)carbamate (189.1 mg, 0.549 mmol) was dissolved in dry DMF (10 ml) and cooled to 0° C. NaH (60% w/w dispersion in mineral oil, 48.3 mg, 1.208 mmol) was added, and the mixture was stirred 5 minutes at 0° C. and then 5 minutes at RT. 4-(2-Chloroethyl)morpholine hydrochloride (123 mg, 0.659 mmol) was added, and the mixture was stirred at RT for overnight. Additional NaH (43.93 mg, 1.098 mmol) was added over 4 days with stirring at RT. The reaction was quenched with water and brine and extracted with Et$_2$O and twice with EtOAc. The combined organic layers were dried over Na$_2$SO$_4$, and the solvent was evaporated under vacuum. The crude product was purified by silica gel cartridge using as eluent:DCM to DCM/EtOAc 2:8 to give tert-butyl 4-methoxy-3-(N-(2-morpholinoethyl)methylsulfonamido)benzyl (methyl)carbamate (114 mg, 0.249 mmol, 45.4% yield).

Step 9: Synthesis of N-(2-methoxy-5-((methylamino)methyl)phenyl)-N-(2-morpholinoethyl)methanesulfonamide hydrochloride (53)

tert-Butyl 4-methoxy-3-(N-(2-morpholinoethyl)methylsulfonamido)benzyl-(methyl)carbamate (114 mg, 0.249 mmol) was dissolved in dry DCM (6 ml), and HCl 4M in dioxane (500 µl, 2.000 mmol) was added. The reaction was stirred at RT for 24 hours. The solvent was evaporated under vacuum and N-(2-methoxy-5-((methylamino)methyl)phenyl)-N-(2-morpholinoethyl)methanesulfonamide was obtained as hydrochloride salt (89 mg, 0.249 mmol, 100% yield, MS/ESI$^+$ 358.1 [MH]$^+$) that was used in the next step without further purification.

Step 10: Synthesis of (S)-3,5-dichloro-4-(2-(3-(cyclopropylmethoxy)-4-(difluoromethoxy)phenyl)-2-(4-methoxy-3-(N-(2-morpholinoethyl)-methylsulfonamido)benzyl)(methyl)carbamoyloxy)ethyl) pyridine 1-oxide (54)

N-(2-methoxy-5-((methylamino)methyl)phenyl)-N-(2-morpholinoethyl)-methanesulfonamide (87 mg, 0.244 mmol), (S)-3,5-dichloro-4-(2-(3-(cyclopropylmethoxy)-4-(difluoromethoxy)phenyl)-2-(4-nitrophenoxy)-carbonyloxy)ethyl)pyridine 1-oxide (prepared with an analogous procedure to that described in Scheme 3, Step 1) (130 mg, 0.222 mmol), and DMAP (57.0 mg, 0.466 mmol) were dissolved in DCM (10 ml) and stirred at RT for 4 hours. The reaction mixture was loaded on a silica gel cartridge and eluted with DCM/EtOAc 1:1 to EtOAc and then with EtOAc/MeOH 95:5. The product was treated with Et$_2$O and evaporated to dryness to give (S)-3,5-dichloro-4-(2-(3-(cyclopropylmethoxy)-4-(difluoromethoxy)phenyl)-2-((4-methoxy-3-(N-(2-morpholinoethyl)-methylsulfonamido)benzyl)(methyl)carbamoyloxy)ethyl)pyridine 1-oxide (112 mg, 0.139 mmol, 62.7% yield, MS/ESI$^+$ 803.18 [MH]$^+$, [$\alpha_D$]=5.44, c=0.55 in DCM).

1H NMR (300 MHz, DMSO-d6) δ ppm 8.38 and 8.56 (s, 2 H), 7.03-7.25 (m, 4 H), 6.86-7.03 (m, 2 H), 7.06 (t, 1 H), 5.80-5.90 and 5.91-6.09 (m, 1 H), 4.12-4.63 (m, 2 H), 3.87-3.95 (m, 2 H), 3.84 (br. s., 3 H), 3.50-3.70 (m, 2 H), 3.33-3.49 (m, 5 H), 3.11-3.25 (m, 1 H), 2.99 and 3.05 (s, 3 H), 2.69 and 2.86 (s, 3 H), 2.14-2.34 (m, 6 H), 1.14-1.22 (m, 1 H), 0.49-0.65 (m, 2 H), 0.26-0.42 (m, 2 H).

Example 5

Synthesis of (S)-3,5-dichloro-4-(2-(3-(cyclopropylmethoxy)-4-(difluoromethoxy)phenyl)-2-((4-(methylsulfonamido)phenylthio)-carbonyloxy)ethyl) pyridine 1-oxide (57)

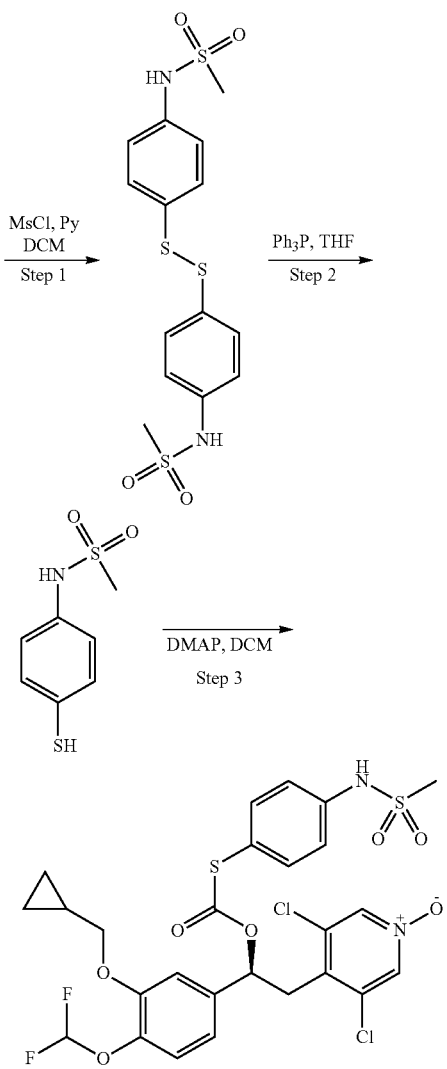

Scheme 5

Step 1: Synthesis of N,N'-(4,4'-disulfanediylbis(4,1-phenylene))dimethanesulfonamide (55)

4,4'-Disulfanediyldianiline (1 g, 4.03 mmol) was dissolved in a mixture of DCM (30 ml) and pyridine (1.303 ml, 16.11 mmol). Methanesulfonyl chloride (0.969 g, 8.46 mmol) was added, and the reaction was stirred at RT for 3 hours, then the mixture was washed with HCl 0.5M, NaHCO$_3$ sat. sol. and brine, dried over Na$_2$SO$_4$ and evaporated affording N,N'-(4,4'-disulfanediylbis(4,1-phenylene))-dimethanesulfonamide (1.5 g, 3.71 mmol, 92% yield) that was used in the next step without further purification.

Step 2: Synthesis of
N-(4-mercaptophenyl)methanesulfonamide (56)

N,N'-(4,4'-disulfanediylbis(4,1-phenylene))dimethanesulfonamide (500 mg, 1.236 mmol) was dissolved in THF (10 ml), and triphenylphosphine (648 mg, 2.472 mmol) was added. The mixture was stirred at RT overnight, then the solvent was evaporated, the crude was dissolved in DCM (30 ml) and washed with NaOH 0.5M (4×). The inorganic fraction were combined and made acid with HCl 6M. The resulting white solid was extracted with EtOAc (4×). The organic layers were combined, dried over Na$_2$SO$_4$ and evaporated affording the desired product (450 mg, 1.214 mmol, 90% yield) that was used in the next step without further purification.

Step 3: Synthesis of (S)-3,5-dichloro-4-(2-(3-(cyclopropylmethoxy)-4-(difluoromethoxy)phenyl)-2-((4-(methylsulfonamido)phenylthio)carbonyloxy)ethyl)pyridine 1-oxide (57)

To a stirred solution of (S)-3,5-dichloro-4-(2-(3-(cyclopropylmethoxy)-4-(difluoromethoxy)phenyl)-2-((4-nitrophenoxy)carbonyloxy)ethyl)pyridine 1-oxide (prepared with an analogous procedure to that described in Scheme 3, Step 1), (200 mg, 0.342 mmol) in DCM (10 ml), DMAP (41.7 mg, 0.342 mmol), and N-(4-mercaptophenyl)methanesulfonamide (83 mg, 0.410 mmol) were sequentially added. The mixture was stirred at RT for 4 hours, then the solvent was removed and the crude purified by flash chromatography on silica gel (DCM:MeOH 10:0.2). The resulting product was further purified by flash chromatography on silica gel (EtOAc:DCM 8:2) and the desired product was obtained (81 mg, 0.125 mmol, 36.5% yield, MS/ESI$^+$ 649.28 [MH]$^+$, [$\alpha_D$]=−59.64, c=0.44 in DCM).

$^1$H NMR (300 MHz, Acetone) δ ppm 8.86 (s, 1 H), 8.31 (s, 2 H), 7.42-7.53 (m, 2 H), 7.34-7.42 (m, 2 H), 7.23 (d, 1 H), 7.19 (d, 1 H), 7.05 (dd, 1 H), 6.93 (t, 1 H), 6.20 (dd, 1 H), 3.99 (d, 2 H), 3.63 (dd, 1 H), 3.38 (dd, 1 H), 3.07 (s, 3 H), 1.23-1.46 (m, 1 H), 0.53-0.73 (m, 2 H), 0.32-0.52 (m, 2 H)

Example 6

Synthesis of (S)-3,5-dichloro-4-(2-(3-(cyclopropylmethoxy)-4-(difluoromethoxy)phenyl)-2-((3-(methylsulfonamido)phenylthio)carbonyloxy)-ethyl) pyridine 1-oxide (60) and (S)-3,5-dichloro-4-(2-(3-(cyclopropylmethoxy)-4-(difluoromethoxy)phenyl)-2-((3-(N-(2-morpholinoethyl)methylsulfonamido)-phenylthio) carbonyloxy)ethyl)pyridine 1-oxide (63)

Scheme 6

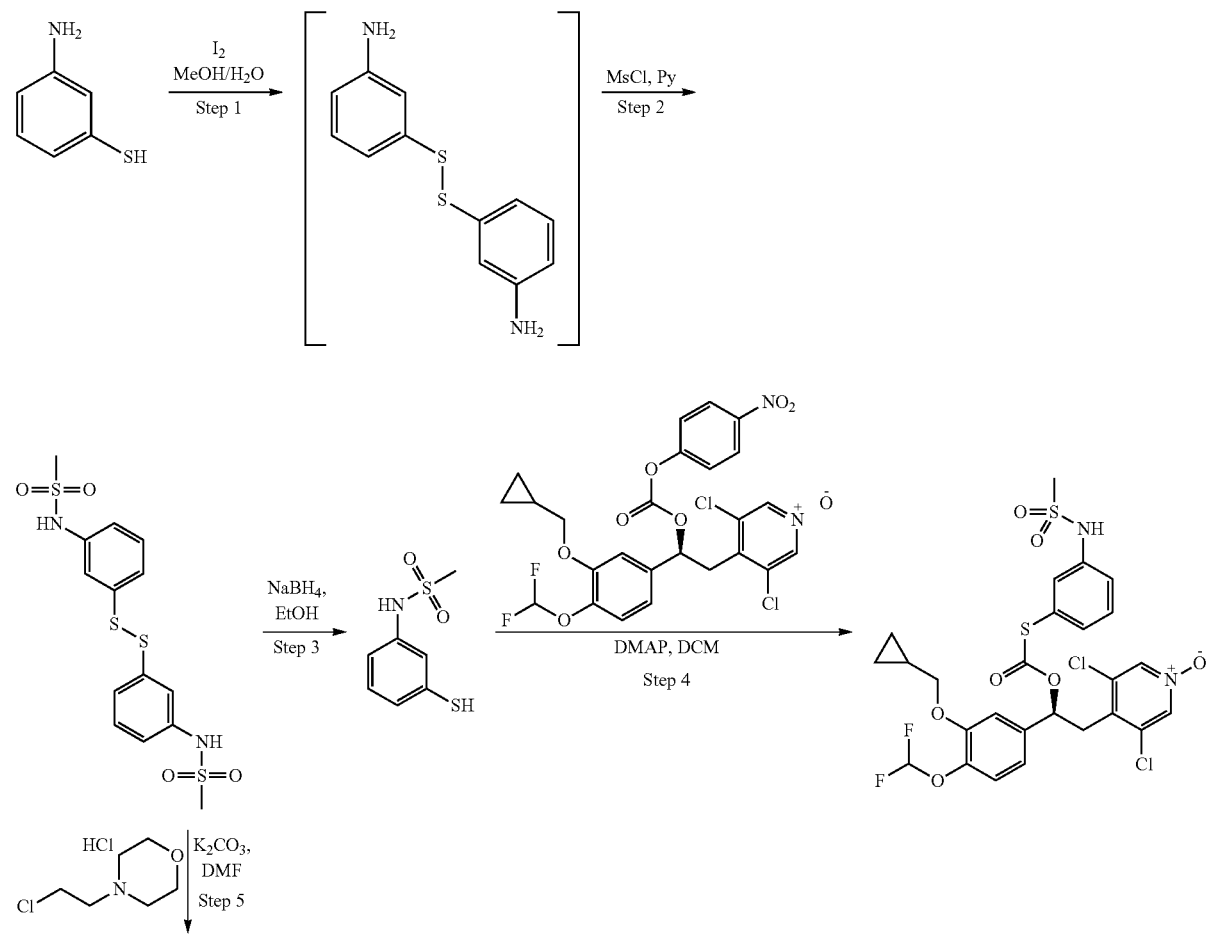

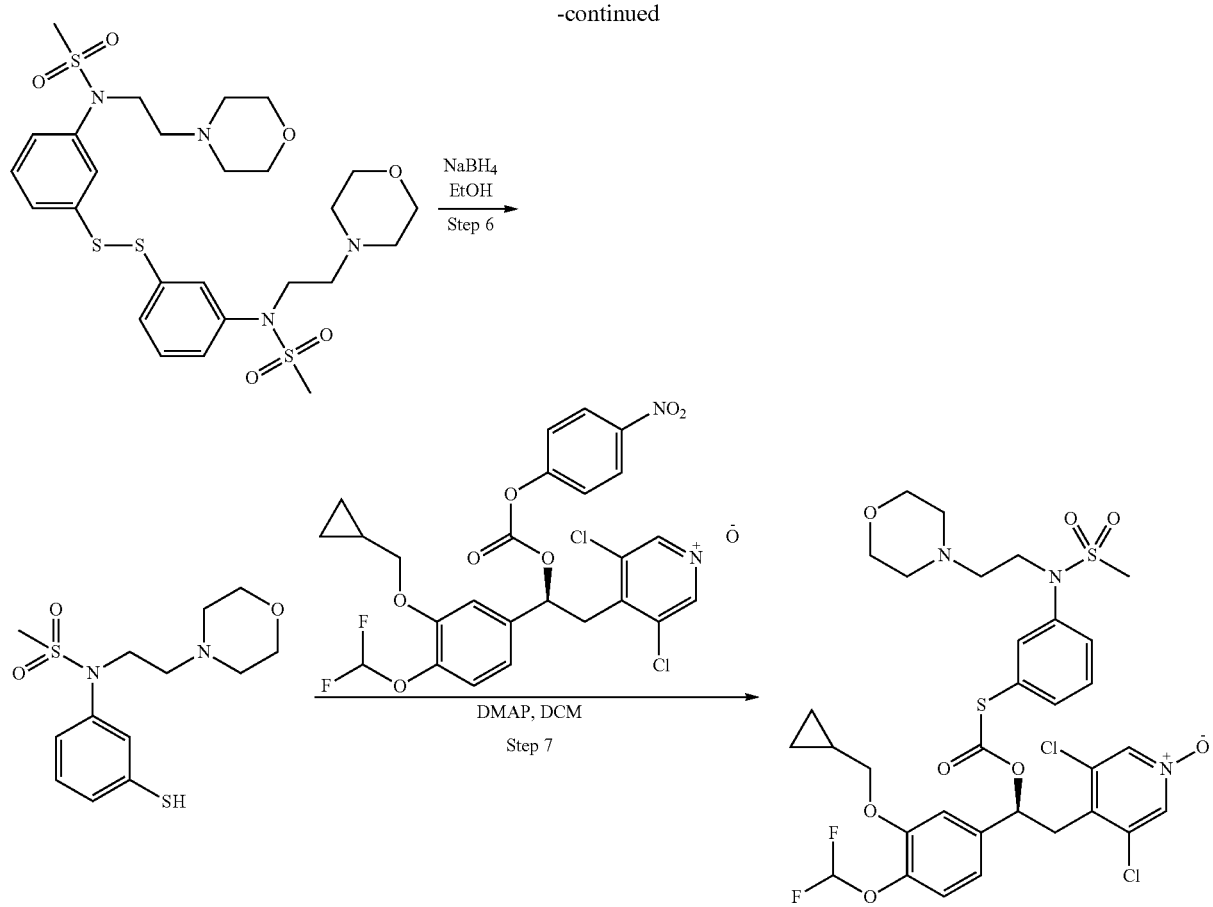

Step 1 and 2: Synthesis of N,N'-(3,3'-disulfanediyl-bis(3,1-phenylene))dimethanesulfonamide (58)

To a stirred solution of 3-aminobenzenethiol (1 ml, 9.42 mmol) in MeOH/H₂O 1:1 (14 ml), a solution of iodine (1.195 g, 4.71 mmol) in MeOH (ca 10 ml) was added dropwise (addition continued till the dark color of the solution of iodine turned into pale yellow). The mixture was stirred at RT overnight. Water was added and the mixture was extracted with EtOAc; the organic layer was dried over Na₂SO₄, filtered and evaporated affording a pale yellow oil. This intermediate was dissolved in pyridine (14 ml), cooled to 0° C. and methanesulfonyl chloride (0.881 ml, 11.30 mmol) was added; the reaction was then warmed to RT and stirred for 3 hours. The solvent was evaporated, HCl 1N was added and the mixture was extracted with DCM. The organic layer was dried over Na₂SO₄, filtered and evaporated. The crude was purified by flash chromatography on silica gel (DCM/MeOH 99.5 to 99:1) affording N,N-(3,3'-disulfanediylbis(3,1-phenylene))dimethanesulfonamide (260 mg, 0.643 mmol, 13.65% yield, MS/ESI⁺ 404.8 [MH]⁺) that was used in the next step without further purification.

Step 3: Synthesis of N-(3-mercaptophenyl)methanesulfonamide (59)

To a solution of N,N'-(3,3'-disulfanediylbis(3,1-phenylene))-dimethanesulfonamide (225 mg, 0.556 mmol) in EtOH (15 ml), NaBH₄ (126 mg, 3.34 mmol) was added, and the reaction was stirred at RT for 4 hours. Sodium borohydride (126 mg, 3.34 mmol) was freshly added, and stirring at RT continued overnight. The mixture was acidified with HCl 1N and extracted with EtOAc; combined organic layers were dried over Na₂SO₄, filtered and evaporated affording N-(3-mercaptophenyl)methanesulfonamide (210 mg, 1.033 mmol, 93% yield, MS/ESI⁺ 203.9 [MH]⁺) that was used in the next step without further purification.

Step 4: Synthesis of (S)-3,5-dichloro-4-(2-(3-(cyclopropylmethoxy)-4-(difluoromethoxy)phenyl)-2-((3-(methylsulfonamido)phenylthio)carbonyloxy)-ethyl) pyridine 1-oxide (60)

To a suspension of N-(3-mercaptophenyl)methanesulfonamide (97 mg, 0.478 mmol) in DCM (15 ml), under nitrogen atmosphere, (S)-3,5-dichloro-4-(2-(3-(cyclopropylmethoxy)-4-(difluoromethoxy)phenyl)-2-((4-nitrophenoxy)-carbonyloxy)ethyl)pyridine 1-oxide (prepared with an analogous procedure to that described in Scheme 3, Step 1) (200 mg, 0.342 mmol), and DMAP (20.87 mg, 0.171 mmol) were added, and the reaction mixture was stirred at RT for 3 hours. The organic solution was washed with K₂CO₃ dil. aq., dried over Na₂SO₄, filtered and evaporated. The crude was triturated with EtOH affording (S)-3,5-dichloro-4-(2-(3-(cyclopropylmethoxy)-4-(difluoromethoxy)phenyl)-2-((3-(methylsulfonamido) phenylthio)carbonyloxy)ethyl)pyridine 1-oxide (162.9 mg, 0.251 mmol, 73.4% yield, MS/ESI⁺ 649.04 [MH]⁺, [α$_D$]=−93.81, c=0.53 in DCM).

¹H NMR (300 MHz, DMSO-d₆) δ ppm 9.94 (br. s., 1 H) 8.58 (s, 2 H) 7.40 (dd, 1 H) 7.08-7.32 (m, 5 H) 6.96 (dd, 1 H)

7.08 (t, 1 H) 6.07 (dd, 1 H) 3.91 (d, 2 H) 3.52 (dd, 1 H) 3.29-3.33 (m, 1 H) 3.00 (s, 3 H) 1.14-1.30 (m, 1 H) 0.49-0.65 (m, 2 H) 0.28-0.42 (m, 2 H)

Step 5: Synthesis of N,N'-(3,3'-disulfanediylbis(3,1-phenylene))bis(N-(2-morpholinoethyl)methanesulfonamide) (61)

A mixture of N,N'-(3,3'-disulfanediylbis(3,1-phenylene))-dimethanesulfonamide (0.135 g, 0.334 mmol), 4-(2-chloroethyl)-morpholine hydrochloride (0.137 g, 0.734 mmol), and potassium carbonate (0.203 g, 1.468 mmol) in DMF (8 ml) was heated at 80° C. for 4 hours. The mixture was portioned between EtOAc and NaHCO$_3$ 5%. The organic phase was washed twice with brine and dried over Na$_2$SO$_4$. The solvent was removed and the crude was purified by filtration on silica gel cartridge (DCM:MeOH=99:1 to 97:3) affording N,N'-(3,3'-disulfanediylbis(3,1-phenylene))bis(N-(2-morpholinoethyl)-methanesulfonamide) (0.165 g, 0.262 mmol, 78% yield, MS/ESI$^+$ 631.0 [MH]$^+$).

Step 6: Synthesis of N-(3-mercaptophenyl)-N-(2-morpholinoethyl)-methanesulfonamide (62)

To a solution of N,N'-(3,3'-disulfanediylbis(3,1-phenylene))bis(N-(2-morpholinoethyl)methanesulfonamide) (0.165 g, 0.262 mmol) in EtOH (8 ml), NaBH$_4$ (0.099 g, 2.62 mmol) was added portion wise, and the mixture was stirred at RT overnight. The mixture was portioned between EtOAc and NH$_4$Cl sat. sol. (pH=7), and the aqueous phase was extracted with EtOAc. The combined organic layers were dried over Na$_2$SO$_4$ and the solvent was removed affording N-(3-mercaptophenyl)-N-(2-morpholinoethyl)methanesulfonamide (0.116 g, 0.367 mmol, 70.1% yield, MS/ESI$^+$ 316.9 [MH]$^+$).

Step 7: Synthesis of (S)-3,5-dichloro-4-(2-(3-(cyclopropylmethoxy)-4-(difluoromethoxy)phenyl)-2-((3-(N-(2-morpholinoethyl)methylsulfonamido)-phenylthio)carbonyloxy)ethyl)pyridine 1-oxide (63)

A mixture of N-(3-mercaptophenyl)-N-(2-morpholinoethyl)-methane-sulfonamide (0.116 g, 0.367 mmol), (S)-3,5-dichloro-4-(2-(3-(cyclopropylmethoxy)-4-(difluoromethoxy)phenyl)-2-((4-nitrophenoxy)-carbonyloxy)ethyl)pyridine 1-oxide (prepared with an analogous procedure to that described in Scheme 3, Step 1) (0.195 g, 0.333 mmol), and DMAP (0.020 g, 0.167 mmol) in DCM (10 ml) was stirred at RT for 3 hours. The mixture was diluted with DCM and washed several times with K$_2$CO$_3$ dil. aq. The organic layer was dried over Na$_2$SO$_4$ and the solvent was removed. The crude was purified by flash chromatography on silica gel cartridge (DCM:EtOAc=50:50 to 25:75; washing with DCM; DCM:MeOH=99:1 to 97:3) affording 0.115 g of a product which was purified by preparative LC/MS (fractions collected and portioned between EtOAc and 5% NaHCO$_3$; organic phase washed with brine; dried over Na$_2$SO$_4$ and evaporated) affording 0.098 g of desired compound as a yellow foam. An additional purification by flash chromatography on silica gel (DCM:MeOH=99:1 to 96:4) was performed to obtain (S)-3,5-dichloro-4-(2-(3-(cyclopropylmethoxy)-4-(difluoromethoxy)phenyl)-2-((3-(N-(2-morpholinoethyl)methylsulfonamido)-phenylthio)carbonyloxy)ethyl)pyridine 1-oxide (0.060 g, 0.079 mmol, 23.61% yield, MS/ESI$^+$ 762.34 [MH]$^+$, [α$_D$]=−49.69, c=0.45 in MeOH).

1H NMR (300 MHz, DMSO-d6) δ ppm 8.59 (s, 2 H), 7.38-7.58 (m, 4 H), 7.21 (d, 1 H), 7.11 (d, 1 H), 6.97 (dd, 1 H), 7.08 (t, 1 H), 6.07 (dd, 1 H), 3.91 (d, 2 H), 3.72 (t, 2 H), 3.53 (dd, 1 H), 3.41-3.47 (m, 4 H), 3.24-3.27 (m, 1 H), 3.02 (s, 3 H), 2.31 (t, 2 H), 2.21-2.28 (m, 4 H), 1.03-1.35 (m, 1 H), 0.48-0.69 (m, 2 H), 0.27-0.48 (m, 2 H)

Example 7

Synthesis of (S)-3,5-dichloro-4-(2-(3-(cyclopropylmethoxy)-4-(difluoromethoxy)phenyl)-2-((3-(cyclopropylmethoxy)-4-(methylsulfonamido)-phenylthio)carbonyloxy)ethyl)pyridine 1-oxide (71)

Scheme 7

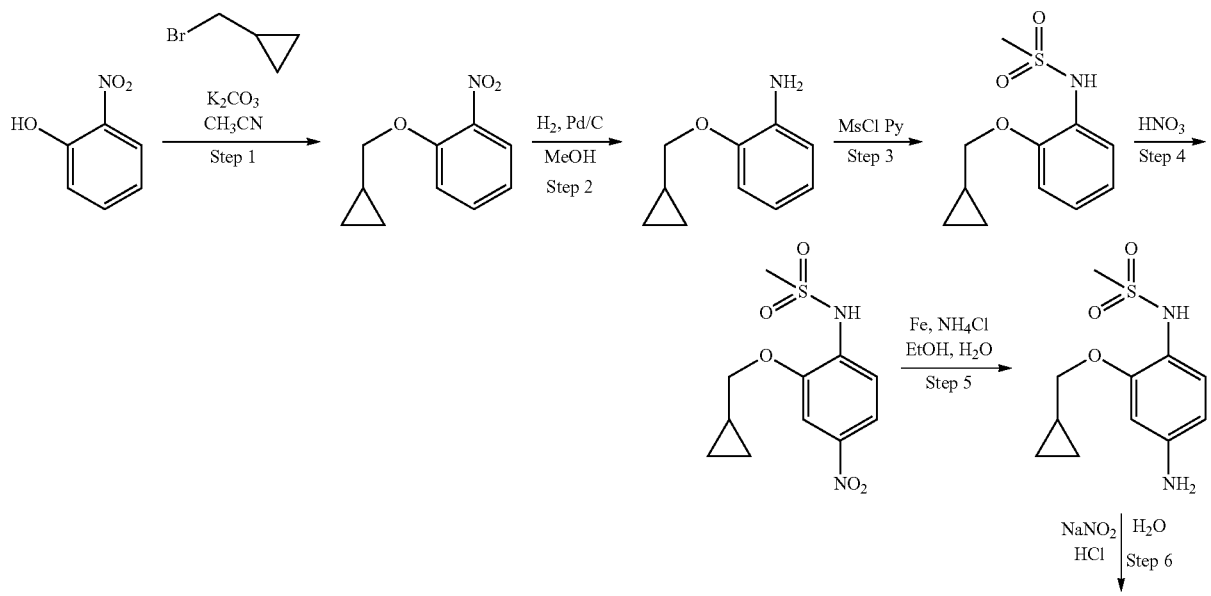

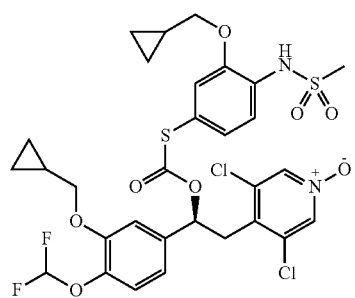
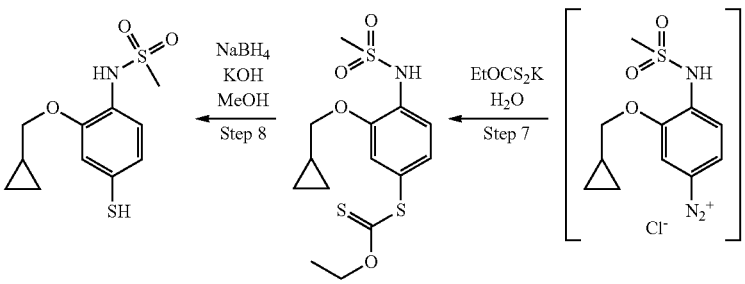

Step 1: Synthesis of 1-(cyclopropylmethoxy)-2-nitrobenzene (64)

A mixture of 2-nitrophenol (1 g, 7.19 mmol), K2CO3 (1.192 g, 8.63 mmol), and (bromomethyl)cyclopropane (0.837 ml, 8.63 mmol) in CH3CN (40 ml) was heated to 85° C. overnight. The mixture was portioned between EtOAc and HCl 1N. The organic phase was dried over $Na_2SO_4$ and the solvent was removed. 1-(cyclopropylmethoxy)-2-nitrobenzene was obtained as a crude (1.352 g, 7.00 mmol, 97% yield) and used in the next step without further purification.

Step 2: Synthesis of 2-(cyclopropylmethoxy)aniline (65)

A mixture of 1-(cyclopropylmethoxy)-2-nitrobenzene (1.352 g, 7.00 mmol) and 10% Pd/C (0.140 g, 0.132 mmol) in MeOH (30 ml) was hydrogenated at 20 psi for 1 hour. The catalyst was filtered off, and the solvent was removed affording 2-(cyclopropylmethoxy)aniline (1.03 g, 6.31 mmol, 90% yield, MS/ESI$^+$ 164.0 [MH]$^+$) that was used in the next step without further purification.

Step 3: Synthesis of N-(2-(cyclopropylmethoxy)phenyl)-methanesulfonamide (66)

A solution of 2-(cyclopropylmethoxy)aniline (1.03 g, 6.31 mmol) in pyridine (20 ml) was cooled to 0° C., and methanesulfonyl chloride (0.541 ml, 6.94 mmol) was added. The mixture was warmed to RT and stirred for 2 hours. The solvent was removed, and the crude was portioned between EtOAc and HCl 1N. The organic phase was washed with brine and dried over $Na_2SO_4$. The solvent was removed and the crude was purified by filtration on silica gel cartridge (petroleum ether:EtOAc=80:20) affording N-(2-(cyclopropylmethoxy)phenyl)methanesulfonamide (1.456 g, 6.03 mmol, 96% yield, MS/ESI$^+$ 263.9 [MNa]$^+$).

Step 4: Synthesis of N-(2-(cyclopropylmethoxy)-4-nitrophenyl)-methanesulfonamide (67)

N-(2-(cyclopropylmethoxy)phenyl)methanesulfonamide (1.3 g, 5.39 mmol) was cooled to 0° C., and nitric acid (0.746 ml, 10.77 mmol) was added. The mixture was stirred at RT for 1 hour. The mixture was diluted with EtOAc and washed with $NaHCO_3$ 5% and brine. The organic phase was dried over $Na_2SO_4$, and the solvent was removed. The crude was purified by flash chromatography on silica gel cartridge (petroleum ether:EtOAc=80:20 to 60:40). 0.390 g of title product were obtained by collection and evaporation of clean fractions. Product obtained from mixed fractions was triturated with EtOAc affording 0.285 g of title compound. The mother liquor from trituration was evaporated and purified by flash chromatography on silica gel (DCM:petroleum ether=80:20) to give 0.155 g of title compound. Title product N-(2-(cyclopropylmethoxy)-4-nitrophenyl)-methanesulfonamide was obtained (0.830 g, 2.90 mmol, 53.8% yield, MS/ESI$^+$ 286.9 [MH]$^+$).

Step 5: Synthesis of N-(4-amino-2-(cyclopropylmethoxy)phenyl)-methanesulfonamide (68)

A mixture of N-(2-(cyclopropylmethoxy)-4-nitrophenyl) methanesulfonamide (0.830 g, 2.90 mmol), iron (0.971 g, 17.39 mmol), and $NH_4Cl$ (0.099 g, 1.848 mmol) in EtOH (15 ml) and water (6 ml) was heated to reflux for 30 minutes. The hot reaction mixture was filtered and the filtrate was evaporated. The residue was portioned between EtOAc and water; the organic phase was washed with brine and dried over $Na_2SO_4$. The solvent was removed affording N-(4-amino-2-(cyclopropylmethoxy)phenyl)-methanesulfonamide (0.679 g, 2.65 mmol, 91% yield, MS/ESI$^+$ 256.9 [MH]$^+$).

Step 6 and Step 7: Synthesis of S-3-(cyclopropylmethoxy)-4-(methylsulfonamido)phenyl O-ethyl carbonodithioate (69)

A solution of sodium nitrite (0.164 g, 2.372 mmol) in water (1 ml) was added dropwise to a suspension of N-(4-amino-2-(cyclopropylmethoxy)phenyl)-methanesulfonamide (0.640 g, 2.497 mmol) in water (10 ml) and conc. HCl (0.789 ml, 9.61 mmol) cooled to 5° C., and the mixture was stirred for 15 minutes between 5 and 10° C. The resulting solution was added dropwise to a solution of potassium O-ethyl carbonodithioate (1.305 g, 8.14 mmol) in water (5 ml) at 65° C. The mixture was stirred at the same temperature for 15 minutes, then the mixture was extracted with toluene and the organic phase was washed with water and brine and dried over $Na_2SO_4$. The solvent was removed and the crude oil (0.903 g, 2.497 mmol, 100% yield, MS/ESI$^+$ 361.9 [MH]+) was kept at 4° C. and used in the next step without purification.

Step 8: Synthesis of N-(2-(cyclopropylmethoxy)-4-mercaptophenyl)-methanesulfonamide (70)

To a solution of crude S-3-(cyclopropylmethoxy)-4-(methylsulfonamido)-phenyl O-ethyl carbonodithioate (prepared as described in Step 7, 0.903 g, 2.497 mmol) in MeOH (15 ml), KOH (0.392 g, 6.99 mmol) was added followed by $NaBH_4$ (0.071 g, 1.873 mmol), and the mixture was stirred at RT for 1 hour. $NaBH_4$ (0.047 g, 1.249 mmol) was freshly added, and the mixture was stirred at RT for 1 hour. Then the mixture was acidified with 10% $H_2SO_4$ (until effervescence ceased). The residue was portioned between EtOAc and water, and the organic layer was washed with water, dried over na2SO4 and evaporated. The residue was purified by flash chromatography on silica gel cartridge (DCM: EtOAc=80:20) affording N-(2-(cyclopropylmethoxy)-4-mercaptophenyl)methanesulfonamide (0.222 g, 0.812 mmol, 32.5% yield, MS/ESI$^+$ 295.9 [MNa]$^+$).

Step 9: Synthesis of (S)-3,5-dichloro-4-(2-(3-(cyclopropylmethoxy)-4-(difluoromethoxy)phenyl)-2-((3-(cyclopropylmethoxy)-4-(methylsulfonamido)-phenylthio)carbonyloxy)ethyl)pyridine 1-oxide (71)

A solution of N-(2-(cyclopropylmethoxy)-4-mercaptophenyl)-methanesulfonamide (0.112 g, 0.410 mmol), (S)-3,5-dichloro-4-(2-(3-(cyclopropylmethoxy)-4-(difluoromethoxy)phenyl)-2-((4-nitrophenoxy)-carbonyloxy) ethyl)pyridine 1-oxide (prepared with an analogous procedure to that described in Scheme 3, Step 1) (0.200 g, 0.342 mmol), and DMAP (0.021 g, 0.171 mmol) in DCM (8 ml) was stirred at RT overnight. The mixture was diluted with DCM and washed several times with diluted aqueous $K_2CO_3$. The organic layer was dried over $Na_2SO_4$ and the solvent was removed. The crude was purified by filtration on silica gel cartridge (DCM:EtOAc=80:20) affording the desired compound as a pale yellow amorphous solid. The product was further purified by flash chromatography on silica gel cartridge (petroleum ether:EtOAc=50:50 to 35:65) and by preparative LC/MS affording (S)-3,5-dichloro-4-(2-(3-(cyclopropylmethoxy)-4-(difluoromethoxy)phenyl)-2-((3-(cyclopropylmethoxy)-4-(methylsulfonamido)phenylthio) carbonyloxy)ethyl)pyridine 1-oxide as an off-white amorphous solid (0.060 g, 0.083 mmol, 24.40% yield, MS/ESI$^+$ 719.23 [MH]$^+$, $[\alpha_D]$=−64.64, c=0.47 in DCM).

$^1$H NMR (300 MHz, DMSO-d$_6$) δ ppm 9.00 (s, 1 H), 8.59 (s, 2 H), 7.29 (d, 1 H), 7.21 (d, 1 H), 7.11 (d, 1 H), 7.07 (d, 1 H), 7.00 (dd, 1 H), 6.97 (dd, 1 H), 7.08 (t, 1 H), 6.07 (dd, 1 H), 3.92 (d, 2 H), 3.86 (d, 2 H), 3.51 (dd, 1 H), 3.27 (dd, 1 H), 3.06 (s, 3 H), 1.08-1.36 (m, 2 H), 0.47-0.65 (m, 4 H), 0.23-0.45 (m, 4 H)

Example 8

Synthesis of 4-((S)-2-((R)-5-acetoxy-2-(3,4-dimethoxyphenylsulfonamido)-pentanoyloxy)-2-(3-(cyclopropylmethoxy)-4-(difluoromethoxy)phenyl) ethyl)-3,5-dichloropyridine 1-oxide (76)

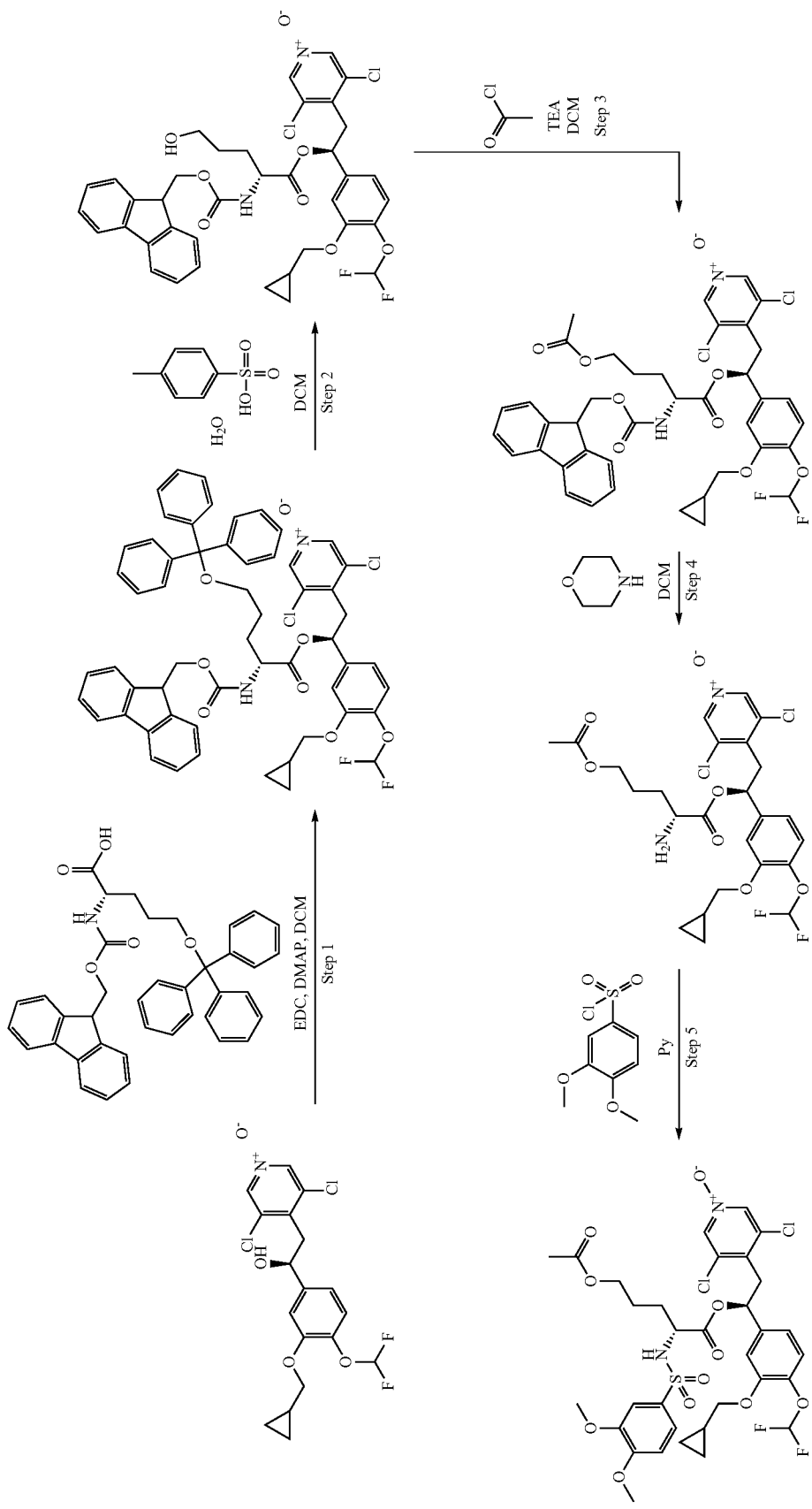

Step 1: Synthesis of 4-((S)-2-((R)-2-(((9H-fluoren-9-yl)methoxy)-carbonylamino)-4-(trityloxy)butanoyloxy)-2-(3-(cyclopropylmethoxy)-4-(difluoromethoxy)phenyl)ethyl)-3,5-dichloropyridine 1-oxide (72)

EDC (174 mg, 0.908 mmol) was added to a solution of (S)-3,5-dichloro-4-(2-(3-(cyclopropylmethoxy)-4-(difluoromethoxy)phenyl)-2-hydroxyethyl)pyridine 1-oxide (293 mg, 0.697 mmol), (S)-2-(((9H-fluoren-9-yl)methoxy)carbonylamino)-5-(trityloxy)-pentanoic acid (500 mg, 0.837 mmol), and DMAP (17 mg, 0.139 mmol) in DCM (5 mL) at RT under nitrogen atmosphere. The mixture was stirred at RT overnight, then diluted with DCM and washed with NaHCO$_3$ sat. sol., HCl 0.1M and Brine. The organic phase was dried over Na$_2$SO$_4$ and the solvent was evaporated, to yield 708 mg of the title compound.

Step 2: Synthesis of 4-((S)-2-((R)-2-(((9H-fluoren-9-yl)methoxy)-carbonylamino)-5-hydroxypentanoyloxy)-2-(3-(cyclopropylmethoxy)-4-(difluoromethoxy)phenyl)ethyl)-3,5-dichloropyridine 1-oxide (73)

To a solution of 4-((S)-2-((R)-2-(((9H-fluoren-9-yl)methoxy)carbonylamino)-4-(trityloxy)butanoyloxy)-2-(3-(cyclopropylmethoxy)-4-(difluoromethoxy)-phenyl)ethyl)-3,5-dichloropyridine 1-oxide (354 mg, 0.354 mmol) in DCM (5 mL), 4-methylbenzenesulfonic acid hydrate (14 mg, 0.071 mmol) was added. The mixture was stirred at room RT overnight. The mixture was then diluted with DCM and washed with NaHCO$_3$ sat. sol. The organic phase was dried over Na$_2$SO$_4$, and the solvent was evaporated, to yield 268 mg of the title compound.

Step 3: Synthesis of 4-((S)-2-((R)-2-(((9H-fluoren-9-yl)methoxy)-carbonylamino)-5-acetoxypentanoyloxy)-2-(3-(cyclopropylmethoxy)-4-(difluoromethoxy)phenyl)ethyl)-3,5-dichloropyridine 1-oxide (74)

To a solution of 4-((S)-2-((R)-2-(((9H-fluoren-9-yl)methoxy)carbonylamino)-5-hydroxypentanoyloxy)-2-(3-(cyclopropylmethoxy)-4-(difluoromethoxy)phenyl)-ethyl)-3,5-dichloropyridine 1-oxide (268 mg, 0.354 mmol) in DCM (5 mL), acetyl chloride (54 µl, 0.757 mmol) and TEA (108 µl, 0.775 mmol) were added. The mixture was stirred at RT for 3 hours. The mixture was then diluted with DCM and washed with NaHCO$_3$ sat. sol., HCl 0.1 M and brine. The organic phase was dried over Na$_2$SO$_4$ and the solvent was evaporated, to yield 284 mg of the title compound.

Step 4: Synthesis of 4-((S)-2-((R)-5-acetoxy-2-aminopentanoyloxy)-2-(3-(cyclopropylmethoxy)-4-(difluoromethoxy)phenyl)ethyl)-3,5-dichloropyridine 1-oxide (75)

To a solution of 4-((S)-2-((R)-2-(((9H-fluoren-9-yl)methoxy)carbonylamino)-5-acetoxypentanoyloxy)-2-(3-(cyclopropylmethoxy)-4-(difluoromethoxy)phenyl)-ethyl)-3,5-dichloropyridine 1-oxide (284 mg, 0.355 mmol) dissolved in DCM (5.7 ml), morpholine (615 µl, 7.10 mmol) was added. The mixture was stirred at RT for 48 hours. The mixture was then diluted with DCM and washed twice with water. The organic phase was dried over Na$_2$SO$_4$ and the solvent was evaporated, to yield 205 mg of the title compound.

Step 5: Synthesis of 4-((S)-2-((R)-5-acetoxy-2-(3,4-dimethoxyphenylsulfonamido)pentanoyloxy)-2-(3-(cyclopropylmethoxy)-4-(difluoromethoxy)phenyl)ethyl)-3,5-dichloropyridine 1-oxide (76)

To a solution of 4-((S)-2-((R)-5-acetoxy-2-aminopentanoyloxy)-2-(3-(cyclopropylmethoxy)-4-(difluoromethoxy)phenyl)ethyl)-3,5-dichloropyridine 1-oxide (205 mg, 0.354 mmol) dissolved in DCM (2.5 mL), pyridine (58 µl, 0.710 mmol) and 3,4-dimethoxybenzene-1-sulfonyl chloride (168 mg, 0.710 mmol) were added. The mixture was stirred at RT for 48 hours. The mixture was then diluted with DCM and washed with NaHCO$_3$ sat. sol., HCl 0.1M and brine. The organic phase was dried over Na$_2$SO$_4$, and the solvent was evaporated, to yield 284 mg of a yellow solid which was purified by preparative reverse-phase HPLC to yield 42 mg of the title compound.

MS/ESI$^+$ 777.6 [MH]$^+$ $^1$H NMR (400 MHz, acetone) δ ppm 8.27 (s, 2 H), 7.32-7.37 (m, 1 H), 7.28-7.31 (m, 1 H), 7.12-7.18 (m, 2 H), 6.99-7.04 (m, 1 H), 6.94-6.99 (m, 1 H), 6.91 (t, J=75.00 Hz, 1 H), 6.78-6.85 (m, 1 H), 5.89-5.97 (m, 1 H), 3.90 (m, 8 H), 3.85 (s, 3 H), 3.40-3.53 (m, 1 H), 3.13-3.31 (m, 1 H), 1.97 (s, 3 H), 1.47-1.86 (m, 4 H), 1.18-1.35 (m, 1 H), 0.50-0.69 (m, 2 H), 0.27-0.45 (m, 2 H).

Example 9

Synthesis of (S)-3,5-dichloro-4-(2-(3-(cyclopropylmethoxy)-4-(difluoromethoxy)phenyl)-2-(3-(3-(cyclopropylmethoxy)-4-(methylsulfonamido)-benzyloxy)-3-oxopropanoyloxy)ethyl)pyridine 1-oxide (81)

Scheme 9

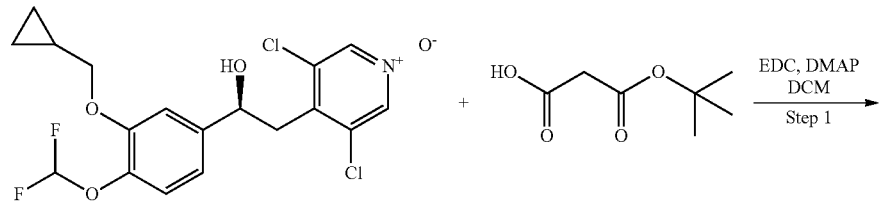

-continued
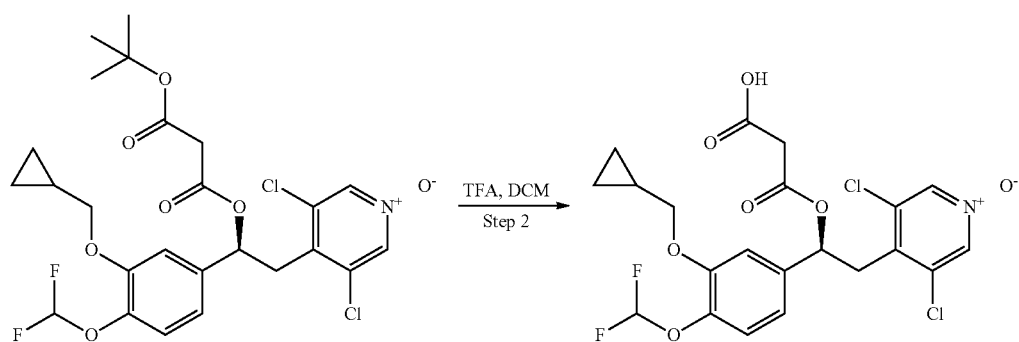
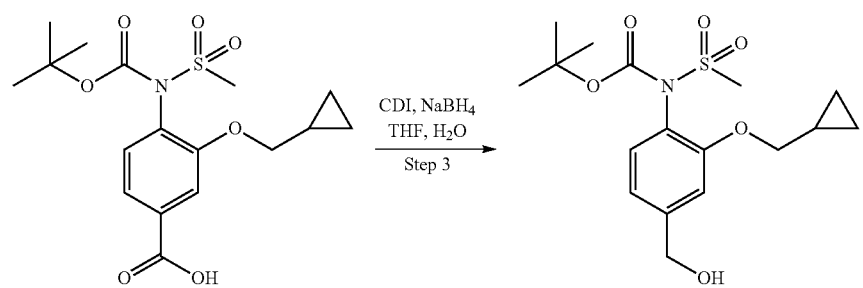
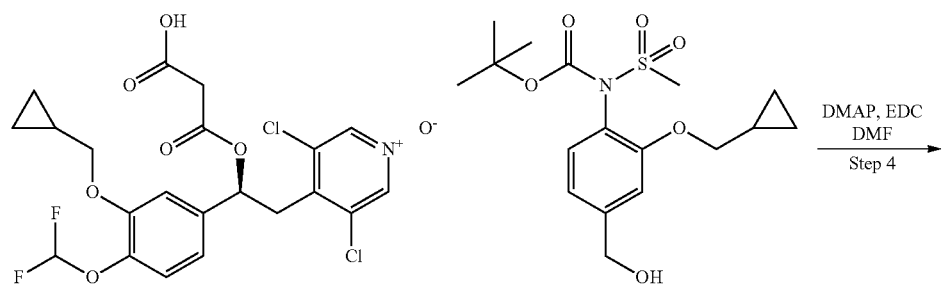
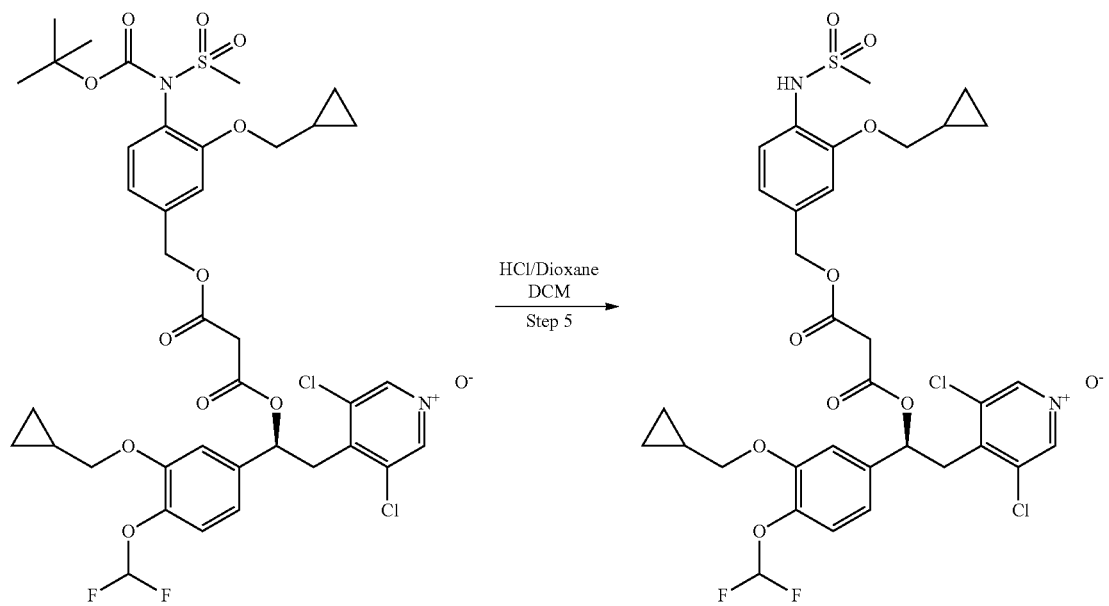

Step 1: Synthesis of (S)-4-(2-(3-tert-butoxy-3-oxo-propanoyloxy)-2-(3-(cyclopropylmethoxy)-4-(difluoromethoxy)phenyl)ethyl)-3,5-dichloropyridine 1-oxide (77)

A mixture of (S)-3,5-dichloro-4-(2-(3-(cyclopropylmethoxy)-4-(difluoromethoxy)phenyl)-2-hydroxyethyl)pyridine 1-oxide (1 g, 2.380 mmol), 3-tert-butoxy-3-oxopropanoic acid (0.457 g, 2.86 mmol), EDC (1.369 g, 7.14 mmol), and DMAP (0.291 g, 2.380 mmol) in DCM (50 ml) was stirred at RT overnight. The reaction mixture was washed with HCl 1N, NaHCO$_3$ 5% and brine. The organic layer was dried over Na$_2$SO$_4$ and evaporated to dryness. The crude was purified by flash chromatography on silica gel column (DCM: EtOAc=40:60) affording (S)-4-(2-(3-tert-butoxy-3-oxopropanoyloxy)-2-(3-(cyclopropylmethoxy)-4-(difluoromethoxy)phenyl)ethyl)-3,5-dichloropyridine 1-oxide (1.1303 g, 2.010 mmol, 84% yield, MS/ESI$^+$ 562.0 [MH]$^+$).

Step 2: Synthesis of (S)-4-(2-(2-carboxyacetoxy)-2-(3-(cyclopropylmethoxy)-4-(difluoromethoxy)phenyl)ethyl)-3,5-dichloropyridine 1-oxide (78)

(S)-4-(2-(3-tert-butoxy-3-oxopropanoyloxy)-2-(3-(cyclopropylmethoxy)-4-(difluoromethoxy)phenyl)ethyl)-3,5-dichloropyridine 1-oxide (1.0561 g, 1.878 mmol) was dissolved in DCM (70 ml) and cooled to 0° C. TFA (1.447 ml, 18.78 mmol) was added slowly, and the reaction was stirred at RT for 3 days. Two more additions of TFA (0.723 ml, 9.39 mmol) were performed, and the stirring was continued overnight. The mixture was evaporated to dryness affording (S)-4-(2-(2-carboxyacetoxy)-2-(3-(cyclopropylmethoxy)-4-(difluoromethoxy)phenyl)ethyl)-3,5-dichloropyridine 1-oxide (0.950 g, 1.876 mmol, 100% yield, MS/ESI$^+$ 505.9 [MH]$^+$).

Step 3: Synthesis of Tert-butyl 2-(cyclopropylmethoxy)-4-(hydroxymethyl)phenyl(methylsulfonyl)carbamate (79)

4-(N-(tert-butoxycarbonyl)methylsulfonamido)-3-(cyclopropylmethoxy)-benzoic acid (for reference procedure see Example 18, WO 2010/089107, which is incorporated herein by reference in its entirety) (200 mg, 0.519 mmol) was dissolved in THF (10.5 ml), then CDI was added (154 mg, 0.95 mmol). The mixture was stirred at RT for 2 days, then H2O (1.75 ml) and NaBH4 (36 mg, 0.95 mmols) were added. The solvent was removed by evaporation under vacuum. The crude was dissolved in EtOAc (80 ml) and washed with water. The organic phase was dried over Na$_2$SO$_4$ and evaporated under vacuum to yield 200 mg of the desired product.

Step 4: Synthesis of (S)-4-(2-(3-(4-(N-(tert-butoxycarbonyl)-methylsulfonamido)-3-(cyclopropylmethoxy)benzyloxy)-3-oxopropanoyloxy)-2-(3-(cyclopropylmethoxy)-4-(difluoromethoxy)phenyl)ethyl)-3,5-dichloropyridine 1-oxide (80)

A mixture of (S)-4-(2-(2-carboxyacetoxy)-2-(3-(cyclopropylmethoxy)-4-(difluoromethoxy)phenyl)ethyl)-3,5-dichloropyridine 1-oxide (50 mg, 0.099 mmol), tert-butyl 2-(cyclopropylmethoxy)-4-(hydroxymethyl)phenyl-(methylsulfonyl)-carbamate (73 mg, 0.2 mmol), DMAP (14.5 mg, 0.12 mmol), and ECD (57 mg, 0.3 mmol) in DMF (1.5 ml) was stirred at RT overnight. The reaction mixture was quenched with water, and the product was extracted with EtOAc. The organic phase was washed with HCl 1M, NaHCO$_3$ sat. sol. and brine. The organic layer was dried over Na$_2$SO$_4$ and evaporated to dryness. The crude (70 mg) was used for the next step without any further purification.

Step 5: Synthesis of (S)-3,5-dichloro-4-(2-(3-(cyclopropylmethoxy)-4-(difluoromethoxy)phenyl)-2-(3-(3-(cyclopropylmethoxy)-4-(methylsulfonamido)-benzyloxy)-3-oxopropanoyloxy)ethyl)pyridine 1-oxide (81)

(S)-4-(2-(3-(4-(N-(tert-butoxycarbonyl)methylsulfonamido)-3-(cyclopropylmethoxy)benzyloxy)-3-oxopropanoyloxy)-2-(3-(cyclopropylmethoxy)-4-(difluoromethoxy)phenyl)ethyl)-3,5-dichloropyridine 1-oxide (70 mg, 0.08 mmol) was dissolved in DCM (1 ml), and HCl 4M in Dioxane (500 μM) was added. The mixture was stirred at RT for 3 hours. The reaction was quenched with water, and the product was extracted with EtOAc. The organic phase was dried over Na$_2$SO$_4$ and evaporated to dryness. The crude was purified by Preparative reverse-phase HPLC to yield 10 mg of the final product (Yield: 16%).

MS/ESI$^+$ 759.60 [MH]$^+$.

$^1$H NMR (400 MHz, acetone) δ ppm 8.22 (s, 2 H), 7.67-7.76 (bs, 1 H), 7.42 (m, 1H), 7.18 (d, J=15.00 Hz, 2 H), 7.02-7.09 (m, 2 H), 6.94-6.96 (m, 1 H), 6.90 (t, J=75.00 Hz, 1 H), 6.04-6.14 (m, 1 H), 5.13 (s, 2 H), 3.95 (t, J=6.17 Hz, 4 H), 3.54 (m, 3 H), 3.26-3.36 (m, 1 H), 3.00 (s, 3 H), 1.21-1.38 (m, 2 H), 0.61 (d, J=7.06 Hz, 4 H), 0.38 (d, J=4.41 Hz, 4 H).

The compounds listed in Table 7 were prepared with an analogous procedure to that described in Example 9, Step 1, 2 and 4, by reacting the appropriate precursors (commercially available or synthesized by a person skilled in the art) with suitable reagents, and where purification step has been performed as indicated in Table 7.

TABLE 7

| Structure | Cmp | 1H NMR | MS/ESI+ [MH]+ [α_D] | Starting Material (and conditions of Step 4, if different) | Purification Method |
|---|---|---|---|---|---|
| 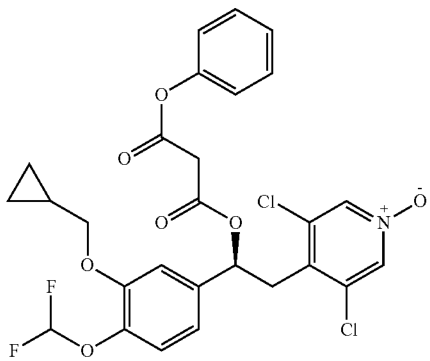 | 82 | 1H NMR (300 MHz, DMSO-d6) δ ppm 8.53 (s, 2 H), 7.39-7.51 (m, 2 H), 7.26-7.33 (m, 1 H), 7.18 (d, 1 H), 7.12 (d, 1 H), 7.05-7.11 (m, 2 H), 7.00 (dd, 1 H), 7.06 (t, 1 H), 6.02 (dd, 1 H), 3.75-3.93 (m, 4 H), 3.49 (dd, 1 H), 3.27 (dd, 1 H), 1.04-1.26 (m, 1 H), 0.45-0.65 (m, 2 H), 0.16-0.43 (m, 2 H) | 582.1 [α_D] = −1.313 (c = 0.32, DCM) | Intermediate of Step 4 (DCM, r.t.) | Flash chromatography on silica gel (petroleum ether/ EtOAc = 1/1 to 4/6) followed by preparative LC/MS |
| 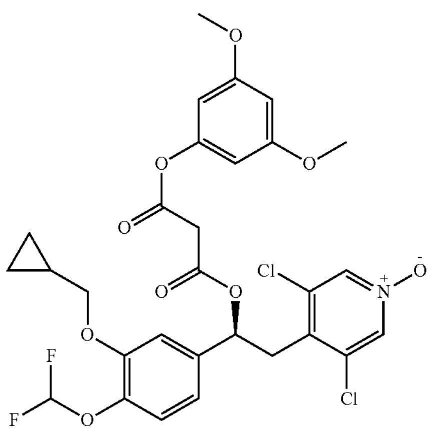 | 83 | 1H NMR (300 MHz, DMSO-d6) δ ppm 8.52 (s, 2 H), 7.18 (d, 1 H), 7.11 (d, 1 H), 6.99 (dd, 1 H), 7.05 (t, 1 H), 6.44 (t, 1 H), 6.26 (d, 2 H), 6.02 (dd, 1 H), 3.81-3.88 (m, 2 H), 3.76-3.81 (m, 2 H), 3.74 (s, 6 H), 3.48 (dd, 1 H), 3.27 (dd, 1 H), 1.06-1.35 (m, 1 H), 0.39-0.77 (m, 2 H), 0.09-0.39 (m, 2 H) | 642.22 [α_D] = +0.650, (c = 0.4, DCM) | Intermediate of Step 4 (DCM, RT) | Flash chromatography on silica gel (DCM/ EtOAc = 7/3), treatment with EtOH and evaporation |
| 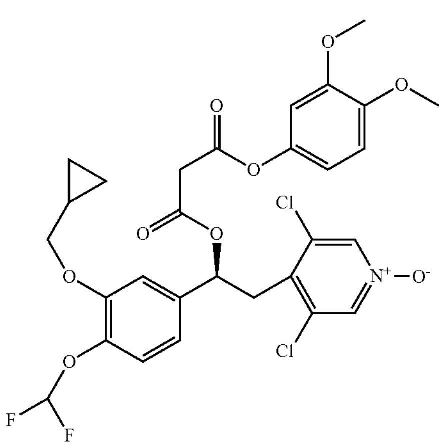 [SMILES: COc1ccc(OC(=O)CC(=O)O[C@@H](Cc2c(Cl)c[n+]([O-])cc2Cl)c2ccc(OC(F)F)c(OCC3CC3)c2)cc1OC] | 84 | 1H NMR (400 MHz, acetone) δ ppm 8.25 (s, 2 H), 7.14-7.28 (m, 2 H), 7.03-7.12 (m, 1 H), 6.87-7.01 (m, 2 H), 6.68-6.74 (m, 1 H), 6.56-6.66 (m, 1 H), 6.01-6.26 (m, 1 H), 3.85-3.95 (m, 2 H), 3.79 and 3.80 (2 s, 2 CH3, 6 H), 3.68-3.76 (m, 2 H), 3.56-3.65 (m, 1 H), 3.32-3.41 (m, 1 H), 1.17-1.34 (m, 1 H), 0.42-0.67 (m, 2 H), 0.18-0.37 (m, 2 H). | 642.4; 664.3 [M + H]+; [M + Na]+ | Intermediate of Step 4 | Preparative reverse-phase HPLC |

Example 10

Synthesis of (S)-3,5-dichloro-4-(2-(3-(cyclopropyl-methoxy)-4-(difluoromethoxy)phenyl)-2-(3-(4-(methylthio)phenylamino)-3-oxopropanoyloxy)ethyl) pyridine 1-oxide (87)

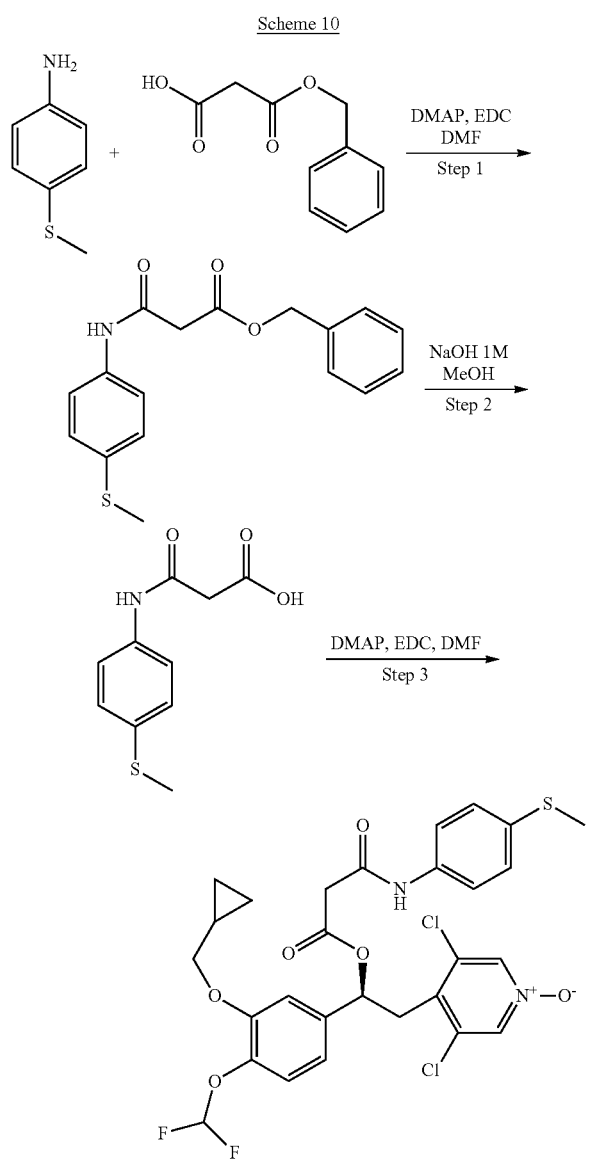

Step 1: Synthesis of benzyl 3-(4-(methylthio)phenylamino)-3-oxopropanoate (85)

4-(methylthio)aniline (500 mg, 3.59 mmol), 3-(benzyloxy)-3-oxopropanoic acid (1046 mg, 5.39 mmol), DMAP (527 mg, 4.31 mmol), and EDC (1377 mg, 7.18 mmol) were dissolved in DMF (7 ml). The reaction was stirred at RT for 4 hours. The reaction mixture was diluted with water, and the precipitate was washed with water, dissolved in EtOAc and extracted with HCl 1N, $Na_2CO_3$ sat. sol. and brine. The organic phase was dried over $Na_2SO_4$ and concentrated under vacuum to give benzyl 3-(4-(methylthio)phenylamino)-3-oxopropanoate (520 mg, 45.9% yield).

Step 2: Synthesis of 3-(4-(methylthio)phenylamino)-3-oxopropanoic acid (86)

Benzyl 3-(4-(methylthio)phenylamino)-3-oxopropanoate (150 mg, 0.476 mmol) was dissolved in MeOH (1.5 ml). NaOH 1M (500 µl) was added, and the reaction was stirred at 40° C. for 2 hours to achieve completion. The reaction mixture was diluted with HCl 1N and extracted with EtOAc. The organic phase was washed with HCl 1N and brine, dried over $Na_2SO_4$ and concentrated under vacuum to give 3-(4-(methylthio)phenylamino)-3-oxopropanoic acid (90 mg, 84% yield).

Step 3: Synthesis of (S)-3,5-dichloro-4-(2-(3-(cyclopropylmethoxy)phenyl)-4-(difluoromethoxy)phenyl)-2-(3-(4-(methylthio)phenylamino)-3-oxopropanoyloxy) ethyl)pyridine 1-oxide (87)

(S)-3,5-dichloro-4-(2-(3-(cyclopropylmethoxy)-4-(difluoromethoxy)phenyl)-2-hydroxyethyl)pyridine 1-oxide (30 mg, 0.071 mmol), 3-(4-(methylthio)-phenylamino)-3-oxopropanoic acid (32.2 mg, 0.143 mmol), DMAP (13.08 mg, 0.107 mmol), and EDC (41.1 mg, 0.214 mmol) were dissolved in DMF (1.5 ml). The reaction was stirred at RT overnight. The reaction mixture was diluted with water and extracted with EtOAc. The organic phase was washed with HCl 1N, $Na_2CO_3$ sat. sol. and brine, dried over $Na_2SO_4$ and concentrated under vacuum. The crude product was purified by preparative reverse-phase HPLC to give (S)-3,5-dichloro-4-(2-(3-(cyclopropylmethoxy)-4-(difluoromethoxy)phenyl)-2-(3-(4-(methylthio)-phenylamino)-3-oxopropanoyloxy)ethyl)pyridine 1-oxide (20 mg, 44.6% yield).

MS/ESI⁺ 627.3; 649.3 [M+H]⁺; [M+Na]+

¹H NMR (400 MHz, acetone) δ ppm 9.30-9.48 (bs, 1 H), 8.20 (s, 2 H), 7.49-7.68 (m, 2 H), 7.26-7.28 (m, 3 H), 7.13-7.20 (m, 1 H), 6.98-7.06 (m, 1 H), 6.91 (t, J=75.00 Hz, 1 H), 6.01-6.17 (m, 1 H), 3.86-4.03 (m, 2 H), 3.40-3.60 (m, 3 H), 3.26-3.37 (m, 1 H), 2.48 (s, 3 H), 1.12-1.35 (m, 1 H), 0.50-0.68 (m, 2 H), 0.28-0.45 (m, 2 H).

Example 11

Synthesis of (S)-3,5-dichloro-4-(2-(3-(cyclopropylmethoxy)-4-(difluoromethoxy)phenyl)-2-(3-(3,4-dimethoxyphenylamino)-3-oxopropanoyloxy)ethyl) pyridine 1-oxide (90)

Scheme 11

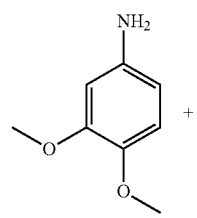

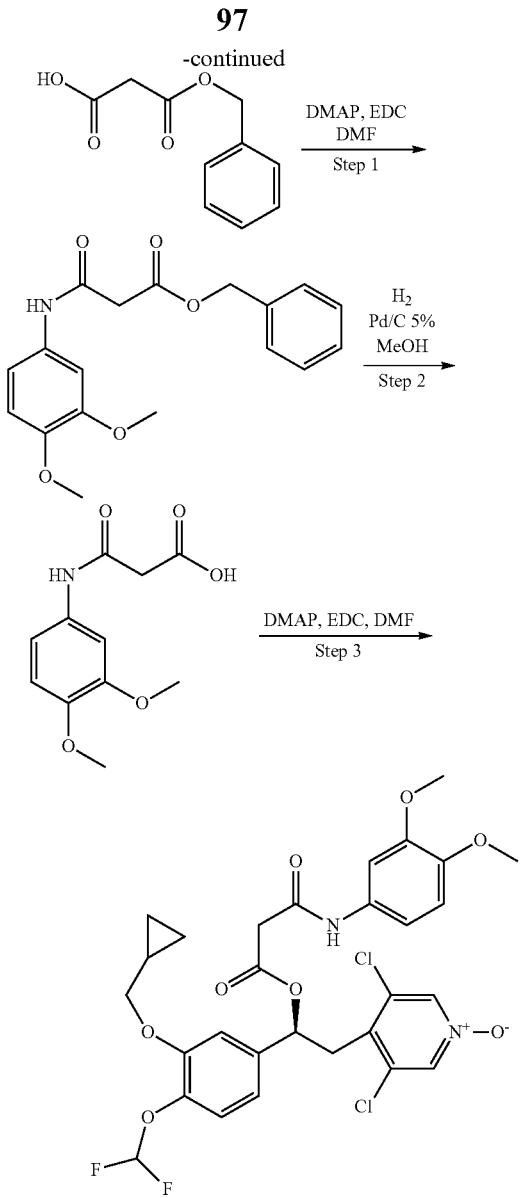

Step 1: Synthesis of benzyl 3-(3,4-dimethoxyphenylamino)-3-oxopropanoate (88)

3,4-dimethoxyaniline (500 mg, 3.26 mmol), 3-(benzyloxy)-3-oxopropanoic acid (1268 mg, 6.53 mmol), DMAP (798 mg, 6.53 mmol), and EDC (1877 mg, 9.79 mmol) were dissolved in DMF (7 ml). The reaction was stirred at RT for 4 hours to achieve completion. The reaction mixture was diluted with water, and the precipitate was washed with water, dissolved in EtOAc and extracted with HCl 1N, $Na_2CO_3$ sat. sol. and brine. The organic phase was dried over $Na_2SO_4$ and concentrated under vacuum to give benzyl 3-(3,4-dimethoxyphenylamino)-3-oxopropanoate (530 mg, 49.3% yield).

Step 2: Synthesis of 3-(3,4-dimethoxyphenylamino)-3-oxopropanoic acid (89)

Benzyl 3-(3,4-dimethoxyphenylamino)-3-oxopropanoate (200 mg, 0.607 mmol) was dissolved in MeOH, and then Pd/C 5% (129 mg, 0.061 mmol) was added. The solution was shaken under hydrogen atmosphere at 30 psi on a Parr apparatus for 30 minutes. The catalyst was filtered off, and the solvent removed under vacuum to give 3-(3,4-dimethoxyphenylamino)-3-oxopropanoic acid (120 mg, 83% yield).

Step 3: Synthesis of (S)-3,5-dichloro-4-(2-(3-(cyclopropylmethoxy)-4-(difluoromethoxy)phenyl)-2-(3-(3,4-dimethoxyphenylamino)-3-oxopropanoyloxy) ethyl)pyridine 1-oxide (90)

(S)-3,5-dichloro-4-(2-(3-(cyclopropylmethoxy)-4-(difluoromethoxy)phenyl)-2-hydroxyethyl)pyridine 1-oxide (30 mg, 0.071 mmol), 3-(3,4-dimethoxyphenylamino)-3-oxopropanoic acid (34.2 mg, 0.143 mmol), DMAP (17.44 mg, 0.143 mmol), and EDC (41.1 mg, 0.214 mmol) were dissolved in DMF (1.5 ml). The reaction was stirred at RT overnight to achieve completion. The reaction mixture was diluted with water and extracted with EtOAc. The organic phase was washed with HCl 1N, $Na_2CO_3$ sat. sol. and brine, dried over $Na_2SO_4$ and concentrated under vacuum. The crude product was purified by Preparative reverse-phase HPLC to give (S)-3,5-dichloro-4-(2-(3-(cyclopropylmethoxy)-4-(difluoromethoxy)phenyl)-2-(3-(3,4-dimethoxyphenylamino)-3-oxopropanoyloxy)-ethyl)pyridine 1-oxide (20 mg, 43.7% yield).

MS/ESI$^+$ 641.3; 663.3[M+H]+; [M+Na]+

$^1$H NMR (400 MHz, acetone) δ ppm 9.07-9.34 (bs, 1 H), 8.20 (s, 2 H), 7.33-7.41 (m, 1 H), 7.26 (m, 1 H), 7.14-7.20 (m, 1 H), 6.72-7.11 (m, 4 H), 6.03-6.18 (m, 1 H), 3.91-4.05 (m, 2 H), 3.78 and 3.80 (2 s, 2 $CH_3$, 6 H), 3.47 (d, J=14.11 Hz, 3 H), 3.26-3.37 (m, 1 H), 1.16-1.37 (m, 1 H), 0.51-0.64 (m, 2 H), 0.36 (br. s., 2 H).

Example 12

Synthesis of (S)-3,5-dichloro-4-(2-(3-(cyclopropylmethoxy)-4-(difluoromethoxy)phenyl)-2-(2-(3,4-dimethoxybenzylamino)acetoxy)ethyl)-pyridine 1-oxide hydrochloride (95) and of (S)-3,5-dichloro-4-(2-(3-(cyclopropylmethoxy)-4-(difluoromethoxy) phenyl)-2-(2-(N-(3,4-dimethoxybenzyl)methylsulfonamido)acetoxy)ethyl)pyridine 1-oxide (96)

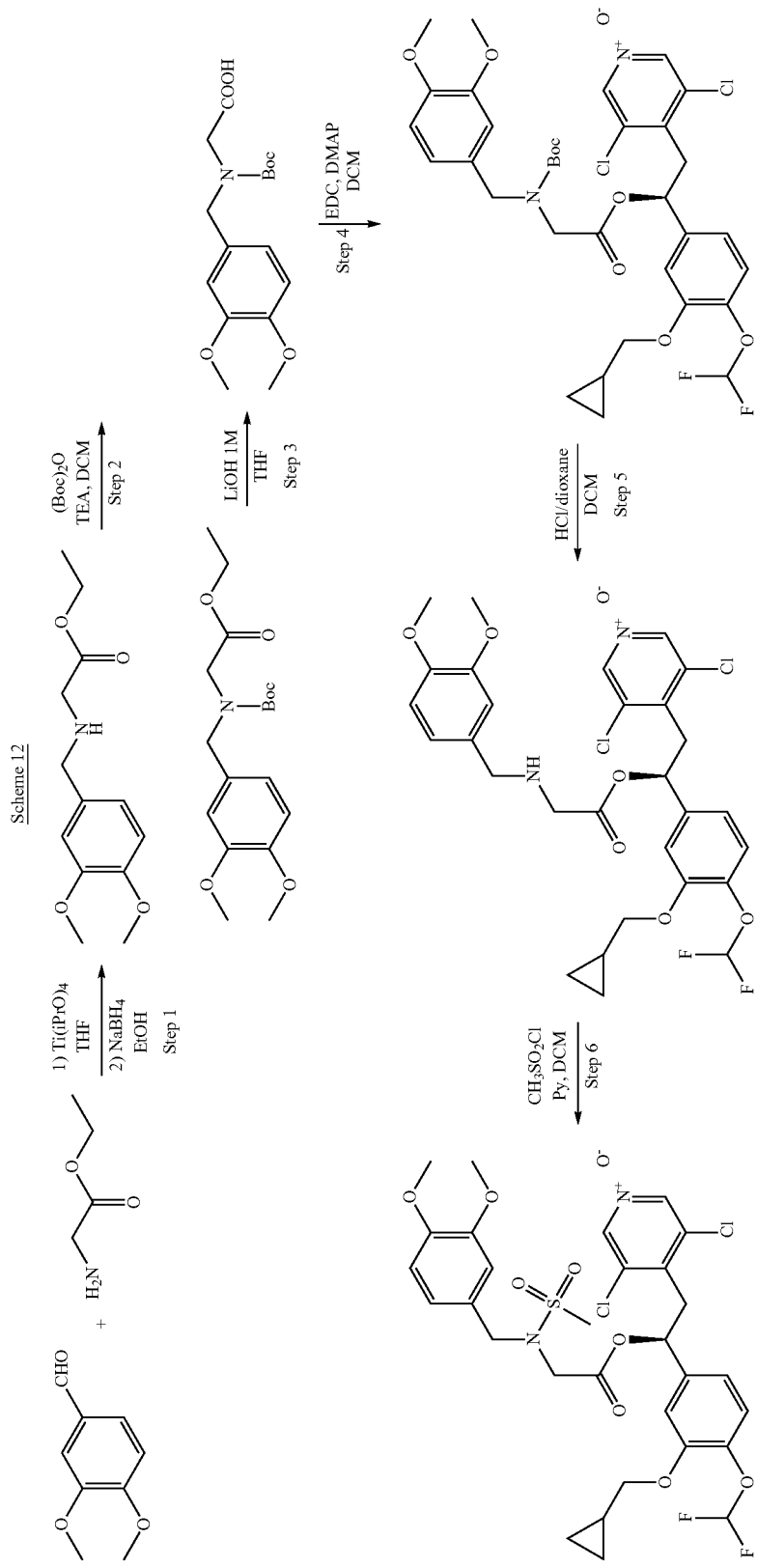

Step 1: Synthesis of ethyl 2-(3,4-dimethoxybenzylamino)acetate (91)

3,4-Dimethoxybenzaldehyde (2.358 g, 14.19 mmol) was dissolved in dry THF (14.19 ml) under nitrogen atmosphere, and a solution of glycine ethyl ester (1.33 g, 12.90 mmol) in dry THF (6.47 ml) was added followed by a solution of tetraisopropoxytitanium (5.73 ml, 19.35 mmol) in dry THF (5.83 ml). The resulting mixture was stirred at RT overnight. NaBH$_4$ (1.366 g, 36.1 mmol) was suspended in abs. EtOH (46.3 ml) and added drop wise to the reaction mixture, stirring for 3 hours. The reaction mixture was treated with water (30 ml) and then filtered through a sintered glass funnel. The filtrate was partitioned between EtOAc and brine and the aqueous phase was extracted with EtOAc (2×). The combined organic layers were dried over Na$_2$SO$_4$ and the solvent was removed under vacuum affording 2.52 g of crude product. 1.4 g of this product were purified by chromatography on silica gel column (DCM:EtOAc=70:30 to 50:50) affording ethyl 2-(3,4-dimethoxybenzylamino)acetate (0.200 g, 0.790 mmol, MS/ESI$^+$ 254.2 [MH]$^+$)

Step 2: Synthesis of ethyl 2-(tert-butoxycarbonyl(3,4-dimethoxybenzyl)-amino)acetate (92)

A solution of ethyl 2-(3,4-dimethoxybenzylamino)acetate (0.200 g, 0.790 mmol), di-tert-butyl dicarbonate (0.183 ml, 0.790 mmol), and TEA (0.110 ml, 0.790 mmol) in DCM (10 ml) was stirred at RT for 1 hour. The reaction mixture was diluted with DCM (10 ml) and washed twice with HCl 1M. The organic phase was dried over Na$_2$SO$_4$ and the solvent was removed under vacuum affording crude ethyl 2-(tert-butoxycarbonyl(3,4-dimethoxybenzyl)amino)acetate, still containing some impurities, (0.260 g, 0.736 mmol, 93% yield, MS/ESI$^+$ 376.2 [MNa]$^+$). This crude was used for the next step without purification.

Step 3: Synthesis of 2-(tert-butoxycarbonyl(3,4-dimethoxybenzyl)amino)-acetic acid (93)

To a solution of ethyl 2-(tert-butoxycarbonyl(3,4-dimethoxybenzyl)amino)-acetate (0.260 g, 0.736 mmol) in THF (1.5 ml), lithium hydroxide 1N (0.883 ml, 0.883 mmol) was added, and the reaction was stirred at RT for 4 hours. The mixture was diluted with EtOAc (15 ml) and acidified with HCl 1M. The organic phase was washed with brine and dried over Na$_2$SO$_4$; the solvent was evaporated to dryness affording 2-(tert-butoxycarbonyl(3,4-dimethoxybenzyl)amino)acetic acid as a yellow oil (0.233 g, 0.716 mmol, 97% yield, MS/ESI$^+$ 348.1 [MNa]$^+$). This product was used without any further purification.

Step 4: Synthesis of (S)-4-(2-(2-(tert-butoxycarbonyl (3,4-dimethoxybenzyl)amino) acetoxy)-2-(3-(cyclopropylmethoxy)-4-(difluoromethoxy)phenyl)ethyl)-3,5-dichloropyridine 1-oxide (94)

A mixture of 2-(tert-butoxycarbonyl(3,4-dimethoxybenzyl)amino)acetic acid (0.209 g, 0.642 mmol), (S)-3,5-dichloro-4-(2-(3-(cyclopropylmethoxy)-4-(difluoromethoxy)phenyl)-2-hydroxyethyl)pyridine 1-oxide (0.150 g, 0.357 mmol), EDC (0.205 g, 1.071 mmol), and DMAP (0.087 g, 0.714 mmol) in DCM (5 ml) was stirred at RT overnight. The reaction mixture was diluted with DCM (20 ml) and washed with HCl 1M and with NaHCO$_3$ 5%. The organic layer was dried over Na$_2$SO$_4$, and the solvent was removed under vacuum. The crude was purified by chromatography on silica gel column (DCM:EtOAc=70:30) affording (S)-4-(2-(2-(tert-butoxycarbonyl(3,4-dimethoxybenzyl) amino) acetoxy)-2-(3-(cyclopropylmethoxy)-4-(difluoromethoxy)phenyl)ethyl)-3,5-dichloropyridine 1-oxide (0.258 g, 0.355 mmol, 99% yield, MS/ESI$^+$ 727.3 [MH]$^+$).

Step 5: Synthesis of (S)-3,5-dichloro-4-(2-(3-(cyclopropylmethoxy)-4-(difluoromethoxy)phenyl)-2-(2-(3,4-dimethoxybenzylamino)acetoxy)-ethyl)pyridine 1-oxide hydrochloride (95)

To a solution of (S)-4-(2-(2-(tert-butoxycarbonyl(3,4-dimethoxybenzyl)-amino)acetoxy)-2-(3-(cyclopropylmethoxy)-4-(difluoromethoxy)phenyl)ethyl)-3,5-dichloropyridine 1-oxide (258 mg, 0.355 mmol) in DCM (24 ml), HCl 4M in dioxane (1.2 ml, 4.80 mmol) was added drop wise, and the reaction was stirred at RT overnight. The volatiles were evaporated under vacuum and the residue was purified by trituration with diethylether affording (S)-3,5-dichloro-4-(2-(3-(cyclopropylmethoxy)-4-(difluoromethoxy)phenyl)-2-(2-(3,4-dimethoxybenzylamino) acetoxy)ethyl)pyridine 1-oxide hydrochloride as a beige solid (0.187 g, 0.282 mmol, 79% yield, MS/ESI$^+$ 626.82 [MH]$^+$, [α$_D$]=−15.57, c=0.56, MeOH).

$^1$H NMR (300 MHz, DMSO-d$_6$) δ ppm 8.55 (s, 2 H) 7.19 (d, 1 H) 7.13 (d, 1 H) 7.08 (d, 1 H) 6.99 (dd, 1 H) 6.85-6.97 (m, 2 H) 7.07 (t, 1 H) 5.98-6.09 (m, 1 H) 3.78-4.04 (m, 6 H) 3.76 (s, 3 H) 3.75 (s, 3 H) 3.48 (dd, 1 H) 3.25 (dd, 1 H) 1.13-1.28 (m, 1 H) 0.50-0.63 (m, 2 H) 0.29-0.39 (m, 2 H).

Step 6: Synthesis of (S)-3,5-dichloro-4-(2-(3-(cyclopropylmethoxy)-4-(difluoromethoxy)phenyl)-2-(2-(N-(3,4-dimethoxybenzyl)methylsulfonamido)-acetoxy)ethyl)pyridine 1-oxide (96)

(S)-3,5-dichloro-4-(2-(3-(cyclopropylmethoxy)-4-(difluoromethoxy)phenyl)-2-(2-(3,4-dimethoxybenzylamino) acetoxy)ethyl)pyridine 1-oxide hydrochloride (42 mg, 0.064 mmol) was dissolved in DCM (1.5 ml). Py (500 μl, 6.18 mmol) and methanesulfonyl chloride (5.96 μl, 0.076 mmol) were added, and the reaction was stirred at RT for 2 hours to achieve completion. The reaction mixture was diluted with HCl 1M and extracted with DCM. The organic phase was dried over Na2SO4 and concentrated under vacuum. The crude product was purified by preparative reverse-phase HPLC to give (S)-3,5-dichloro-4-(2-(3-(cyclopropylmethoxy)-4-(difluoromethoxy)phenyl)-2-(2-(N-(3,4-dimethoxybenzyl)methylsulfonamido)-acetoxy)ethyl)pyridine 1-oxide (20 mg, 44.5% yield).

MS/ESI$^+$ 706.55 [MH]$^+$ $^1$H NMR (400 MHz, acetone) δ ppm 8.26 (s, 2 H), 7.16-7.24 (m, 2 H), 7.01 (dd, J=8.38, 1.76 Hz, 1 H), 6.86-6.95 (m, 3 H), 6.73 (d, J=2.21 Hz, 1 H), 6.12-6.19 (m, 1 H), 4.33 (s, 2 H), 3.98-4.01 (m, 2 H), 3.95 (d, J=7.06 Hz, 2 H), 3.81 (s, 3 H), 3.75 (s, 3 H), 3.51 (d, J=9.26 Hz, 1 H), 3.33 (d, J=4.85 Hz, 1 H), 2.96 (s, 3 H), 1.22-1.35 (m, 1 H), 0.61 (dd, J=8.16, 1.54 Hz, 2 H), 0.33-0.42 (m, 2 H).

Example 13

Synthesis of (S)-3,5-dichloro-4-(2-(3-(cyclopropylmethoxy)-4-(difluoromethoxy)phenyl)-2-(2-(methyl (4-(methylsulfonamido)benzyl)amino)-acetoxy) ethyl)pyridine 1-oxide hydrochloride (105)

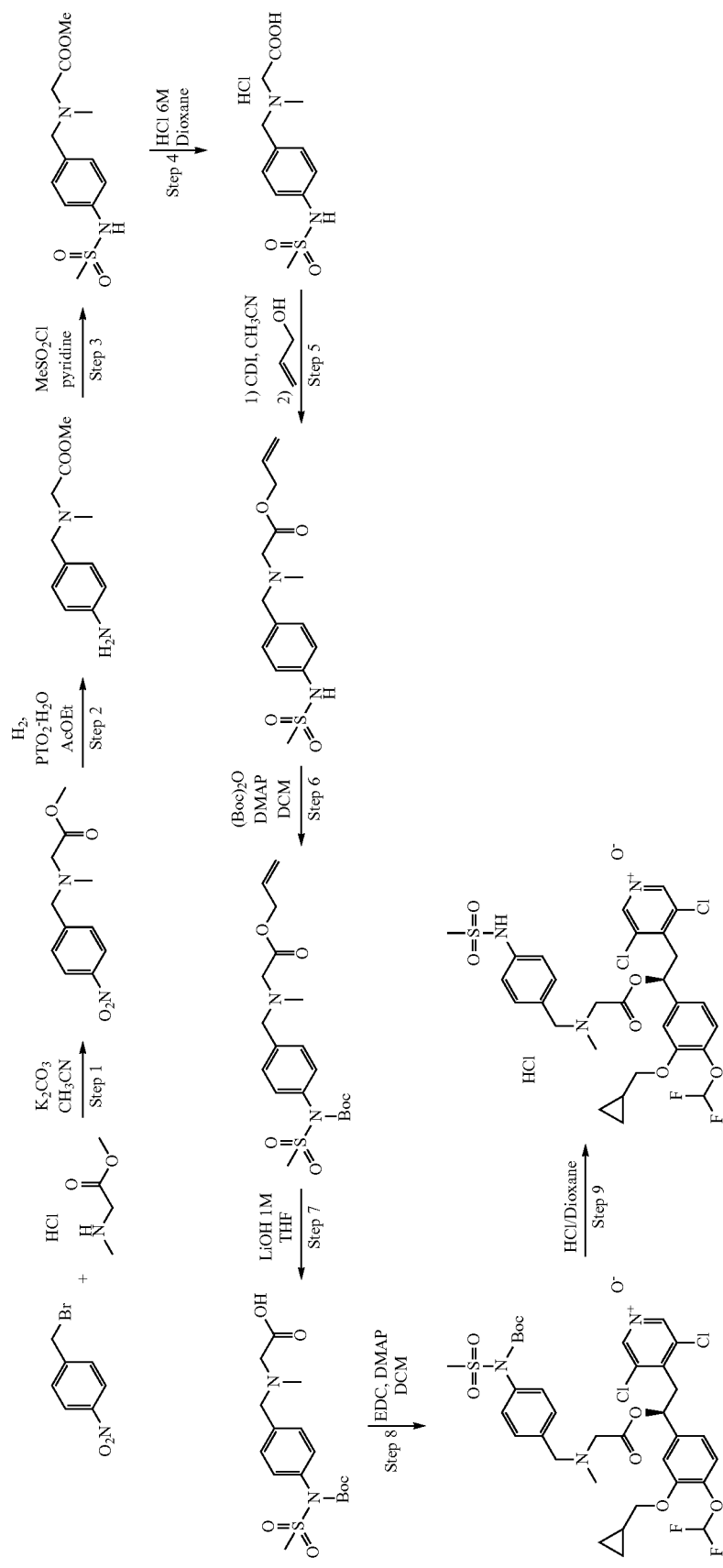

Step 1: Synthesis of methyl 2-(methyl(4-nitrobenzyl)amino)acetate (97)

A mixture of 1-(bromomethyl)-4-nitrobenzene (1 g, 4.63 mmol), methyl 2-(methylamino)acetate hydrochloride (0.646 g, 4.63 mmol), and $K_2CO_3$ (0.960 g, 6.94 mmol) in $CH_3CN$ (20 ml) was heated under MW irradiation at 60° C. for 1.5 hours. The mixture was portioned between EtOAc and water, and the organic layer was washed with brine ad dried over $Na_2SO_4$. The solvent was removed and the crude was purified by filtration on SCX cartridge (DCM/MeOH 1/1; MeOH/conc.aq.NH4OH 90/10). The basic fraction was evaporated to dryness to give methyl 2-(methyl(4-nitrobenzyl)amino)acetate (0.800 g, 3.36 mmol, 72.5% yield, MS/ESI$^+$ 239.1 [MH]$^+$).

Step 2: Synthesis of methyl 2-((4-aminobenzyl)(methyl)amino)acetate (98)

A mixture of methyl 2-(methyl(4-nitrobenzyl)amino)acetate (0.800 g, 3.36 mmol) and $Pt_2O$ (0.080 g, 0.352 mmol) in EtOAc (30 ml) was hydrogenated at 15 psi for 1 hour. The catalyst was filtered off, and the solvent was removed. Methyl 2-((4-aminobenzyl)(methyl)amino)acetate was obtained (0.680 g, 3.27 mmol, 97% yield, MS/ESI$^+$ 209.2 [MH]$^+$) and used in the next step without further purification.

Step 3: Synthesis of methyl 2-(methyl(4-(methylsulfonamido)-benzyl)amino)acetate (99)

A solution of methyl 2-((4-aminobenzyl)(methyl)amino) acetate (0.680 g, 3.27 mmol) in pyridine (15 ml) was cooled to 0° C., and methane sulfonylchloride (0.280 ml, 3.59 mmol) was added. The mixture was warmed to RT and stirred for 1 hour. The solvent was removed, and the crude was portioned between DCM and water. The aqueous phase was basified with solid K2CO3 and extracted with EtOAc. The combined organic layers were dried over $Na_2SO_4$, and the solvent was evaporated. The crude was filtered on SCX cartridge (DCM/MeOH 1/1; MeOH/conc.aq.NH4OH 90/10). The basic fraction was evaporated to dryness to give methyl 2-(methyl(4-(methylsulfonamido)-benzyl)amino)acetate (0.750 g, 2.62 mmol, 80% yield, MS/ESI$^+$ 287.2 [MH]$^+$).

Step 4: Synthesis of 2-(methyl(4-(methylsulfonamido)benzyl)amino)acetic acid hydrochloride (100)

A solution of methyl 2-(methyl(4-(methylsulfonamido) benzyl)amino)acetate (0.977 g, 3.41 mmol) and HCl 6N (14.22 ml, 85 mmol) in dioxane (100 ml) was heated at 70° C. overnight. The solvent was removed and crude 2-(methyl(4-(methylsulfonamido)-benzyl)amino)acetic acid hydrochloride was obtained (1.054 g, 3.41 mmol, 100% yield, MS/ESI$^+$ 273.1 [MH]$^+$) and used in the next step without further purification.

Step 5: Synthesis of allyl 2-(methyl(4-(methylsulfonamido)benzyl)-amino)acetate (101)

A mixture of 2-(methyl(4-(methylsulfonamido)benzyl) amino)acetic acid hydrochloride (1.054 g, 3.41 mmol), CDI (1.107 g, 6.83 mmol), and TEA (0.952 ml, 6.83 mmol) in CH3CN (80 ml) was heated at 75° C. for 3 hours. The solvent was evaporated; the residue was dissolved in prop-2-en-1-ol (30 ml, 439 mmol) and heated at 75° C. for 1 hour. The mixture was diluted with EtOAc and washed several times with NH4Cl sat. sol. The organic phase was dried over $Na_2SO_4$, the solvent was removed, and the residue was filtered on SCX cartridge (DCM/MeOH 1/1; conc.aq.NH4OH/ MeOH 1/9). The basic fraction was evaporated to dryness to give allyl 2-(methyl(4-(methylsulfonamido)benzyl)-amino) acetate as a brown oil (0.942 g, 3.02 mmol, 88% yield, MS/ESI$^+$ 313.2 [MH]$^+$).

Step 6: Synthesis of allyl 2-((4-(N-(tert-butoxycarbonyl)methylsulfonamido)-benzyl)(methyl)amino)acetate (102)

A solution of allyl 2-(methyl(4-(methylsulfonamido)benzyl)amino)acetate (0.942 g, 3.02 mmol), di-tert-butyl dicarbonate (0.724 g, 3.32 mmol), and DMAP (0.405 g, 3.32 mmol) in DCM (70 ml) was stirred at RT for 1 hour. The mixture was washed with aqueous HCl (pH=5) and NaHCO3 5%. The organic layer was dried over $Na_2SO_4$ and the solvent was removed. The crude was purified by flash chromatography on silica gel (DCM/MeOH 99/1) to give allyl 2-((4-(N-(tert-butoxycarbonyl)methylsulfonamido)-benzyl)(methyl) amino)acetate (1.003 g, 2.432 mmol, 81% yield, MS/ESI$^+$ 313.2 [MH]$^+$).

Step 7: Synthesis of 2-((4-(N-(tert-butoxycarbonyl) methylsulfonamido)benzyl)(methyl)-amino)acetic acid (103)

To a solution of allyl 2-((4-(N-(tert-butoxycarbonyl)methylsulfonamido)-benzyl)(methyl)amino)acetate (0.390 g, 0.945 mmol) in THF (22 ml), LiOH 1N (0.945 ml, 0.945 mmol) was added, and the mixture was stirred at RT for 3 days. The mixture was diluted with water and washed twice with EtOAc. The aqueous phase was acidified with 0.189 ml of HCl 1N and frozen dry. The residue was dissolved in DCM/MeOH and transferred in a small container. 2-((4-(N-(tert-butoxycarbonyl)methylsulfonamido)-benzyl)(methyl) amino)acetic acid was obtained (0.313 g, 0.840 mmol, 89% yield, MS/ESI$^+$ 373.2 [MH]$^+$) and used without any further purification.

Step 8: Synthesis of (S)-4-(2-(2-((4-(N-(tert-butoxycarbonyl)methylsulfonamido)-benzyl)(methyl) amino)acetoxy)-2-(3-(cyclopropylmethoxy)-4-(difluoromethoxy)-phenyl)ethyl)-3,5-dichloropyridine 1-oxide (104)

A mixture of 2-((4-(N-(tert-butoxycarbonyl)methylsulfonamido)benzyl)-(methyl)amino)acetic acid (0.398 g, 1.069 mmol), (S)-3,5-dichloro-4-(2-(3-(cyclopropylmethoxy)-4-(difluoromethoxy)phenyl)-2-hydroxyethyl)pyridine 1-oxide (0.345 g, 0.822 mmol), EDC (0.473 g, 2.466 mmol), and DMAP (0.151 g, 1.233 mmol) in DCM was stirred at RT for 30 minutes. $CH_3CN$ (10 ml) and DMF (5 ml) were added to dissolve insoluble residue, and the mixture was stirred at RT for 2 days. The mixture was diluted with DCM and washed twice with HCl 1N and with $NaHCO_3$. The organic layer was dried over $Na_2SO_4$, and the solvent was removed. The crude was purified by filtration on SCX cartridge (DCM/MeOH 1/1; MeOH/conc.aq.NH4OH 90/10). The basic fraction was portioned between EtOAc and water, and the organic phase was washed with brine and dried over $Na_2SO_4$. The solvent was removed, and the crude (S)-4-(2-(2-((4-(N-(tert-butoxycarbonyl)-methylsulfonamido)benzyl)(methyl)amino)acetoxy)-2-(3-(cyclopropylmethoxy)-4-(difluoromethoxy) phenyl)ethyl)-3,5-dichloropyridine 1-oxide was obtained as a colorless amorphous solid (0.250 g, 0.323 mmol, 39.3% yield, MS/ESI$^+$ 774.5 [MH]$^+$) and used in the next step without any further purification.

Step 9: Synthesis of (S)-3,5-dichloro-4-(2-(3-(cyclopropylmethoxy)-4-(difluoromethoxy)phenyl)-2-(2-(methyl(4-(methylsulfonamido)benzyl)-amino)acetoxy)ethyl)pyridine 1-oxide hydrochloride (105)

To a solution of (S)-4-(2-(2-((4-(N-(tert-butoxycarbonyl) methylsulfonamido)benzyl)(methyl)amino)acetoxy)-2-(3-

(cyclopropylmethoxy)-4-(difluoromethoxy)-phenyl)ethyl)-3,5-dichloropyridine 1-oxide (0.250 g, 0.323 mmol) in DCM (15 ml), HCl 4M in dioxane (2 ml, 8.00 mmol) was added, and the solution was stirred at RT overnight. The mixture was portioned between DCM and 5% NaHCO₃, and the organic layer was dried over sodium sulfate. The solvent was removed, and the crude was purified by flash chromatography on silica gel cartridge (DCM:MeOH=99:1 to 97:3) to give (S)-3,5-dichloro-4-(2-(3-(cyclopropylmethoxy)-4-(difluoromethoxy)phenyl)-2-(2-(methyl(4-(methylsulfonamido)benzyl)amino)-acetoxy)ethyl)pyridine 1-oxide, free base (0.120 g, 0.178 mmol, 55.1% yield, as a colorless amorphous solid. This product was dissolved in DCM (12 ml) and HCl 4M in dioxane (0.089 ml, 0.356 mmol) was added; the mixture was stirred at RT for 2 hours, and volatiles were removed under vacuum. The product was further dissolved in DCM and washed with 5% NaHCO₃. The organic phase was dried over Na₂SO₄, and the crude was purified by chromatography on silica gel cartridge (DCM/EtOAc 90/10 to EtOAc 100%) followed by a further filtration through a silica gel cartridge (DCM/MeOH 99/1 to 98/2) to give 0.090 g of free base. This product was dissolved in 5 ml of DCM, and HCl 4M in dioxane (0.044 ml, 0.177 mmol) was added. The mixture was stirred at RT for 1 hour. The solvent was removed to give (S)-3,5-dichloro-4-(2-(3-(cyclopropylmethoxy)-4-(difluoromethoxy)phenyl)-2-(2-(methyl-(4-(methylsulfonamido)benzyl)amino)acetoxy)ethyl)pyridine 1-oxide hydrochloride (0.095 g, 0.134 mmol, 41.5% yield, MS/ESI⁺ 673.99 [MH]⁺)

¹H NMR (300 MHz, DMSO-d₆) δ ppm 10.49 (br. s., 1 H), 10.00 (br. s., 1 H), 8.55 (s, 2 H), 7.41 (m, 2 H), 7.24 (m, 2 H), 7.20 (d, 1 H), 7.14 (d, 1 H), 6.99 (dd, 1 H), 7.07 (t, 1 H), 6.03 (dd, 1 H), 4.00-4.37 (m, 4 H), 3.92 (d, 2 H), 3.51 (dd, 1 H), 3.28 (dd, 1 H), 3.04 (s, 3 H), 2.67 (br. s., 3 H), 1.10-1.35 (m, 1 H), 0.46-0.66 (m, 2 H), 0.14-0.46 (m, 2 H)

The compounds listed in Table 8 were prepared with an analogous procedure to that described in Example 13, Step 8, by reacting the appropriate precursors (commercially available or synthesized by a person skilled in the art) with suitable reagents, and where purification step has been performed as indicated in Table 8.

TABLE 8

| Structure | Cmp | ¹H NMR | MS/ESI⁺ [MH]⁺ | Salt Name | Starting Material | Purification method |
|---|---|---|---|---|---|---|
| (structure shown) | 106 | ¹H NMR (300 MHz, DMSO-d₆) δ ppm 8.55 (s, 2 H), 7.18 (d, 1 H), 7.10 (d, 1 H), 6.98 (dd, 1 H), 6.86 (d, 1 H), 6.83 (d, 1 H), 7.06 (t, 1 H), 6.70 (dd, 1 H), 6.04 (dd, 1 H), 3.82-3.94 (m, 2 H), 3.73 (s, 3 H), 3.70 (s, 3 H), 3.47 (s, 2 H), 3.44 (d, 1 H), 3.37 (d, 1 H), 3.24 (dd, 1 H), 3.20 (d, 1 H), 2.15 (s, 3 H), 1.11-1.24 (m, 1 H), 0.47-0.62 (m, 2 H), 0.25-0.39 (m, 2 H) | 641.0 | Hydrochloride | (structure shown) | Flash chromatography on silica gel (EtOAc), then dissolution in DCM and treatment with HCl 4M in dioxane to obtain HCl salt. Final purification by trituration with Et₂O |

Example 14

Synthesis of (S)-3,5-dichloro-4-(2-(3-(cyclopropylmethoxy)-4-(difluoromethoxy)phenyl)-2-(2-(N-(3,4-dimethoxyphenyl)sulfamoyl)acetoxy)-ethyl)pyridine 1-oxide (112)

Scheme 14

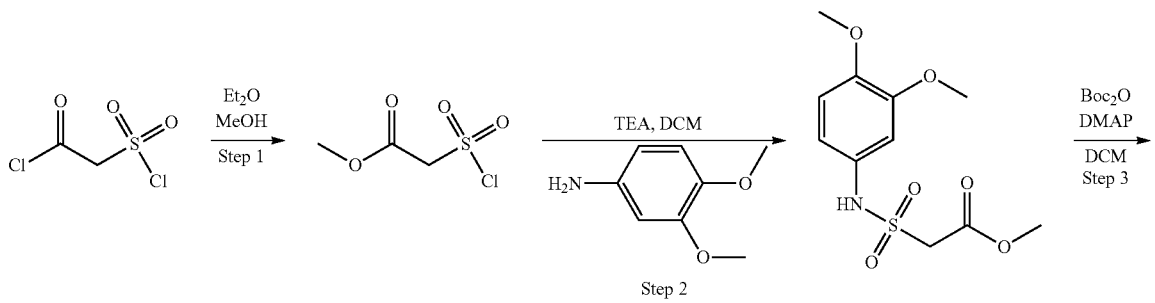

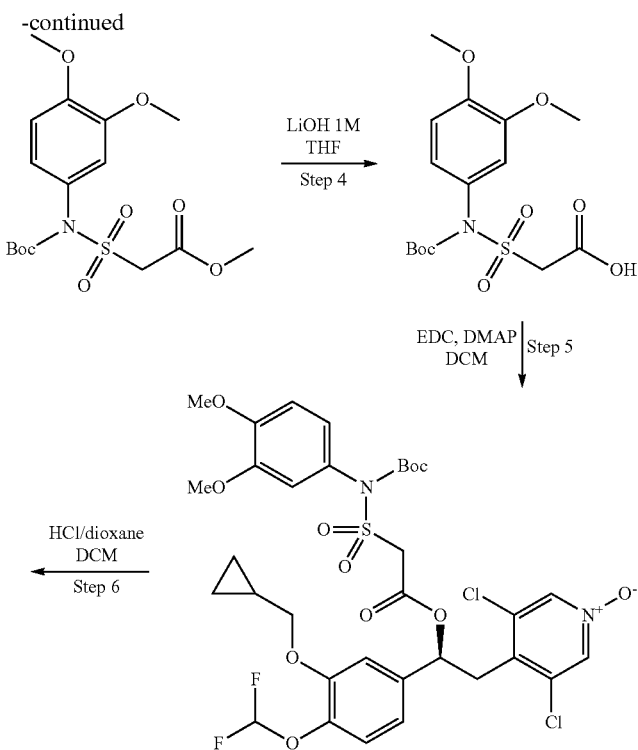

Step 1: Synthesis of methyl 2-(chlorosulfonyl)acetate (107)

To a solution of 2-(chlorosulfonyl)acetyl chloride (1 g, 5.65 mmol) in dry Et₂O (5 ml) cooled to 0° C., a solution of methanol (0.286 g, 6.21 mmol) in dry Et₂O (1 ml) was added dropwise. After 15 minutes, the mixture was warmed to RT and stirred for 2 hours. The solvent was evaporated and the desired compound was obtained (1 g, 5.36 mmol, 95% yield) and used in the next step without further purification.

Step 2: Synthesis of ethyl 2-(N-(3,4-dimethoxyphenyl)sulfamoyl)acetate (108)

To a solution of 3,4-dimethoxyaniline (0.740 g, 4.83 mmol) and triethylamine (0.587 g, 5.80 mmol) in dry DCM (10 ml), a solution of methyl 2-(chlorosulfonyl)acetate (1 g, 5.36 mmol) in dry DCM (5 ml) was added dropwise at RT. The mixture was stirred for 2 hours, then the solvent was removed under vacuum; the residue was dissolved in EtOAc, washed with HCl 1N, NaHCO₃ sat. sol, and brine, dried over Na₂SO₄, filtered and evaporated to give 1.6 g of a dark oil. After trituration with iPrOH (8 ml) and filtration, the desired product was obtained (0.74 g, 2.440 mmol, 50.5% yield, MS/ESI⁺ 311.9 [MNa]⁺) and used in the next step without further purification.

Step 3: Synthesis of methyl 2-(N-(tert-butoxycarbonyl)-N-(3,4-dimethoxyphenyl)-sulfamoyl)acetate (109)

To a solution of methyl 2-(N-(3,4-dimethoxyphenyl)sulfamoyl)acetate (260 mg, 0.899 mmol) and DMAP (121 mg, 0.989 mmol) in dry DCM (10 ml), di-tert-butyl dicarbonate (216 mg, 0.989 mmol) was added at RT, and the mixture was stirred for 2 hours. Then the solvent was evaporated, and the residue was treated with EtOAc and HCl 1N. The organic layer was washed with NaHCO₃ sat. sol. and brine; dried over Na₂SO₄, filtered and evaporated. The residue was purified by flash chromatography on silica gel (eluent: petroleum ether/EtOAc 7/3) to give methyl 2-(N-(tert-butoxycarbonyl)-N-(3, 4-dimethoxyphenyl)sulfamoyl)acetate (237 mg, 0.609 mmol, 67.7% yield, MS/EST⁺ 411.9 [MNa]⁺).

Step 4: Synthesis of 2-(N-(tert-butoxycarbonyl)-N-(3,4-dimethoxyphenyl)sulfamoyl)-acetic acid (110)

A solution of LiOH (28.1 mg, 0.669 mmol) in water (0.66 ml) was added to a solution of methyl 2-(N-(tert-butoxycarbonyl)-N-(3,4-dimethoxyphenyl)sulfamoyl)-acetate (237 mg, 0.609 mmol) in THF (3 ml), and the mixture was stirred at RT for 2 hours. EtOAc was added, and the solution was washed with HCl 1N (6 ml); the organic phase was washed with brine, dried over Na₂SO₄, filtered and evaporated, to give 2-(N-(tert-butoxycarbonyl)-N-(3,4-dimethoxyphenyl) sulfamoyl)acetic acid (200 mg, 0.533 mmol, 88% yield, MS/ESI⁺ 397.9 [MNa]⁺) that was used in the next step without further purification.

Step 5: Synthesis of N-tert-butoxycarbonyl-(3,4-Dimethoxy-phenylsulfamoyl)-acetic acid (S)-1-(3-cyclopropylmethoxy-4-difluoromethoxy-phenyl)-2-(3,5-dichloro-1-oxy-pyridin-4-yl)-ethyl ester (111)

To a solution of (S)-3,5-dichloro-4-(2-(3-(cyclopropylmethoxy)-4-(difluoromethoxy)phenyl)-2-hydroxyethyl)pyridine 1-oxide (179 mg, 0.426 mmol) in dry DCM (15 ml), DMAP (52.1 mg, 0.426 mmol), EDC (245 mg, 1.279 mmol) and 2-(N-(tert-butoxycarbonyl)-N-(3,4-dimethoxyphenyl)-sulfamoyl)acetic acid (200 mg, 0.533 mmol) were added, and the resulting mixture was stirred at RT for 2 days. The solvent was removed under vacuum, the residue was dissolved in EtOAc, washed with HCl 1N, NaHCO₃ sat. sol and brine, dried over Na₂SO₄, filtered and evaporated. The residue was purified by flash chromatography on silica gel (eluent: dichloromethane/acetone 8/2) and the desired compound was obtained (195 mg, 0251 mmol, 58.8% yield, MS/ESI⁺ 777.1 [MH]⁺).

Step 6: Synthesis of (S)-3,5-dichloro-4-(2-(3-(cyclopropylmethoxy)-4-(difluoromethoxy)phenyl)-2-(2-(N-(3,4-dimethoxyphenyl)sulfamoyl)acetoxy)-ethyl) pyridine 1-oxide (112)

N-tert-butoxycarbonyl-(3,4-Dimethoxy-phenylsulfamoyl)-acetic acid (S)-1-(3-cyclopropylmethoxy-4-difluoromethoxy-phenyl)-2-(3,5-dichloro-1-oxy-pyridin-4-yl)-ethyl ester (195 mg, 0.251 mmol) was dissolved in dry DCM (3 ml); HCl 4M in dioxane (188 μl, 0.752 mmol) was added; and the mixture was stirred at RT for 4 days. The solvent was evaporated, and the residue was purified by flash chromatography on silica gel (eluent: DCM/MeOH/32% NH₄OH 98/2/0.2). The product so obtained was triturated with iPr₂O, filtered and dried under vacuum to give (S)-3,5-dichloro-4-(2-(3-(cyclopropylmethoxy)-4-(difluoromethoxy)phenyl)-2-(2-(N-(3,4-dimethoxyphenyl)sulfamoyl)acetoxy)ethyl) pyridine 1-oxide as a white powder (35 mg, 0.052 mmol, 20.60% yield, MS/ESI⁺ 677.24 [MH]⁺, [α_D]=−11.28, c=0.5, MeOH).
¹H NMR (300 MHz, DMSO-d6) δ ppm 8.50 (s, 2 H), 7.15 (d, 1 H), 7.12 (d, 1 H), 6.92 (dd, 1 H), 6.89 (d, 1 H), 7.06 (t, 1 H), 6.79 (d, 1 H), 6.70 (dd, 1 H), 5.95 (dd, 1 H), 4.04-4.21 (m, 2 H), 3.89 (d, 2 H), 3.73 (s, 3 H), 3.70 (s, 3 H), 3.41 (dd, 1 H), 3.16-3.26 (m, 1 H), 1.08-1.36 (m, 1 H), 0.44-0.67 (m, 2 H), 0.27-0.44 (m, 2 H)

Example 15

Synthesis of (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzoyloxy)acetoxy)ethyl)pyridine 1-oxide (117)

Scheme 15

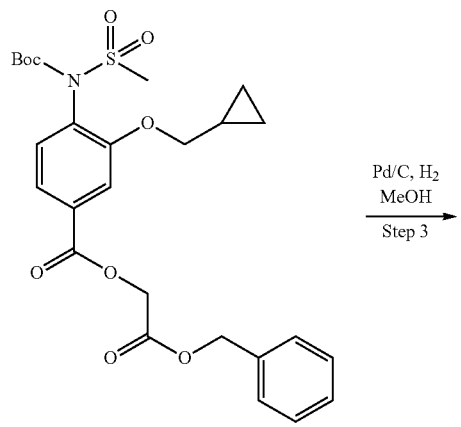

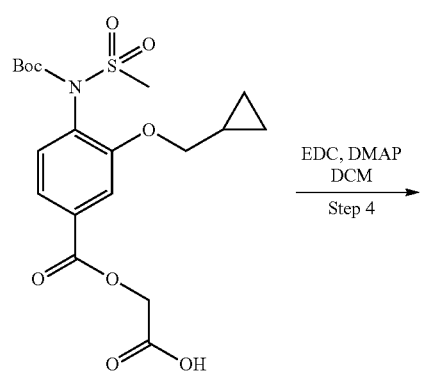

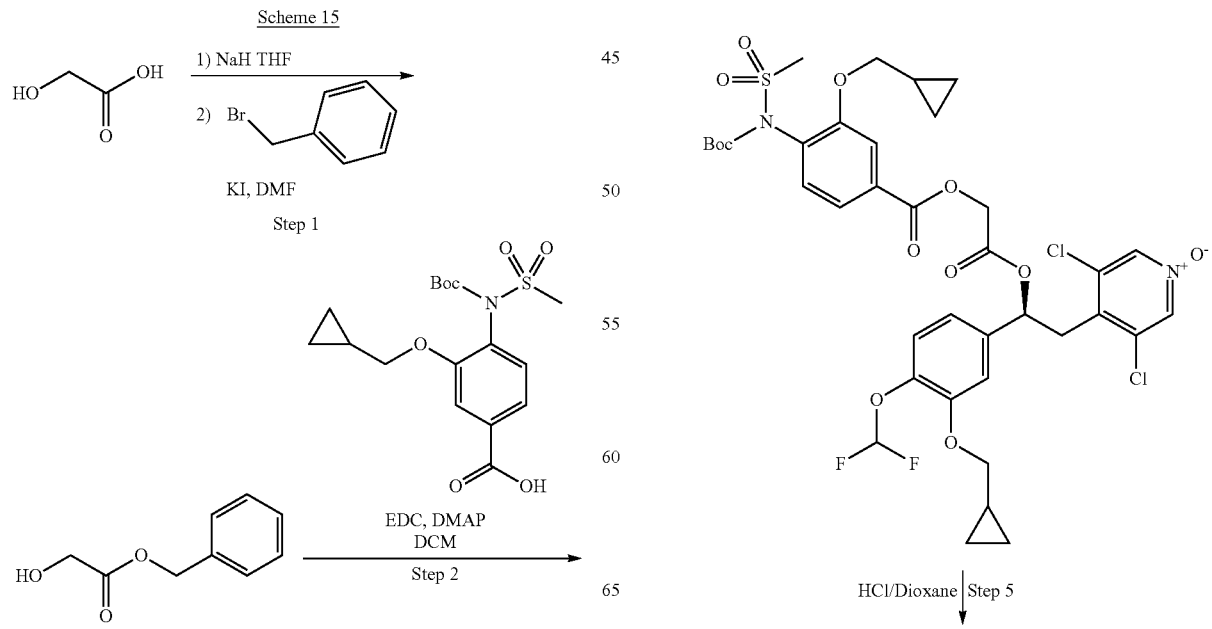

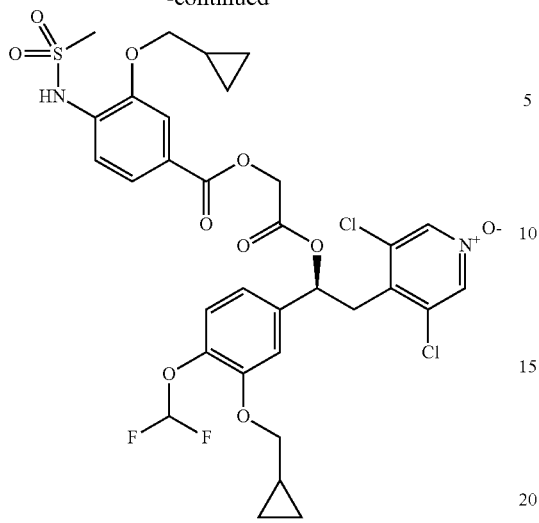

Step 1: Synthesis of benzyl 2-hydroxyacetate (113)

NaH (6.31 g, 158 mmol) was suspended in dry THF (500 ml) and cooled to 0° C. 2-hydroxyacetic acid (12 g, 158 mmol) was added portion wise, and the mixture was stirred at RT for 1 hour. The solvent was removed, and the residue was suspended in DMF (500 ml); KI (2.488 g, 14.99 mmol) and benzyl bromide (18.77 ml, 158 mmol) were added; and the mixture was heated to 100° C. for 24 hours. The solvent was removed, and the crude was portioned between EtOAc (600 ml) and water (200 ml). The organic phase was washed with brine and dried over $Na_2SO_4$. The solvent was removed and the crude was purified by flash chromatography on silica gel (petroleum ether/EtOAc 80/20). Benzyl 2-hydroxyacetate was obtained (18.089 g, 69% yield).

Step 2: Synthesis of 2-(benzyloxy)-2-oxoethyl 4-(N-(tert-butoxycarbonyl)methyl-sulfonamido)-3-(cyclopropylmethoxy)benzoate (114)

4-(N-(tert-butoxycarbonyl)methylsulfonamido)-3-(cyclopropylmethoxy)-benzoic acid (see for reference procedure Example 18, WO 2010/089107, which is incorporated herein by reference in its entirety) (2.5 g, 6.49 mmol), benzyl 2-hydroxyacetate (1.078 g, 6.49 mmol), EDC (3.73 g, 19.46 mmol) and DMAP (0.396 g, 3.24 mmol) were mixed in DCM (150 ml), and the resulting mixture was stirred at RT for 24 hours. Then the mixture was washed with HCl 1N and NaHCO3 sat. sol.; the organic layer was dried over $Na_2SO_4$, and the solvent was evaporated. The crude was sonicated in MeOH; 2-(benzyloxy)-2-oxoethyl 4-(N-(tert-butoxycarbonyl)methylsulfonamido)-3-(cyclopropylmethoxy)benzoate precipitated (2.6 g, 4.87 mmol, 75% yield, MS/ESI+ 556.0 [MNa]+), it was filtered and used as such in the following reaction without further purification.

Step 3: Synthesis of 2-((4-((N-(tert-butoxycarbonyl)methylsulfonamido)-3-(cyclopropylmethoxy)benzoyloxy)acetic acid (115)

2-(benzyloxy)-2-oxoethyl 4-(N-(tert-butoxycarbonyl)methylsulfonamido)-3-(cyclopropylmethoxy)benzoate (2.6 g, 4.87 mmol) was suspended in EtOAc (30 ml) and MeOH (10 ml) in a 250 ml Parr bottle; 10% Pd/C (0.176 g, 0.165 mmol) was added; and the mixture was hydrogenated at the Parr apparatus for 2 hours (H2 pressure: 30 psi), then the catalyst was filtered over a pad of celite and the solvent was evaporated to dryness; 2-(4-(N-(tert-butoxycarbonyl)methylsulfonamido)-3-(cyclopropylmethoxy)benzoyloxy)-acetic acid was obtained as a white amorphous solid (1.7 g, 3.83 mmol, 79% yield, MS/ESI+ 465.9 [MNa]+) and used as such in the following reaction without further purification.

Step 4: Synthesis of (S)-4-(2-(2-(4-(N-(tert-butoxycarbonyl)methylsulfonamido)-3-(cyclopropylmethoxy)benzoyloxy)-acetoxy)-2-(3-(cyclopropylmethoxy)-4-(difluoromethoxy)phenyl)ethyl)-3,5-dichloropyridine 1-oxide (116)

2-(4-(N-(tert-butoxycarbonyl)methylsulfonamido)-3-(cyclopropylmethoxy)-benzoyloxy)acetic acid (1.7 g, 3.83 mmol), (S)-3,5-dichloro-4-(2-(3-(cyclopropylmethoxy)-4-(difluoromethoxy)phenyl)-2-hydroxyethyl)pyridine 1-oxide (1.611 g, 3.83 mmol), EDC (2.205 g, 11.50 mmol), and DMAP (0.702 g, 5.75 mmol) were dissolved in DCM (60 ml); the mixture was stirred at RT for 2 days. Then it was concentrated to about half volume, diluted with EtOAc (about 200 ml) and washed with HCl 1N and $NaHCO_3$ sat. sol. The organic layer was dried over $Na_2SO_4$, and the solvent was evaporated to dryness. The crude (3.35 g) was purified by flash chromatography on silica gel (eluent: Et20/EtOAc 2/1); (S)-4-(2-(2-(4-(N-(tert-butoxycarbonyl)methyl-sulfonamido)-3-(cyclopropylmethoxy)benzoyloxy)acetoxy)-2-(3-(cyclopropylmethoxy)-4-(difluoromethoxy)phenyl)ethyl)-3,5-dichloropyridine 1-oxide was obtained as a white amorphous solid (2.52 g, 2.98 mmol, 78% yield, MS/ESI+ 846.0 [MH]+).

Step 5: Synthesis of (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzoyloxy)acetoxy)ethyl)pyridine 1-oxide (117)

To a solution of (S)-4-(2-(2-(4-(N-(tert-butoxycarbonyl)methylsulfonamido)-3-(cyclopropylmethoxy)benzoyloxy)acetoxy)-2-(3-(cyclopropylmethoxy)-4-(difluoromethoxy)phenyl)ethyl)-3,5-dichloropyridine 1-oxide (2.457 g, 2.91 mmol) in dry DCM (85 ml), HCl 4M in dioxane (7.26 ml, 29.1 mmol) was added, and the reaction was stirred at RT overnight. Then the solvent was evaporated and the residue was purified by flash chromatography on silica gel (eluent: DCM/MeOH 99:1). Combined fractions were evaporated and the resulting solid was triturated with EtOH/MeOH 95:5 to afford (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzoyloxy)acetoxy)ethyl)pyridine 1-oxide as a white solid (1.761 g, 2.362 mmol, 81% yield, MS/ESI+ 745.13 [MH]+, $[\alpha_D]$=−34.69, c=0.49, DCM).

$^1$H NMR (300 MHz, DMSO-$d_6$) δ ppm 9.15 (br. s., 1 H), 8.48 (s, 2 H), 7.57 (dd, 1 H), 7.48 (d, 1 H), 7.45 (d, 1 H), 7.18 (d, 1 H), 7.09 (d, 1 H), 6.97 (dd, 1 H), 7.07 (t, 1 H), 6.05 (dd, 1 H), 4.92 (d, 1 H), 4.86 (d, 1 H), 3.95 (d, 2 H), 3.90 (d, 2 H), 3.37-3.53 (m, 1 H), 3.24 (dd, 1 H), 3.14 (s, 3 H), 1.13-1.41 (m, 2 H), 0.51-0.67 (m, 4 H), 0.30-0.45 (m, 4 H)

The compounds listed in Table 9 were prepared with an analogous procedure to that described in Example 15, Step 1-4, by reacting the appropriate precursors (commercially available or synthesized by a person skilled in the art) with suitable reagents, and where purification step has been performed as indicated in Table 9.

TABLE 9

| Structure | Cmp | NMR characterization | MS/ESI+ [MH]+ | Starting Material (and Conditions, if different) | Purification method |
|---|---|---|---|---|---|
| 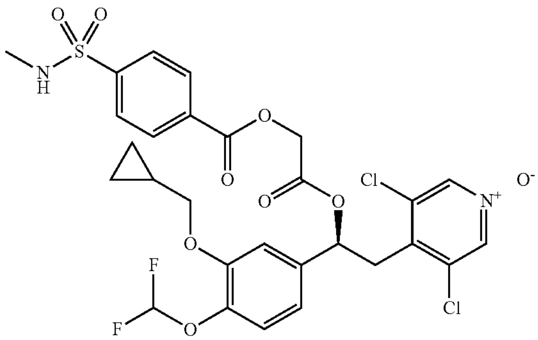 | 118 | 1H NMR (300 MHz, DMSO-d6) δ ppm 8.51 (s, 2 H), 8.09-8.24 (m, 2 H), 7.85-7.90 (m, 2 H), 7.67 (q, 1 H), 7.19 (d, 1 H), 7.10 (d, 1 H), 6.98 (dd, 1 H), 7.07 (t, 1 H), 6.06 (dd, 1 H), 5.02 (d, 1 H), 4.94 (d, 1 H), 3.91 (d, 2 H), 3.46 (dd, 1 H), 3.26 (dd, 1 H), 2.46 (d, 3 H), 1.08-1.38 (m, 1 H), 0.49-0.67 (m, 2 H), 0.23-0.44 (m, 2 H) | 675.24 | Intermediate of Step 2 (Step 3: EtOAc, 25 psi) | Preparative reverse-phase HPLC |

Example 16

Synthesis of (S)-3,5-dichloro-4-(2-(3-(cyclopropylmethoxy)-4-(difluoromethoxy)phenyl)-2-(3-(3-(cyclopropylmethoxy)-4-(methylsulfonamido)benzoyloxy)propanoyloxy)ethyl)pyridine 1-oxide (124)

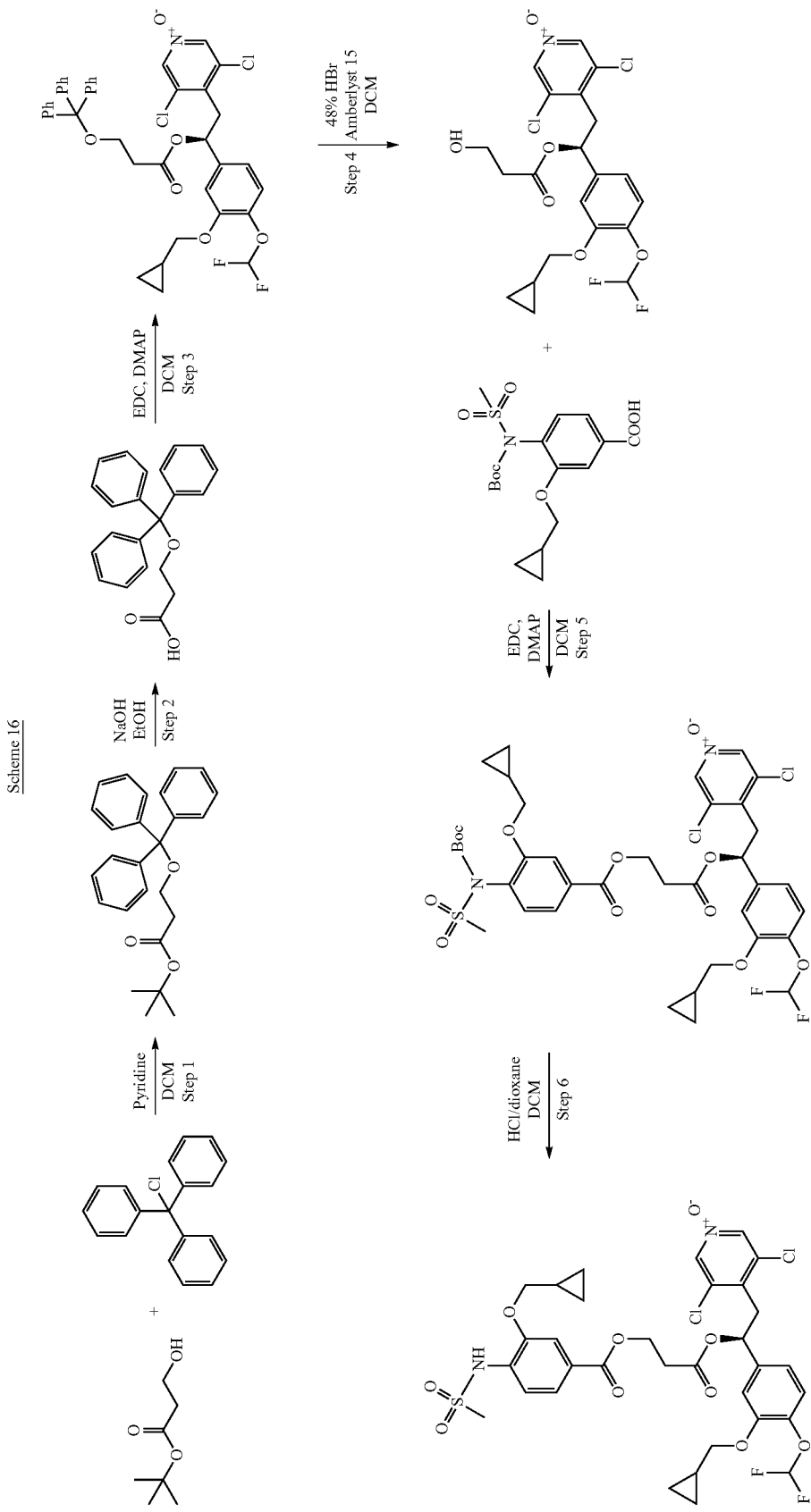

Step 1: Synthesis of tert-butyl 3-(trityloxy)propanoate (119)

To a solution of tert-butyl 3-hydroxypropanoate (2 g, 13.68 mmol) in dry DCM (50 ml), pyridine (3.32 ml, 41.0 mmol) was added. The solution was cooled to 5° C., and (chloromethanetriyl)tribenzene (3.81 g, 13.68 mmol) was added portion-wise; the ice cooling was removed and stirring was continued for 20 hours. The solvent was evaporated and the residue was portioned between EtOAc and water; the organic layer was washed with a 3% aqueous solution of citric acid, with brine and dried over $Na_2SO_4$. The solvent was removed and the residue was purified by flash chromatography on silica gel column (petroleum ether:EtOAc=95:5) affording tert-butyl 3-(trityloxy)propanoate (3.5 g, 9.01 mmol, 65.8% yield, MS/ESI$^+$ 411.3 [MNa]$^+$).

Step 2: Synthesis of 3-(trityloxy)propanoic acid (120)

A solution of tert-butyl 3-(trityloxy)propanoate (3.5 g, 9.01 mmol) and 6M NaOH (3.00 ml, 18.02 mmol) in ethanol was heated to reflux for 3 hours. After cooling the solvent was removed under vacuum and the residue was partitioned between DCM and aqueous 3% citric acid. The organic layer was washed with brine dried over $Na_2SO_4$. The solvent was evaporated and the crude was triturated with $iPr_2O$ and filtered affording 3-(trityloxy)propanoic acid (2.3 g, 6.92 mmol, 77% yield).

Step 3: Synthesis of (S)-3,5-dichloro-4-(2-(3-(cyclopropylmethoxy)-4-(difluoromethoxy)phenyl)-2-(3-(trityloxy)propanoyloxy)ethyl)pyridine 1-oxide (121)

To a mixture of 3-(trityloxy)propanoic acid (0.5 g, 1.504 mmol) and EDC (0.865 g, 4.51 mmol) in dry DCM (20 ml), (S)-3,5-dichloro-4-(2-(3-(cyclopropylmethoxy)-4-(difluoromethoxy)phenyl)-2-hydroxyethyl)pyridine 1-oxide (0.632 g, 1.504 mmol) and DMAP (0.184 g, 1.504 mmol) were added, and the resulting solution was stirred at RT overnight. The solvent was evaporated and the residue was partitioned between EtOAc and a sat. sol. of $NaHCO_3$. The organic layer was washed with aqueous 3% citric acid, with brine and dried over $Na_2SO_4$. The solvent was removed under vacuum and the residue was purified by flash chromatography on silica gel column (DCM:MeOH: 32% aq. $NH_4OH$=98:2:0.2) affording (S)-3,5-dichloro-4-(2-(3-(cyclopropylmethoxy)-4-(difluoromethoxy)phenyl)-2-(3-(trityloxy)propanoyloxy)ethyl)pyridine 1-oxide (0.6 g, 0.817 mmol, 54.3% yield, MS/ESI$^+$ 756.3 [MNa]$^+$).

Step 4: Synthesis of (S)-3,5-dichloro-4-(2-(3-(cyclopropylmethoxy)-4-(difluoromethoxy)phenyl)-2-(3-hydroxypropanoyloxy)ethyl)pyridine 1-oxide (122)

To a mixture of (S)-3,5-dichloro-4-(2-(3-(cyclopropylmethoxy)-4-(difluoromethoxy)phenyl)-2-(3-(trityloxy)propanoyloxy)ethyl)pyridine 1-oxide (0.600 g, 0.817 mmol) and Amberlyst 15 (4.7 meq/g, 0.050 g) in dry DCM (20 ml), 3 drops of HBr 48% were added at RT. After 1 hour, the reaction mixture was washed with $NaHCO_3$ sat. sol. and with brine. The organic layer was dried over $Na_2SO_4$, the solvent was removed under reduced pressure and the residue was purified by flash chromatography on silica gel column (DCM:MeOH: 32% aq. NH4OH=90:10:1) affording (S)-3,5-dichloro-4-(2-(3-(cyclopropylmethoxy)-4-(difluoromethoxy)-phenyl)-2-(3-hydroxy propanoyloxy)ethyl)pyridine 1-oxide (0.311 g, 0.632 mmol, 77% yield, MS/ESI$^+$ 492.1 [MH]$^+$).

Step 5: Synthesis of (S)-4-(2-(3-(4-(N-(tert-butoxycarbonyl)-methylsulfonamido)-3-(cyclopropylmethoxy)benzoyloxy)propanoyloxy)-2-(3-(cyclopropylmethoxy)-4-(difluoromethoxy)phenyl)ethyl)-3,5-dichloropyridine 1-oxide (123)

To a solution of (S)-3,5-dichloro-4-(2-(3-(cyclopropylmethoxy)-4-(difluoromethoxy)phenyl)-2-(3-hydroxypropanoyloxy)ethyl)pyridine 1-oxide (0.311 g, 0.632 mmol), 4-(N-(tert-butoxycarbonyl)methylsulfonamido)-3-(cyclopropylmethoxy)benzoic acid (0.243 g, 0.632 mmol), and EDC (0.363 g, 1.895 mmol) in dry DCM (15 ml), DMAP (0.077 g, 0.632 mmol) was added and the resulting mixture was stirred at RT for 3 hours. The solvent was evaporated, and the residue was partitioned between EtOAc and a $NaHCO_3$ sat. sol. The organic layer was washed with brine and dried over $Na_2SO_4$. The solvent was removed and the residue was purified by flash chromatography on silica gel column (DCM:MeOH:32% NH4OH=95:5:0.5) affording (S)-4-(2-(3-(4-(N-(tert-butoxycarbonyl)-methylsulfonamido)-3-(cyclopropylmethoxy)benzoyloxy)propanoyloxy)-2-(3-(cyclopropylmethoxy)-4-(difluoromethoxy)phenyl)ethyl)-3,5-dichloropyridine 1-oxide (0.450 g, 0.523 mmol, 83% yield, MS/ESI$^+$ 859.0 [MH]$^+$).

Step 6: Synthesis of (S)-3,5-dichloro-4-(2-(3-(cyclopropylmethoxy)-4-(difluoromethoxy)phenyl)-2-(3-(3-(cyclopropylmethoxy)-4-(methylsulfonamido)-benzoyloxy)propanoyloxy)ethyl)pyridine 1-oxide (124)

To a solution of (S)-4-(2-(3-(4-(N-(tert-butoxycarbonyl)methylsulfonamido)-3-(cyclopropylmethoxy)benzoyloxy)propanoyloxy)-2-(3-(cyclopropylmethoxy)-4-(difluoromethoxy)phenyl)ethyl)-3,5-dichloropyridine 1-oxide (0.450 g, 0.523 mmol) in dry DCM (15 ml), 4M HCl in dioxane (0.654 ml, 2.62 mmol) was added. The resulting mixture was stirred at RT for 4 days. The solvent was evaporated and the residue was purified by trituration with $Et_2O$ (30 ml) affording (S)-3,5-dichloro-4-(2-(3-(cyclopropylmethoxy)-4-(difluoromethoxy)phenyl)-2-(3-(3-(cyclopropylmethoxy)-4-(methylsulfonamido)benzoyloxy)propanoyloxy)ethyl)pyridine 1-oxide (0.340 g, 0.448 mmol, 86% yield, MS/ESI$^+$759.31 [MH]$^+$, [$\alpha_D$]=−8.9, c=0.6, DCM).

$^1$H NMR (300 MHz, DMSO-d$_6$) δ ppm 9.11 (br. s., 1 H), 8.45 (s, 2 H), 7.35-7.42 (m, 2 H), 7.35 (dd, 1 H), 7.11 (d, 1 H), 7.08 (d, 1 H), 6.95 (dd, 1 H), 7.02 (t, 1 H), 5.98 (dd, 1 H), 4.32-4.53 (m, 2 H), 3.89 (d, 2 H), 3.87 (d, 2 H), 3.43 (dd, 1 H), 3.20 (dd, 1 H), 3.12 (s, 3 H), 2.82 (t, 2 H), 1.24-1.35 (m, 1 H), 1.09-1.24 (m, 1 H), 0.50-0.64 (m, 4 H), 0.28-0.42 (m, 4 H)

Example 17

Synthesis of (S)-3,5-dichloro-4-(2-(2-(3-(cyclopropylmethoxy)-4-(N-(2-(4-methylpiperazin-1-yl)ethyl)methylsulfonamido)benzoyloxy)acetoxy)-2-(3-(cyclopropylmethoxy)-4-(difluoromethoxy)phenyl)ethyl)pyridine 1-oxide 2,2,2-trifluoroacetate (132)

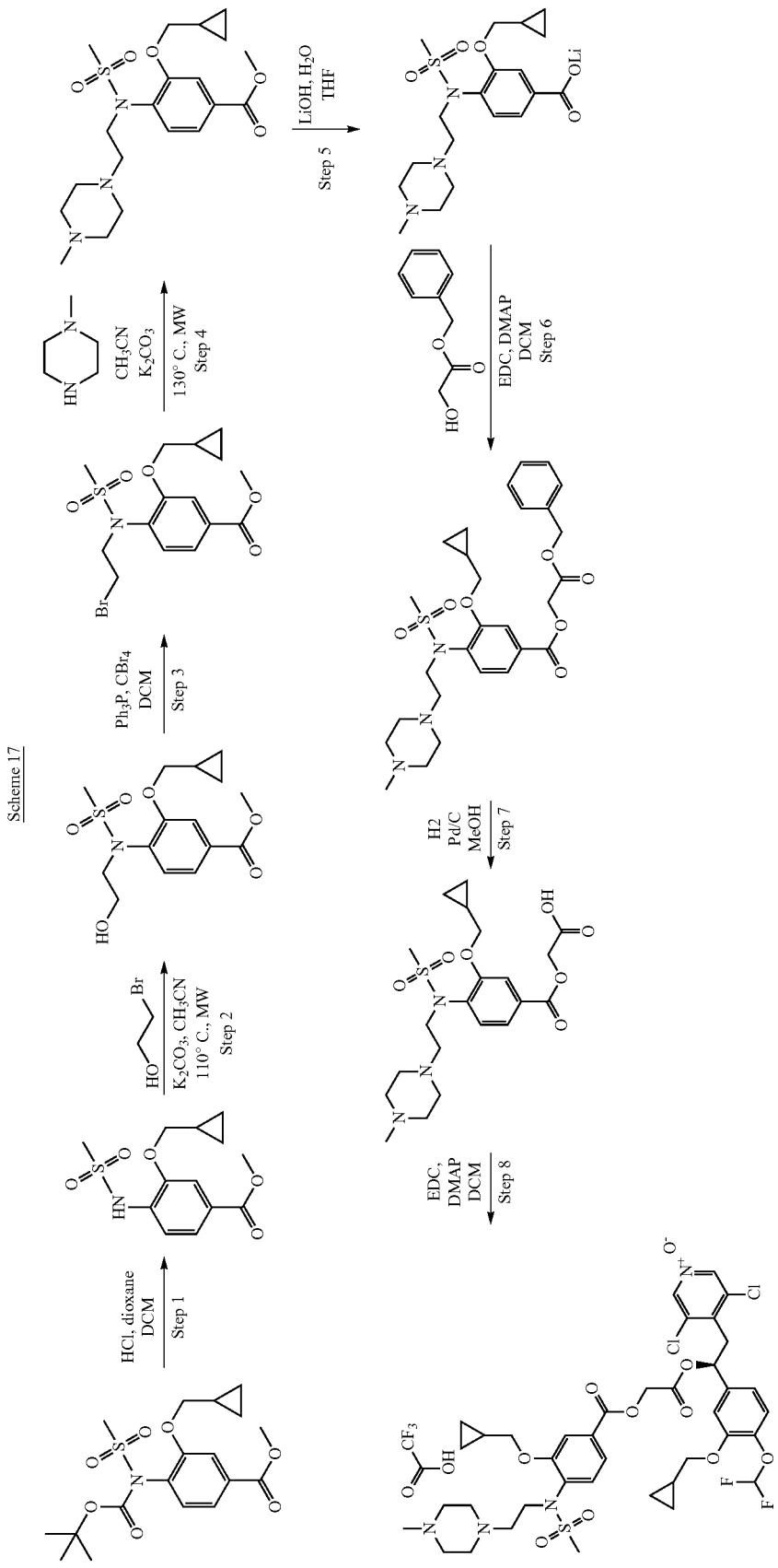

Step 1: Synthesis of methyl 3-(cyclopropylmethoxy)-4-(methylsulfonamido)benzoate (125)

To a solution of methyl 4-(N-(tert-butoxycarbonyl)methylsulfonamido)-3-(cyclopropylmethoxy)benzoate (for reference procedure see Example 18, WO 2010/089107, which is incorporated herein by reference) (3.00 g, 7.51 mmol) in dry DCM (40 ml), HCl 4M in Dioxane (9.39 ml, 37.6 mmol) was added, and the mixture was stirred at RT for 3 days. The solvent was evaporated, the residue was triturated with iPr$_2$O (50 ml) and filtered to give methyl 3-(cyclopropylmethoxy)-4-(methylsulfonamido)benzoate as an off-white powder (2.15 g, 7.18 mmol, 96% yield, MS/ESI$^+$ 299.9 [MH]$^+$).

Step 2: Synthesis of methyl 3-(cyclopropylmethoxy)-4-(N-(2-hydroxyethyl)methylsulfonamido)benzoate (126)

A mixture of methyl 3-(cyclopropylmethoxy)-4-(methylsulfonamido)benzoate (1 g, 3.34 mmol), 2-bromoethanol (0.835 g, 6.68 mmol), and K$_2$CO$_3$ (0.923 g, 6.68 mmol) in CH$_3$CN (12 ml) was heated at 110° C. under microwave irradiation for 12 hours. After cooling the solvent was evaporated and the residue was dissolved in EtOAc and filtered; the solvent was evaporated and the residue was purified by flash chromatography (eluent: EtOAc/petroleum ether 1/1) to give methyl 3-(cyclopropylmethoxy)-4-(N-(2-hydroxyethyl)methylsulfonamido)benzoate as a light brown oil (0.764 g, 2.225 mmol, 66.6% yield, /ESI$^+$ 365.9 [MNa]$^+$).

Step 3: Synthesis of methyl 4-(N-(2-bromoethyl)methylsulfonamido)-3-(cyclopropylmethoxy)benzoate (127)

To a solution of methyl 3-(cyclopropylmethoxy)-4-(N-(2-hydroxyethyl)-methylsulfonamido)benzoate (0.690 g, 2.009 mmol) in dry DCM (15 ml), CBr$_4$ (0.866 g, 2.61 mmol) was added, followed by triphenylphosphine (0.685 g, 2.61 mmol), and stirring was continued for 2 hours at RT. The solvent was evaporated, and the residue was purified by flash chromatography on silica gel (eluent: EtOAc/petroleum ether 2/8) to give methyl 4-(N-(2-bromoethyl)methylsulfonamido)-3-(cyclopropylmethoxy)benzoate as a colorless oil (0.630 g, 1.551 mmol, 77% yield, MS/ESI$^+$ 405.8, [MH]$^+$).

Step 4: Synthesis of methyl 3-(cyclopropylmethoxy)-4-(N-(2-(4-methylpiperazin-1-yl)ethyl)methylsulfonamido)benzoate (128)

The mixture of methyl 4-(N-(2-bromoethyl)methylsulfonamido)-3-(cyclopropylmethoxy)benzoate (630 mg, 1.551 mmol), 1-methylpiperazine (155 mg, 1.551 mmol) and K$_2$CO$_3$ (321 mg, 2.326 mmol) in dry CH$_3$CN (14 ml) was heated at 130° C. under microwave irradiation for 3 hours. After cooling the inorganic salts were filtered, the solvent was evaporated and the residue was purified by flash chromatography on silica gel (eluent: DCM/MeOH/32% NH$_4$OH 95/5/0.5) to give methyl 3-(cyclopropylmethoxy)-4-(N-(2-(4-methylpiperazin-1-yl)ethyl)-methylsulfonamido)benzoate as a light brown oil (520 mg, 1.222 mmol, 79% yield, MS/ESI$^+$ 426.0 [MH]$^+$).

Step 5: Synthesis of lithium 3-(cyclopropylmethoxy)-4-(N-(2-(4-methylpiperazin-1-yl)ethyl)methylsulfonamido)benzoate (129)

To a solution of methyl 3-(cyclopropylmethoxy)-4-(N-(2-(4-methylpiperazin-1-yl)ethyl)methylsulfonamido)benzoate (370 mg, 0.869 mmol) in THF (3 ml), a solution of LiOH 1M (43.8 mg, 1.043 mmol) was added. The final solution was stirred at RT for 6 hours, then the solvent was evaporated and the residue was dried under vacuum to give lithium 3-(cyclopropylmethoxy)-4-(N-(2-(4-methylpiperazin-1-yl)ethyl)methyl-sulfonamido)benzoate as a pale yellow solid (380 mg, yield considered to be quantitative, MS/ESI$^+$ 412.0 [MH]$^+$) that was used in the following step without further purification.

Step 6: Synthesis of 2-(benzyloxy)-2-oxoethyl 3-(cyclopropylmethoxy)-4-(N-(2-(4-methylpiperazin-1-yl)ethyl)methylsulfonamido)benzoate (130)

To a solution of lithium 3-(cyclopropylmethoxy)-4-(N-(2-(4-methylpiperazin-1-yl)ethyl)methylsulfonamido)benzoate (theoric 0.869 mmol) and EDC (349 mg, 1.821 mmol) in dry DCM (3 ml), benzyl 2-hydroxyacetate (151 mg, 0.910 mmol) and DMAP (111 mg, 0.910 mmol) were added at RT. The final mixture was stirred for 2 days, then the solvent was evaporated, the residue was portioned between water and EtOAc, the organic layer was washed with NaHCO$_3$ sat. sol. and brine, dried over Na$_2$SO$_4$ and evaporated. The crude was purified by flash chromatography on silica gel (eluent: DCM/MeOH/32% NH$_4$OH 95/5/0.5) to give 2-(benzyloxy)-2-oxoethyl 3-(cyclopropylmethoxy)-4-(N-(2-(4-methylpiperazin-1-yl)ethyl)-methylsulfonamido)benzoate as a colorless oil (370 mg, 0.661 mmol, 76% yield over 2 steps, MS/ESI$^+$ 560.1 [MH]$^+$).

Step 7: Synthesis of 2-(3-(cyclopropylmethoxy)-4-(N-(2-(4-methylpiperazin-1-yl)ethyl)methylsulfonamido)benzoyloxy)acetic acid (131)

The mixture of 2-(benzyloxy)-2-oxoethyl 3-(cyclopropylmethoxy)-4-(N-(2-(4-methylpiperazin-1-yl)ethyl)methylsulfonamido)benzoate (370 mg, 0.661 mmol) and a catalytic amount of 10% Pd/C in MeOH (20 ml) was hydrogenated at 20 psi for 2 hours. The catalyst was filtered off and the solvent was evaporated to give 2-(3-(cyclopropylmethoxy)-4-(N-(2-(4-methylpiperazin-1-yl)ethyl)methylsulfonamido)-benzoyloxy)acetic acid (270 mg, 0.575 mmol, 87% yield, MS/ESI$^+$ 470.0 [MH]$^+$) that was used in the following step without further purification.

Step 8: Synthesis of (S)-3,5-dichloro-4-(2-(2-(3-(cyclopropylmethoxy)-4-(N-(2-(4-methylpiperazin-1-yl)ethyl)methylsulfonamido)benzoyloxy)acetoxy)-2-(3-(cyclopropylmethoxy)-4-(difluoromethoxy)phenyl)ethyl)pyridine 1-oxide 2,2,2-trifluoroacetate (132)

To a solution of 2-(3-(cyclopropylmethoxy)-4-(N-(2-(4-methylpiperazin-1-yl)ethyl)methylsulfonamido)benzoyloxy)acetic acid (140 mg, 0.298 mmol) and EDC (171 mg, 0.894 mmol) in dry DCM (5 ml), (S)-3,5-dichloro-4-(2-(3-(cyclopropylmethoxy)-4-(difluoromethoxy)phenyl)-2-hydroxyethyl)pyridine 1-oxide (125 mg, 0.298 mmol) and DMAP (36.4 mg, 0.298 mmol) were added, and the mixture was stirred at RT for 24 hours. The solvent was evaporated, and the residue was portioned between water and EtOAc; the organic phase was washed with brine, dried over Na$_2$SO$_4$ and evaporated. The crude was purified by flash chromatography on silica gel (eluent: DCM/MeOH/32% NH$_4$OH 95/5/0.5) to give 140 mg of an oil that was further purified by preparative HPLC. (S)-3,5-dichloro-4-(2-(2-(3-(cyclopropylmethoxy)-4-(N-(2-(4-methylpiperazin-1-yl)ethyl)methylsulfonamido)-benzoyloxy)acetoxy)-2-(3-(cyclopropylmethoxy)-4-(difluoromethoxy)phenyl)ethyl)-pyridine 1-oxide was obtained as 2,2,2-trifluoroacetate (80 mg, 0.081 mmol, 27.2% yield, MS/ESI⁺ 871.36 [MH]⁺, $[\alpha_D]$=−23.00, c=0.50, DCM).

$^1$H NMR (300 MHz, DMSO-$d_6$) δ ppm 8.44 (s, 2 H) 7.56 (dd, 1 H) 7.51 (d, 1 H) 7.47 (d, 1 H) 7.20 (d, 1 H) 7.11 (d, 1 H) 6.99 (dd, 1 H) 7.08 (t, 1 H) 6.05 (dd, 1 H) 4.95 (d, 1 H) 4.89 (d, 1 H) 3.99 (d, 2 H) 3.93 (d, 2 H) 3.73 (t, 2 H) 3.46 (dd, 1 H) 3.33 (br. s., 2 H) 3.26 (dd, 1 H) 3.13 (s, 3 H) 2.92 (br. s., 4 H) 2.76 (s, 3 H) 2.21-2.48 (m, 4 H) 1.13-1.39 (m, 2 H) 0.49-0.71 (m, 4 H) 0.23-0.49 (m, 4 H)

Example 18

Synthesis of (S)-3,5-dichloro-4-(2-(3-(cyclopropylmethoxy)-4-(difluoromethoxy)phenyl)-2-(2-(4-methoxy-3-(methylsulfonamido)benzoyloxy)-acetoxy)ethyl)pyridine 1-oxide (140) and of (S)-3,5-dichloro-4-(2-(3-(cyclopropylmethoxy)-4-(difluoromethoxy)phenyl)-2-(2-(4-methoxy-3-(N-(2-morpholinoethyl)methylsulfonamido)benzoyloxy)acetoxy)ethyl)pyridine 1-oxide (142)

Scheme 18
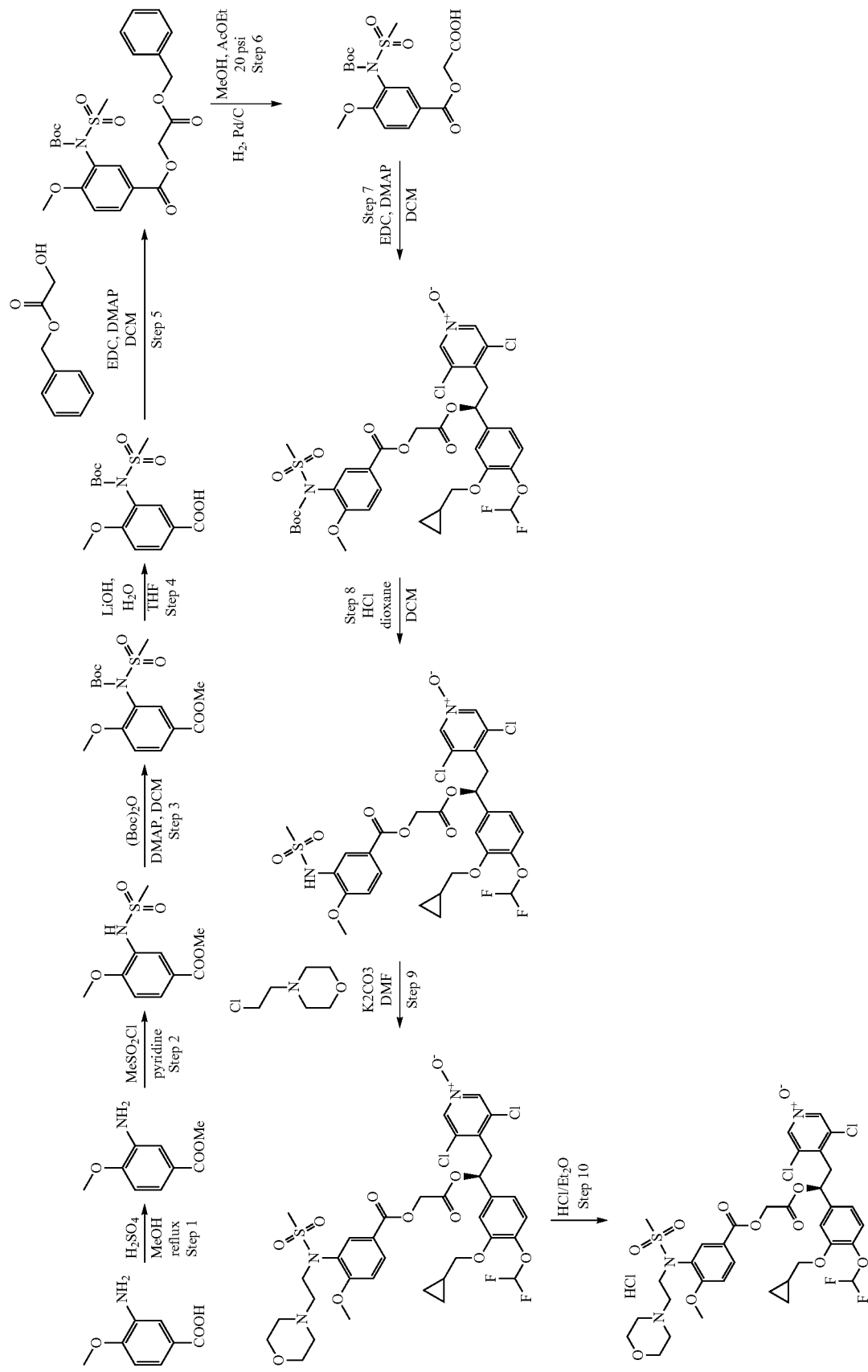

Step 1: Synthesis of methyl 3-amino-4-methoxybenzoate (133)

A mixture of 3-amino-4-methoxybenzoic acid (0.500 g, 2.99 mmol) and a catalytic amount of aqueous conc. sulfuric acid in MeOH (30 ml) was heated to reflux for 48 hours. The solvent was removed, and the crude was portioned between EtOAc and NaHCO$_3$ 5%. The organic phase was dried over Na$_2$SO$_4$ and the solvent was removed affording methyl 3-amino-4-methoxybenzoate (0.509 g, 2.81 mmol, 94% yield, MS/ESI$^+$ 181.9 [MH]$^+$). This product was used without purification.

Step 2: Synthesis of methyl 4-methoxy-3-(methylsulfonamido)benzoate (134)

To a solution of methyl 3-amino-4-methoxybenzoate (0.509 g, 2.81 mmol) in pyridine (10 ml), methanesulfonyl chloride (0.285 ml, 3.65 mmol) was added drop wise and the mixture was stirred at RT for 2 hours. The solvent was removed under vacuum, and the crude was portioned between EtOAc and HCl 1N. The organic phase was dried over Na$_2$SO$_4$ and the solvent was removed. The crude was purified by filtration through a silica gel cartridge (DCM:EtOAc=90:10) to give methyl 4-methoxy-3-(methylsulfonamido)benzoate (0.673 g, 2.60 mmol, 92% yield, MS/ESI$^+$ 259.9 [MH]$^+$).

Step 3: Synthesis of methyl 3-(N-(tert-butoxycarbonyl)methylsulfonamido)-4-methoxybenzoate (135)

A solution of methyl 4-methoxy-3-(methylsulfonamido)benzoate (0.673 g, 2.60 mmol), di-tert-butyl dicarbonate (0.623 g, 2.86 mmol), and DMAP (0.349 g, 2.86 mmol) in DCM (30 ml) was stirred for 2 hours at RT. The mixture was washed with HCl 1N and with NaHCO$_3$ 5%. The organic phase was dried over Na$_2$SO$_4$, and the solvent was removed; the residue was suspended in MeOH and the solvent was evaporated to dryness affording methyl 3-(N-(tert-butoxycarbonyl)-methylsulfonamido)-4-methoxybenzoate (0.882 g, 2.454 mmol, 95% yield, MS/ESI$^+$ 381.9 [MNa]$^+$). This product was used without any further purification.

Step 4: Synthesis of 3-(N-(tert-butoxycarbonyl)methylsulfonamido)-4-methoxybenzoic acid (136)

To a solution of methyl 3-(N-(tert-butoxycarbonyl)methylsulfonamido)-4-methoxybenzoate (0.882 g, 2.454 mmol) in THF (15 ml), LiOH 1N (2.94 ml, 2.94 mmol) was added and the mixture was stirred at RT for 24 hours. The mixture was acidified with HCl 1N and extracted with EtOAc; the organic phase was washed with brine ad dried over Na$_2$SO$_4$. The solvent was removed and the residue was triturated with Et$_2$O to afford after filtration 3-(N-(tert-butoxycarbonyl)-methylsulfonamido)-4-methoxybenzoic acid (0.487 g, 1.410 mmol, 57.5% yield, MS/ESI$^+$ 367.9 [MNa]$^+$).

Step 5: Synthesis of 2-(benzyloxy)-2-oxoethyl 3-(N-(tert-butoxycarbonyl)methylsulfonamido)-4-methoxybenzoate (137)

To a solution of benzyl 2-hydroxyacetate (0.234 g, 1.410 mmol), EDC (0.541 g, 2.82 mmol) and DMAP (0.086 g, 0.705 mmol) in DCM (25 ml), 3-(N-(tert-butoxycarbonyl)methylsulfonamido)-4-methoxybenzoic acid (0.487 g, 1.410 mmol) was added, and the reaction was stirred at RT for 1 hour. The mixture was washed with HCl 1N and with NaHCO$_3$ 5%; the organic phase was dried over Na$_2$SO$_4$, and the solvent was removed. The crude was purified by flash chromatography on silica gel cartridge (petroleum ether:EtOAc=80:20 to 70:30) to give 2-(benzyloxy)-2-oxoethyl 3-(N-(tert-butoxycarbonyl)-methylsulfonamido)-4-methoxybenzoate (0.508 g, 1.029 mmol, 73.0% yield, MS/ESI$^+$ 515.9 [MNa]$^+$).

Step 6: Synthesis of 2-(3-(N-(tert-butoxycarbonyl) methylsulfonamido)-4-methoxybenzoyloxy)acetic acid (138)

To a solution of 2-(benzyloxy)-2-oxoethyl 3-(N-(tert-butoxycarbonyl)-methylsulfonamido)-4-methoxybenzoate (0.508 g, 1.029 mmol) in MeOH (30 m) and EtOAc (3 ml), 10% w/w Pd/C (a catalytic amount) was added, and the mixture was hydrogenated in a Parr apparatus at 20 psi for 3 hours. The catalyst was filtered off and the filtrate was evaporated to dryness affording 2-(3-(N-(tert-butoxycarbonyl)methyl-sulfonamido)-4-methoxybenzoyloxy)acetic acid (0.387 g, 0.959 mmol, 93% yield, MS/ESI$^+$not detectable [MH]$^+$). This product was used without any further purification.

Step 7: Synthesis of (S)-4-(2-(2-(3-(N-(tert-butoxycarbonyl)-methylsulfonamido)-4-methoxybenzoyloxy)acetoxy)-2-(3-(cyclopropylmethoxy)-4-(difluoromethoxy)phenyl)ethyl)-3,5-dichloropyridine 1-oxide (139)

A mixture of 2-(3-(N-(tert-butoxycarbonyl)methylsulfonamido)-4-methoxybenzoyloxy)acetic acid (0.192 g, 0.476 mmol), (S)-3,5-dichloro-4-(2-(3-(cyclopropylmethoxy)-4-(difluoromethoxy)phenyl)-2-hydroxyethyl)pyridine 1-oxide (0.200 g, 0.476 mmol), EDC (0.274 g, 1.428 mmol), and DMAP (0.058 g, 0.476 mmol) in DCM (20 ml) was stirred at RT for 2 hours. The mixture was washed with HCl 1N and with NaHCO$_3$ 5%; the organic layer was dried over Na$_2$SO$_4$, and the solvent was removed. The crude was purified by flash chromatography on silica gel cartridge (DCM:MeOH=99:1) to afford (S)-4-(2-(2-(3-(N-(tert-butoxycarbonyl)methylsulfonamido)-4-methoxybenzoyloxy)acetoxy)-2-(3-(cyclopropylmethoxy)-4-(difluoromethoxy)phenyl)ethyl)-3,5-dichloropyridine 1-oxide (0.296 g, 0.367 mmol, 77% yield, MS/ESI$^+$ 805.0 [MH]$^+$).

Step 8: Synthesis of (S)-3,5-dichloro-4-(2-(3-(cyclopropylmethoxy)-4-(difluoromethoxy)phenyl)-2-(2-(4-methoxy-3-(methylsulfonamido)benzoyloxy)-acetoxy)ethyl)pyridine 1-oxide (140)

To a solution of (S)-4-(2-(2-(3-(N-(tert-butoxycarbonyl) methylsulfonamido)-4-methoxybenzoyloxy)acetoxy)-2-(3-(cyclopropylmethoxy)-4-(difluoromethoxy)-phenyl)ethyl)-3,5-dichloropyridine 1-oxide (0.296 g, 0.367 mmol) in DCM (20 ml), HCl 4M in dioxane (0.919 ml, 3.67 mmol) was added, and the mixture was stirred at RT for 3 days. Additional HCl 4M in dioxane (1.838 ml, 7.34 mmol) was added over 2 days with stirring at the same temperature. The volatiles was removed under vacuum, and the crude was triturated with MeOH. The precipitate was collected by filtration and washed with Et$_2$O to give (S)-3,5-dichloro-4-(2-(3-(cyclopropylmethoxy)-4-(difluoromethoxy)phenyl)-2-(2-(4-methoxy-3-(methylsulfonamido)benzoyloxy)-acetoxy)ethyl)pyridine 1-oxide as a white solid (0.215 g, 0.305 mmol, 83% yield, MS/ESI$^+$ 705.25 [MH]$^+$, [$\alpha_D$]=−28.15, c=0.53, DCM).

$^1$H NMR (300 MHz, DMSO-d$_6$) δ ppm 9.16 (br. s., 1 H), 8.50 (s, 2 H), 7.89 (d, 1 H), 7.81 (dd, 1 H), 7.22 (d, 1 H), 7.18 (d, 1 H), 7.08 (d, 1 H), 6.97 (dd, 1 H), 7.07 (t, 1 H), 6.04 (dd, 1 H), 4.93 (d, 1 H), 4.86 (d, 1 H), 3.92 (s, 3 H), 3.89 (d, 2 H), 3.45 (dd, 1 H), 3.25 (dd, 1 H), 2.98 (s, 3 H), 1.10-1.33 (m, 1 H), 0.50-0.73 (m, 2 H), 0.16-0.50 (m, 2 H)

Step 9: Synthesis of (S)-3,5-dichloro-4-(2-(3-(cyclopropylmethoxy)-4-(difluoromethoxy)-phenyl)-2-(2-((4-methoxy-3-(N-(2-morpholinoethyl)methylsulfonamido)-benzoyloxy)acetoxy)ethyl)pyridine 1-oxide (141)

(S)-3,5-dichloro-4-((2-(3-(cyclopropylmethoxy)-4-(difluoromethoxy)phenyl)-2-(2-(4-methoxy-3-(methylsulfonamido)benzoyloxy)acetoxy)ethyl)pyridine 1-oxide, (152 mg, 0.21 mmol) was dissolved in DMF (2 ml). K₂CO₃ (35 mg, 0.25 mmol) and 4-(2-chloroethyl)morpholine (161 mg, 1.08 mmol) were added, and the mixture was stirred at 40° C. for 8 hours. The reaction was diluted with water and extracted with EtOAc. The organic phase was washed with water and brine, dried over Na₂SO₄ and evaporated under vacuum to give 133 mg of final product (Yield: 77%)

Step 10: Synthesis of (S)-3,5-dichloro-4-(2-(3-(cyclopropylmethoxy)-4-(difluoromethoxy)phenyl)-2-(2-(4-methoxy-3-(N-(2-morpholinoethyl)-methylsulfonamido)benzoyloxy)acetoxy)ethyl)pyridine 1-oxide hydrochloride (142)

(S)-3,5-dichloro-4-(2-(3-(cyclopropylmethoxy)-4-(difluoromethoxy)phenyl)-2-(2-(4-methoxy-3-(N-(2-morpholinoethyl)methylsulfonamido)benzoyloxy)-acetoxy)ethyl)pyridine 1-oxide (21 mg, 0.026 mmol) was dissolved in EtOAc (1 ml). HCl 2M in Et₂O (15 µl) was added, then Et₂O (5 ml) was added. The precipitate was filtered and dried in the vacuum oven to give 14 mg of final product.

MS/ESI⁺ 818.66 [MH]⁺

¹H NMR (400 MHz, acetone) δ ppm 13.28-13.53 (m, 1 H), 8.24 (s, 2 H), 8.05-8.13 (m, 1 H), 7.93-8.03 (m, 1 H), 7.26-7.40 (m, 1 H), 7.17-7.25 (m, 2 H), 7.03-7.12 (m, 1 H), 6.93 (t, J=75.00 Hz, 1 H), 6.11-6.32 (m, 1 H), 4.88 (s, 2 H), 4.22-4.43 (m, 2 H), 4.09 (m, 5 H), 4.00 (d, J=6.62 Hz, 2 H), 3.88-3.97 (m, 2 H), 3.52-3.75 (m, 1 H), 3.12-3.50 (m, 7 H), 3.09 (s, 3 H), 1.25-1.40 (m, 1 H), 0.54-0.75 (m, 2 H), 0.32-0.49 (m, 2 H).

Example 19

Synthesis of (S)-4-(2-(2-(3-(N-(2-amino-2-oxoethyl)methylsulfonamido)-4-methoxybenzoyloxy)acetoxy)-2-(3-(cyclopropylmethoxy)-4-(difluoromethoxy)-phenyl)ethyl)-3,5-dichloropyridine 1-oxide (149)

Scheme 19

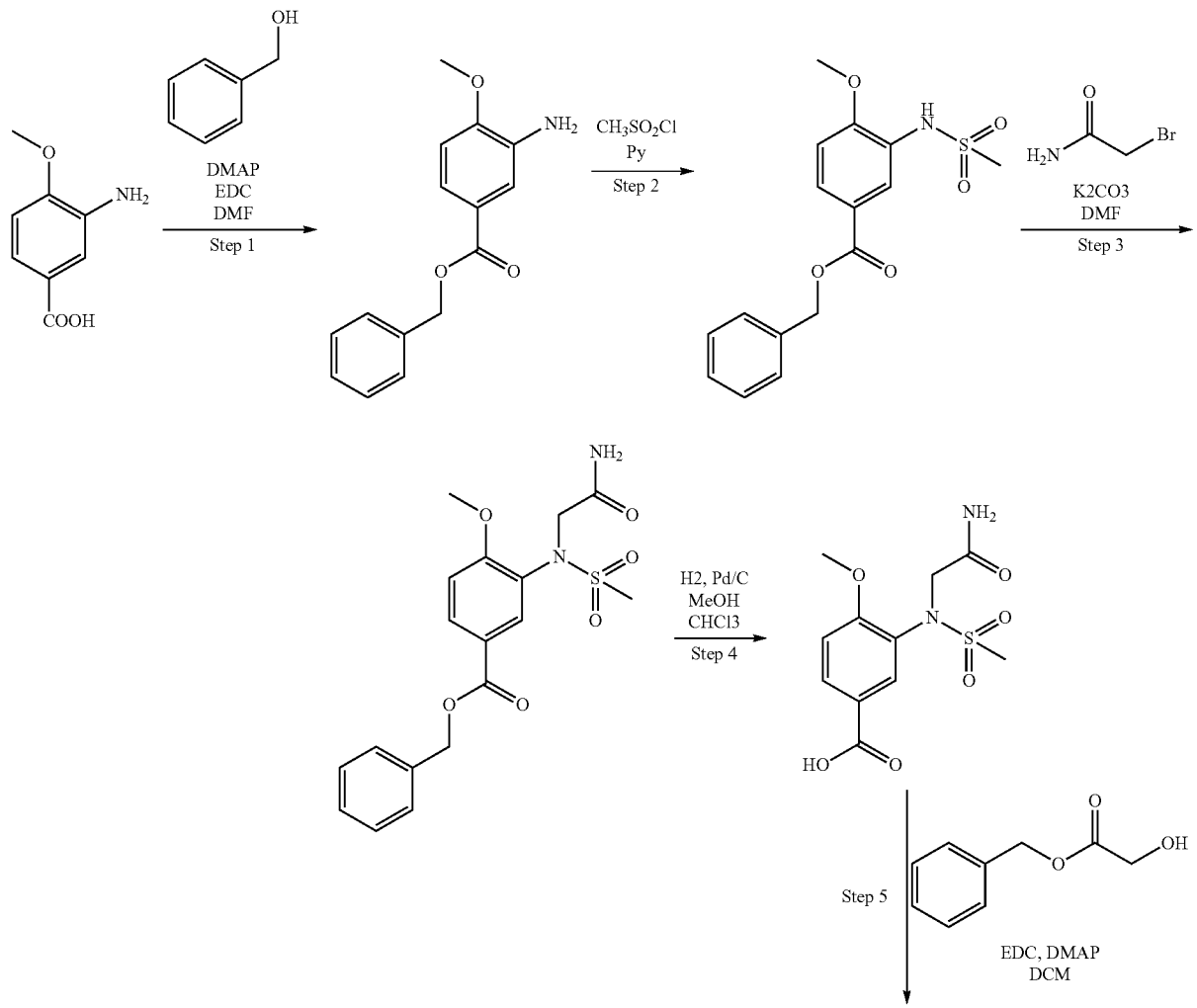

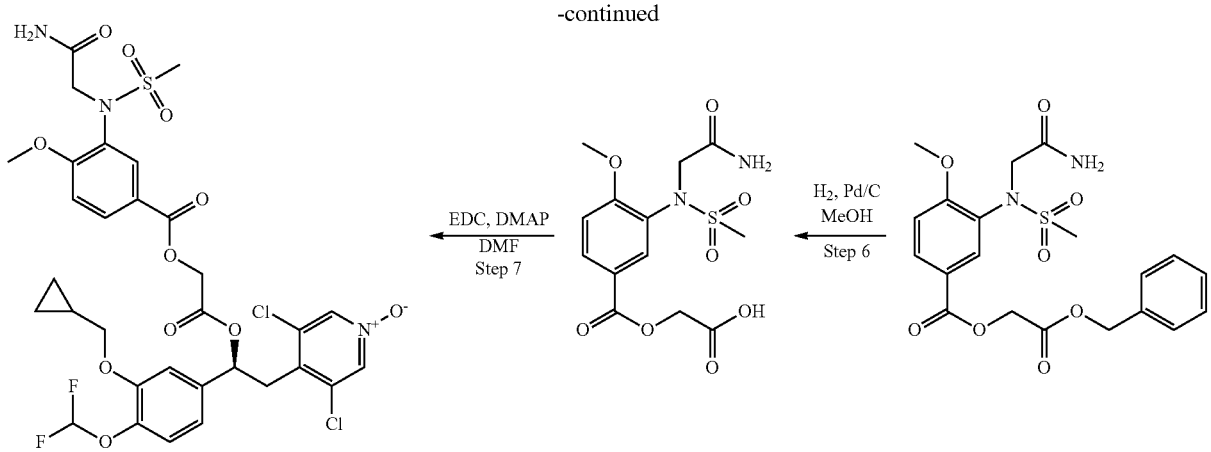

Step 1: Synthesis of benzyl 3-amino-4-methoxybenzoate (143)

3-amino-4-methoxybenzoic acid (20 g, 120 mmol), phenylmethanol (12.94 g, 120 mmol), DMAP (14.62 g, 120 mmol), and EDC (22.94 g, 120 mmol) were dissolved in DMF (100 ml). The reaction was stirred at RT for 2 hours. The reaction mixture was filtered, and the mother liquor was diluted with water and extracted with EtOAc. The organic phase was extracted with water, dried over $Na_2SO_4$ and evaporated under vacuum. The crude product was crystallized in EtOAc. The mother liquor are purified by flash chromatography (Petroleum Ether/EtOAc 80/20). The overall amount of the desired product was 16 g (Yield: 52%).

Step 2: Synthesis of benzyl 4-methoxy-3-(methylsulfonamido)benzoate (144)

Benzyl 3-amino-4-methoxybenzoate (300 mg, 1.17 mmol) was dissolved in Py (5 ml). Methanesulfonyl chloride (140 mg, 1.22 mmol) was added at 0° C. and under Argon atmosphere. The mixture was stirred at RT for 1 hour, then it was diluted with HCl 1N and extracted with EtOAc. The organic phase was washed with HCl 1M, dried over $Na_2SO_4$ and concentrated under vacuum to give benzyl 4-methoxy-3-(methylsulfonamido)benzoate (247 mg, 63.2% yield).

Step 3: Synthesis of benzyl 3-(N-(2-amino-2-oxoethyl)methylsulfonamido)-4-methoxybenzoate (145)

Benzyl 4-methoxy-3-(methylsulfonamido)benzoate (200 mg, 0.596 mmol) was dissolved in DMF (2 ml). 2-bromoacetamide (247 mg, 1.789 mmol) and $K_2CO_3$ (165 mg, 1.193 mmol) were added, and the reaction was stirred at RT overnight. The reaction mixture was diluted with water and filtered. The precipitate was washed with water and dried in the vacuum oven to give benzyl 3-(N-(2-amino-2-oxoethyl)methylsulfonamido)-4-methoxybenzoate (220 mg, 94% yield).

Step 4: Synthesis of 3-(N-(2-amino-2-oxoethyl)methylsulfonamido)-4-methoxybenzoic acid (146)

Benzyl 3-(N-(2-amino-2-oxoethyl)methylsulfonamido)-4-methoxybenzoate (220 mg, 0.561 mmol) was dissolved in MeOH (20 ml) and $CHCl_3$ (5 ml), then Pd/C 5% (119 mg, 0.056 mmol) was added. The solution was shaken under hydrogen atmosphere at 30 psi on a Parr apparatus for 30 minutes. The catalyst was filtered off and the solvent removed under vacuum to give 3-(N-(2-amino-2-oxoethyl)methylsulfonamido)-4-methoxybenzoic acid (150 mg, 89% yield).

Step 5: Synthesis of 2-(benzyloxy)-2-oxoethyl 3-(N-(2-amino-2-oxoethyl)methylsulfonamido)-4-methoxybenzoate (147)

3-(N-(2-amino-2-oxoethyl)methylsulfonamido)-4-methoxybenzoic acid (150 mg, 0.496 mmol), benzyl 2-hydroxyacetate (165 mg, 0.992 mmol), DMAP (121 mg, 0.992 mmol), and EDC (285 mg, 1.489 mmol) were dissolved in DMF (2 ml). The reaction was stirred at RT for 3 h to achieve completion. The reaction mixture was diluted with water, and extracted with EtOAc. The organic phase was washed with HCl 1N, $Na_2CO_3$ sat. sol. and brine, dried over $Na_2SO_4$ and concentrated under vacuum to give 2-(benzyloxy)-2-oxoethyl 3-(N-(2-amino-2-oxoethyl)-methylsulfonamido)-4-methoxybenzoate (180 mg, 81% yield).

Step 6: Synthesis of 2-(3-(N-(2-amino-2-oxoethyl) methylsulfonamido)-4-methoxybenzoyloxy)acetic acid (148)

2-(benzyloxy)-2-oxoethyl 3-(N-(2-amino-2-oxoethyl)methylsulfonamido)-4-methoxybenzoate (180 mg, 0.400 mmol) was dissolved in MeOH (10 ml), then Pd/C 5% (85 mg, 0.040 mmol) was added. The solution was shaken under hydrogen atmosphere at 35 psi on a Parr apparatus for 30 minutes. The catalyst was filtered off, and the solvent removed under vacuum to give 2-(3-(N-(2-amino-2-oxoethyl)methylsulfonamido)-4-methoxybenzoyloxy)acetic acid (130 mg, 90% yield).

Step 7: Synthesis of (S)-4-(2-(2-(3-(N-(2-amino-2-oxoethyl)-methylsulfonamido)-4-methoxybenzoyloxy)acetoxy)-2-(3-(cyclopropylmethoxy)-4-(difluoromethoxy)phenyl)ethyl)-3,5-dichloropyridine 1-oxide (149)

(S)-3,5-dichloro-4-(2-(3-(cyclopropylmethoxy)-4-(difluoromethoxy)phenyl)-2-hydroxyethyl)pyridine 1-oxide (30 mg, 0.071 mmol), 2-(3-(N-(2-amino-2-oxoethyl)methylsulfonamido)-4-methoxybenzoyloxy)acetic acid (51.4 mg, 0.143 mmol), DMAP (15 mg, 0.123 mmol), and EDC (100 mg, 0.522 mmol) were dissolved in DMF (2 ml). The reaction was stirred at RT for 3 hours to achieve completion. The reaction mixture was diluted with Water, and the precipitate was washed with water, dissolved in EtOAc and extracted with HCl 1N, Na$_2$CO$_3$ sat. sol. and brine. The organic phase was dried over Na$_2$SO$_4$ and concentrated under vacuum. The crude product was crystallized in EtOH to give (S)-4-(2-(2-(3-(N-(2-amino-2-oxoethyl)methylsulfonamido)-4-methoxybenzoyloxy)acetoxy)-2-(3-(cyclopropylmethoxy)-4-(difluoromethoxy)phenyl)ethyl)-3,5-dichloropyridine 1-oxide (20 mg, 0.026 mmol, 36.7% yield).

MS/ESI$^+$ 818.66 [MH]$^+$ $^1$H NMR (400 MHz, acetone) δ ppm 8.21-8.28 (m, 3 H), 8.03 (dd, J=8.82, 2.20 Hz, 1 H), 7.29 (d, J=8.82 Hz, 1 H), 7.16-7.23 (m, 2 H), 7.06 (dd, J=8.38, 1.76 Hz, 2 H), 6.93 (t, J=75.00 Hz, 1 H), 6.59 (br. s., 1 H), 6.19 (dd, J=9.70, 4.41 Hz, 1 H), 4.88 (s, 2 H), 4.26 (s, 2 H), 4.06 (s, 3 H), 3.97 (d, J=7.06 Hz, 2 H), 3.57 (dd, J=14.11, 9.26 Hz, 1 H), 3.33 (dd, J=14.33, 4.63 Hz, 1 H), 3.11 (s, 3 H), 1.22-1.35 (m, 1 H), 0.56-0.69 (m, 2 H), 0.34-0.43 (m, 2 H).

Example 20

Synthesis of (S)-3,5-dichloro-4-(2-(3-(cyclopropylmethoxy)-4-(difluoromethoxy)phenyl)-2-(2-(4-methoxy-3-(N-(2-morpholinoethyl)-methylsulfonamido)benzamido)acetoxy)ethyl)pyridine 1-oxide (153)

Scheme 20

Step 1: Synthesis of benzyl 4-methoxy-3-(N-(2-morpholinoethyl)methyl-sulfonamido)benzoate (151)

Benzyl 4-methoxy-3-(methylsulfonamido)benzoate (1.5 g, 4.47 mmol, Compound 144 may be prepared in analogous manner as described in Scheme 19, Step 1 and 2) was dissolved in DMF (10 ml), then 4-(2-chloroethyl)morpholine (6.69 g, 44.7 mmol) and $K_2CO_3$ (1.23 g, 8.94 mmol) were added, and the mixture was stirred at 80° C. for 3 hours. The reaction was quenched with water, and the product was extracted with EtOAc. The organic phase was washed with water (3×), then dried over $Na_2SO_4$ and evaporated under vacuum to yield 1.5 g of crude.

Step 2: Synthesis of 4-methoxy-3-(N-(2-morpholinoethyl)-methylsulfonamido)benzoic acid (152)

Benzyl 4-methoxy-3-(N-(2-morpholinoethyl)methylsulfonamido)benzoate (1.5 g, 3.34 mmol) was dissolved in MeOH (20 ml), then Pd/C 5% (0.33 mmol, 702 mg) was added, and the mixture was hydrogenated in a Parr apparatus ($H_2$:35 psi) for 30 minutes. The reaction was diluted with $CHCl_3$ (300 ml) and MeOH (300 ml) to dissolve the product that precipitated in MeOH, and the catalyst was filtered over a celite pad, and the solvent is evaporated under vacuum, to yield 700 mg of white solid.

Step 3: Synthesis of (S)-3,5-dichloro-4-(2-(3-(cyclopropylmethoxy)-4-(difluoromethoxy)phenyl)-2-(2-(4-methoxy-3-(N-(2-morpholinoethyl)-methylsulfonamido)benzamido)acetoxy)ethyl)pyridine 1-oxide (153)

20 mg of the title compound were obtained after Preparative Reverse Phase HPLC purification (Yield: 41%), starting from (S)-4-(2-(2-aminoacetoxy)-2-(3-(cyclopropylmethoxy)-4-(difluoromethoxy)phenyl)ethyl)-3,5-dichloropyridine 1-oxide (30 mg, 0.06 mmol, Compound 3 may be prepared as in analogous manner as described in Scheme 1, Step 1 and 2) and 4-methoxy-3-(N-(2-morpholinoethyl)methyl-sulfonamido)benzoic acid (Compound 152, 43 mg, 0.12 mmol), with DMAP (16 mg, 0.13 mmol) and EDC (58 mg, 0.3 mmol) in DMF (2 ml) using an analogous procedure to that described in Scheme 1, Step 3.

MS/ESI$^+$817.2 [MH]$^+$ $^1$H NMR (400 MHz, acetone) δ ppm 8.22 (s, 2 H), 8.16 (bs, 1 H), 7.83-8.00 (m, 2H), 7.16-7.25 (m, 3 H), 7.05 (dd, J=8.16, 1.98 Hz, 1 H), 6.92 (t, 1 H, CHF2), 6.12 (dd, J=9.48, 4.63 Hz, 1 H), 4.12 (dd, J=11.25, 5.95 Hz, 2 H), 3.96-4.08 (m, 5 H), 3.42-3.57 (m, 5 H), 3.32 (dd, J=13.89, 4.63 Hz, 1 H), 3.03 (s, 3 H), 2.40 (t, J=6.62 Hz, 2 H), 2.32 (m., 4 H), 1.18-1.36 (m, 1 H), 0.56-0.67 (m, 2 H), 0.35-0.47 (m, 2 H).

The compounds listed in Table 10 were prepared with an analogous procedure to that described in Example 20 by reacting the appropriate precursors (commercially available or synthesized by a person skilled in the art) with suitable reagents, and where purification step has been performed as indicated in Table 10.

TABLE 10

| Structure | Compound | $^1$H NMR | MS/ESI$^+$ [MH]$^+$ | Starting Materials | Purification Method |
|---|---|---|---|---|---|
| 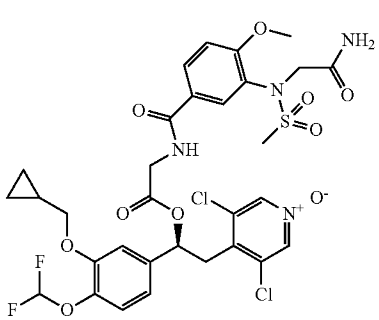 | 154 | 1H NMR (400 MHz, acetone) δ ppm 8.23 (s, 2 H), 8.11 (d, J = 2.20 Hz, 2 H), 7.96 (dd, J = 8.82, 2.21 Hz, 1 H), 7.14-7.29 (m, 3 H), 7.05 (dd, J = 8.16, 1.98 Hz, 2 H), 6.92 (t, J = 75.00 Hz, 1 H), 6.41-6.61 (m, 1 H), 6.14 (dd, J = 9.70, 4.41 Hz, 1 H), 4.20-4.31 (m, 2 H), 3.94-4.19 (m, 7 H), 3.53 (dd, J = 14.11, 9.70 Hz, 1 H), 3.31 (dd, J = 14.11, 4.41 Hz, 1 H), 3.16 (s, 3 H), 1.20-1.41 (m, 1 H), 0.62 (dd, J = 8.16, 1.54 Hz, 2 H), 0.41 (d, J = 5.29 Hz, 2 H) | 761.57 | Intermediates of Step 2 | Preparative reverse-phase HPLC |

The compounds listed in Table 11 were prepared with an analogous procedure to that described in Example 20, Step 4, by reacting the appropriate precursors (commercially available or synthesized by a person skilled in the art) with suitable reagents, and where purification step has been performed as indicated in Table 11.

TABLE 11

| Structure | Cmp | $^1$H NMR | MS/ESI$^+$ [MH]$^+$ | Starting Material | Purification Method |
|---|---|---|---|---|---|
| (structure) | 155 | $^1$H NMR (400 MHz, acetone) δ ppm 8.35-8.44 (m, 1 H), 8.25 (s, 2 H), 8.20 (dd, J = 8.16, 1.10 Hz, 2 H), 7.66-7.79 (m, 1 H), 7.49-7.63 (m, 2 H), 7.24 (d, J = 2.21 Hz, 1 H), 7.20 (d, J = 8.38 Hz, 1 H), 7.07 (dd, J = 8.16, 1.98 Hz, 1 H), 6.92 (t, J = 75.00 Hz, 1 H), 6.18 (dd, J = 9.48, 4.63 Hz, 1 H), 4.12-4.27 (m, 2 H), 3.98 (d, J = 6.17 Hz, 2 H), 3.58 (dd, J = 14.11, 9.26 Hz, 1 H), 3.35 (dd, J = 14.11, 4.41 Hz, 1 H), 1.18-1.36 (m, 1 H), 0.48-0.70 (m, 2 H), 0.29-0.43 (m, 2 H). | 609.40 | (structure) | Crystallization in EtOH |

Example 21

Synthesis of (S)-3,5-dichloro-4-(2-(2-(2-(4-(cyclopropylmethoxy)-3-(methylsulfonamido)phenyl)acetoxy)acetoxy)-2-(3-(cyclopropylmethoxy)-4-(difluoromethoxy)phenyl)ethyl)pyridine 1-oxide (166)

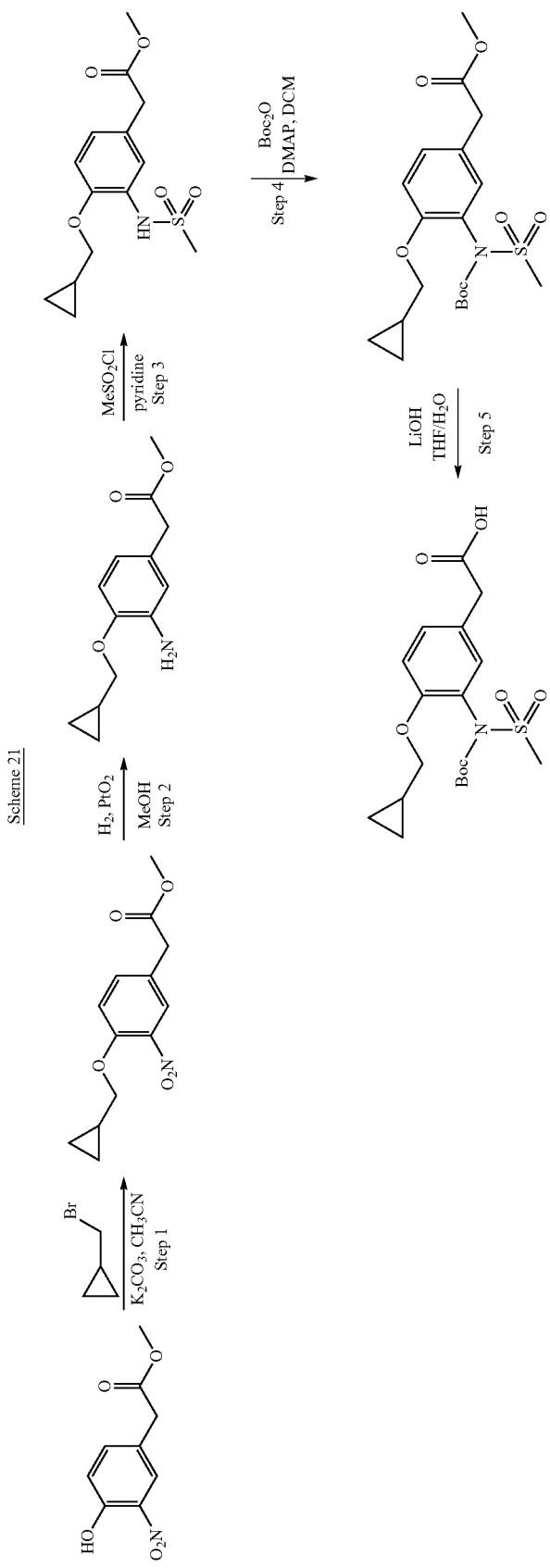
Scheme 21

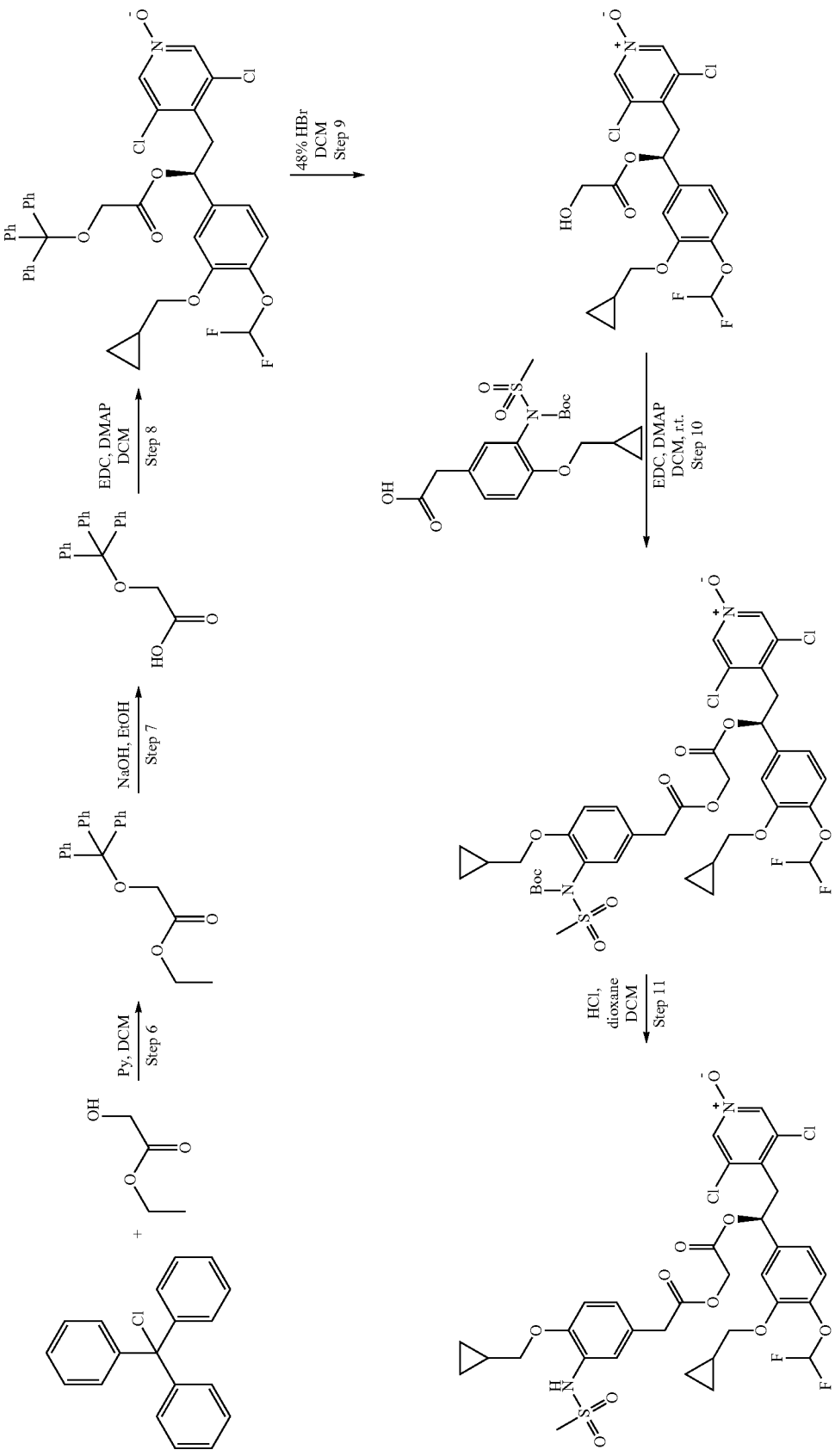

Step 1: Synthesis of methyl 2-(4-(cyclopropylmethoxy)-3-nitrophenyl)acetate (156)

To a solution of methyl 2-(4-hydroxy-3-nitrophenyl)acetate (1.0 g, 4.74 mmol) in $CH_3CN$ (10 ml), $K_2CO_3$ (0.327 g, 2.37 mmol) and (bromomethyl)cyclopropane (0.460 ml, 4.74 mmol) were added and the mixture was heated under MW irradiation at 100° C. for 1 hour. The insoluble inorganic salts were filtered off and the filtrate was evaporated to dryness to give crude methyl 2-(4-(cyclopropylmethoxy)-3-nitrophenyl)acetate (1.3 g, yield considered to be quantitative, MS/ESI$^+$265.9 [MH]$^+$). This crude was used without any additional purification.

Step 2: Synthesis of methyl 2-(3-amino-4-(cyclopropylmethoxy)phenyl)acetate (157)

To a solution of crude methyl 2-(4-(cyclopropylmethoxy)-3-nitrophenyl)acetate (theoric 4.74 mmol) in MeOH (50 ml), a catalytic amount of $PtO_2$ was added and the mixture was hydrogenated in a Parr apparatus at 30 psi for 15 minutes. The catalyst was filtered off, and the solvent was removed to give crude methyl 2-(3-amino-4-(cyclopropylmethoxy)phenyl)acetate (1.2 g, yield considered to be quantitative, MS/ESI$^+$ 236.0 [MH]$^+$). This crude was used without any additional purification.

Step 3: Synthesis of methyl 2-(4-(cyclopropylmethoxy)-3-(methylsulfonamido) phenyl)acetate (158)

To a solution of crude methyl 2-(3-amino-4-(cyclopropylmethoxy)phenyl)acetate (theoric 4.74 mmol) in pyridine (50 ml), methanesulfonyl chloride (0.406 ml, 5.10 mmol) was added, and the mixture was reacted for 3 hours at RT. The solvent was evaporated to dryness, and the residue was partitioned between EtOAc and HCl 1N; the aqueous phase was extracted with EtOAc (3×), and the combined organic layers were dried over $Na_2SO_4$. The solvent was removed under vacuum affording methyl 2-(4-(cyclopropylmethoxy)-3-(methylsulfonamido)phenyl)acetate (1.4 g, 4.47 mmol, 94.3% yield over 3 steps, MS/ESI$^+$ 313.9 [MH]$^+$). This intermediate was used without any additional purification.

Step 4: Synthesis of methyl 2-(3-(N-(tert-butoxycarbonyl)-methylsulfonamido)-4-(cyclopropylmethoxy) phenyl)acetate (159)

To a solution of methyl 2-(4-(cyclopropylmethoxy)-3-(methylsulfonamido)-phenyl)acetate (1.4 g, 4.47 mmol) in DCM (50 ml), DMAP (0.819 g, 6.70 mmol) and di-tert-butyl dicarbonate (1.463 g, 6.70 mmol) were added, and the mixture was stirred at RT for 2 hours. The mixture was partitioned between DCM and HCl 1N, and the organic phase was extracted three times with DCM. The combined organic layers were dried over $Na_2SO_4$ and the solvent was removed affording methyl 2-(3-(N-(tert-butoxycarbonyl)methylsulfonamido)-4-(cyclopropylmethoxy)phenyl)acetate (1.2 g, 2.90 mmol, 65% yield, MS/ESI$^+$ 435.9 [MNa]$^+$). This intermediate was used without any additional purification.

Step 5: Synthesis of 2-(3-(N-(tert-butoxycarbonyl) methylsulfonamido)-4-(cyclopropylmethoxy)phenyl) acetic acid (160)

To a solution of methyl 2-(3-(N-(tert-butoxycarbonyl)methylsulfonamido)-4-(cyclopropylmethoxy)phenyl)acetate (1.2 g, 2.90 mmol) in THF:water=1:1 (35 ml), LiOH (0.695 g, 29.0 mmol) was added, and the mixture was reacted for 30 minutes at RT. THF was evaporated, and the aqueous residue was acidified with HCl 6N (pH=7). The mixture was extracted with EtOAc (3×), and the combined organic layers were dried over $Na_2SO_4$. The solvent was removed under vacuum affording 2-(3-(N-(tert-butoxycarbonyl)methylsulfonamido)-4-(cyclopropylmethoxy)phenyl)acetic acid (1.1 g, 2.75 mmol, 95% yield, MS/ESI$^+$ 400.0 [MH]$^+$). This intermediate was used without any additional purification.

Step 6: Synthesis of ethyl 2-(trityloxy)acetate (161)

To a solution of (chloromethanetriyl)tribenzene (9.8 g, 35.2 mmol) in DCM (500 ml), ethyl 2-hydroxyacetate (4.33 ml, 45.7 mmol) and Py (3.70 ml, 45.7 mmol) were added at RT. The reaction was heated at 50° C. for 9 hours. HCl 2N was added to the mixture, and the organic phase was separated, dried over $Na_2SO_4$ and evaporated under vacuum. The resulting white solid was triturated in Hexane. Ethyl 2-(trityloxy)acetate was obtained (8.2 g, 23.67 mmol, 67.3% yield) and used in the following step without further purification.

Step 7: Synthesis of 2-(trityloxy)acetic acid (162)

To a suspension of ethyl 2-(trityloxy)acetate (8.2 g, 23.67 mmol) in EtOH (350 ml), NaOH 6M (7.89 ml, 47.3 mmol) was added at RT. The suspension slowly turned into a solution. After 1 hour, EtOH was removed under vacuum and the remaining crude was partitioned between HCl 2N and DCM. The organic phase was separated, dried over $Na_2SO_4$ and evaporated under vacuum. 2-(Trityloxy)acetic acid was obtained (7.42 g, 23.31 mmol, 98% yield) and used as such in the following reaction without further purification.

Step 8: Synthesis of (S)-3,5-dichloro-4-(2-(3-(cyclopropylmethoxy)-4-(difluoromethoxy)phenyl)-2-(2-(trityloxy)acetoxy)ethyl)pyridine 1-oxide (163)

To a solution of 2-(trityloxy)acetic acid (7.2 g, 22.62 mmol) in DCM (250 ml), (S)-3,5-dichloro-4-(2-(3-(cyclopropylmethoxy)-4-(difluoromethoxy)phenyl)-2-hydroxyethyl)pyridine 1-oxide (7.92 g, 18.85 mmol), EDC (4.34 g, 22.62 mmol), and DMAP (4.60 g, 37.7 mmol) were added at RT. The solution was stirred at the same temperature overnight. A sat. sol. of $K_2CO_3$ was added, and the organic phase was separated, washed with HCl 2N and brine, dried over $Na_2SO_4$ and evaporated under vacuum. The resulting brown crude was purified by flash chromatography on silica gel (DCM 100% as eluent). (S)-3,5-dichloro-4-(2-(3-(cyclopropylmethoxy)-4-(difluoromethoxy)phenyl)-2-(2-(trityloxy)acetoxy)ethyl)pyridine 1-oxide was obtained (8.53 g, 11.84 mmol, 62.8% yield, MS/ESI$^+$ 720.1 [MH]$^+$).

Step 9: Synthesis of (S)-3,5-dichloro-4-(2-(3-(cyclopropylmethoxy)-4-(difluoromethoxy)phenyl)-2-(2-hydroxyacetoxy)ethyl)pyridine 1-oxide (164)

To a solution of (S)-3,5-dichloro-4-(2-(3-(cyclopropylmethoxy)-4-(difluoromethoxy)phenyl)-2-(2-(trityloxy)acetoxy)ethyl)pyridine 1-oxide (4.0 g, 5.55 mmol) in DCM (1 Lt) cooled at 0° C., 160 drops of 48% HBr were added, and the reaction was stirred for 1 hour (temperature below 10° C.). Water was added to the mixture, the organic phase was separated, dried over $Na_2SO_4$ and evaporated under vacuum (bath temperature=25° C.). The crude compound was dissolved in DCM, and hexanes was added. The white precipitate thus formed was filtered and washed with plenty of hexanes. After drying, (S)-3,5-dichloro-4-(2-(3-(cyclopropylmethoxy)-4-(difluoromethoxy)phenyl)-2-(2-hydroxyacetoxy)ethyl)pyridine 1-oxide was obtained (2.26 g, 4.73 mmol, 76% yield, MS/ESI$^+$ 478.0 [MH]$^+$) and used in the following step without further purification.

Step 10: Synthesis of (S)-4-(2-(2-(2-(3-(N-(tert-butoxycarbonyl)-methylsulfonamido)-4-(cyclopropylmethoxy)phenyl)acetoxy)acetoxy)-2-(3-(cyclopropylmethoxy)-4-(difluoromethoxy)phenyl)ethyl)-3,5-dichloropyridine 1-oxide (165)

To a solution of 2-(3-(N-(tert-butoxycarbonyl)methylsulfonamido)-4-(cyclopropylmethoxy)phenyl)acetic acid (0.200 g, 0.501 mmol) in DCM (5 ml), (S)-3,5-dichloro-4-(2-(3-(cyclopropylmethoxy)-4-(difluoromethoxy)phenyl)-2-(2-hydroxyacetoxy)ethyl)pyridine 1-oxide (0.239 g, 0.501 mmol), EDC (0.288 g, 1.502 mmol), and DMAP (0.0306 g, 0.250 mmol) were added, and the mixture was reacted for 5 hours. A 1N solution of HCl was added, and the desired compound was extracted with DCM (3×) recovering the crude desired product (0.450 g, yield considered to be quantitative, MS/ESI$^+$ 859.3 [MH]$^+$) that was used in the following step without further purification.

Step 11: Synthesis of (S)-3,5-dichloro-4-(2-(2-(2-(4-(cyclopropylmethoxy)-3-(methylsulfonamido)phenyl)acetoxy)acetoxy)-2-(3-(cyclopropylmethoxy)-4-(difluoromethoxy)phenyl)ethyl)pyridine 1-oxide (166)

To a solution of crude (S)-4-(2-(2-(2-(3-(N-(tert-butoxycarbonyl)-methylsulfonamido)-4-(cyclopropylmethoxy)phenyl)acetoxy)acetoxy)-2-(3-(cyclopropylmethoxy)-4-(difluoromethoxy)phenyl)ethyl)-3,5-dichloropyridine 1-oxide (theoric 0.501 mmol) in DCM (5 ml), HCl 4M in dioxane (1.309 ml, 5.23 mmol) was added and the mixture was reacted for 4 hours at RT. The solvents were evaporated to dryness, and the resulting crude was purified by preparative LC-MS recovering the desired product (102.5 mg, 0.135 mmol, 26.9% yield over two steps, MS/ESI$^+$ 759.46 [MH]$^+$, [α$_D$]=+ 47.84, c=0.25, DCM).

$^1$H NMR (300 MHz, DMSO-d$_6$) δ ppm 8.76 (s, 1 H), 8.53 (s, 2 H), 7.11-7.22 (m, 2 H), 7.02-7.11 (m, 2 H), 6.98 (d, 1 H), 6.92 (dd, 1 H), 7.06 (t, 1 H), 5.99 (dd, 1 H), 4.73 (d, 1 H), 4.65 (d, 1 H), 3.81-3.97 (m, 4 H), 3.68 (s, 2 H), 3.43 (dd, 1 H), 3.23 (dd, 1 H), 2.99 (s, 3 H), 1.02-1.44 (m, 2 H), 0.44-0.69 (m, 4 H), 0.15-0.44 (m, 4 H)

The compounds listed in Table 12 were prepared with an analogous procedure to that described in Example 21, Step 6-10, by reacting the appropriate precursors (commercially available or synthesized by a person skilled in the art) with suitable reagents, and where purification step has been performed as indicated in Table 12 or under appropriate conditions known to the person skilled in the art.

TABLE 12

| Structure | Cmp | NMR characterization | MS/ESI$^+$ [MH]$^+$ [α$_D$] | Starting Material | Purification method |
|---|---|---|---|---|---|
| 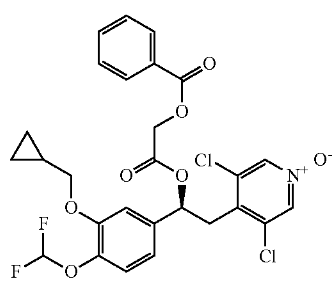 | 167 | $^1$H NMR (300 MHz, DMSO-d$_6$) δ ppm 8.51 (s, 2 H), 7.92-8.06 (m, 2 H), 7.65-7.77 (m, 1 H), 7.48-7.63 (m, 2 H), 7.18 (d, 1 H), 7.08 (d, 1 H), 6.97 (dd, 1 H), 7.07 (t, 1 H), 6.06 (dd, 1 H), 4.97 (d, 1 H), 4.89 (d, 1 H), 3.89 (d, 2 H), 3.45 (dd, 1 H), 3.25 (dd, 1 H), 1.07-1.34 (m, 1 H), 0.46-0.67 (m, 2 H), 0.25-0.45 (m, 2 H) | 582.17 [α$_D$] = −25.65 (c = 0.361, DCM) | Intermediate of Step 10 | Flash chromatography on silica gel (DCM/MeOH = 100/2) |
| 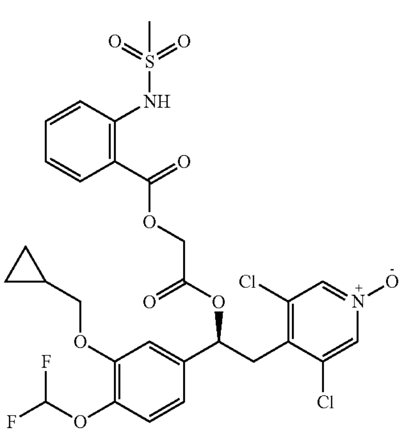 | 168 | $^1$H NMR (300 MHz, DMSO-d$_6$) δ ppm 9.78 (s, 1 H), 8.51 (s, 2 H), 7.99 (dd, 1 H), 7.70 (td, 1 H), 7.61 (d, 1 H), 7.27 (td, 1 H), 7.19 (d, 1 H), 7.11 (d, 1 H), 6.99 (dd, 1 H), 7.13 (t, 1 H), 6.08 (dd, 1 H), 5.02 (d, 1 H), 4.92 (d, 1 H), 3.89 (d, 2 H), 3.48 (dd, 1 H), 3.25 (d, 1 H), 3.19 (s, 3 H), 0.99-1.34 (m, 1 H), 0.46-0.68 (m, 2 H), 0.16-0.45 (m, 2 H) | 675.37 [α$_D$] = −54.72 (c = 0.246, DCM) | Intermediate of Step 10 | Flash chromatography on silica gel (DCM/MeOH = 100/2) |

TABLE 12-continued

| Structure | Cmp | NMR characterization | MS/ESI+ [MH]+ [α_D] | Starting Material | Purification method |
|---|---|---|---|---|---|
| 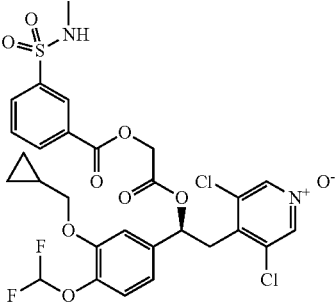 | 169 | $^1$H NMR (300 MHz, DMSO-d$_6$) δ ppm 8.52 (s, 2 H), 8.33 (t, 1 H), 8.20 (dt, 1 H), 8.09 (dt, 1 H), 7.82 (t, 1 H), 7.66 (s, 1 H), 7.19 (d, 1 H), 7.10 (d, 1 H), 6.98 (dd, 1 H), 7.07 (t, 1 H), 6.06 (dd, 1 H), 5.03 (d, 1 H), 4.95 (d, 1 H), 3.90 (d, 2 H), 3.47 (dd, 1 H), 3.26 (dd, 1 H), 2.44 (s, 3 H), 1.02-1.39 (m, 1 H), 0.48-0.72 (m, 2 H), 0.14-0.48 (m, 2 H) | 675.21 [α_D] = −60.82 (c = 0.388 DCM) | 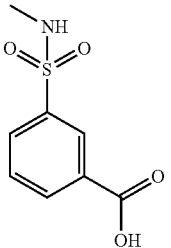 Intermediate of Step 10 | Flash chromatography on silica gel (DCM/MeOH = 100/2) followed by crystallization from abs. EtOH |
| 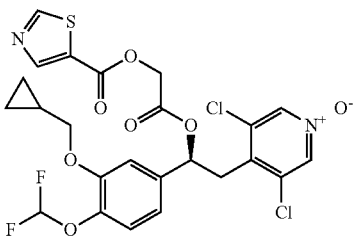 | 317 | $^1$H NMR (300 MHz, DMSO-d$_6$) d ppm 9.43 (δ, 1 H), 8.58 (d, 1 H), 8.52 (s, 2 H), 7.18 (d, 1 H), 7.08 (d, 1 H), 6.97 (dd, 1 H), 7.08 (t, 1 H), 6.04 (dd, 1 H), 4.98 (d, 1 H), 4.90 (d, 1 H), 3.90 (d, 2 H), 3.46 (dd, 1 H), 3.25 (dd, 1 H), 1.14-1.33 (m, 1 H), 0.48-0.66 (m, 2 H), 0.18-0.47 (m, 2 H) | 589.07 −34.44 c = 0.5 MeOH | 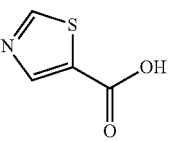 | |
| 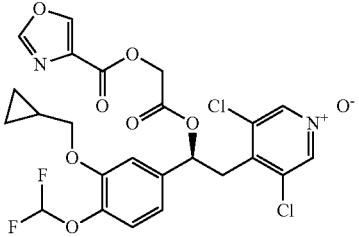 | 318 | $^1$H NMR (300 MHz, DMSO-d$_6$) d ppm 8.93 (δ, 1 H), 8.59 (d, 1 H), 8.52 (s, 2 H), 7.18 (d, 1 H), 7.08 (d, 1 H), 6.97 (dd, 1 H), 7.07 (t, 1 H), 6.04 (dd, 1 H), 4.94 (d, 1 H), 4.86 (d, 1 H), 3.91 (d, 2 H), 3.45 (dd, 1 H), 3.25 (dd, 1 H), 1.14-1.33 (m, 1 H), 0.48-0.71 (m, 2 H), 0.23-0.47 (m, 2 H) | 573.2 −22 c = 0.5 DCM | 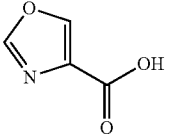 | |
| 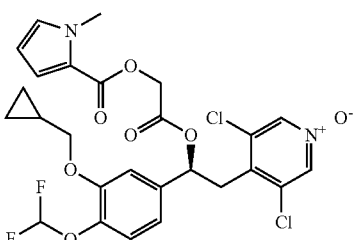 | 319 | $^1$H NMR (300 MHz, DMSO-d$_6$) δ ppm 8.49 (s, 2 H), 7.13-7.26 (m, 2 H), 7.10 (d, 1 H), 6.98 (dd, 1 H), 6.90 (dd, 1 H), 7.07 (t, 1 H), 6.13 (dd, 1 H), 6.06 (dd, 1 H), 4.81 (d, 1 H), 4.74 (d, 1 H), 3.90 (d, 2 H), 3.81 (s, 3 H), 3.46 (dd, 1 H), 3.25 (dd, 1 H), 1.17-1.28 (m, 1 H), 0.51-0.66 (m, 2 H), 0.28-0.40 (m, 2 H) | 585.24 −58.36 c = 0.5 MeOH | 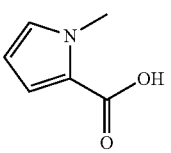 | |
| 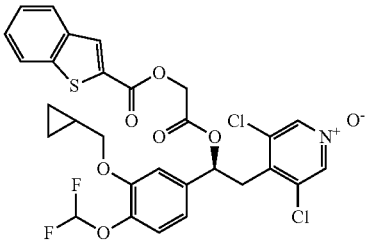 | 320 | $^1$H NMR (300 MHz, DMSO-d$_6$) δ ppm 8.52 (s, 2 H), 8.27 (s, 1 H), 8.00-8.15 (m, 2 H), 7.58 (ddd, 1 H), 7.46-7.54 (m, 1 H), 7.18 (d, 1 H), 7.09 (d, 1 H), 6.98 (dd, 1 H), 7.07 (t, 1 H), 6.06 (dd, 1 H), 5.02 (d, 1 H), 4.94 (d, 1 H), 3.88 (d, 2 H), 3.47 (dd, 1 H), 3.26 (dd, 1 H), 1.13-1.23 (m, 1 H), 0.50-0.63 (m, 2 H), 0.25-0.41 (m, 2 H) | 638.24 −51.68 c = 0.5 MeOH | 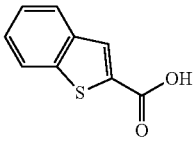 [SMILES: O=C(O)c1cc2ccccc2s1] | |

TABLE 12-continued

| Structure | Cmp | NMR characterization | MS/ESI+ [MH]+ [α_D] | Starting Material | Purification method |
|---|---|---|---|---|---|
| 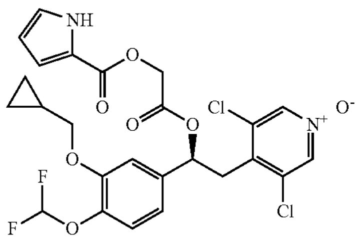 | 321 | 1H NMR (300 MHz, DMSO-d6) δ ppm 11.94 (br. s., 1 H), 8.51 (s, 2 H), 7.17 (d, 1 H), 7.04-7.09 (m, 2 H), 6.96 (dd, 1 H), 6.82-6.87 (m, 1 H), 7.07 (t, 1 H), 6.17-6.25 (m, 1 H), 6.03 (dd, 1 H), 4.85 (d, 1 H), 4.78 (d, 1 H), 3.88 (d, 2 H), 3.45 (dd, 1 H), 3.25 (dd, 1 H), 1.13-1.28 (m, 1 H), 0.46-0.68 (m, 2 H), 0.23-0.46 (m, 2 H) | 571.30 −37.78 c = 0.5 MeOH | | |
| 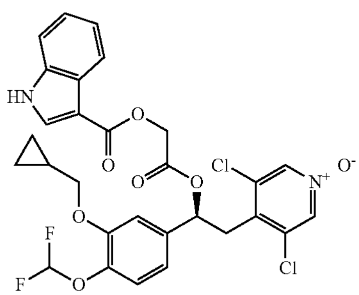 | 322 | 1H NMR (300 MHz, DMSO-d6) δ ppm 12.01 (br. s., 1 H), 8.52 (s, 2 H), 8.11 (d, 1 H), 7.99 (dd, 1 H), 7.50 (dd, 1 H), 7.14-7.27 (m, 3 H), 7.10 (d, 1 H), 6.98 (dd, 1 H), 6.94 (t, 1 H), 6.07 (dd, 1 H), 4.90 (d, 1 H), 4.85 (d, 1H), 3.87 (d, 2 H), 3.46 (dd, 1 H), 3.24 (d, 1 H), 1.14-1.23 (m, 1 H), 0.43-0.64 (m, 2 H), 0.19-0.43 (m, 2 H) | 621.30 −23.04 c = 0.5 MeOH | | |
| 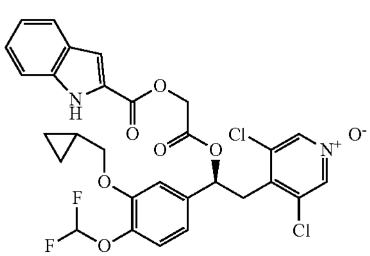 | 323 | 1H NMR (300 MHz, DMSO-d6) δ ppm 11.96 (s, 1 H), 8.53 (s, 2 H), 7.69 (d, 1 H), 7.47 (dd, 1 H), 7.25-7.32 (m, 1 H), 7.22 (d, 1 H), 7.18 (d, 1 H), 7.06-7.14 (m, 2 H), 6.98 (dd, 1 H), 7.07 (t, 1 H), 6.06 (dd, 1 H), 4.99 (d, 1 H), 4.91 (d, 1 H), 3.87 (d, 2 H), 3.47 (dd, 1 H), 3.26 (dd, 1 H), 1.04-1.23 (m, 1 H), 0.44-0.65 (m, 2 H), 0.18-0.44 (m, 2 H) | −62.72 c = 0.5 MeOH | | |

The compounds listed in Table 13 were prepared with an analogous procedure to that described in Example 21, Step 2-11, by reacting the appropriate precursors (commercially available or synthesized by a person skilled in the art) with suitable reagents, and where purification step has been performed as indicated in Table 13.

TABLE 13

| Structure | Cmp | NMR characterization | MS/ESI+ [MH]+ [α$_D$] | Starting Material (and conditions, if different) | Purification method |
|---|---|---|---|---|---|
| 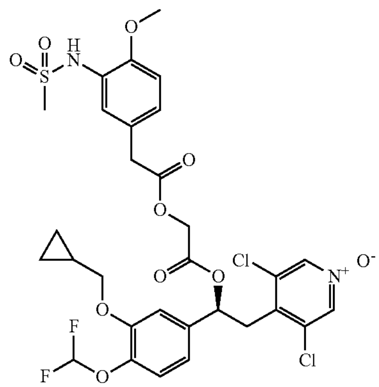 | 170 | $^1$H NMR (300 MHz, DMSO-d$_6$) δ ppm 8.82 (s, 1 H), 8.54 (s, 2 H), 7.19 (d, 1 H), 7.16 (d, 1 H), 7.08 (dd, 1 H), 7.05 (d, 1 H), 7.01 (d, 1 H), 6.93 (dd, 1 H), 7.06 (t, 1 H), 5.99 (dd, 1 H), 4.73 (d, 1 H), 4.65 (d, 1 H), 3.89 (d, 2 H), 3.81 (s, 3 H), 3.69 (s, 2 H), 3.46-3.54 (m, 1 H), 3.23 (dd, 1 H), 2.94 (s, 3 H), 1.11-1.37 (m, 1 H), 0.47-0.66 (m, 2 H), 0.25-0.47 (m, 2 H) | 719.41 [α$_D$] = −47.52 (c = 0.25 DCM) | | Preparative LC/MS |
| 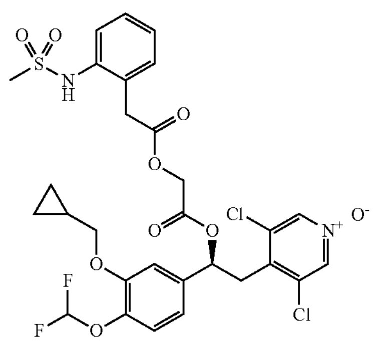 | 171 | $^1$H NMR (300 MHz, DMSO-d$_6$) δ ppm 9.10 (s, 1 H), 8.54 (s, 2 H), 7.28-7.40 (m, 3 H), 7.20-7.27 (m, 1 H), 7.17 (d, 1 H), 7.07 (d, 1 H), 6.95 (dd, 1 H), 7.06 (t, 1 H), 6.00 (dd, 1 H), 4.73 (d, 1 H), 4.65 (d, 1 H), 3.91 (s, 2 H), 3.88 (d, 2 H), 3.45 (dd, 1 H), 3.25 (dd, 1 H), 2.91 (s, 3 H), 1.05-1.33 (m, 1 H), 0.46-0.64 (m, 2 H), 0.18-0.41 (m, 2 H) | 689.39 [α$_D$] = −35.50 (c = 0.25 DCM) | | Preparative LC MS |
| 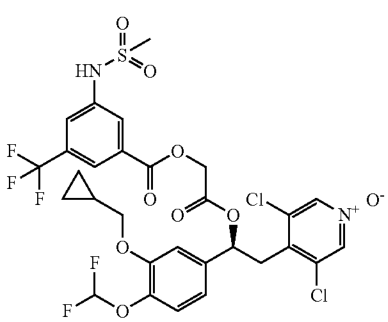 | 172 | $^1$H NMR (300 MHz, DMSO-d$_6$) δ ppm 9.80-11.14 (m, 1 H), 8.51 (s, 2 H), 8.04 (s, 1 H), 7.82 (s, 1 H), 7.74 (s, 1 H), 7.18 (d, 1 H), 7.09 (d, 1 H), 6.98 (dd, 1 H) 6.82 (t, 1 H), 6.05 (dd, 1 H), 5.02 (d, 1 H), 4.94 (d, 1 H), 3.90 (d, 2 H), 3.39-3.56 (m, 1 H), 3.24 (d, 1 H), 3.07 (s, 3 H), 1.05-1.35 (m, 1 H), 0.45-0.65 (m, 2 H), 0.13-0.42 (m, 2 H) | 743.1 [α$_D$] = −63.77 (c = 0.26, DCM) | (Step 2: 10% Pd/C, MeOH, 30 psi; Step 3: DCM, pyridine (3 eq.), r.t. Step 4: HCl | Trituration with MeOH/acetone mixture |
| 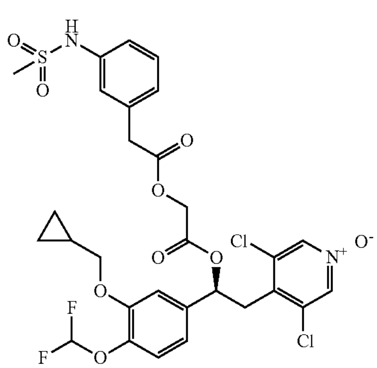 | 173 | $^1$H NMR (300 MHz, DMSO-d$_6$) δ ppm 9.73 (br. s., 1 H), 8.54 (s, 2 H), 7.24-7.30 (m, 1 H), 7.16 (d, 1 H), 7.08-7.13 (m, 2 H), 7.05 (d, 1 H), 7.00 (d, 1 H), 6.93 (dd, 1 H), 7.06 (t, 1 H), 5.99 (dd, 1 H), 4.74 (d, 1 H), 4.66 (d, 1 H), 3.89 (d, 2 H), 3.73 (s, 2 H), 3.43 (dd, 1 H), 3.23 (dd, 1 H), 2.96 (s, 3 H), 1.01-1.33 (m, 1 H), 0.42-0.67 (m, 2 H), 0.15-0.45 (m, 2 H) | 689.37 [α$_D$] = −64.08 (c = 0.25 DCM) | | Preparative LC MS followed by trituration with MeOH |

TABLE 13-continued

| Structure | Cmp | NMR characterization | MS/ESI+ [MH]+ [α_D] | Starting Material (and conditions, if different) | Purification method |
|---|---|---|---|---|---|
| (structure shown) | 174 | ¹H NMR (300 MHz, DMSO-d₆) δ ppm 9.67 (s, 1 H), 8.53 (s, 2 H), 7.20-7.27 (m, 2 H), 7.11-7.19 (m, 3 H), 7.05 (d, 1 H), 6.92 (dd, 1 H), 7.06 (dd, 1 H), 5.99 (dd, 1 H), 4.74 (d, 1 H), 4.66 (d, 1 H), 3.88 (d, 2 H), 3.71 (s, 2 H), 3.46-3.54 (m, 1 H), 3.23 (dd, 1 H), 2.96 (s, 3 H), 1.10-1.30 (m, 1 H), 0.46-0.68 (m, 2 H), 0.23-0.45 (m, 2 H) | 689.32 [α_D] = −48.96 (c = 0.125 DCM) | (structure shown with NO₂) | Two preparative LC MS |

The compounds listed in Table 14 were prepared with an analogous procedure to that described in Example 21, Step 3-11, by reacting the appropriate precursors (commercially available or synthesized by a person skilled in the art) with suitable reagents, and where purification step has been performed as indicated in Table 14.

TABLE 14

| Structure | Cmp | NMR characterization | MS/ESI+ [MH]+ [α_D] | Starting Material (and conditions, if different) | Purification method |
|---|---|---|---|---|---|
| (structure shown) | 175 | ¹H NMR (300 MHz, DMSO-d₆) δ ppm 10.38 (br. s., 1 H), 8.50 (s, 2 H), 7.92 (m, 2 H), 7.32 (m, 2 H), 7.18 (d, 1 H), 7.08 (d, 1 H), 6.97 (dd, 1 H), 7.07 (t, 1 H), 6.05 (dd, 1 H), 4.92 (d, 1 H), 4.85 (d, 1 H), 3.89 (d, 2 H), 3.45 (dd, 1 H), 3.25 (dd, 1 H), 3.13 (s, 3 H), 1.11-1.34 (m, 1 H), 0.47-0.70 (m, 2 H), 0.18-0.44 (m, 2 H) | 675.17 [α_D] = −37.86 (c = 0.327 DCM) | (structure shown with H₂N) Step 3: DCM, pyridine (2 eq.), RT Step 5: MeOH, RT Step 10: HCl 4N in dioxane was directly added to the reaction mixture | Flash chromatography on silica gel (DCM/MeOH = 100/2) followed by flash chromatography on silica gel (toluene/EtOAc = 1/1.2) |
| (structure shown) | 175 bis | ¹H NMR (300 MHz, DMSO-d₆) δ ppm 10.03 (br. s., 1 H), 8.51 (s, 2 H), 7.84 (d, 1 H), 7.62-7.76 (m, 1 H), 7.44-7.59 (m, 2 H), 7.18 (d, 1 H), 7.09 (d, 1 H), 6.97 (dd, 1 H), 7.07 (t, 1 H), 6.05 (dd, 1 H), 4.97 (d, 1 H), 4.90 (d, 1 H), 3.89 (d, 2 H), 3.46 (dd, 1 H), 3.19-3.28 (m, 1 H), 3.02 (s, 3 H), 1.08-1.32 (m, 1 H), 0.49-0.69 (m, 2 H), 0.25-0.40 (m, 2 H) | 675.15 [α_D] = −48.70 (c = 0.522 DCM) | (structure shown with NH₂) Step 3: DCM, pyridine (2 eq.), r.t. Step 5: MeOH, r.t Step 10: HCl 4N in dioxane was directly added to the reaction mixture | Flash chromatography on silica gel (DCM/MeOH = 100/2) |

The compounds listed in Table 15 were prepared with an analogous procedure to that described in Example 21, Step 3 and 5-10, by reacting the appropriate precursors (commercially available or synthesized by a person skilled in the art) with suitable reagents, and where purification step has been performed as indicated in Table 15.

TABLE 15

| Structure | Cmp | NMR characterization | MS/ESI+ [MH]+ [α_D] | Starting Material (and Conditions, if different) | Purification method |
|---|---|---|---|---|---|
| (structure shown) | 177 | ¹H NMR (300 MHz, DMSO-d₆) δ ppm 10.03 (br. S., 1 H), 8.51 (s, 2 H), 7.45 (t, 1 H), 7.15-7.23 (m, 2 H), 7.04-7.10 (m, 2 H), 6.98 (dd, 1 H), 7.07 (t, 1 H), 6.05 (dd, 1 H), 4.96 (d, 1 H), 4.88 (d, 1 H), 3.89 (d, 2 H), 3.81 (s, 3 H), 3.46 (dd, 1 H), 3.26 (dd, 1 H), 3.02 (s, 3 H), 1.08-1.32 (m, 1 H), 0.48-0.65 (m, 2 H), 0.27-0.44 (m, 2 H) | 705.29 [α_D] = −49.01 (c = 0.322, DCM) | (structure shown) Step 3: DCM, pyridine (2 eq.), RT Step 5: MeOH, reflux | Flash chromatography on silica gel (petroleum ether/ EtOAc = 21/1) followed by cystallization from EtOH |

Example 22

Synthesis of (S)-3,5-dichloro-4-(2-(3-(cyclopropylmethoxy)-4-(difluoromethoxy)phenyl)-2-(2-(4-(methylsulfonamidomethyl)benzoyloxy)-acetoxy)ethyl) pyridine 1-oxide (181)

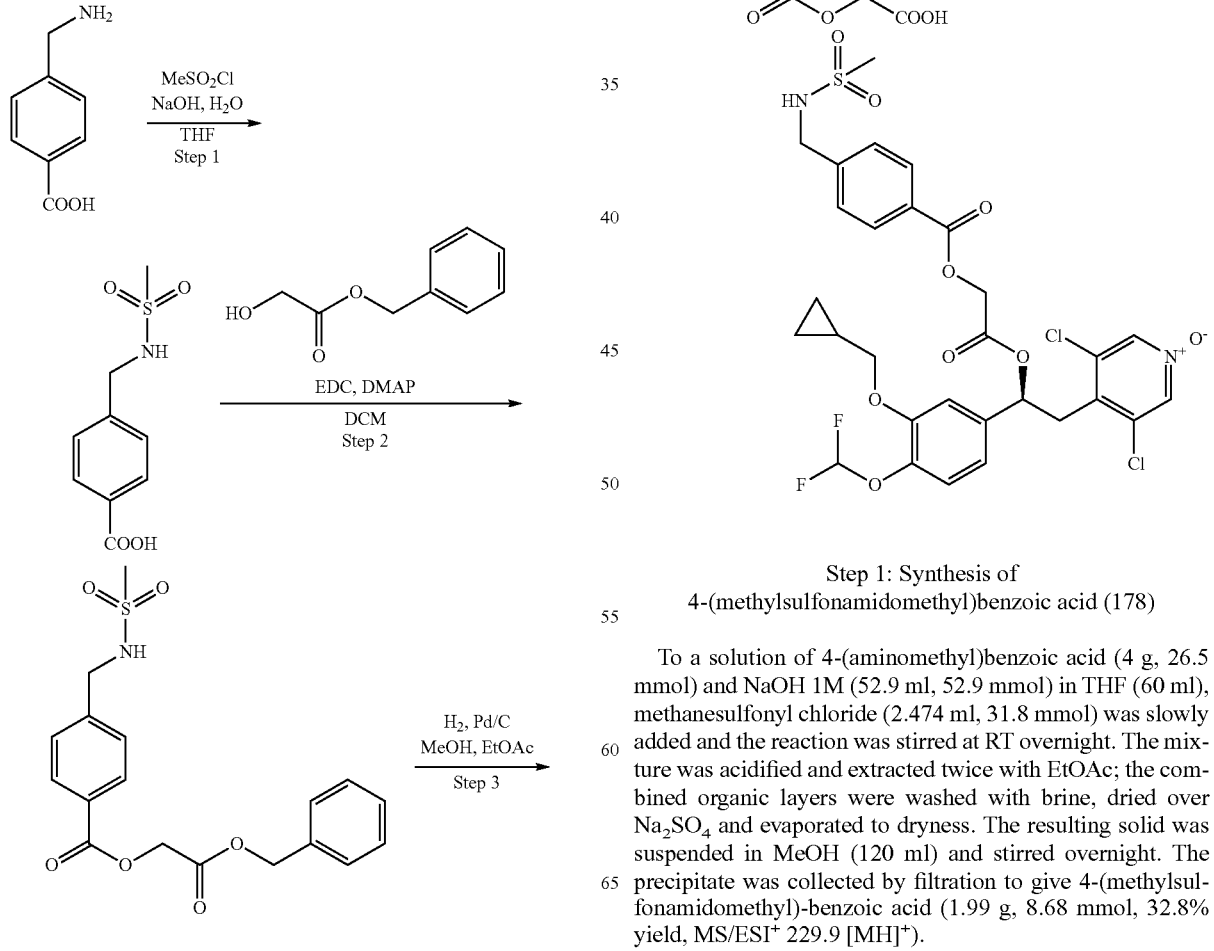

Scheme 22

Step 1: Synthesis of 4-(methylsulfonamidomethyl)benzoic acid (178)

To a solution of 4-(aminomethyl)benzoic acid (4 g, 26.5 mmol) and NaOH 1M (52.9 ml, 52.9 mmol) in THF (60 ml), methanesulfonyl chloride (2.474 ml, 31.8 mmol) was slowly added and the reaction was stirred at RT overnight. The mixture was acidified and extracted twice with EtOAc; the combined organic layers were washed with brine, dried over Na₂SO₄ and evaporated to dryness. The resulting solid was suspended in MeOH (120 ml) and stirred overnight. The precipitate was collected by filtration to give 4-(methylsulfonamidomethyl)-benzoic acid (1.99 g, 8.68 mmol, 32.8% yield, MS/ESI⁺ 229.9 [MH]⁺).

Step 2: Synthesis of 2-(benzyloxy)-2-oxoethyl 4-(methylsulfonamidomethyl)benzoate (179)

To a solution of 4-(methylsulfonamidomethyl)benzoic acid (0.4 g, 1.745 mmol) and benzyl 2-hydroxyacetate (0.290 g, 1.745 mmol) in a mixture of DCM and THF 1/1 (50 ml), EDC (0.334 g, 1.745 mmol) and DMAP (0.256 g, 2.094 mmol) were added in one portion. The reaction was stirred at RT for 3 hours. The solvent was removed under vacuum and the resulting crude was portioned between EtOAc and HCl 2N. The organic phase was separated, washed with brine and dried over Na$_2$SO$_4$. The solvent was removed under vacuum affording 2-(benzyloxy)-2-oxoethyl 4-(methylsulfonamidomethyl)benzoate (0.4 g, 1.060 mmol, 60.7% yield, MS/ESI$^+$ 377.9 [MH]$^+$). This product was employed in the following step without any further purification.

Step 3: Synthesis of 2-(4-(methylsulfonamidomethyl)benzoyloxy)acetic acid (180)

A mixture of 2-(benzyloxy)-2-oxoethyl 4-(methylsulfonamidomethyl)-benzoate (0.4 g, 1.060 mmol) and 10% w/w Pd/C (0.056 g, 0.053 mmol) in EtOAc and MeOH 1/1 (30 ml) was shaken under H$_2$ atmosphere (25 psi) for 4 hours. The catalyst was removed by filtration and the filtrate was evaporated to dryness affording 2-(4-(methyl-sulfonamidomethyl)benzoyloxy)acetic acid (0.3 g, 1.044 mmol, 99% yield). The product was used without purification.

Step 4: Synthesis of (S)-3,5-dichloro-4-(2-(3-(cyclopropylmethoxy)-4-(difluoromethoxy)phenyl)-2-(2-(4-(methylsulfonamidomethyl)benzoyloxy)-acetoxy)ethyl)pyridine 1-oxide (181)

The final product was purified by preparative HPLC to give 0.1 g of the title compound (0.145 mmol, 13.89% yield) starting from (S)-3,5-dichloro-4-(2-(3-(cyclopropylmethoxy)-4-(difluoromethoxy)phenyl)-2-hydroxyethyl)pyridine 1-oxide (0.527 g, 1.253 mmol) and 2-(4-(methylsulfonamidomethyl)benzoyloxy)acetic acid (0.3 g, 1.044 mmol, Compound 180) with DMAP (0.153 g, 1.253 mmol) and EDC (0.200 g, 1.044 mmol) in DCM/THF=1/1 (70 ml), using an analogous procedure to that described in Scheme 15, Step 4.

MS/ESI$^+$ 689.27 [MH]$^+$, [α$_D$]=−24.36, c 0.5, DCM $^1$H NMR (300 MHz, DMSO-d6) δ ppm 8.51 (s, 2 H), 7.90-7.99 (m, 2 H), 7.66 (t, 1 H), 7.49-7.57 (m, 2 H), 7.18 (d, 1 H), 7.08 (d, 1 H), 6.97 (dd, 1 H), 7.07 (t, 1 H), 6.05 (dd, 1 H), 4.96 (d, 1 H), 4.88 (d, 1 H), 4.27 (d, 2 H), 3.90 (d, 2 H), 3.45 (dd, 1 H), 3.25 (dd, 1 H), 2.90 (s, 3 H), 1.02-1.37 (m, 1 H), 0.49-0.73 (m, 2 H), 0.26-0.45 (m, 2 H).

Example 23

Synthesis of (S)-3,5-dichloro-4-(2-(2-(4-(cyclopropylmethoxy)-3-(methylsulfonyloxy)benzoyloxy)acetoxy)-2-(3-(cyclopropylmethoxy)-4-(difluoromethoxy)phenyl)ethyl)pyridine 1-oxide (187)

Scheme 23

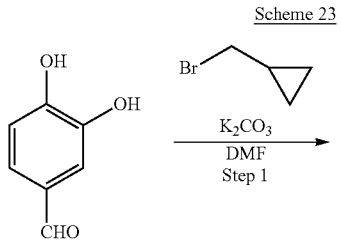

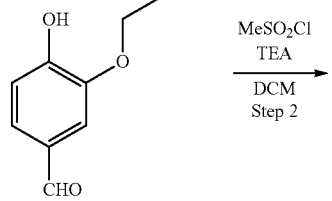

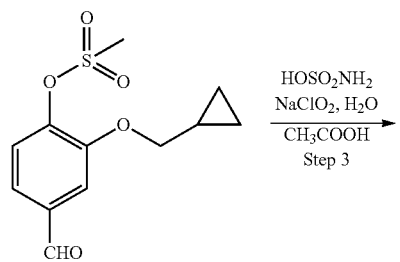

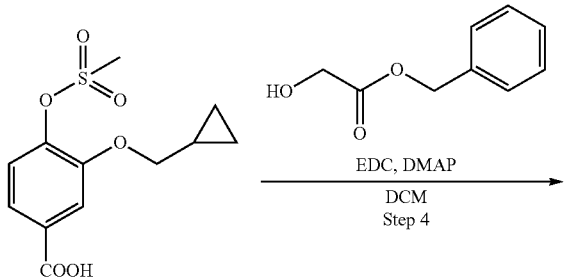

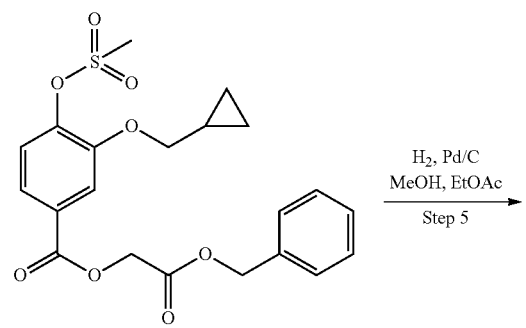

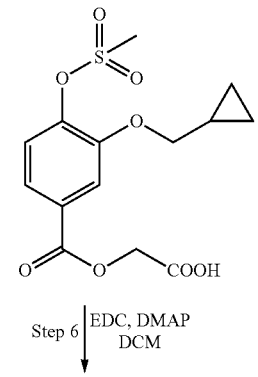

-continued

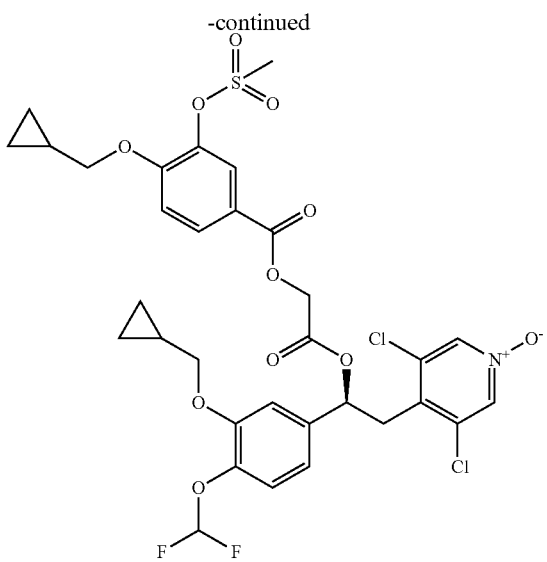

Step 1: Synthesis of 4-(cyclopropylmethoxy)-3-hydroxybenzaldehyde (182)

A mixture of 3,4-dihydroxybenzaldehyde (0.5 g, 3.62 mmol), $K_2CO_3$ (0.550 g, 3.98 mmol) and (bromomethyl)cyclopropane (0.386 ml, 3.98 mmol) in DMF (12 ml) was heated to 50° C. overnight. The reaction mixture was portioned between EtOAc and HCl 1N. The organic phase was washed several times with brine and dried over $Na_2SO_4$; the solvent was removed; and the crude was purified by flash chromatography on silica gel cartridge (petroleum ether:EtOAc=90:10 to 85:15) to give 4-(cyclopropylmethoxy)-3-hydroxybenzaldehyde (0.370 g, 1.925 mmol, 53.2% yield, MS/ESI$^+$ 193.0 [MH]$^+$).

Step 2: Synthesis of 2-(cyclopropylmethoxy)-5-formylphenyl methanesulfonate (183)

To a solution of 4-(cyclopropylmethoxy)-3-hydroxybenzaldehyde (0.440 g, 2.289 mmol) in DCM (20 m), TEA (0.479 ml, 3.43 mmol) was added followed by methanesulfonyl chloride (0.196 ml, 2.52 mmol), and the mixture was stirred at RT overnight. A second portion of TEA (0.096 ml, 0.687 mmol) and methanesulfonyl chloride (0.054 ml, 0.687 mmol) was added, and the reaction was stirred at RT for additional 3 hours. The mixture was washed with HCl 1N and twice with $K_2CO_3$ 1N. The organic layer was dried over $Na_2SO_4$, and the solvent was removed under vacuum affording 2-(cyclopropylmethoxy)-5-formylphenyl methanesulfonate (0.565 g, 2.090 mmol, 91% yield, MS/ESI$^+$ 270.9 [MH]$^+$). This crude was used for the next step without purification.

Step 3: Synthesis of 4-(cyclopropylmethoxy)-3-(methylsulfonyloxy)benzoic acid (184)

A mixture of 2-(cyclopropylmethoxy)-5-formylphenyl methanesulfonate (0.565 g, 2.090 mmol) and sulfamic acid (0.223 g, 2.299 mmol) in acetic acid (8 ml) was cooled to 0° C., and a solution of sodium chlorite (0.378 g, 4.18 mmol) in water (3 ml) was added. The resulting yellow mixture was allowed to warm to RT and stirred for 2 hours. Additional sulfamic acid (0.081 g, 0.836 mmol) and sodium chlorite (0.133 g, 1.463 mmol) in water (2 ml) were added over 1 hour. The reaction mixture was diluted with water (15 ml), and the precipitate was collected by filtration, washed with water and dried to obtain 4-(cyclopropylmethoxy)-3-(methylsulfonyloxy)benzoic acid (0.521 g, 1.820 mmol, 87% yield, MS/ESI$^+$ 286.9 [MH]$^+$). This product was employed in the next step without purification.

Step 4: Synthesis of 4 2-(benzyloxy)-2-oxoethyl 4-(cyclopropylmethoxy)-3-(methylsulfonyloxy)benzoate (185)

A solution of 4-(cyclopropylmethoxy)-3-(methylsulfonyloxy)benzoic acid (0.300 g, 1.048 mmol), benzyl 2-hydroxyacetate (0.174 g, 1.048 mmol), EDC (0.603 g, 3.14 mmol), and DMAP (0.128 g, 1.048 mmol) in DCM (25 ml) was stirred at RT for 2 hours. The mixture was diluted with DCM and washed with HCl 1N and NaHCO$_3$ 5%. The organic phase was dried over $Na_2SO_4$, the solvent was removed under vacuum, and the crude was purified by flash chromatography on silica gel cartridge (petroleum ether:EtOAc=80:20 to 75:25). A further purification by trituration with EtOH was required to obtain 2-(benzyloxy)-2-oxoethyl 4-(cyclopropylmethoxy)-3-(methylsulfonyloxy)benzoate (0.238 g, 0.548 mmol, 52.3% yield, MS/ESI$^+$ 434.9 [MH]$^+$).

Step 5: Synthesis of 2-(4-(cyclopropylmethoxy)-3-(methylsulfonyloxy)-benzoyloxy)acetic acid (186)

A mixture of 2-(benzyloxy)-2-oxoethyl 4-(cyclopropylmethoxy)-3-(methylsulfonyloxy)benzoate (0.238 g, 0.548 mmol) and 10% w/w Pd/C (0.030 g, 0.028 mmol) in MeOH (17 ml) and EtOAc (3 ml) was hydrogenated at 20 psi for 2 hours. The catalyst was filtered off, and the solvent was removed under vacuum affording 2-(4-(cyclopropylmethoxy)-3-(methylsulfonyloxy)benzoyloxy)acetic acid (0.178 g, 0.517 mmol, 94% yield, MS/ESI$^+$ 344.9 [MH]$^+$). The product was used without any further purification.

Step 6: Synthesis of (S)-3,5-dichloro-4-(2-(2-(4-(cyclopropylmethoxy)-3-(methylsulfonyloxy)benzoyloxy)acetoxy)-2-(3-(cyclopropylmethoxy)-4-(difluoromethoxy)phenyl)ethyl)pyridine 1-oxide (187)

The title compound was obtained by purification by trituration with MeOH, washing with Et$_2$O (0.275 g, 0.368 mmol, 71% yield) starting from (S)-3,5-dichloro-4-(2-(3-(cyclopropylmethoxy)-4-(difluoromethoxy)phenyl)-2-hydroxyethyl)pyridine 1-oxide (0.217 g, 0.517 mmol) and 2-(4-(cyclopropylmethoxy)-3-(methylsulfonyloxy)-benzoyloxy)acetic acid (0.178 g, 0.517 mmol, Compound 186) with DMAP (0.063 g, 0.517 mmol) and EDC (0.297 g, 1.551 mol) in DCM (15 ml), using an analogous procedure to that described in Scheme 15, Step 4.

MS/ESI$^+$ 746.23 [MH]$^+$, [α$_D$]=−30.34, c 0.53, DCM $^1$H NMR (300 MHz, DMSO-d6) δ ppm 8.50 (s, 2 H), 7.91 (dd, 1 H), 7.79 (d, 1 H), 7.34 (d, 1 H), 7.18 (d, 1 H), 7.08 (d, 1 H), 6.97 (dd, 1 H), 7.07 (t, 1 H), 6.05 (dd, 1 H), 4.94 (d, 1 H), 4.87 (d, 1 H), 4.05 (d, 2 H), 3.90 (d, 2 H), 3.43 (s, 3 H), 3.45 (dd, 1 H), 3.25 (dd, 1 H), 1.08-1.40 (m, 2 H), 0.51-0.73 (m, 4 H), 0.21-0.50 (m, 4 H).

The compounds listed in Table 16 were prepared with an analogous procedure to that described in Example 23, Step 2-6, by reacting the appropriate precursors (commercially available or synthesized by a person skilled in the art) with suitable reagents, and where purification step has been performed as indicated in Table 16.

TABLE 16

| Structure | Cmp | NMR characterization | MS/ESI+ [MH]+ [α_D] | Starting Material (and Conditions, if different) | Purification method |
|---|---|---|---|---|---|
| (structure 188) | 188 | ¹H NMR (300 MHz, DMSO-d6) δ ppm 8.50 (s, 2 H), 7.83 (d, 1 H), 7.18 (d, 1 H), 7.16 (d, 1 H), 7.09 (d, 1 H), 7.05 (dd, 1 H), 6.98 (dd, 1 H), 7.07 (t, 1 H), 6.04 (dd, 1 H), 4.90 (d, 1 H), 4.83 (d, 1 H), 3.90 (d, 2 H), 3.86 (s, 3 H), 3.47 (s, 3 H), 3.46 (dd, 1 H), 3.26 (dd, 1 H), 1.07-1.29 (m, 1 H), 0.47-0.66 (m, 2 H), 0.22-0.43 (m, 2 H) | 706.24 [α_D] = −19.44 (c = 0.5 DCM) | (structure) Step 5: MeOH, 25 psi | Preparative HPLC |
| (structure 189) | 189 | ¹H NMR (300 MHz, DMSO-d6) δ ppm 8.50 (s, 2 H), 7.95 (dd, 1 H), 7.82 (d, 1 H), 7.38 (d, 1 H), 7.18 (d, 1 H), 7.08 (d, 1 H), 6.97 (dd, 1 H), 7.07 (t, 1 H), 6.05 (dd, 1 H), 4.94 (d, 1 H), 4.87 (d, 1 H), 3.96 (s, 3 H), 3.90 (d, 2 H), 3.45 (dd, 1 H), 3.40 (s, 3 H), 3.25 (dd, 1 H), 1.00-1.36 (m, 1 H), 0.46-0.67 (m, 2 H), 0.21-0.46 (m, 2 H) | 706.11 [α_D] = −31.07 (c = 0.45 DCM) | (structure) | Trituration with MeOH and washing with Et₂O followed by dissolution in DCM/MeOH and evaporation |

Example 24

Synthesis of 4-((2S)-2-(3-(acetylthio)-3-methyl-2-(phenylsulfonamido)-butanoyloxy)-2-(3-(cyclopropylmethoxy)-4-(difluoromethoxy)phenyl)ethyl)-3,5-dichloropyridine 1-oxide (194)

Scheme 24

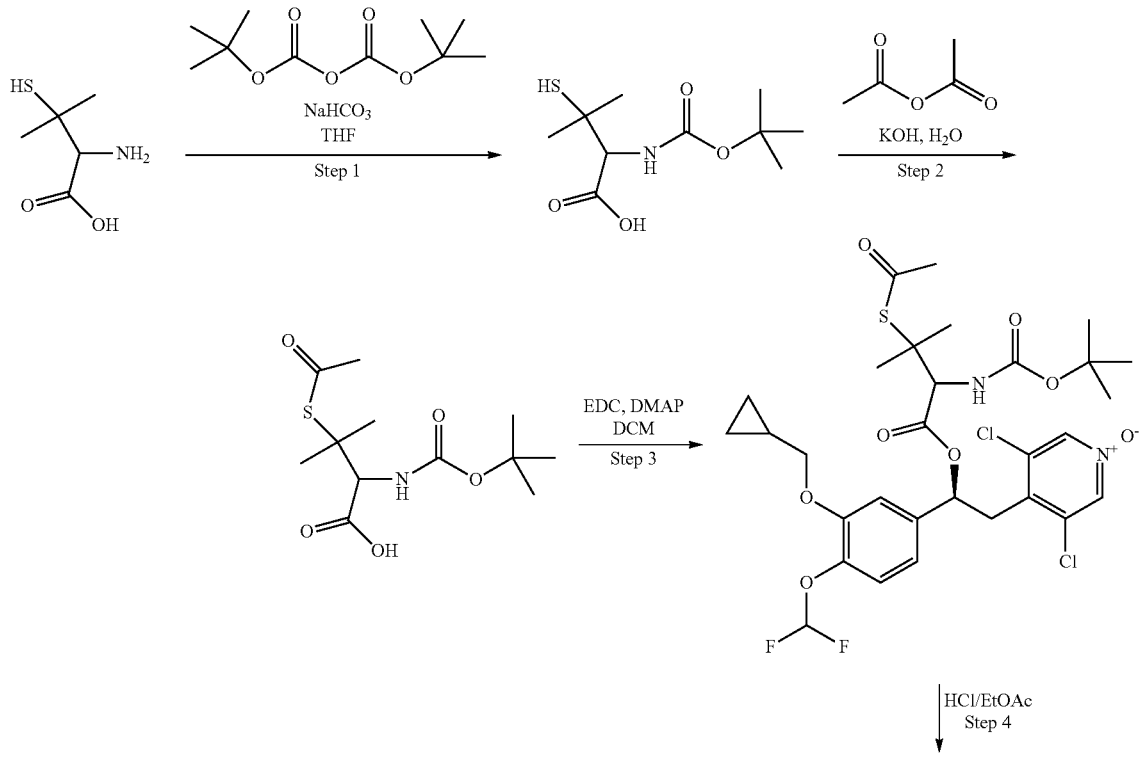

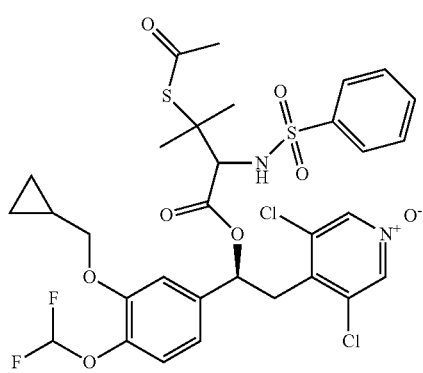

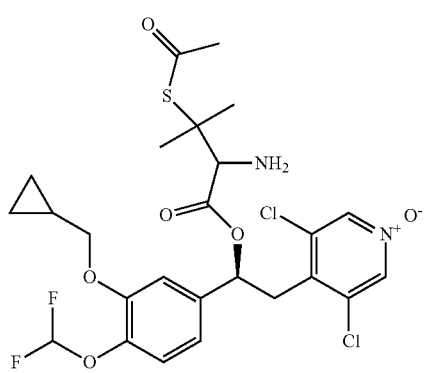

Step 5

Step 1: Synthesis of 2-(tert-butoxycarbonylamino)-3-mercapto-3-methylbutanoic acid (190)

To a solution of 2-amino-3-mercapto-3-methylbutanoic acid (2 g, 13.4 mmol) in THF (40 ml), NaHCO₃ sat. sol. (4 ml) and di-tert-butyl dicarbonate (4.39 g, 20.11 mmol) were added. The mixture was stirred at RT for 2 hours. Then THF was evaporated under vacuum and the reaction mixture partitioned between HCl 1M and EtOAc. The aqueous layer was extracted 2 times with EtOAc. The combined organic layers were washed with brine and dried over Na₂SO₄, filtered and solvent removed under vacuum. Crude compound was used in the next step without further purification (2.96 g, Yield: 89%).

Step 2: Synthesis of 3-(acetylthio)-2-(tert-butoxycarbonylamino)-3-methylbutanoic acid (191)

2-(tert-butoxycarbonylamino)-3-mercapto-3-methylbutanoic acid (2.96 g, 11.87 mmol) was suspended in water (33 ml) and cooled with an ice/water bath. KOH (1.67 g, 29.7 mmol) dissolved in water (16 ml) followed by acetic anhydride (1.41 ml, 14.9 mmol) were added to the reaction flask and stirred at 0-5° C. for 4 hours (a white precipitated appears after ca. 30 minutes of stirring). The reaction mixture was partitioned between EtOAc and HCl 1M. The aqueous layer was extracted 3 times with EtOAc. The combined organic layers were washed with brine and dried over Na₂SO₄, filtered and solvent removed under vacuum. Crude compound was used in the next step without further purification. (3.45 g, quantitative yield).

Step 3: Synthesis of 4-((2S)-2-(3-(acetylthio)-2-(tert-butoxycarbonylamino)-3-methylbutanoyloxy)-2-(3-(cyclopropylmethoxy)-4-(difluoromethoxy)phenyl)ethyl)-3,5-dichloropyridine 1-oxide (192)

3-(acetylthio)-2-(tert-butoxycarbonylamino)-3-methylbutanoic acid (693 mg, 2.38 mmol) was dissolved in DCM (10 ml). DMAP (73 mg, 0.59 mmol), EDC (342 mg, 1.79 mmol), and (S)-3,5-dichloro-4-(2-(3-(cyclopropylmethoxy)-4-(difluoromethoxy)phenyl)-2-hydroxyethyl)pyridine 1-oxide (500 mg, 1.19 mmol) were added, and the mixture stirred for 4 hours at RT. The reaction mixture was diluted with DCM and washed with NaHCO₃ sat. sol. (10 ml), HCl 1N, brine, dried over Na₂SO₄ and evaporated under vacuum to give 1.06 g. Crude compound was used in the next step without further purification.

Step 4: Synthesis of 4-((2S)-2-(3-(acetylthio)-2-amino-3-methylbutanoyloxy)-2-(3-(cyclopropylmethoxy)-4-(difluoromethoxy)-phenyl)ethyl)-3,5-dichloropyridine 1-oxide (193)

4-((2S)-2-(3-(acetylthio)-2-(tert-butoxycarbonylamino)-3-methylbutanoyloxy)-2-(3-(cyclopropylmethoxy)-4-(difluoromethoxy)phenyl)ethyl)-3,5-dichloropyridine 1-oxide (118 mg, 0.170 mmol) was dissolved in DCM (1 ml). HCl 4N in dioxane (425 µl, 1.70 mmol) was added and the mixture stirred for 30 minutes at RT. The reaction mixture was diluted with DCM. The organic layer was washed with NaHCO₃ sat. sol. (2×) and brine, dried over Na₂SO₄ and evaporated under vacuum. The crude product was purified by preparative reverse-phase HPLC to give 101 mg of the desired compound (quantitative yield).

Step 5: Synthesis of 4-((2S)-2-(3-(acetylthio)-3-methyl-2-(phenylsulfonamido)-butanoyloxy)-2-(3-(cyclopropylmethoxy)-4-(difluoromethoxy)phenyl)ethyl)-3,5-dichloropyridine 1-oxide (194)

4-((2S)-2-(3-(acetylthio)-2-amino-3-methylbutanoyloxy)-2-(3-(cyclopropylmethoxy)-4-(difluoromethoxy)phenyl)ethyl)-3,5-dichloropyridine 1-oxide (101 mg, 0.170 mmol) was dissolved in pyridine (1 ml), then benzenesulfonyl chloride (60 mg, 0.340 mmol) was added at 0° C., and the mixture was stirred at RT for 2 hours. The reaction was quenched with HCl 1N, and the product was extracted with EtOAc. The organic phase was washed with HCl 1N (2×) and brine, then dried over Na₂SO₄. The solvent was removed and the crude product was purified by preparative reverse-phase HPLC to give 10 mg of the desired compound (Yield 8%).

MS/ESI⁺ 733.1 [M+H]+

Retention Time on Acquity Waters UPLC: 4.15, 4.21. Diastereomeric Ratio: 55/45.

This retention time was determined using the analytical method described below:

LC/UV/MS Analytical Method:

LC instrument: Acquity Waters UPLC (or equivalent)

Column: Kinetex 1.7u XB-C18 100A 100×2.1 mm (Phenomenex)

Column Temperature (° C.) 50.0

Mobile phases: HCOONH₄ 0.025M pH3 (A); Acetonitrile (B)

Flow (ml/min) 0.65 (split in MS 1:3)
Stop Time (mins) 10.0
Gradient:
| Time (min) | % A | % B |
|---|---|---|
| 0.00 | 80.0 | 20.0 |
| 5.50 | 20.0 | 80.0 |
| 7.50 | 20.0 | 80.0 |
| 8.00 | 80.0 | 20.0 |
| 10.00 | 80.0 | 20.0 |
UV detection: wavelength 254 nm
Injection Volume (ul)-2.00
Sample solvents: Acetonitrile
Example 25
Synthesis of (S)-3,5-dichloro-4-(2-(2-(4-(cyclopropylmethoxy)-3-(morpholinomethyl)benzoyloxy)acetoxy)-2-(3-(cyclopropylmethoxy)-4-(difluoromethoxy)phenyl)ethyl)pyridine 1-oxide (200)
Scheme 25
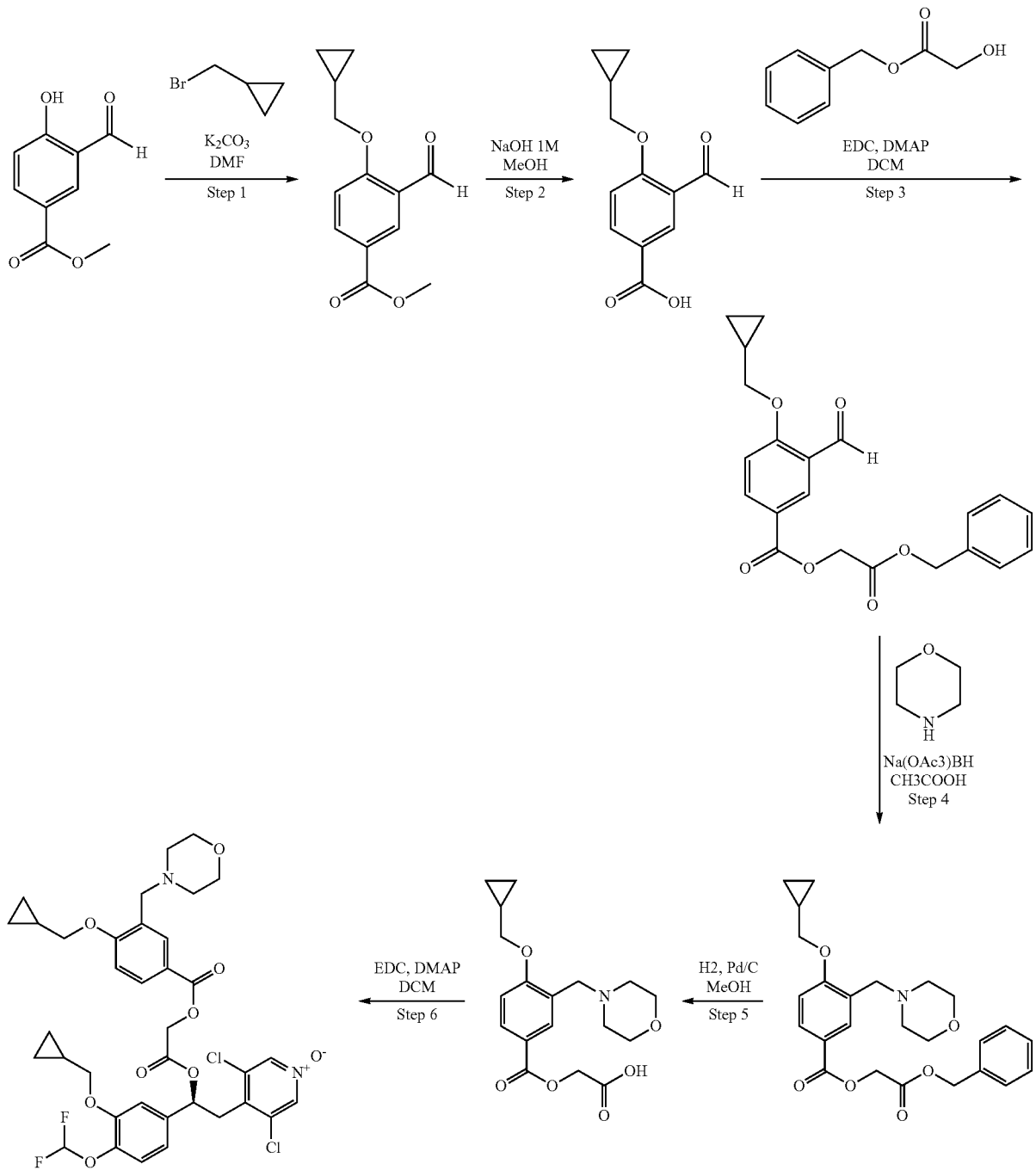

Step 1: Synthesis of methyl 4-(cyclopropylmethoxy)-3-formylbenzoate (195)

To a solution of methyl 3-formyl-4-hydroxybenzoate (2 g, 11.10 mmol) in DMF (20 ml), $K_2CO_3$ (3.07 mg, 22.2 mmol) and (bromomethyl)cyclopropane (2.156 ml, 22.2 mmol) were added. The mixture was stirred at RT for 2 hours. The reaction was quenched with water, and the product was extracted with EtOAc. The organic layer was washed with water (2×) and NaCl sat. sol., dried over $Na_2SO_4$ and evaporated under vacuum to give 2.6 g of the desired compound (quantitative yield).

Step 2: Synthesis of 4-(cyclopropylmethoxy)-3-formylbenzoic acid (196)

Methyl 4-(cyclopropylmethoxy)-3-formylbenzoate (2.6 g, 11.87 mmol) was dissolved in MeOH (40 mL), and NaOH 1 N (17 ml, 17.09 mmol) was added. The mixture was stirred at 40° C. for 4 hours. MeOH was evaporated under vacuum, and the reaction mixture was partitioned between EtOAc and HCl 1 M. The aqueous layer was extracted 3 times with EtOAc. The combined organic layers were washed with brine and dried over $Na_2SO_4$, filtered and solvent removed under vacuum to give 2.42 g. (quantitative yield).

Step 3: Synthesis of 2-(benzyloxy)-2-oxoethyl 4-(cyclopropylmethoxy)-3-formylbenzoate (197)

EDC (2.52 g, 13.16 mmol) was added to a solution of compound benzyl 2-hydroxyacetate (2.02 g, 12.15 mmol), 4-(cyclopropylmethoxy)-3-formylbenzoic acid (2.23 g, 10.13 mmol), and DMAP (247 mg, 2.03 mmol) in DCM (20 ml) at RT under nitrogen atmosphere. The mixture was stirred at RT overnight. The mixture was then diluted with DCM and washed with $NaHCO_3$ sat. sol., HCl 0.1M and brine. The organic phase was dried over $Na_2SO_4$, and the solvent was evaporated. 2-(benzyloxy)-2-oxoethyl 4-(cyclopropylmethoxy)-3-formylbenzoate was obtained (3.73 g, quantitative yield).

Step 4: Synthesis of 2-(benzyloxy)-2-oxoethyl 4-(cyclopropylmethoxy)-3-(morpholinomethyl)benzoate (198)

A solution of 2-(benzyloxy)-2-oxoethyl 4-(cyclopropylmethoxy)-3-formylbenzoate (3.73 g, 10.13 mmol) and morpholine (1.15 g, 13.17 mmol) in dry THF (50 ml), under argon atmosphere, was stirred for 15 minutes at RT. $Na(OAc)_3BH$ (2.79 g, 13.17 mmol) and $CH_3COOH$ (754 µl, 13.17 mmol) were added. $CH_3COOH$ was added to reach a pH between 5 and 6. The mixture stirred at RT for 24 hours. The solvent was removed, and the crude was dissolved in EtOAc and washed with $NaHCO_3$ sat. sol. and brine. The organic phase was dried over $Na_2SO_4$, and the solvent was removed to give 2-(benzyloxy)-2-oxoethyl 4-(cyclopropylmethoxy)-3-(morpholinomethyl)benzoate (4.45 g, quantitative yield).

Step 5: Synthesis of 2-(4-(cyclopropylmethoxy)-3-(morpholinomethyl)benzoyloxy)acetic acid (199)

2-(benzyloxy)-2-oxoethyl 4-(cyclopropylmethoxy)-3-(morpholinomethyl)-benzoate (4.55 g, 10.35 mmol) was dissolved in MeOH (50 ml), then Pd/C 5% (1.10 g, 0.340 mmol) was added. The solution was shaken under hydrogen atmosphere at 60 psi on a Parr apparatus for 1 hour. The catalyst was filtered off and the solvent removed under vacuum to give 3.18 g of the desired compound (yield 88%).

Step 6: Synthesis of (S)-3,5-dichloro-4-(2-(2-(4-(cyclopropylmethoxy)-3-(morpholinomethyl)benzoyloxy)acetoxy)-2-(3-(cyclopropylmethoxy)-4-(difluoromethoxy)phenyl)ethyl)pyridine 1-oxide (200)

EDC (82 mg, 0.429 mmol) was added to a solution of compound (S)-3,5-dichloro-4-(2-(3-(cyclopropylmethoxy)-4-(difluoromethoxy)phenyl)-2-hydroxyethyl)pyridine 1-oxide (120 mg, 0.286 mmol), 2-(4-(cyclopropylmethoxy)-3-(morpholinomethyl)-benzoyloxy)acetic acid (300 mg, 0.859 mmol) and DMAP (18 mg, 0.143 mmol) in DCM (1 ml) at RT under nitrogen atmosphere. The mixture was stirred at RT overnight. The mixture was then diluted with DCM and washed with NaHCO3 sat. sol., HCl 0.1N and brine. The organic phase was dried over $Na_2SO_4$, and the solvent was evaporated. The crude was purified through Preparative HPLC to give (S)-3,5-dichloro-4-(2-(2-(4-(cyclopropylmethoxy)-3-(morpholinomethyl)-benzoyloxy)acetoxy)-2-(3-(cyclopropylmethoxy)-4-(difluoromethoxy)phenyl)-ethyl)pyridine 1-oxide (150 mg, 70% yield).

MS/ESI⁺ 751.2 [MH]⁺.

¹H NMR (400 MHz, DMSO-d6) δ ppm 12.31-13.04 (bs, 1 H), 8.40 (s, 2 H), 7.75-8.06 (m, 2 H), 6.74-7.47 (m, 6 H), 6.03 (dd, J=8.82, 4.41 Hz, 1 H), 4.64-5.03 (m, 2 H), 3.78-4.13 (m, 4 H), 3.50-3.65 (m, 7 H), 3.37-3.48 (m, 1 H), 2.41 (m, 4 H), 1.23 (dd, J=13.23, 7.06 Hz, 2 H), 0.45-0.72 (m, 4 H), 0.19-0.43 (m, 4 H).

Example 26

Synthesis of (S)-3,5-dichloro-4-(2-(3-(cyclopropylmethoxy)-4-(difluoromethoxy)phenyl)-2-(2-(4-methoxy-3-(methylsulfonyloxy)benzamido)-acetoxy)ethyl)pyridine 1-oxide (201)

Scheme 26

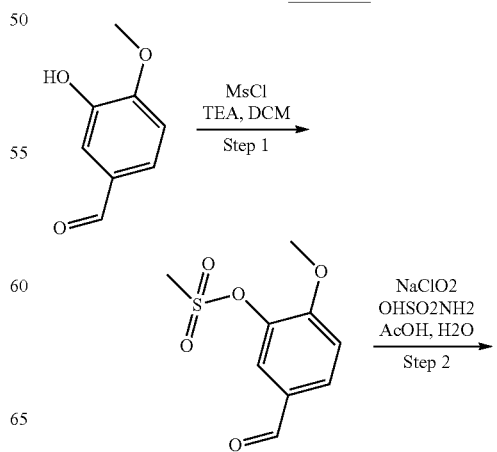

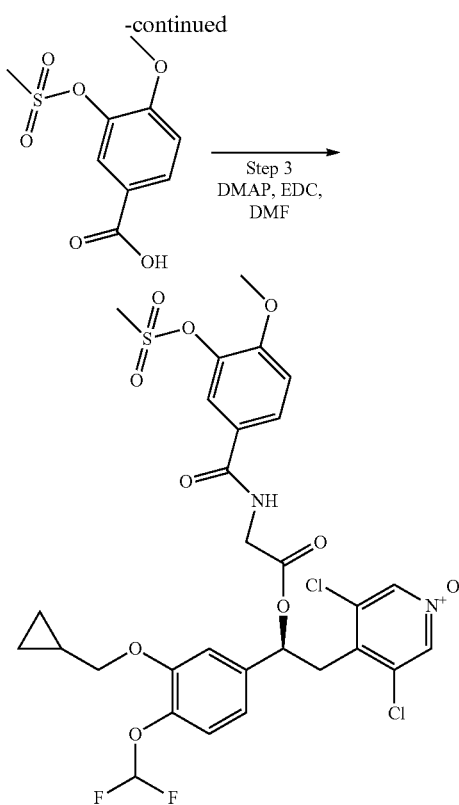

Step 1: Synthesis of 5-formyl-2-methoxyphenyl methanesulfonate:

3-hydroxy-4-methoxybenzaldehyde (2.5 g, 16.4 mmol) was dissolved in DCM (50 ml), then methanesulfonyl chloride (2 g, 17.5 mmol) and TEA (4 ml, 28.6 mmol) were added, and the reaction was stirred at RT for 12 hours. DCM was evaporated, and the mixture was dissolved in ethyl acetate and extracted with HCl 1M, dried over Na2SO4 and evaporated under vacuum to yield 3.3 g of the desired product. (Yield: 87%).

Step 2: Synthesis of 4-methoxy-3-(methylsulfonyloxy)benzoic acid:

5-formyl-2-methoxyphenyl methanesulfonate (3.3 g, 14 mmol) was dissolved in acetic acid (50 ml) and sulfamic acid (500 mg, 5.15 mmol) was added. Sodium chlorite (3 g, 33.2 mmol) was dissolved in H$_2$O (20 ml) and added dropwise. The reaction was stirred at RT overnight, then the precipitate was filtered and washed with HCl 1 M, MeOH and dried in the vacuum oven, to give 3.4 g of the desired product (Yield: 99%).

Step 3: Synthesis of (S)-3,5-dichloro-4-(2-(3-(cyclopropylmethoxy)-4-(difluoromethoxy)-phenyl)-2-(2-(4-methoxy-3-(methylsulfonyloxy)-benzamido)acetoxy)ethyl)pyridine 1-oxide (201)

The final product was purified by crystallization from ethyl acetate, obtaining 20 mg of the title compound (Yield: 29%), starting from (S)-4-(2-(2-aminoacetoxy)-2-(3-(cyclopropylmethoxy)-4-(difluoromethoxy)phenyl)ethyl)-3,5-dichloropyridine 1-oxide (50 mg, 0.1 mmol, Compound 3 may be prepared as in analogous manner as described in Scheme 1, Step 1 and 2) and 4-methoxy-3-(methylsulfonyloxy)benzoic acid (50 mg, 0.2 mmol), with DMAP (30 mg, 0.24 mmol) and EDC (50 mg, 0.26 mmol), in DMF (3 ml), and using an analogous procedure to that described in Scheme 1, Step 3.

MS/ESI$^+$ 706.51 [MH]$^+$ $^1$H NMR (400 MHz, acetone) δ ppm 8.21 (m, 3 H), 7.85 (d, J=1.76 Hz, 2 H), 7.24-7.35 (m, 1 H), 7.19 (d, J=17.64 Hz, 2 H), 6.67-7.13 (m, 2 H), 6.04-6.19 (m, 1 H), 3.87-4.21 (m, 7 H), 3.42-3.60 (m, 1 H), 3.32 (s, 4 H), 1.24-1.40 (m, 1 H), 0.62 (d, J=7.06 Hz, 2 H), 0.40 (d, J=4.85 Hz, 2 H).

Example 27

Synthesis of (S)-3,5-dichloro-4-(2-(3-(cyclopropylmethoxy)-4-(difluoromethoxy)phenyl)-2-(2-(5-(N-(cyclopropylmethyl)methylsulfonamido)-2-hydroxybenzoyloxy)acetoxy)ethyl)pyridine 1-oxide (210)

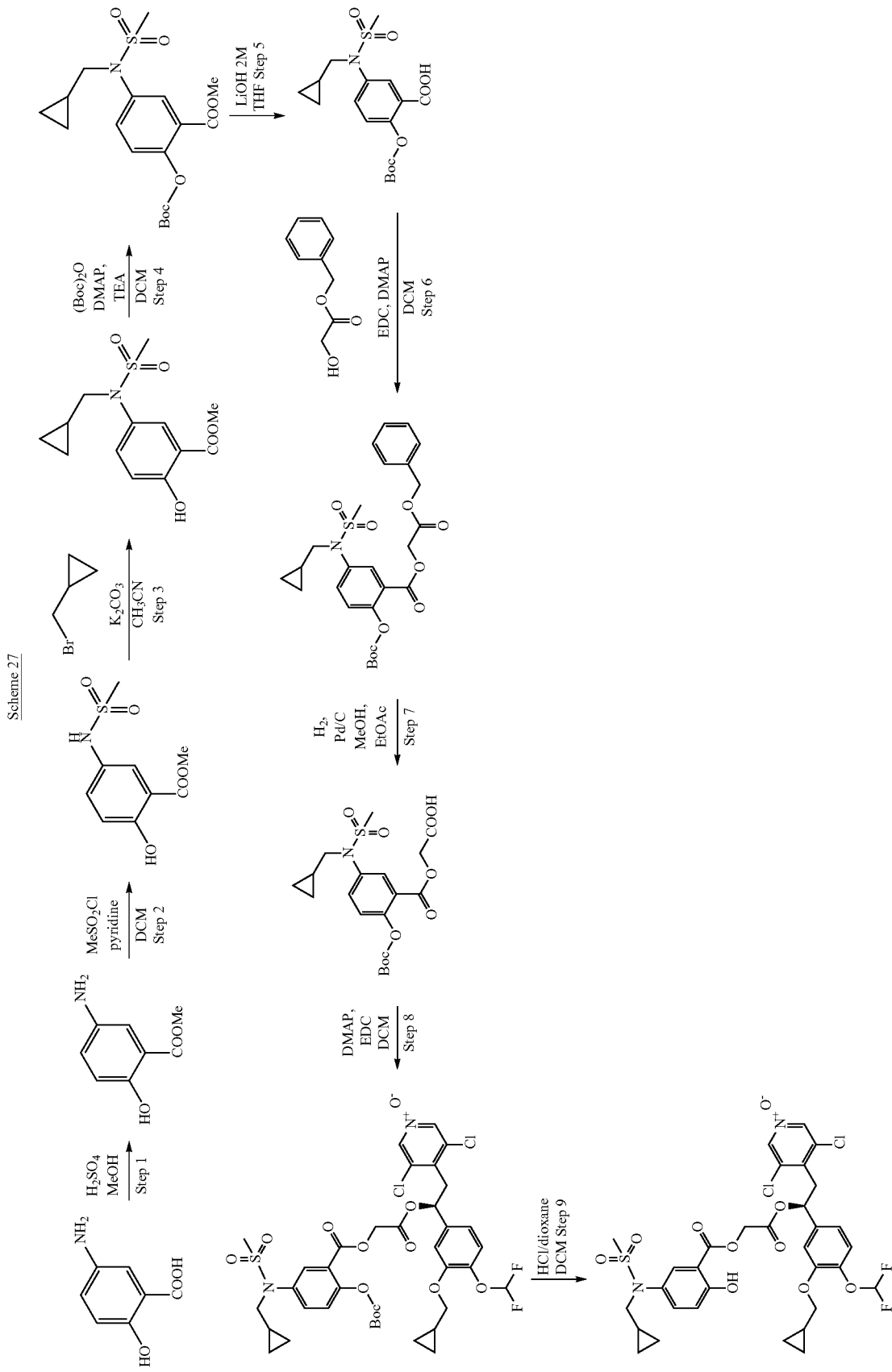
Scheme 27

Step 1: Synthesis of methyl 5-amino-2-hydroxybenzoate (202)

5-Amino-2-hydroxybenzoic acid (10 g, 65.3 mmol) was suspended in MeOH (150 ml), and aqueous 96% sulfuric acid (12 ml, 225 mmol) was added drop wise. The mixture was heated to reflux for 96 hours. After cooling to RT, the solvent was partially removed under vacuum; the remaining solution was basified with NaHCO$_3$ 5% and extracted with EtOAc. The organic layer was washed with brine and dried over Na$_2$SO$_4$. The solvent was evaporated under vacuum affording methyl 5-amino-2-hydroxybenzoate as a solid (9.68 g, 57.9 mmol, 89% yield, MS/EST$^+$168.0 [MH]$^+$).

Step 2: Synthesis of methyl 2-hydroxy-5-(methylsulfonamido)benzoate (203)

To a solution of methyl 5-amino-2-hydroxybenzoate (9.58 g, 57.3 mmol) in DCM (150 ml), pyridine (9.27 ml, 115 mmol) was added followed by methanesulfonyl chloride (4.47 ml, 57.3 mmol). The reaction mixture was stirred at RT for 4 hours. Water (50 ml) and HCl 6M (15 ml) were added, and the resulting precipitate was collected by filtration, washed with water and dried to give methyl 2-hydroxy-5-(methylsulfonamido)benzoate (13 g, 53.0 mmol, 92% yield, MS/ESI$^+$ 246.0 [MH]$^+$).

Step 3: Synthesis of methyl 5-(N-(cyclopropylmethyl)methylsulfonamido)-2-hydroxybenzoate (204)

To a solution of methyl 2-hydroxy-5-(methylsulfonamido)benzoate (6.8 g, 27.72 mmol) in CH$_3$CN (200 ml), (bromomethyl)cyclopropane (5.62 g, 41.58 mmol) and K$_2$CO$_3$ (7.66 g, 55.4 mmol) were added, and the reaction was stirred at RT for 4 days. The reaction mixture was poured into ice-water (400 ml), acidified with HCl 36% (pH=1) and extracted with EtOAc. The organic layer was dried over Na$_2$SO$_4$ and evaporated to dryness. The resulting crude was purified by chromatography on silica gel column (petroleum ether:EtOAc=4:1) affording methyl 5-(N-(cyclopropylmethyl)methylsulfonamido)-2-hydroxybenzoate (6 g, 20.32 mmol, 73.3% yield).

Step 4: Synthesis of methyl 2-(tert-butoxycarbonyloxy)-5-(N-(cyclopropylmethyl)methylsulfonamido)benzoate (205)

To a solution of methyl 5-(N-(cyclopropylmethyl)methylsulfonamido)-2-hydroxybenzoate (6 g, 20.04 mmol) in DCM (150 ml), DMAP (0.490 g, 4.01 mmol), TEA (2.81 ml, 20.04 mmol) and di-tert-butyl dicarbonate (5.25 g, 24.05 mmol) were sequentially added, and the resulting mixture was stirred at RT for 3 hours. The volatiles were removed under reduced pressure, and the residue was dissolved in DCM and washed with HCl 0.5N (2×). The organic layer was dried over Na$_2$SO$_4$ and evaporated to dryness. The solid residue was purified by crystallization with EtOH affording methyl 2-(tert-butoxycarbonyloxy)-5-(N-(cyclopropylmethyl)-methylsulfonamido)benzoate (6.54 g, 16.37 mmol, 82% yield, MS/ESI$^+$ 422.0 [MNa]$^+$).

Step 5: Synthesis of 2-(tert-butoxycarbonyloxy)-5-(N-(cyclopropylmethyl) methylsulfonamido)benzoic acid (206)

Methyl 2-(tert-butoxycarbonyloxy)-5-(N-(cyclopropylmethyl)-methylsulfonamido)benzoate (6 g, 15.02 mmol) was dissolved in THF (50 ml); LiOH 2M (15.02 ml, 30.0 mmol) was added; and the mixture was stirred at RT for 24 hours. The volatiles were removed under vacuum, and the residue was dissolved in water, neutralized with HCl 1M (pH 6) and extracted with EtOAc. The organic layer was dried over Na$_2$SO$_4$ and evaporated to dryness. The resulting crude was purified by flash chromatography on silica gel column (DCM:MeOH=10:0.5) affording 2-(tert-butoxycarbonyloxy)-5-(N-(cyclopropylmethyl)methylsulfonamido)benzoic acid (3 g, 7.78 mmol, 51.8% yield, MS/ESI$^+$ 407.9 [MNa]$^+$).

Step 6: Synthesis of 2-(benzyloxy)-2-oxoethyl 2-(tert-butoxycarbonyloxy)-5-(N-(cyclopropylmethyl)methylsulfonamido)benzoate (207)

A mixture of 2-(tert-butoxycarbonyloxy)-5-(N-(cyclopropylmethyl)-methylsulfonamido)benzoic acid (0.300 g, 0.778 mmol), benzyl 2-hydroxyacetate (0.129 g, 0.778 mmol), EDC (0.448 g, 2.335 mmol) and DMAP (0.048 g, 0.389 mmol) in DCM (30 ml) was stirred at RT overnight. The reaction mixture was washed twice with HCl 1N and then with NaHCO$_3$ 5%. The organic phase was dried over Na$_2$SO$_4$, and the solvent was removed under vacuum. The crude was purified by filtration on silica gel cartridge (petroleum ether:EtOAc=80:20 to 70:30) to give 2-(benzyloxy)-2-oxoethyl 2-(tert-butoxycarbonyloxy)-5-(N-(cyclopropylmethyl)methylsulfonamido)benzoate (0.288 g, 0.540 mmol, 69.3% yield, MS/ESI$^+$ 555.96 [MNa]$^+$).

Step 7: Synthesis of 2-(2-(tert-butoxycarbonyloxy)-5-(N-(cyclopropylmethyl) methylsulfonamido)benzoyloxy)acetic acid (208)

A mixture of 2-(benzyloxy)-2-oxoethyl 2-(tert-butoxycarbonyloxy)-5-(N-(cyclopropylmethyl)methylsulfonamido) benzoate (0.288 g, 0.540 mmol) and 10% w/w Pd/C (0.030 g, 0.028 mmol) in MeOH (20 ml) and EtOAc (5 ml) was hydrogenated at 20 psi for 3 hours. The catalyst was filtered off and the solvent was removed affording 2-(2-(tert-butoxycarbonyloxy)-5-(N-(cyclopropylmethyl)-methylsulfonamido)benzoyloxy)-acetic acid (0.215 g, 0.485 mmol, 90% yield). This product was used without purification.

Step 8: Synthesis of (S)-4-(2-(2-(2-(tert-butoxycarbonyloxy)-5-(N-(cyclopropyl-methyl)methylsulfonamido)benzoyloxy)acetoxy)-2-(3-(cyclopropylmethoxy)-4-(difluoromethoxy)phenyl)ethyl)-3,5-dichloropyridine 1-oxide (209)

A mixture of 2-(2-(tert-butoxycarbonyloxy)-5-(N-(cyclopropylmethyl)-methylsulfonamido)benzoyloxy)acetic acid (0.215 g, 0.485 mmol), (S)-3,5-dichloro-4-(2-(3-(cyclopropylmethoxy)-4-(difluoromethoxy)phenyl)-2-hydroxyethyl) pyridine 1-oxide (204 g, 0.485 mmol), EDC (0.279 g, 1.454 mmol), and DMAP (0.059 g, 0.485 mmol) in DCM (25 mL) was stirred at RT overnight. The mixture was diluted with DCM and washed with 1N HCl and 5% NaHCO$_3$. The organic phase was dried over sodium sulfate and the solvent was removed. The crude was purified by chromatography on silica gel cartridge (DCM:MeOH=99:1) affording (S)-4-(2-(2-(2-(tert-butoxycarbonyloxy)-5-(N-(cyclopropylmethyl) methylsulfonamido)-benzoyloxy)acetoxy)-2-(3-(cyclopropylmethoxy)-4-(difluoromethoxy)phenyl)ethyl)-3,5-dichloropyridine 1-oxide (0.326 g, 0.385 mmol, 80% yield, MS/ESI$^+$ 845.1 [MH]$^+$).

Step 9: Synthesis of (S)-3,5-dichloro-4-(2-(3-(cyclopropylmethoxy)-4-(difluoromethoxy)phenyl)-2-(2-(5-(N-(cyclopropylmethyl)methylsulfonamido)-2-hydroxybenzoyloxy)acetoxy)ethyl)pyridine 1-oxide (210)

To a solution of (S)-4-(2-(2-(2-(tert-butoxycarbonyloxy)-5-(N-(cyclopropyl-methyl)methylsulfonamido)benzoyloxy)acetoxy)-2-(3-(cyclopropylmethoxy)-4-(difluoromethoxy)phenyl)ethyl)-3,5-dichloropyridine 1-oxide (0.326 g, 0.385 mmol) in DCM (15 ml), HCl 4M in dioxane (1 ml, 4.00 mmol) was added, and the mixture was stirred at RT overnight. Additional HCl 4M in dioxane (1 ml, 4.00 mmol) was added, and the mixture was stirred at the same temperature for 3 days. The solvent was removed and the crude was triturated with MeOH. The solid was collected by filtration and washed with ethyl ether. A further trituration with EtOAc was required to afford (S)-3,5-dichloro-4-(2-(3-(cyclopropylmethoxy)-4-(difluoromethoxy)phenyl)-2-(2-(5-(N-(cyclopropylmethyl)-methylsulfonamido)-2-hydroxybenzoyloxy)acetoxy)ethyl)pyridine 1-oxide as a white solid (0.160 g, 0.215 mmol, 55.7% yield, MS/ESI$^+$ 745.19 [MH]$^+$, [$\alpha_D$]=−36.29, c=0.49, DCM).
$^1$H NMR (300 MHz, DMSO-d6) δ ppm 10.26 (br. s., 1 H), 8.51 (s, 2 H), 7.77 (d, 1 H), 7.60 (dd, 1 H), 7.19 (d, 1 H), 7.10 (d, 1 H), 7.06 (d, 1 H), 6.99 (dd, 1 H), 7.07 (t, 1 H), 6.07 (dd, 1 H), 4.99 (d, 1 H), 4.90 (d, 1 H), 3.90 (d, 2 H), 3.47 (dd, 1 H), 3.44 (d, 2 H), 3.21-3.27 (m, 1 H), 2.97 (s, 3 H), 1.02-1.34 (m, 1 H), 0.71-0.95 (m, 1 H), 0.49-0.67 (m, 2 H), 0.26-0.46 (m, 4 H), −0.03-0.15 (m, 2 H)

Example 28

Synthesis of (S)-3,5-dichloro-4-(2-(3-(cyclopropylmethoxy)-4-(difluoromethoxy)phenyl)-2-((4-methoxy-3-(N-(2-morpholinoethyl)-methylsulfonamido)phenoxy)carbonyloxy)ethyl)pyridine 1-oxide (217)

Scheme 28

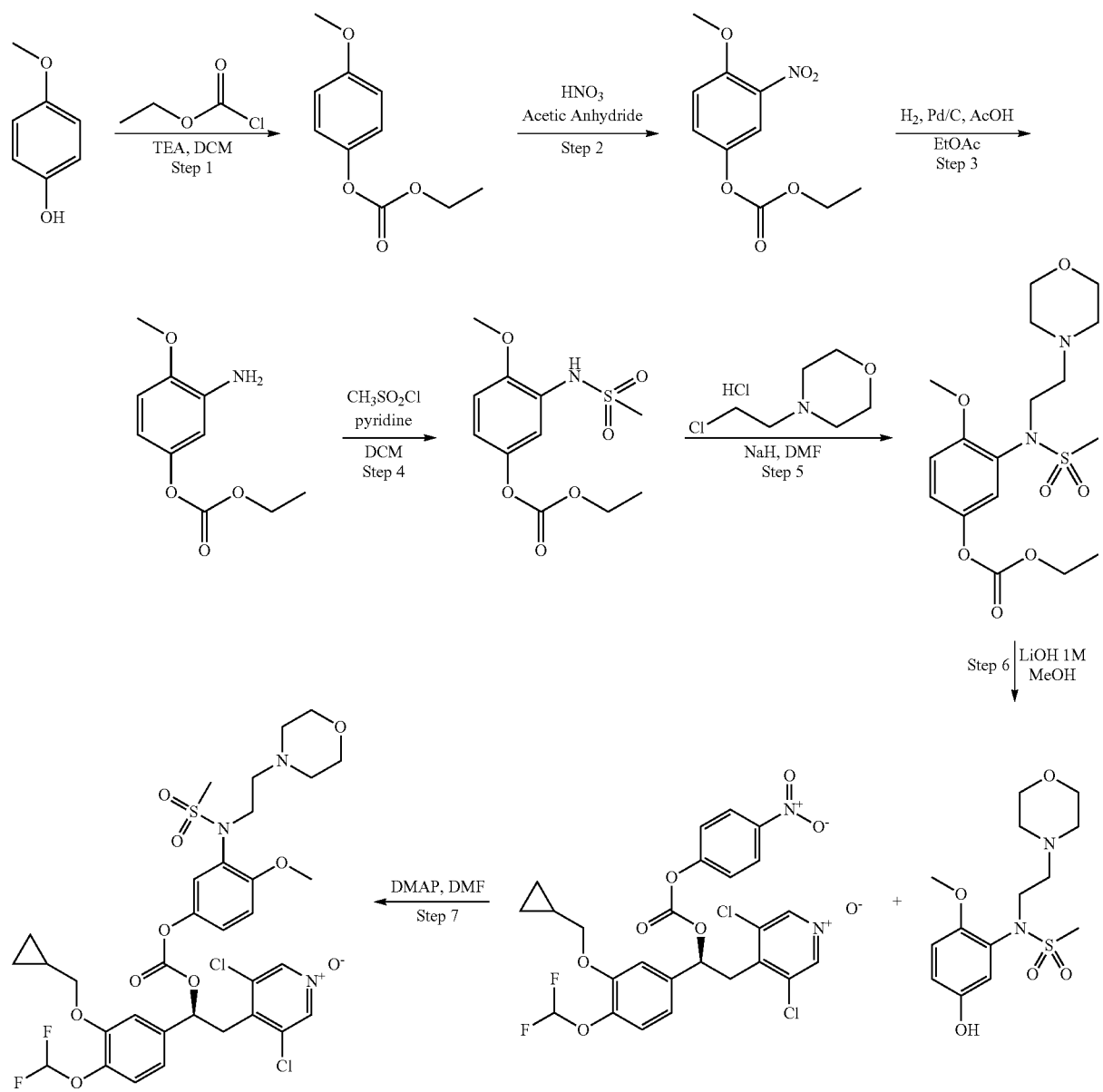

Step 1: Synthesis of ethyl 4-methoxyphenyl carbonate (211)

To a solution of 4-methoxyphenol (5 g, 40.3 mmol) and TEA (6.78 ml, 48.3 mmol) in dry DCM (30 ml), ethyl chloroformate (4.62 ml, 48.3 mmol) was added drop-wise, and the resulting mixture was stirred at RT for 3 hours. The reaction mixture was washed with water and brine; the organic layer was dried over $Na_2SO_4$ and the solvent was evaporated under reduced pressure. The crude ethyl 4-methoxyphenyl carbonate (7.6 g, 38.7 mmol, 96% yield) was used for the next step without any further purification.

Step 2: Synthesis of ethyl 4-methoxy-3-nitrophenyl carbonate (212)

Ethyl 4-methoxyphenyl carbonate (0.700 g, 3.57 mmol) was dissolved in acetic anhydride (2 mL, 21.20 mmol), and the solution was cooled to 0° C. with an ice-water bath. 65% nitric acid (0.4 mL, 5.78 mmol) was added drop-wise at the same temperature. When the addition was completed, the cold bath was removed and the resulting mixture was allowed to warm to RT and stirred for 2 hours. The reaction mixture was poured into ice-water, and the resulting precipitate was collected by filtration affording ethyl 4-methoxy-3-nitrophenyl carbonate (0.720 g, 2.99 mmol, 88% yield, MS/ESI$^+$ 242.2 [MH]$^+$).

Step 3: Synthesis of 3-amino-4-methoxyphenyl ethyl carbonate (213)

Ethyl 4-methoxy-3-nitrophenyl carbonate (0.720 g, 2.99 mmol) was dissolved in EtOAc (20 ml), and glacial acetic acid (0.200 ml, 3.49 mmol) was added followed by 10% palladium on carbon (0.100 g, 0.094 mmol). The mixture was stirred in a Parr apparatus under hydrogen atmosphere (25 psi) for 2 hours. The catalyst was filtered off, and the filtrate was evaporated under reduced pressure. The resulting crude 3-amino-4-methoxyphenyl ethyl carbonate (0.600 g, 2.84 mmol, 95% yield, MS/ESI$^+$ 212.3 [MH]$^+$), was used for the next step without any further purification.

Step 4: Synthesis of ethyl 4-methoxy-3-(methylsulfonamido)phenyl carbonate (214)

To a solution of 3-amino-4-methoxyphenyl ethyl carbonate (0.650 g, 3.08 mmol) and pyridine (2.2 ml, 27.2 mmol) in dry DCM (20 ml), methanesulfonyl chloride (1.0 ml, 12.83 mmol) was added at RT, and the resulting mixture was stirred for 3 hours. The volatiles were removed under reduced pressure affording crude ethyl 4-methoxy-3-(methylsulfonamido)phenyl carbonate (0.850 g, 2.94 mmol, 95% yield, MS/ESI$^+$312.1 [MNa]$^+$) which was used for the next step without purification.

Step 5: Synthesis of ethyl 4-methoxy-3-(N-(2-morpholinoethyl)-methylsulfonamido)phenyl carbonate (215)

A solution of ethyl 4-methoxy-3-(methylsulfonamido) phenyl carbonate (0.850 g, 2.94 mmol) in dry DMF (15 ml) was cooled to 0° C. under nitrogen atmosphere, and sodium hydride (60% w/w, 0.300 g, 7.50 mmol) was added portionwise. After 10 minutes, the cold bath was removed, 4-(2-chloroethyl)morpholine hydrochloride (0.680 mg, 3.65 mmol) was added, and the mixture was heated to 90° C. for 2 hours. After cooling to RT, the reaction mixture was diluted with DCM and washed with water. The organic layer was washed with brine and dried over $Na_2SO_4$; the solvent was evaporated and the crude was purified by flash chromatography on silica gel column (DCM:MeOH=10:0.1) affording ethyl 4-methoxy-3-(N-(2-morpholinoethyl)methylsulfonamido)-phenyl carbonate (0.250 g, 0.621 mmol, 21.14% yield, UPLC-MS purity: 97%, MS/ESI$^+$ 403.1 [MH]$^+$).

Step 6: Synthesis of N-(5-hydroxy-2-methoxyphenyl)-N-(2-morpholinoethyl)methanesulfonamide (216)

To a solution of ethyl 4-methoxy-3-(N-(2-morpholinoethyl)-methylsulfonamido)-phenyl carbonate (0.250 g, 0.621 mmol) in MeOH (5 ml), LiOH 1M (1.242 ml, 1.242 mmol) was added, and the mixture was stirred at RT for 4 hours. The volatiles were removed under vacuum, and the solid residue was partitioned between EtOAc and a diluted aqueous solution of HCl (pH=5). The organic layer was dried over $Na_2SO_4$, the solvent was evaporated and the crude was purified by chromatography on silica gel column (DCM: MeOH=10:0.2) affording N-(5-hydroxy-2-methoxyphenyl)-N-(2-morpholinoethyl)methanesulfonamide (0.180 g, 0.545 mmol, 88% yield, MS/ESI$^+$ 331.0 [MH]$^+$).

Step 7: Synthesis of (S)-3,5-dichloro-4-(2-(3-(cyclopropylmethoxy)-4-(difluoromethoxy)phenyl)-2-((4-methoxy-3-(N-(2-morpholinoethyl)-methylsulfonamido)phenoxy)carbonyloxy)ethyl)pyridine 1-oxide (217)

To a solution of (S)-3,5-dichloro-4-(2-(3-(cyclopropylmethoxy)-4-(difluoromethoxy)phenyl)-2-((4-nitrophenoxy) carbonyloxy)ethyl)pyridine I-oxide (prepared in an analogous manner to that described in Scheme 3, Step 1) (0.250 g, 0.427 mmol) and DMAP (0.052 g, 0.427 mmol) in dry DMF (5 ml), N-(5-hydroxy-2-methoxyphenyl)-N-(2-morpholinoethyl)methanesulfonamide (0.180 g, 0.545 mmol) was added, and the resulting mixture was stirred at RT for 7 hours. The reaction mixture was treated with water and extracted with DCM (3×). The combined organic layers were washed with brine and dried over $Na_2SO_4$; the solvent was removed under vacuum and the crude was purified by flash chromatography on silica gel column (DCM:acetone=6:4) affording (S)-3,5-dichloro-4-(2-(3-(cyclopropylmethoxy)-4-(difluoromethoxy)phenyl)-2-((4-methoxy-3-(N-(2-morpholinoethyl)methylsulfonamido)phenoxy)carbonyloxy)-ethyl) pyridine 1-oxide (0.130 g, 0.167 mmol, 39.2% yield, LC-MS purity (BPI): 100%, MS/ESI$^+$ 776.34 [MH]$^+$, [δ$_D$]−27.42, c=0.542, DCM).

$^1$H NMR (300 MHz, DMSO-d$_6$) δ ppm 8.57 (s, 2 H), 7.21 (d, 1 H), 7.15 (d, 1 H), 7.12 (br. s., 3 H), 7.02 (dd, 1 H), 7.08 (t, 1 H), 5.89 (dd, 1 H), 3.92 (d, 2 H), 3.84 (s, 3 H), 3.57 (dd, 1 H), 3.52-3.66 (m, 2 H), 3.43 (br. s., 4 H), 3.34 (dd, 1 H), 3.03 (s, 3 H), 2.15-2.38 (m, 6 H), 1.16-1.31 (m, 1 H), 0.49-0.67 (m, 2 H), 0.24-0.43 (m, 2 H)

Example 29

Synthesis of (S)-3,5-dichloro-4-(2-(3-(cyclopropylmethoxy)-4-(difluoromethoxy)phenyl)-2-(2-(3-(cyclopropylmethoxy)-4-(methylsulfonamido)benzoylthio)acetoxy)ethyl)pyridine 1-oxide (220)

Scheme 29

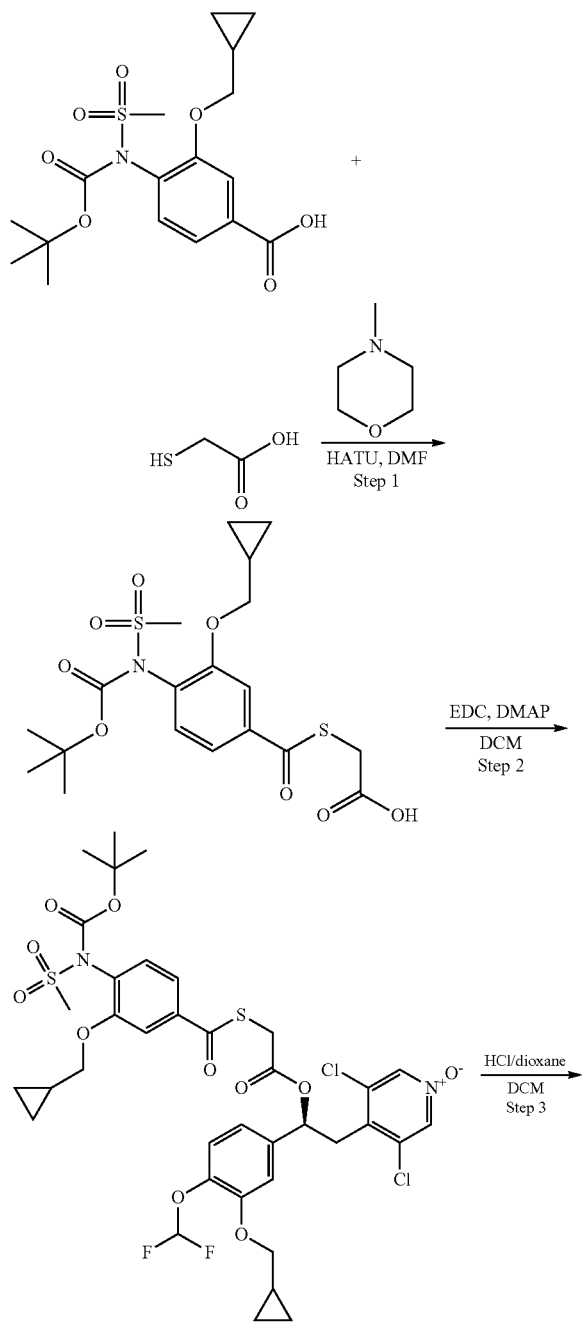

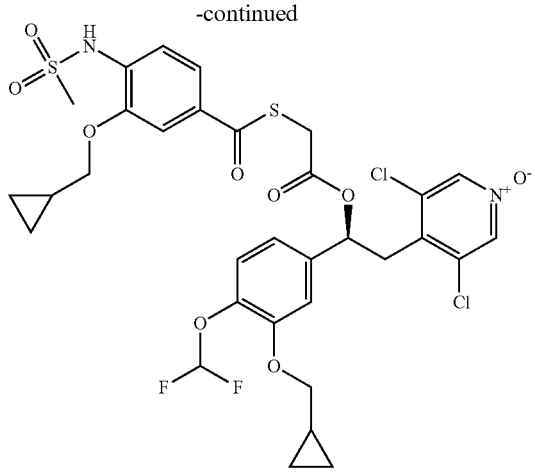

Step 1: Synthesis of 2-(4-(N-(tert-butoxycarbonyl)methylsulfonamido)-3-(cyclopropylmethoxy)benzoylthio)acetic acid (218)

To a solution of 4-(N-(tert-butoxycarbonyl)methylsulfonamido)-3-(cyclopropylmethoxy)benzoic acid (for reference procedure see Example 18, WO2010/089107, which is incorporated herein by reference in its entirety) (0.2 g, 0.519 mmol), in dry DMF (6 ml), HATU (0.198 g, 0.521 mmol) and 4-methylmorpholine (0.057 ml, 0.521 mmol) were added and the mixture was stirred at RT until the complete conversion of the carboxylic acid into the activated ester occurred. 2-mercaptoacetic acid (0.030 ml, 0.434 mmol) was then added drop-wise, and the reaction mixture was stirred in the same conditions overnight. DMF was removed under reduced pressure and the crude was partitioned between EtOAc and HCl 1N; the organic layer was dried over $Na_2SO_4$, and the resulting crude was purified by trituration with $Et_2O$ affording 2-(4-(N-(tert-butoxycarbonyl)methylsulfonamido)-3-(cyclopropylmethoxy)benzoylthio)acetic acid as an off-white solid containing some impurities (0.253 g, yield supposed to be quantitative, MS/ESI$^+$ 459.7 [MH]$^+$). The product was used for the next step without any further purification.

Step 2: Synthesis of (S)-4-(2-(2-(4-(N-(tert-butoxycarbonyl)-methylsulfonamido)-3-(cyclopropylmethoxy)benzoylthio)acetoxy)-2-(3-(cyclopropylmethoxy)-4-(difluoromethoxy)phenyl)ethyl)-3,5-dichloropyridine 1-oxide (219)

To a solution of 2-(4-(N-(tert-butoxycarbonyl)methylsulfonamido)-3-(cyclopropylmethoxy)benzoylthio)acetic acid (0.12 g, 0.261 mmol) in dry DCM (8 ml), EDC (0.083 g, 0.435 mmol) and DMAP (0.027 g, 0.218 mmol) were added, followed by (S)-3,5-dichloro-4-(2-(3-(cyclopropylmethoxy)-4-(difluoromethoxy)phenyl)-2-hydroxyethyl)pyridine 1-oxide (0.091 g, 0.218 mmol). The resulting solution was stirred at RT overnight under $N_2$ atmosphere. The mixture was partitioned between DCM and HCl 1N; the organic layer was then washed with $NaHCO_3$ sat. sol. and brine and dried over $Na_2SO_4$. The solvent was removed under vacuum and the crude was purified by flash chromatography on silica gel cartridge (DCM:MeOH=95:5) affording 0.101 g of an unclean product, which was further purified by preparative HPLC. (S)-4-(2-(2-(4-(N-(tert-butoxycarbonyl)methylsulfonamido)-3-(cyclopropylmethoxy)benzoylthio)acetoxy)-2-

(3-(cyclopropylmethoxy)-4-(difluoromethoxy)phenyl) ethyl)-3,5-dichloropyridine 1-oxide was obtained as a colorless oil (0.046 g, 0.053 mmol, 24.53% yield, MS/ESI+ 861.1 [MH]+).

Step 3: Synthesis of (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzoylthio)acetoxy)ethyl)pyridine 1-oxide (220)

To a solution of (S)-4-(2-(2-(4-(N-(tert-butoxycarbonyl) methylsulfonamido)-3-(cyclopropylmethoxy)benzoylthio) acetoxy)-2-(3-(cyclopropylmethoxy)-4-(difluoromethoxy) phenyl)ethyl)-3,5-dichloropyridine 1-oxide (0.046 g, 0.053 mmol) in DCM (2 ml), HCl 4M in dioxane (0.013 ml, 0.053 mmol) was added and the resulting mixture was stirred at RT overnight. Three more additions of HCl 4M in dioxane (0.265 ml, 1.06 mmol) over five days were performed. The volatiles were removed under vacuum and the crude was purified by filtration through a silica gel cartridge (DCM:Et2O=7:3) affording (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzoylthio)acetoxy)ethyl)pyridine 1-oxide as a colorless oil (0.032 g, 0.042 mmol, 79% yield, MS/ESI+ 761.26 [MH]+, [α$_D$]=−46.44, c=0.5, MeOH).

$^1$H NMR (300 MHz, DMSO-d$_6$) δ ppm 9.20 (s, 1 H), 8.49 (s, 2 H), 7.55 (dd, 1 H), 7.46 (d, 1 H), 7.36 (d, 1 H), 7.19 (d, 1 H), 7.11 (d, 1 H), 7.00 (dd, 1 H), 7.07 (t, 1 H), 6.03 (dd, 1 H), 4.00 (d, 2 H), 3.99 (d, 1 H), 3.91 (d, 2 H), 3.88 (d, 1 H), 3.47 (dd, 1 H), 3.25 (dd, 1 H), 3.14 (s, 3 µl), 1.12-1.39 (m, 2 H), 0.50-0.66 (m, 4 H), 0.21-0.47 (m, 4 H).

Example 30

Synthesis of (S)-3,5-dichloro-4-(2-(3-(cyclopropylmethoxy)-4-(difluoromethoxy)phenyl)-2-(2-(4-methoxy-3-(methylsulfonyloxy)benzoylthio)-acetoxy) ethyl)pyridine 1-oxide (222)

Scheme 30

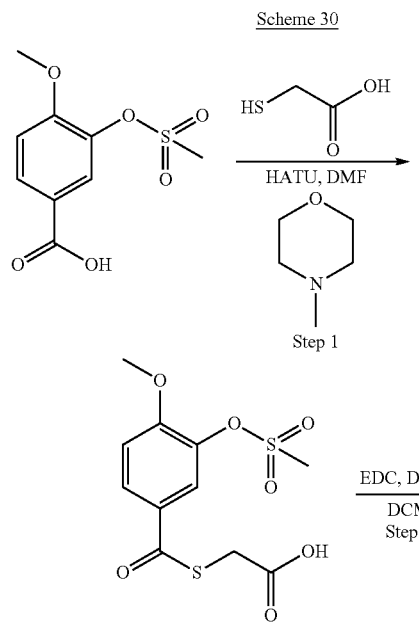

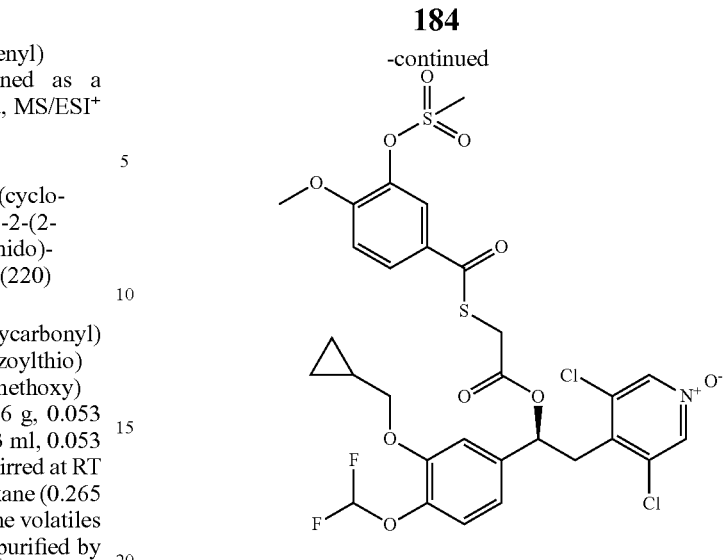

Step 1: Synthesis of 2-(4-methoxy-3-(methylsulfonyloxy)benzoylthio)acetic acid (221)

To a solution of 4-methoxy-3-(methylsulfonyloxy)benzoic acid (prepared in an analogous manner to that described in Scheme 23, Step 2 and 3) (0.362 g, 1.470 mmol) in dry DMF (10.7 ml), HATU (0.559 g, 1.470 mmol) and N-methylmorpholine (0.162 ml, 1.470 mmol) were added. The resulting mixture was stirred at 50° C. under nitrogen until complete conversion of the starting acid into the activated specie (detected by UPLC-MS). Then the solution was allowed to warm to RT and 2-mercaptoacetic acid (0.102 ml, 1.470 mmol) was added drop wise; the resulting mixture was stirred overnight at RT. The solvent was removed under vacuum and the residue was partitioned between EtOAc and HCl 1N; the organic phase was dried over Na$_2$SO$_4$ and the solvent was removed. The crude was purified by preparative HPLC to afford 2-(4-methoxy-3-(methylsulfonyloxy)-benzoylthio)acetic acid (0.152 g, 0.474 mmol, 32.3% yield, MS/ESI+ 342.9 [MNa]+).

Step 2: Synthesis of (S)-3,5-dichloro-4-(2-(3-(cyclopropylmethoxy)-4-(difluoromethoxy)phenyl)-2-(2-(4-methoxy-3-(methylsulfonyloxy)benzoylthio)-acetoxy)ethyl)pyridine 1-oxide (222)

To a solution of 2-(4-methoxy-3-(methylsulfonyloxy)benzoylthio)acetic acid (0.150 g, 0.468 mmol) in dry DCM (12 ml), EDC (0.090 g, 0.468 mmol) and DMAP (0.057 g, 0.468 mmol) were added followed by (S)-3,5-dichloro-4-(2-(3-(cyclopropylmethoxy)-4-(difluoromethoxy)phenyl)-2-hydroxyethyl)pyridine 1-oxide (0.197 g, 0.468 mmol) and the reaction was stirred at RT for 48 hours. The mixture was partitioned between DCM and HCl 1N; the organic phase was washed with NaHCO$_3$ sat. sol., and dried over Na$_2$SO$_4$. The solvent was removed and the crude was purified by preparative HPLC to afford (S)-3,5-dichloro-4-(2-(3-(cyclopropylmethoxy)-4-(difluoromethoxy)phenyl)-2-(2-(4-methoxy-3-(methylsulfonyloxy)benzoylthio)-acetoxy)ethyl)pyridine 1-oxide (0.080 g, 0.111 mmol, 23.64% yield, MS/ESI+ 722.38 [MH]+, [α$_D$]=−34.72, c=0.5, DCM).

$^1$H NMR (300 MHz, DMSO-d$_6$) δ ppm 8.51 (s, 2 H), 7.93 (dd, 1 H), 7.75 (d, 1 H), 7.38 (d, 1 H), 7.18 (d, 1 H), 7.11 (d, 1 H), 6.99 (dd, 1 H), 7.07 (t, 1 H), 6.02 (dd, 1 H), 4.01 (d, 1 H), 3.97 (s, 3 H), 3.91 (d, 2 H), 3.92 (d, 1 H), 3.47 (dd, 1 H), 3.43 (s, 3 H), 3.24 (dd, 1 H), 1.09-1.33 (m, 1 H), 0.50-0.65 (m, 2 H), 0.25-0.42 (m, 2 H)

Example 31

Synthesis of (S)-3,5-dichloro-4-(2-(3-(cyclopropylmethoxy)-4-(difluoromethoxy)phenyl)-2-(2-(4-methoxy-3-(N-(2-morpholinoethyl)-methylsulfonamido)benzoylthio)acetoxy)ethyl)pyridine 1-oxide hydrochloride (227)

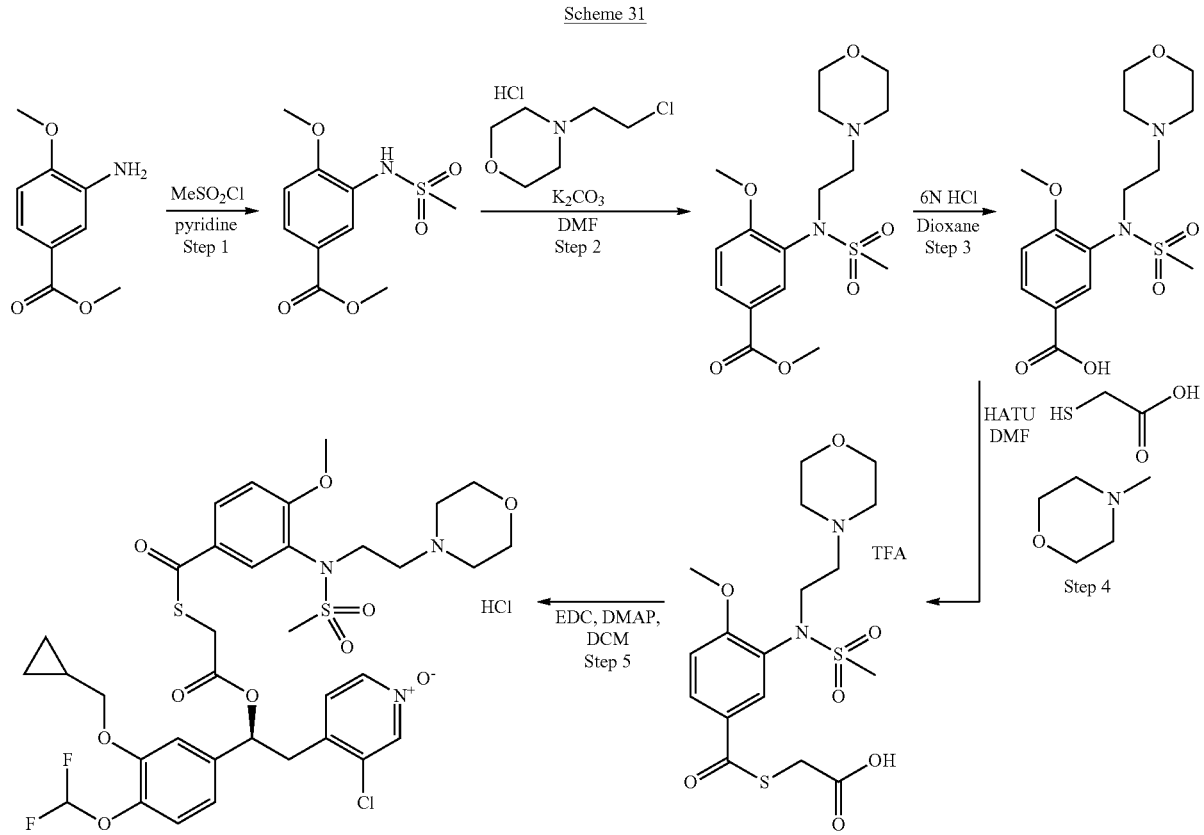

Scheme 31

Step 1: Synthesis of methyl 4-methoxy-3-(methylsulfonamido)benzoate (223)

A solution of methyl 3-amino-4-methoxybenzoate (prepared in an analogous manner to that described in Scheme 17, Step 1) (2.00 g, 11.04 mmol) in dry pyridine (25 ml) was cooled to 0° C.; methanesulfonyl chloride (1.115 ml, 14.35 mmol) was added drop wise, and the mixture was warmed to RT and stirred for 3 hours. The solvent was evaporated under vacuum, and the residue was partitioned between DCM and HCl 2N. The organic layer was washed with brine and dried over $Na_2SO_4$; the solvent was removed; and the residue was triturated with $iPr_2O$ to give methyl 4-methoxy-3-(methylsulfonamido)benzoate (2.6 g, 10.03 mmol, 91% yield, MS/ESI$^+$ 260.1 [MH]$^+$).

Step 2: Synthesis of methyl 4-methoxy-3-(N-(2-morpholinoethyl)methyl-sulfonamido)benzoate (224)

To a solution of ethyl 4-methoxy-3-(methylsulfonamido)benzoate (0.600 g, 2.314 mmol) in dry DMF (23 ml), 4-(2-chloroethyl)morpholine hydrochloride (0.517 g, 2.78 mmol) and $K_2CO_3$ (0.704 g, 5.09 mmol) were sequentially added stirring at RT under nitrogen, and the reaction was heated at 70° C. overnight. Water (40 ml) was added, and the mixture was extracted $Et_2O$ (3×) and then with EtOAc (3×). The combined organic layers were dried over $Na_2SO_4$, and the solvent was removed. The crude was purified by flash chromatography on silica gel column (EtOAc:MeOH=97:3) affording methyl 4-methoxy-3-(N-(2-morpholinoethyl)methylsulfonamido)-benzoate (0.902 g, yield supposed to be quantitative, MS/ESI$^+$ 373.0 [MH]$^+$). This crude was used as such, without any further purification.

Step 3: Synthesis of 4-methoxy-3-(N-(2-morpholinoethyl)methylsulfonamido)benzoic acid (225)

To a solution of methyl 4-methoxy-3-(N-(2-morpholinoethyl)-methylsulfonamido)benzoate (0.902 g, theoric 2.314 mmol) in dioxane (23 ml), HCl 6N (4.63 ml, 27.8 mmol) was added, and the mixture was heated to 100° C. Additional HCl 6N (3.47 ml, 20.83 mmol) was added in two portion over 24 hours with stirring at the same temperature. The volatiles were removed under vacuum and the residue was dissolved in water (20 ml) and basified with $NaHCO_3$ sat sol. (pH 7-8). The aqueous phase was washed with EtOAc and evaporated to dryness. The residue was purified by flash chromatography on silica gel column (DCM:MeOH=9:1 to 7:3) affording 4-methoxy-3-(N-(2-morpholinoethyl)methylsulfonamido)benzoic acid (0.758 g, 2.115 mmol, 91% yield over two steps, MS/ESI$^+$ 358.9 [MH]$^+$).

Step 4: Synthesis of 4-(2-(N-(5-((carboxymethylthio) carbonyl)-2-methoxyphenyl)methylsulfonamido) ethyl)morpholin-4-ium 2,2,2-trifluoroacetate (226)

4-Methoxy-3-(N-(2-morpholinoethyl)methylsulfonamido)benzoic acid (0.250 g, 0.698 mmol) was suspended in dry DMF (6.975 ml), and HATU (398 mg, 1.046 mmol) was added followed by 4-methylmorpholine (0.092 ml, 0.837 mmol). The mixture was stirred at RT for 70 minutes, until complete conversion into the activated ester intermediate was observed. 2-Mercaptoacetic acid (0.097 ml, 1.395 mmol) was added, and the solution was reacted at the same temperature for 2 hours. The solvent was evaporated, and the crude was purified by preparative LC/MS. After evaporation 4-(2-(N-(5-((carboxymethylthio)carbonyl)-2-methoxyphenyl)-methylsulfonamido)ethyl)-morpholin-4-ium 2,2,2-trifluoroacetate was obtained (0.194 g, 0.355 mmol, 50.9% yield, MS/ESI$^+$ 433.0 [MH]$^+$).

Step 5: Synthesis of (S)-3,5-dichloro-4-(2-(3-(cyclopropylmethoxy)-4-(difluoromethoxy)phenyl)-2-(2-(4-methoxy-3-(N-(2-morpholinoethyl)-methylsulfonamido)benzoylthio)acetoxy)ethyl)pyridine 1-oxide hydrochloride (227)

4-(2-(N-(5-((carboxymethylthio)carbonyl)-2-methoxyphenyl)-methylsulfonamido)-ethyl)morpholin-4-ium 2,2,2-trifluoroacetate (0.194 g, 0.355 mmol) was suspended in dry DCM (3.5 ml), and (S)-3,5-dichloro-4-(2-(3-(cyclopropylmethoxy)-4-(difluoromethoxy)phenyl)-2-hydroxyethyl)pyridine 1-oxide (0.115 g, 0.273 mmol), EDC (0.157 g, 0.819 mmol), and DMAP (0.0667 g, 0.546 mmol) were sequentially added with stirring at RT under nitrogen. The resulting yellow solution was stirred at the same temperature for 24 hours. The mixture was diluted with DCM and washed twice with 1N HCl and then with brine. The organic phase was dried over Na2SO4, and the solvent was removed under vacuum. The crude was purified by flash chromatography on silica gel column (DCM:MeOH=96:4) followed by preparative HPLC under neutral conditions. The fraction obtained after solvent evaporation was dissolved in Et$_2$O and HCl in Et$_2$O was added; the resulting suspension was stirred at RT for few minutes. The volatiles were removed, and the residue was dried affording (S)-3,5-dichloro-4-(2-(3-(cyclopropylmethoxy)-4-(difluoromethoxy)phenyl)-2-(2-(4-methoxy-3-(N-(2-morpholinoethyl)-methylsulfonamido)benzoylthio)acetoxy)-ethyl)pyridine 1-oxide hydrochloride (0.103 g, 0.118 mmol, 43.3% yield, LC-MS purity (BPI): 99.7%, MS/ESI$^+$ 834.34 [MH]$^+$, [$\alpha_D$]=−54.00, c=0.5, MeOH).
$^1$H NMR (300 MHz, DMSO-d$_6$) δ ppm 8.50 (s, 2 H), 7.99 (dd, 1 H), 7.85 (d, 1 H), 7.34 (dd, 1 H), 7.20 (d, 1 H), 7.14 (d, 1 H), 7.01 (dd, 1 H), 7.08 (t, 1 H), 6.04 (dd, 1 H), 3.98 (s, 3 H), 3.86-4.07 (m, 8 H), 3.63-3.80 (m, 2 H), 3.48 (dd, 1 H), 3.37-3.57 (m, 2H), 3.26 (dd, 1 H), 3.14-3.29 (m, 2 H), 3.11 (s, 3 H), 3.03-3.20 (m, 2 H), 1.15-1.35 (m, 1 H), 0.46-0.68 (m, 2 H), 0.26-0.46 (m, 2 H)

Example 32

Synthesis of (S)-3,5-dichloro-4-(2-(3-(cyclopropylmethoxy)-4-(difluoromethoxy)phenyl)-2-(2-(4-methoxy-3-(methylsulfonamido)-benzoylthio)acetoxy) ethyl)pyridine 1-oxide (232)

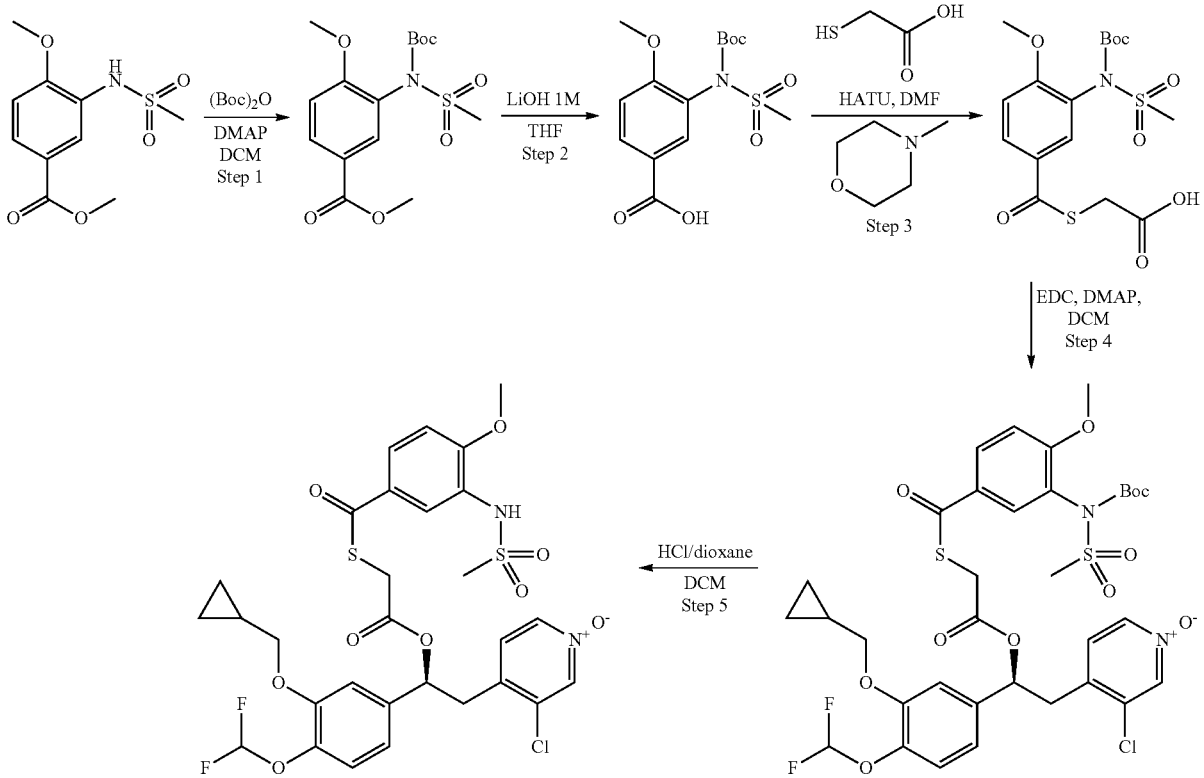

Scheme 32

Step 1: Synthesis of methyl 3-(N-(tert-butoxycarbonyl)methylsulfonamido)-4-methoxybenzoate (228)

To a solution of methyl 4-methoxy-3-(methylsulfonamido) benzoate (prepared in an analogous manner to that described in Scheme 18, Step 1 and 2) (1.658 g, 6.39 mmol) in DCM (75 ml), di-tert-butyl dicarbonate (1.535 g, 7.03 mmol) was added followed by DMAP (0.859 g, 7.03 mmol), and the resulting solution was stirred for 3 hours at RT. The solvent was removed under vacuum, and the residue was partitioned between EtOAc and HCl 1N; the organic phase was washed with brine and dried over $Na_2SO_4$. The solvent was removed to afford methyl 3-(N-(tert-butoxycarbonyl)methylsulfonamido)-4-methoxybenzoate (2.260 g, 6.29 mmol, 98% yield, MS/ESI$^+$ 381.9 [MNa]$^+$). This intermediate was used without purification.

Step 2: Synthesis of 3-(N-(tert-butoxycarbonyl)methylsulfonamido)-4-methoxybenzoic acid (229)

To a solution of methyl 3-(N-(tert-butoxycarbonyl)methylsulfonamido)-4-methoxybenzoate (2.260 g, 6.29 mmol) in THF (25 ml), aqueous 1M LiOH (6.29 ml, 6.29 mmol) was added, and the reaction was stirred at RT for 6 hours. Additional 1M LiOH (12.58 ml, 12.58 mmol) was added over 3 days with stirring at the same temperature. The solvents were removed under vacuum, and the residue was partitioned between EtOAc and 2N HCl; the organic phase was dried over $Na_2SO_4$ and the solvent was removed. The crude was purified by chromatography on silica gel column (DCM:MeOH=98:2 to 9:1) to afford 3-(N-(tert-butoxycarbonyl)methylsulfonamido)-4-methoxybenzoic acid (1.240 g, 3.59 mmol, 57.1% yield, MS/ESI$^+$ 368.0 [MHNa]$^+$).

Step 3: Synthesis of 2-(3-(N-(tert-butoxycarbonyl)methylsulfonamido)-4-methoxybenzoylthio)acetic acid (230)

To a solution of 3-(N-(tert-butoxycarbonyl)methylsulfonamido)-4-methoxybenzoic acid (0.25 g, 0.724 mmol) in dry DMF (7.5 ml), HATU (0.275 g, 0.724 mmol) and 4-methylmorpholine (0.080 ml, 0.724 mmol) were added, and the resulting solution was stirred under nitrogen at RT until complete conversion of starting acid into the activated ester intermediate (UPLC-MS check). Then 2-mercaptoacetic acid (0.042 ml, 0.603 mmol) was added drop wise, and the reaction was stirred at RT overnight. Additional 2-mercaptoacetic acid (0.008 ml, 0.120 mmol) was added, and the mixture was stirred at the same temperature for 5 days. The solvent was removed under vacuum and the residue was partitioned between EtOAc and HCl 1N; the organic phase was dried over $Na_2SO_4$ and the solvent was evaporated. The crude was purified by chromatography on silica gel column (DCM:MeOH=95:5) to afford 2-(3-(N-(tert-butoxycarbonyl)methylsulfonamido)-4-methoxybenzoylthio)acetic acid (0.206 g, 0.491 mmol, 81% yield, MS/ESI$^+$ 419.9 [MH]$^+$). This intermediate was used as such without any further purification.

Step 4: Synthesis of (S)-4-(2-(2-(3-(N-(tert-butoxycarbonyl)-methylsulfonamido)-4-methoxybenzoylthio)acetoxy)-2-(3-(cyclopropylmethoxy)-4-(difluoromethoxy)phenyl)ethyl)-3,5-dichloropyridine 1-oxide (231)

To a solution of 2-(3-(N-(tert-butoxycarbonyl)methylsulfonamido)-4-methoxybenzoylthio)acetic acid (0.206 g, 0.491 mmol) in dry DCM (16 ml), EDC (0.157 g, 0.818 mmol) and DMAP (0.050 g, 0.409 mmol) were added followed by (S)-3,5-dichloro-4-(2-(3-(cyclopropylmethoxy)-4-(difluoromethoxy)phenyl)-2-hydroxyethyl)pyridine 1-oxide (0.172 g, 0.409 mmol), and the resulting solution was stirred overnight at RT. Additional EDC (0.080 g, 0.42 mmol) and DMAP (0.025 g, 0.20 mmol) were added, and the reaction was stirred at the same temperature for 24 hours. The mixture was partitioned between DCM and HCl 1N; the organic phase was washed with aqueous $NaHCO_3$ and dried over $Na_2SO_4$. The solvent was removed and the crude was purified by preparative HPLC affording (S)-4-(2-(2-(3-(N-(tert-butoxycarbonyl)methylsulfonamido)-4-methoxybenzoylthio)acetoxy)-2-(3-(cyclopropylmethoxy)-4-(difluoromethoxy)phenyl)ethyl)-3,5-dichloropyridine 1-oxide (0.082 g, 0.100 mmol, 24.4% yield, MS/ESI$^+$ 821.1 [MH]$^+$).

Step 5: Synthesis of (S)-3,5-dichloro-4-(2-(3-(cyclopropylmethoxy)-4-(difluoromethoxy)phenyl)-2-(2-(4-methoxy-3-(methylsulfonamido)-benzoylthio)acetoxy)ethyl)pyridine 1-oxide (232)

To a solution of (S)-4-(2-(2-(3-(N-(tert-butoxycarbonyl)methylsulfonamido)-4-methoxybenzoylthio)acetoxy)-2-(3-(cyclopropylmethoxy)-4-(difluoromethoxy)-phenyl)ethyl)-3,5-dichloropyridine 1-oxide (0.082 g, 0.100 mmol) in DCM (4 ml), HCl 4M in dioxane was added, and the reaction was stirred at RT for 3 days. The volatiles were removed under vacuum, and the residue was purified by chromatography on silica gel column (DCM:MeOH=95:5) to afford (S)-3,5-dichloro-4-(2-(3-(cyclopropylmethoxy)-4-(difluoromethoxy)phenyl)-2-(2-(4-methoxy-3-(methylsulfonamido)benzoylthio)acetoxy)ethyl)pyridine 1-oxide (0.042 g, 0.058 mmol, 58.3% yield, MS/ESI$^+$ 721.32 [MH]$^+$, [$\alpha_D$]=−31.40, c=0.5, MeOH).

$^1$H NMR (300 MHz, DMSO-d$_6$) δ ppm 9.20 (s, 1 H), 8.50 (s, 2 H), 7.82 (d, 1 H), 7.77 (dd, 1 H), 7.23 (d, 1 H), 7.18 (d, 1 H), 7.11 (d, 1 H), 6.98 (dd, 1 H), 7.06 (t, 1 H), 6.00 (dd, 1 H), 3.98 (d, 1 H), 3.94 (s, 3 H), 3.91 (d, 2 H), 3.91 (d, 1 H), 3.46 (dd, 1 H), 3.25 (dd, 1 H), 3.01 (s, 3 H), 1.13-1.24 (m, 1 H), 0.50-0.64 (m, 2 H), 0.28-0.40 (m, 2 H)

Example 33

Synthesis of (S)-3,5-dichloro-4-(2-(3-(cyclopropylmethoxy)-4-(difluoromethoxy)phenyl)-2-(2-(N-(2-(methoxycarbonyl)phenyl)-methylsulfonamido)acetoxy)ethyl)pyridine 1-oxide (235)

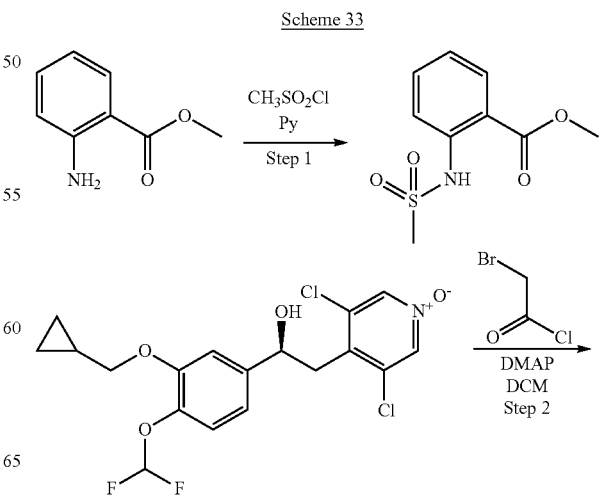

Scheme 33

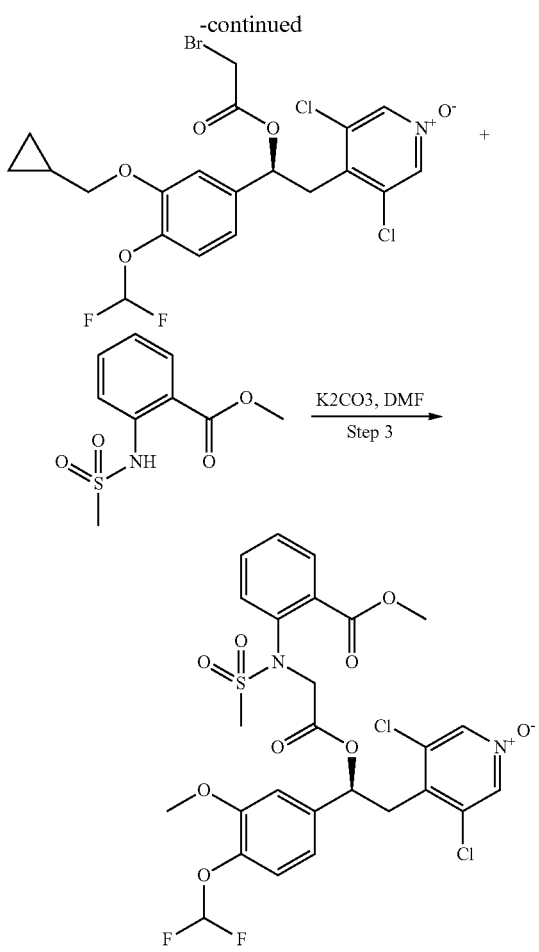

Step 1: Synthesis of methyl 2-(methylsulfonamido)benzoate (233)

500 mg of the desired product were obtained, starting from methyl 2-aminobenzoate (500 mg, 3.3 mmol) and methanesulfonyl chloride (416 mg, 3.63 mmol) in pyridine (2 ml), using an analogous procedure to that described in Scheme 4, Step 5.

Step 2: Synthesis of (S)-4-(2-(2-bromoacetoxy)-2-(3-(cyclopropylmethoxy)-4-(difluoromethoxy)phenyl) ethyl)-3,5-dichloropyridine 1-oxide (234)

(S)-3,5-dichloro-4-(2-(3-(cyclopropylmethoxy)-4-(difluoromethoxy)phenyl)-2-hydroxyethyl)pyridine 1-oxide (500 mg, 1.2 mmol) was dissolved in DCM (15 ml), and TEA (180 mg, 1.8 mmol) and 2-bromoacetyl chloride (243 mg, 1.55 mmol) were added. The mixture was stirred at RT for 2 hours, then was diluted with DCM (50 ml) and washed with HCl 1N (2×). The organic phase was dried over $Na_2SO_4$ and evaporated under vacuum, obtaining a crude (550 mg) containing the title compound (MS/ESI$^+$ 541.17 [MH]$^+$) which was employed in the next step without any further purification.

Step 3: Synthesis of (S)-3,5-dichloro-4-(2-(3-(cyclopropylmethoxy)-4-(difluoromethoxy)phenyl)-2-(2-(N-(2-(methoxycarbonyl)phenyl)-methylsulfonamido)acetoxy)ethyl)pyridine 1-oxide (235)

The mixture obtained in step 2, containing (S)-4-(2-(2-bromoacetoxy)-2-(3-(cyclopropylmethoxy)-4-(difluoromethoxy)phenyl)ethyl)-3,5-dichloropyridine (100 mg) was dissolved in DMF (2 ml), and $K_2CO_3$ (30 mg, 0.22 mmol) and methyl 2-(methylsulfonamido)benzoate (82 mg, 0.36 mmol) were added. The mixture was stirred at RT for 5 hours. The reaction was diluted with water, and the product was extracted with EtOAc. The organic layer was washed with water, dried over $Na_2SO_4$ and evaporated under vacuum. The crude product was purified by preparative reverse-phase HPLC to give 105 mg of the desired product (Yield: 85%, MS/ESI$^+$ 689.5 [MH]$^+$).

$^1$H NMR (400 MHz, acetone) δ ppm 8.15 (s, 2 H), 7.91 (d, J=7.50 Hz, 1 H), 7.48-7.63 (m, 3 H), 7.14-7.24 (m, 2 H), 7.05 (d, J=8.38 Hz, 1 H), 6.91 (t, J=75.00 Hz, 1 H), 6.18-6.27 (m, 1 H), 4.41-4.84 (m, 2 H), 3.95 (dd, J=6.40, 3.31 Hz, 2 H), 3.88 (s, 3 H), 3.48-3.60 (m, 1 H), 3.23-3.38 (m, 1 H), 2.97 (s, 3 H), 1.22-1.33 (m, 1 H), 0.60 (d, J=7.94 Hz, 2 H), 0.37 (d, J=4.85 Hz, 2 H).

The compounds listed in Table 17 were prepared with an analogous procedure to that described in Example 33 by reacting the appropriate precursors (commercially available or synthesized by a person skilled in the art) with suitable reagents, and where purification step has been performed as indicated in Table 17.

TABLE 17

| Structure | Cmp | NMR characterization | MS/ESI$^+$ [MH]$^+$ | Starting Material |
|---|---|---|---|---|
| (structure) | 236 | $^1$H NMR (400 MHz, acetone) δ ppm 8.25 (s, 2 H), 7.99 (d, J = 8.38 Hz, 2 H), 7.43 (d, J = 7.94 Hz, 2 H), 7.16-7.24 (m, 2 H), 7.01 (dd, J = 8.38, 1.76 Hz, 1 H), 6.93 (t, J = 75.00 Hz, 1 H), 6.15 (d, J = 4.41 Hz, 1 H), 4.50 (d, J = 3.09 Hz, 2 H), 4.07 (s, 2 H), 3.95 (d, J = 7.06 Hz, 2 H), 3.89 (s, 3 H), 3.51 (d, J = 9.26 Hz, 1 H), 3.33 (d, J = 4.85 Hz, 1 H), 2.99 (s, 3 H), 1.14-1.35 (m, 1 H), 0.61 (dd, J = 8.16, 1.54 Hz, 2 H), 0.30-0.46 (m, 2 H). | 703.54 | (structure) |

Example 34

Synthesis of (S)-3,5-dichloro-4-(2-(3-(cyclopropylmethoxy)-4-(difluoromethoxy)phenyl)-2-(2-(N-(4-(methylthio)phenyl)methylsulfonamido)-acetoxy)ethyl)pyridine 1-oxide (240)

Scheme 34

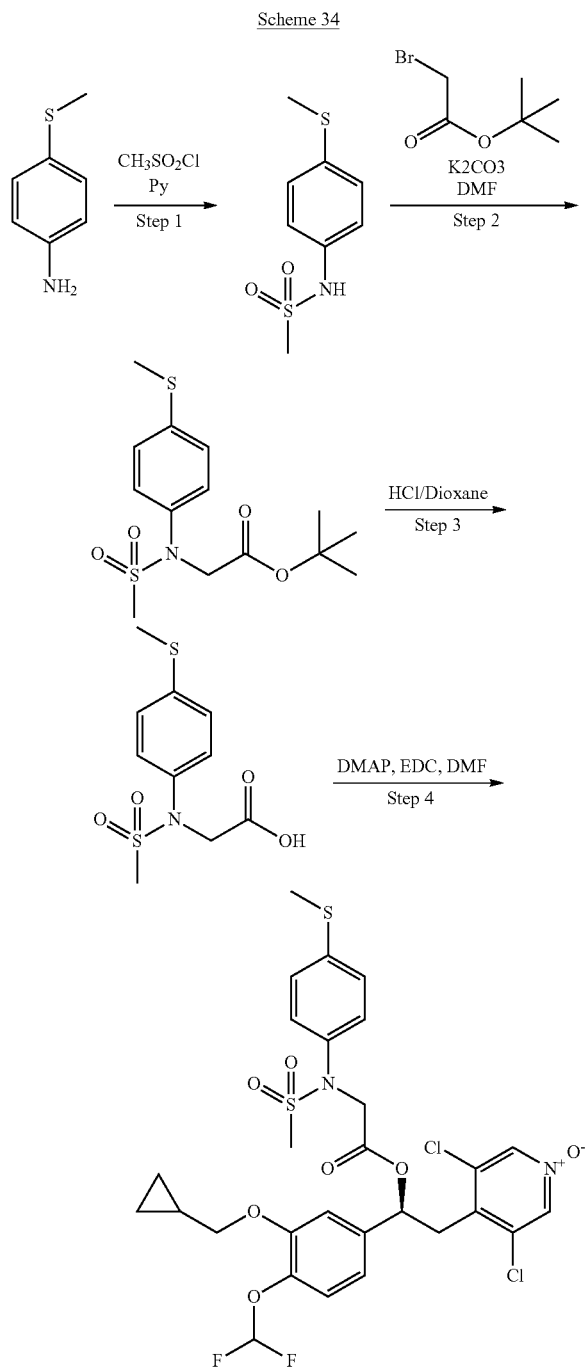

Step 1: Synthesis of N-(4-(methylthio)phenyl)methanesulfonamide (237)

4-(methylthio)aniline (500 mg, 3.59 mmol) was dissolved in DCM (10 ml, 155 mmol). Pyridine (1 ml, 12.36 mmol) and methanesulfonyl chloride (0.336 ml, 4.31 mmol) were added, and the reaction was stirred at RT for 3 hours to achieve completion. The reaction mixture was diluted with HCl 1N and extracted with DCM. The organic phase was dried over $Na_2SO_4$ and concentrated under vacuum. The crude product was triturated in Petroleum Ether to give N-(4-(methylthio)phenyl)methanesulfonamide (550 mg, 70.5% yield).

Step 2: Synthesis of tert-butyl 2-(N-(4-(methylthio)phenyl)methylsulfonamido)acetate (238)

N-(4-(methylthio)phenyl)methanesulfonamide (200 mg, 0.920 mmol) was dissolved in DMF (3 ml). $K_2CO_3$ (254 mg, 1.841 mmol) and tert-butyl 2-bromoacetate (359 mg, 1.841 mmol) were added, and the reaction was stirred at RT for 4 hours. The reaction mixture was diluted with water and filtered. The precipitate was dissolved in EtOAc and extracted with water and HCl 1M, dried over $Na_2SO_4$ and concentrated under vacuum to give tert-butyl 2-(N-(4-(methylthio)phenyl)methylsulfonamido)acetate (220 mg, 72.1% yield).

Step 3: Synthesis of 2-(N-(4-(methylthio)phenyl)methylsulfonamido)acetic acid (239)

Tert-butyl 2-(N-(4-(methylthio)phenyl)methylsulfonamido)acetate (220 mg, 0.664 mmol) was dissolved in HCl 4M in Dioxane (4 ml). The reaction was stirred at RT for 8 hours. The reaction mixture was diluted with water and extracted with EtOAc. The organic phase was dried over $Na_2SO_4$ and concentrated under vacuum, and the crude product was triturated with Petroleum Ether to give 2-(N-(4-(methylthio)phenyl)methyl-sulfonamido)acetic acid (150 mg, 82% yield).

Step 4: Synthesis of (S)-3,5-dichloro-4-(2-(3-(cyclopropylmethoxy)-4-(difluoromethoxy)phenyl)-2-(2-(N-(4-(methylthio)phenyl)methylsulfonamido)-acetoxy)ethyl)pyridine 1-oxide (240)

(S)-3,5-dichloro-4-(2-(3-(cyclopropylmethoxy)-4-(difluoromethoxy)phenyl)-2-hydroxyethyl)pyridine 1-oxide 30 mg, 0.071 mmol), 2-(N-(4-(methylthio)phenyl)methyl-sulfonamido)acetic acid (39.3 mg, 0.143 mmol), DMAP (17.44 mg, 0.143 mmol), and EDC (41.1 mg, 0.214 mmol) were dissolved in DMF (1.5 ml). The reaction was stirred at RT overnight to achieve completion. The reaction mixture was diluted with water and extracted with EtOAc. The organic phase was washed with HCl 1N, Na2CO3 sat. sol. and brine, dried over Na2SO4 and concentrated under vacuum. The crude product was purified by Preparative reverse-phase HPLC to give (S)-3,5-dichloro-4-(2-(3-(cyclopropylmethoxy)-4-(difluoromethoxy)phenyl)-2-(2-(N-(4-(methylthio)phenyl)methylsulfonamido)-acetoxy)ethyl)pyridine 1-oxide (20 mg, 41.3% yield).

MS/ESI$^+$ 677.2; 699.2 [M+H]+; [M+Na]+

$^1$H NMR (400 MHz, acetone) δ ppm 8.19 (s, 2 H), 7.24-7.37 (m, 4 H), 7.15-7.23 (m, 2 H), 7.00-7.08 (m, 1 H), 6.92 (t, J=75.00 Hz, 1 H), 6.20 (dd, J=9.26, 4.41 Hz, 1 H), 4.38-4.70 (m, 2 H), 3.96 (d, J=7.06 Hz, 2 H), 3.55 (dd, J=14.11, 9.70 Hz, 1 H), 3.32 (dd, J=14.33, 4.19 Hz, 1 H), 2.99 (s, 3 H), 2.53 (s, 3 H), 1.19-1.37 (m, 1 H), 0.52-0.72 (m, 2 H), 0.31-0.46 (m, 2 H).

The compounds listed in Table 18 were prepared with an analogous procedure to that described in Example 34 by reacting the appropriate precursors (commercially available or synthesized by a person skilled in the art) with suitable reagents, and where purification step has been performed as indicated in Table 18.

TABLE 18

| Structure | Cmp | NMR characterization | MS/ESI+ [MH]+ | Starting Material |
|---|---|---|---|---|
| 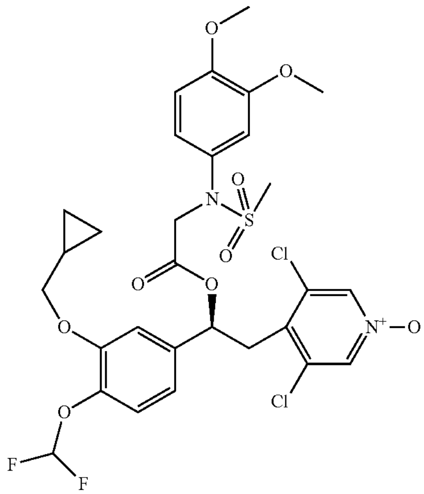 [SMILES: COc1ccc(N(CC(=O)O[C@@H](Cc2c(Cl)c[n+](O)cc2Cl)c2ccc(OC(F)F)c(OCC3CC3)c2)S(C)(=O)=O)cc1OC] | 241 | ¹H NMR (400 MHz, acetone) δ ppm 8.17 (s, 2 H), 7.13-7.25 (m, 2 H), 6.98-7.05 (m, 2 H), 6.85-6.94 (m, 3 H), 6.19 (dd, J = 9.48, 4.63 Hz, 1 H), 4.36-4.64 (m, 2 H), 3.93 (dd, J = 6.84, 2.87 Hz, 2 H), 3.83 (s, 3 H), 3.74 (s, 3 H), 3.53 (dd, J = 14.11, 9.26 Hz, 1 H), 3.31 (dd, J = 14.11, 4.41 Hz, 1 H), 2.98 (s, 3 H), 1.13-1.34 (m, 1 H), 0.54-0.64 (m, 2 H), 0.33-0.39 (m, 2 H). | 691.4; 713.2 [M + H]+; [M + Na]+ | |

Example 35

Synthesis of 4-((S)-2-((S)-2-amino-3-(4-(methylsulfonyloxy)phenyl)-propanoyloxy)-2-(3-(cyclopropylmethoxy)-4-(difluoromethoxy)phenyl)ethyl)-3,5-dichloropyridine 1-oxide hydrochloride (245) and 3,5-dichloro-4-((S)-2-(3-(cyclopropylmethoxy)-4-(difluoromethoxy)phenyl)-2-((S)-2-(methylsulfonamido)-3-(4-(methylsulfonyloxy)phenyl)-propanoyloxy)ethyl)pyridine 1-oxide (246)

Scheme 35

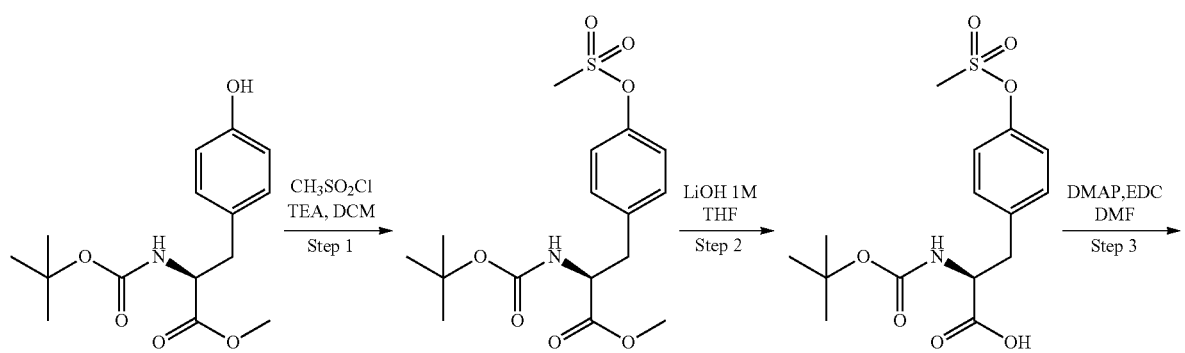

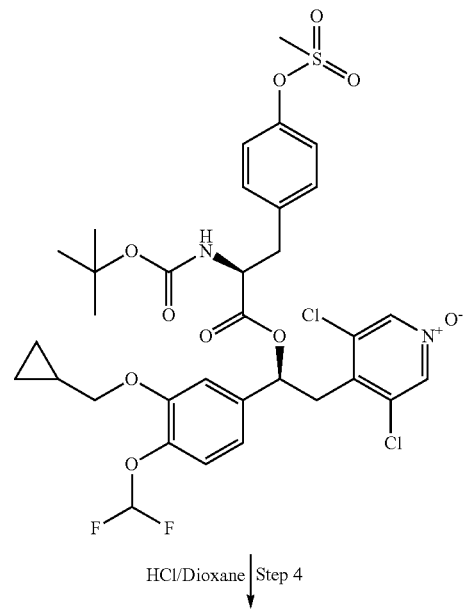

HCl/Dioxane | Step 4

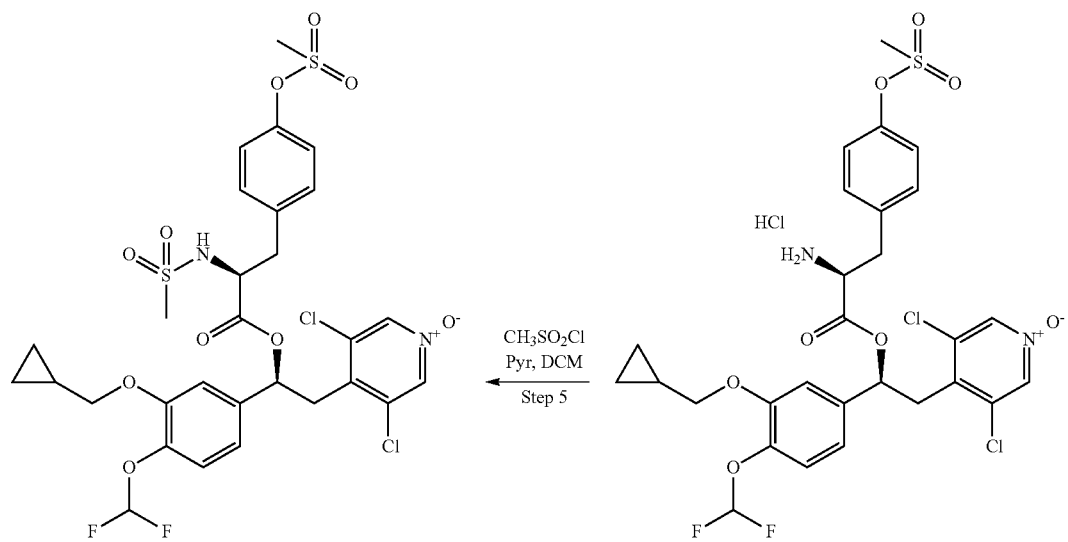

Step 1: Synthesis of (S)-methyl 2-(tert-butoxycarbonylamino)-3-(4(methylsulfonyloxy)phenyl)propanoate (242)

(S)-methyl 2-(tert-butoxycarbonylamino)-3-(4-hydroxyphenyl)propanoate (500 mg, 1.7 mmol) was dissolved in DCM (10 ml), and TEA (343 mg, 3.4 mmol) and methanesulfonyl chloride (290 mg, 2.6 mmol) were added. The mixture was stirred at RT for 2 hours, then was washed with HCl 1N (2x). The organic layer was dried over $Na_2SO_4$ and evaporated under vacuum to give 570 mg (90%) of the title compound which was employed in the next step without any further purification. MS/ESI+ 374.12 [MH]+.

Step 2: Synthesis of (S)-2-(tert-butoxycarbonylamino)-3-(4-(methylsulfonyloxy)phenyl)propanoic acid (243)

(S)-methyl 2-(tert-butoxycarbonylamino)-3-(4-(methylsulfonyloxy)phenyl)-propanoate (300 mg, 0.8 mmol) was dissolved in THF (5 ml), and LiOH 1M (2 ml) was added. The mixture was stirred at RT for 5 hours, then HCl 1M was added, and the product was extracted with EtOAc. The organic layer was dried over $Na_2SO_4$ and evaporated under vacuum to give 229 mg (80%) of the title compound which was employed in the next step without any further purification. MS/ESI+ 360.39 [MH]+.

Step 3: Synthesis of 4-((S)-2-((S)-2-(tert-butoxycarbonylamino)-3-(4(methylsulfonyloxy)phenyl)propanoyloxy)-2-(3-(cyclopropylmethoxy)-4-(difluoromethoxy)phenyl)ethyl)-3,5-dichloropyridine 1-oxide (244)

(S)-3,5-dichloro-4-(2-(3-(cyclopropylmethoxy)-4-(difluoromethoxy)phenyl)-2-hydroxyethyl)pyridine 1-oxide (100 mg, 0.24 mmol) and (S)-2-(tert-butoxycarbonylamino)-3-(4-(methylsulfonyloxy)phenyl)propanoic acid (172 mg, 0.48 mmol) were dissolved in DMF (3 ml). DMAP (35 mg, 0.29 mmol) and EDC (92 mg, 0.48 mmol) were added, and the mixture was stirred at RT for 3 hours, then was quenched with HCl 1N and extracted with EtOAc. The organic layer was washed with HCl 1N and NaHCO$_3$ sat. sol., then was dried over Na$_2$SO$_4$ and evaporated under vacuum to give 155 mg (85%) of the title compound which was employed in the next step without any further purification. MS/ESI$^+$ 761.14 [MH]$^+$.

Step 4: Synthesis of 4-((S)-2-((S)-2-amino-3-(4-(methylsulfonyloxy)-phenyl)propanoyloxy)-2-(3-(cyclopropylmethoxy)-4-(difluoromethoxy)phenyl)-ethyl)-3,5-dichloropyridine 1-oxide hydrochloride (245)

4-((S)-2((S)-2-(tert-butoxycarbonylamino)-3-(4-(methylsulfonyloxy)-phenyl)propanoyloxy)-2-(3-(cyclopropylmethoxy)-4-(difluoromethoxy)phenyl)-ethyl)-3,5-dichloropyridine 1-oxide (100 mg, 0.13 mmol) was dissolved in EtOAc (2 ml), and then HCl 7M in EtOAc (2 ml) was added. The mixture was stirred at RT for 3 hours, then was washed with WATER (2×). The crude was purified by preparative reverse-phase HPLC to give 69 mg (80%) of the title compound.
MS/ESI+661.09 [MH]+.
$^1$H NMR (400 MHz, CHLOROFORM-d) δ ppm 7.06-7.20 (m, 4 H), 6.83-6.88 (m, 3 H), 6.88 (m, 1 H), 6.71 (t, J=75.00 Hz, 1 H), 6.63 (m, 1 H), 6.14 (m, 1 H), 3.91 (d, J=6.65 Hz, 2 H), 3.41-3.62 (m, 2 H), 2.92-3.28 (m, 6 H), 1.54-1.68 (bs, 2 H), 1.24-1.38 (m, 1 H), 0.59-0.76 (m, 2 H), 0.42 (q, J=4.96 Hz, 2 H).

Step 5: Synthesis of 3,5-dichloro-4-((S)-2-(3-(cyclopropylmethoxy)-4-(difluoromethoxy)phenyl)-2-((S)-2-(methylsulfonamido)-3-(4-(methylsulfonyloxy)phenyl)propanoyloxy)ethyl)pyridine 1-oxide (246)

4-((S)-2-((S)-2-amino-3-(4-(methylsulfonyloxy)phenyl)propanoyloxy)-2-(3-(cyclopropylmethoxy)-4-(difluoromethoxy)phenyl)ethyl)-3,5-dichloropyridine 1-oxide hydrochloride (30 mg, 0.05 mmol) was dissolved in DCM (2 ml) and pyridine (100 μl), then methanesulfonyl chloride (7 mg, 0.06 mmol) was added. The mixture was stirred at RT for 2 h, then was washed with HCl 1N (2×). The crude was purified by semi-preparative HPLC to give 29 mg of the final compound (Yield: 80%)
MS/ESI$^+$ 738.9; 760.9 [M+H]+; [M+Na]+
$^1$H NMR (400 MHz, acetone) δ ppm 8.26 (s, 2 H), 7.32-7.38 (m, 2 H), 7.21-7.27 (m, 3 H), 7.15-7.21 (m, 1 H), 6.98-7.06 (m, 1 H), 6.82 (t, J=75.00 Hz, 1 H), 6.51-6.60 (m, 1 H), 6.07-6.16 (m, 1 H), 4.29-4.42 (m, 1 H), 3.92-4.01 (m, 2 H), 3.52-3.66 (m, 1 H), 3.30-3.38 (m, 1 H), 3.25 (m, 4 H), 2.96-3.06 (m, 1 H), 2.57 (s, 3 H), 1.20-1.34 (m, 1 H), 0.53-0.65 (m, 2 H), 0.31-0.42 (m, 2 H).

Example 36

Synthesis of (S)-3,5-dichloro-4-(2-(3-(cyclopropylmethoxy)-4-(difluoromethoxy)phenyl)-2-(2-(3,4-dimethoxyphenylsulfonamido)-acetoxy)ethyl)pyridine 1-oxide (247) and of (S)-3,5-dichloro-4-(2-(3-(cyclopropylmethoxy)-4-(difluoromethoxy)phenyl)-2-(2-(3,4-dimethoxy-N-(2-morpholinoethyl)phenylsulfonamido)acetoxy)ethyl)pyridine 1-oxide (248)

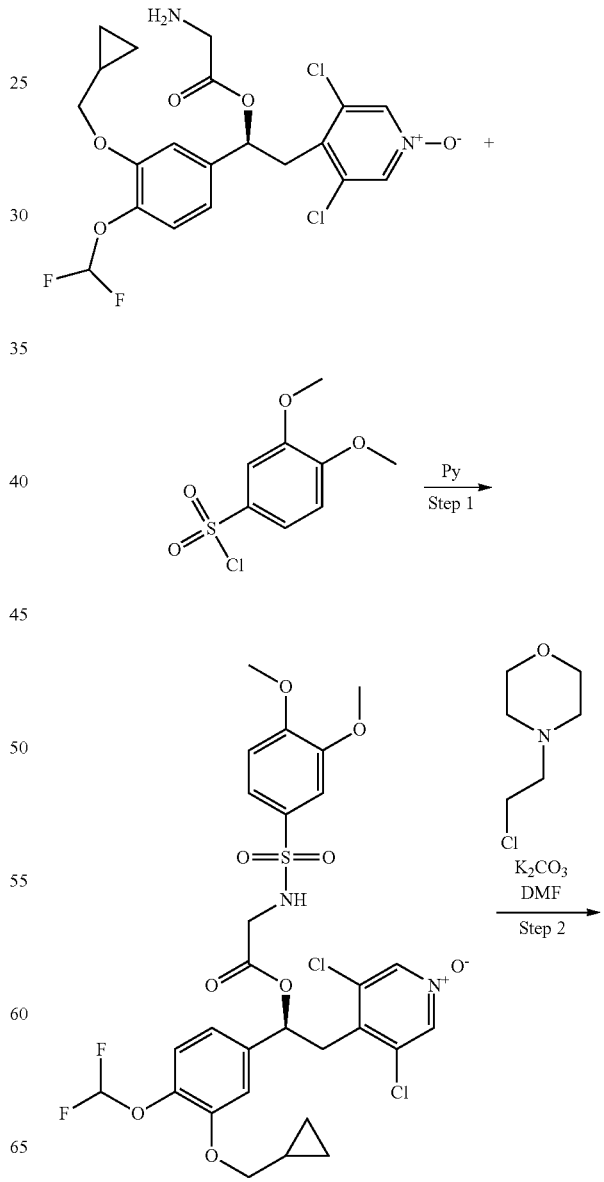

Scheme 36

Step 1: Synthesis of (S)-3,5-dichloro-4-(2-(3-(cyclo-propylmethoxy)-4-(difluoromethoxy)phenyl)-2-(2-(3,4-dimethoxyphenylsulfonamido)-acetoxy)ethyl) pyridine 1-oxide (247)

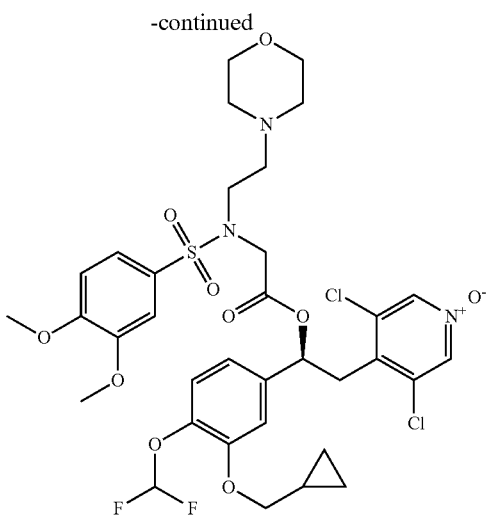

(S)-4-(2-(2-aminoacetoxy)-2-(3-(cyclopropylmethoxy)-4-(difluoromethoxy)-phenyl)ethyl)-3,5-dichloropyridine 1-oxide (prepared in an analogous manner to that described in Scheme 1, Step 1-2) (70 mg, 0.15 mmol) was dissolved in pyridine (1 ml), then Dimethoxybenzenesulfonylchloride (46 mg, 0.19 mmol) was added, and the mixture was stirred at RT for 3 hours. The reaction was diluted with HCl 1N, and the product was extracted with EtOAc. The organic phase was dried over Na$_2$SO$_4$ and evaporated under vacuum. The crude product was purified by Preparative reverse-phase HPLC to give 60 mg of the final product.

MS/ESI$^+$ 677.50 [MH]$^+$ $^1$H NMR (400 MHz, acetone) δ ppm 8.24 (s, 2 H), 7.37 (dd, J=8.38, 2.21 Hz, 1 H), 7.32 (d, J=2.20 Hz, 1 H), 7.12-7.19 (m, 2 H), 7.02 (d, J=8.82 Hz, 1 H), 6.97 (dd, J=8.16, 1.98 Hz, 1 H), 6.92 (t, J=75.00 Hz, 1 H), 6.73 (m, 1 H), 6.01 (dd, J=9.04, 5.07 Hz, 1 H), 3.95 (d, J=7.06 Hz, 2 H), 3.89 (s, 3 H), 3.81-3.86 (m, 5 H), 3.48 (dd, J=14.11, 8.82 Hz, 1 H), 3.23-3.32 (m, 1 H), 1.19-1.33 (m, 1 H), 0.52-0.67 (m, 2 H), 0.38 (d, J=4.85 Hz, 2 H).

Step 2: Synthesis of (S)-3,5-dichloro-4-(2-(3-(cyclopropylmethoxy)-4-(difluoromethoxy)phenyl)-2-(2-(3,4-dimethoxy-N-(2-morpholinoethyl)-phenylsulfonamido)acetoxy)ethyl)pyridine 1-oxide (248)

(S)-3,5-dichloro-4-(2-(3-(cyclopropylmethoxy)-4-(difluoromethoxy)phenyl)-2-(2-(3,4-dimethoxyphenylsulfonamido)acetoxy)ethyl)pyridine 1-oxide (30 mg, 0.04 mmol) was dissolved in DMF (1 ml), then 4-(2 chloroethyl)morpholine free base (33 mg, 0.22 mmol), K$_2$CO$_3$ (12 mg, 0.088 mmol) and KI (7 mg, 0.0044 mmol) were added, and the mixture was stirred at 40° C. for 6 hours. The reaction was diluted with water, and the product was extracted with EtOAc. The organic phase was dried over Na$_2$SO$_4$ and evaporated under vacuum. The crude product was purified by Preparative reverse-phase HPLC to give 25 mg of the final product.

MS/ESI$^+$ 790.3; 812.4[M+H]+; [M+Na]+

$^1$H NMR (400 MHz, acetone) δ ppm 8.28 (s, 2 H), 7.34-7.43 (m, 1 H), 7.25-7.31 (m, 1 H), 7.16-7.23 (m, 2 H), 6.98-7.07 (m, 2 H), 6.91 (t, J=75.00 Hz, 1 H), 6.00-6.15 (m, 1 H), 4.18-4.36 (m, 2 H), 3.94-4.03 (m, 2 H), 3.89 (s, 3 H), 3.83 (s, 3 H), 3.49-3.62 (m, 1 H), 3.39-3.47 (m, 4 H), 3.20-3.37 (m, 3 H), 2.37-2.45 (m, 2 H), 2.21-2.30 (m, 4 H), 1.18-1.38 (m, 1 H), 0.54-0.68 (m, 2 H), 0.31-0.44 (m, 2 H).

The compounds listed in Table 19 were prepared with an analogous procedure to that described in Example 37, Step 1, by reacting the appropriate precursors (commercially available or synthesized by a person skilled in the art) with suitable reagents, and where purification step has been performed as indicated in Table 19.

TABLE 19

| Structure | Cmp | $^1$H NMR | MS/ESI$^+$ [MH]$^+$ | Starting Material (and Conditions, if different) | Purification Method |
| --- | --- | --- | --- | --- | --- |
| 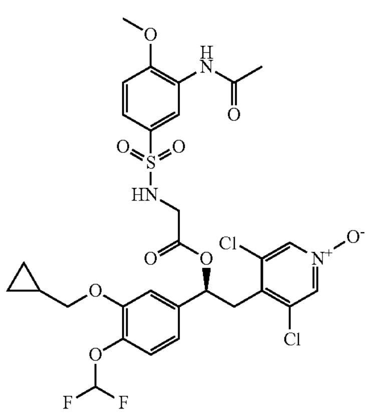 [SMILES: COc1ccc(S(=O)(=O)NCC(=O)O[C@@H](Cc2c(Cl)c[n+]([O-])cc2Cl)c2ccc(OC(F)F)c(OCC3CC3)c2)cc1NC(C)=O] | 249 | $^1$H NMR (400 MHz, acetone) δ ppm 8.86 (s, 1 H), 8.76 (bs, 1 H), 8.25 (s, 2 H), 7.48 (dd, J = 8.60, 2.43 Hz, 1 H), 7.13-7.24 (m, 2 H), 7.10 (d, J = 8.38 Hz, 1 H), 6.98 (dd, J = 8.38, 1.76 Hz, 1 H), 6.92 (t, J = 75.00 Hz, 1 H), 6.83 (t, J = 6.17 Hz, 1 H), 6.02 (dd, J = 9.04, 5.07 Hz, 1 H), 3.92-4.00 (m, 5 H), 3.81-3.87 (m, 2 H), 3.48 (dd, J = 14.11, 8.82 Hz, 1 H), 3.27 (dd, J = 14.11, 5.29 Hz, 1 H), 2.18 (s, 3 H), 1.22-1.34 (m, 1 H), 0.57-0.66 (m, 2 H), 0.28-0.42 (m, 2 H). | 704.52 |  | Sulphonylation in DMAP (1.5 eq) and DCM at RT |

TABLE 19-continued

| Structure | Cmp | $^1$H NMR | MS/ESI$^+$ [MH]$^+$ | Starting Material (and Conditions, if different) | Purification Method |
|---|---|---|---|---|---|
| 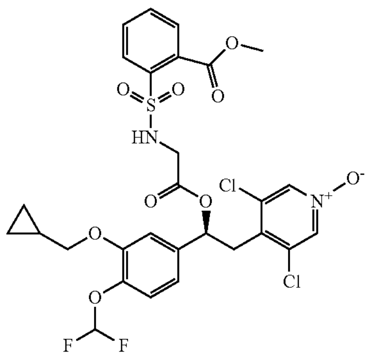 [SMILES: COC(=O)c1ccccc1S(=O)(=O)NCC(=O)O[C@@H](Cc1c(Cl)c[n+]([O-])cc1Cl)c1ccc(OC(F)F)c(OCC2CC2)c1] | 250 | $^1$H NMR (400 MHz, acetone) δ ppm 8.24 (s, 2 H), 7.86-7.94 (m, 1 H), 7.76-7.84 (m, 1 H), 7.66-7.75 (m, 2 H), 7.13-7.21 (m, 2 H), 6.97 (dd, J = 8.16, 1.98 Hz, 1 H), 6.92 (t, 1 H, CHF2), 6.70-6.81 (m, 1 H), 6.00 (dd, J = 9.26, 4.85 Hz, 1 H), 3.88-4.08 (m, 7 H), 3.49 (dd, J = 14.11, 9.26 Hz, 1 H), 3.25 (dd, J = 14.11, 4.85 Hz, 1 H), 1.21-1.36 (m, 1 H), 0.56-0.68 (m, 2 H), 0.33-0.44 (m, 2 H). | 675.48 | Sulphonylation in DMAP (1.5 eq) and DCM at RT | |
| 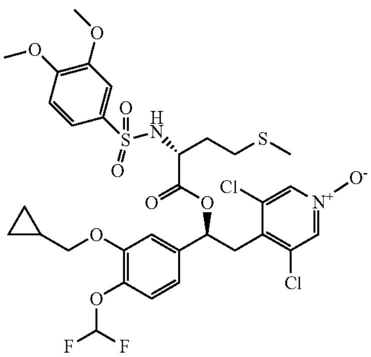 [SMILES: COc1ccc(S(=O)(=O)N[C@H](CCSC)C(=O)O[C@@H](Cc2c(Cl)c[n+]([O-])cc2Cl)c2ccc(OC(F)F)c(OCC3CC3)c2)cc1OC] | 251 | $^1$H NMR (400 MHz, acetone) δ ppm 8.75-8.83 (m, 1 H), 8.26 (s, 2 H), 7.36 (dd, J = 8.60, 1.98 Hz, 1 H), 7.26 (d, J = 1.76 Hz, 1 H), 7.11-7.18 (m, 2 H), 6.93-6.99 (m, 1 H), 6.80-6.93 (m, 2 H), 5.95 (dd, J = 9.04, 5.51 Hz, 1 H), 4.13 (m, 1 H), 3.95 (dd, J = 6.84, 2.87 Hz, 2 H), 3.86 (s, 3 H), 3.77 (s, 3 H), 3.44 (d, J = 9.26 Hz, 1 H), 3.27 (d, J = 5.29 Hz, 1 H), 2.40 (t, J = 7.28 Hz, 2 H), 1.99 (s, 3 H), 1.73 - 1.95 (m, 2 H), 1.29 (m, 1 H), 0.54-0.66 (m, 2 H), 0.32-0.45 (m, 2 H). | 750.74 | | Evaporation of Ethyl Acetate |
| 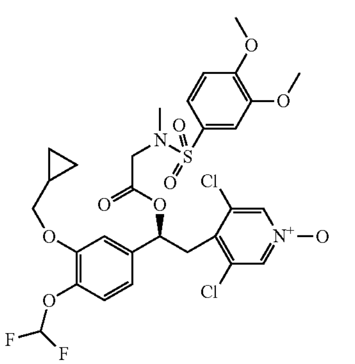 [SMILES: COc1ccc(S(=O)(=O)N(C)CC(=O)O[C@@H](Cc2c(Cl)c[n+](O)cc2Cl)c2ccc(OC(F)F)c(OCC3CC3)c2)cc1OC] | 252 | $^1$H NMR (400 MHz, acetone) δ ppm 8.27 (s, 2 H), 7.34 (dd, J = 8.38, 2.21 Hz, 1 H), 7.25 (d, J = 2.20 Hz, 1 H), 7.16-7.21 (m, 2 H), 7.08 (m, 1 H), 7.03 (d, J = 2.21 Hz, 1 H), 6.93 (t, J = 75.00 Hz, 1 H), 6.05-6.13 (m, 1 H), 4.04 (d, J = 2.21 Hz, 2 H), 3.97 (d, J = 6.62 Hz, 2 H), 3.90 (s, 3 H), 3.85 (s, 3 H), 3.49-3.62 (m, 1 H), 3.28-3.36 (m, 1 H), 2.76 (s, 3 H), 1.20-1.34 (m, 1 H), 0.61 (dd, J = 8.16, 1.54 Hz, 2 H), 0.38 (d, J = 4.41 Hz, 2 H) | 691.3; 713.2 [M + H]+; [M + Na]+ | Sulphonylation in Pyridine and DCM at RT | |

TABLE 19-continued

| Structure | Cmp | ¹H NMR | MS/ESI⁺ [MH]⁺ | Starting Material (and Conditions, if different) | Purification Method |
|---|---|---|---|---|---|
| 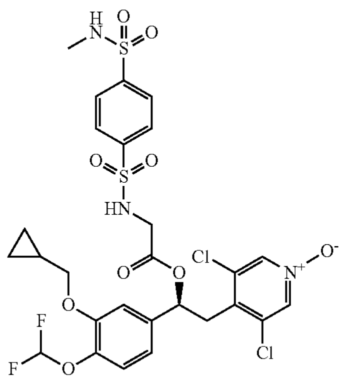 [SMILES: CNS(=O)(=O)c1ccc(S(=O)(=O)NCC(=O)O[C@@H](Cc2c(Cl)c[n+]([O-])cc2Cl)c2ccc(OC(F)F)c(OCC3CC3)c2)cc1] | 253 | ¹H NMR (400 MHz, acetone) δ ppm 8.29 (s, 2 H), 7.99 (d, J = 3.97 Hz, 4 H), 7.16-7.28 (m, 3 H), 6.98-7.07 (m, 1 H), 6.94 (t, J = 75.00 Hz, 1 H), 6.55-6.68 (m, 1 H), 5.92-6.12 (m, 1 H), 3.97 (d, J = 7.06 Hz, 4 H), 3.45-3.60 (m, 1 H), 3.23-3.35 (m, 1 H), 2.63 (d, J = 4.85 Hz, 3 H), 1.20-1.38 (m, 1 H), 0.62 (dd, J = 7.94, 1.32 Hz, 2 H), 0.39 (d, J = 4.41 Hz, 2 H) | 710.1 | | |
| 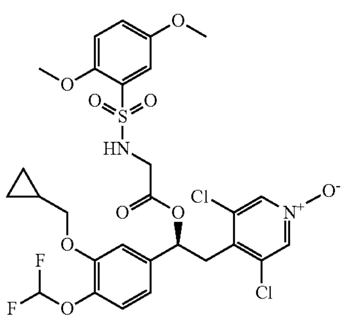 [SMILES: COc1ccc(OC)c(S(=O)(=O)NCC(=O)O[C@@H](Cc2c(Cl)c[n+]([O-])cc2Cl)c2ccc(OC(F)F)c(OCC3CC3)c2)c1] | 254 | ¹H NMR (400 MHz, acetone) δ ppm 8.23 (s, 2 H), 7.30 (d, J = 3.09 Hz, 1 H), 7.05-7.21 (m, 4 H), 6.94-7.01 (m, 1 H), 6.91 (t, J = 75.00 Hz, 1 H), 6.48-6.59 (m, 1 H), 5.99-6.10 (m, 1 H), 3.95 (d, J = 7.06 Hz, 2 H), 3.86-3.91 (m, 2 H), 3.82 (d, J = 6.17 Hz, 6 H), 3.46 (d, J = 9.26 Hz, 1 H), 3.29 (d, J = 5.29 Hz, 1 H), 1.22-1.32 (m, 1 H), 0.61 (dd, J = 8.16, 1.54 Hz, 2 H), 0.32-0.43 (m, 2 H). | 677.1 | | Triturated in EtOH |
| 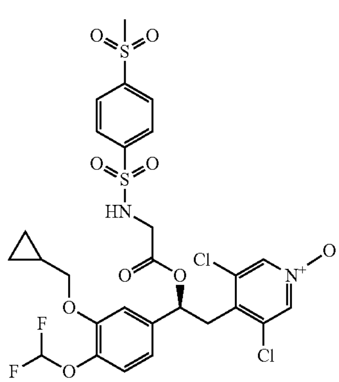 [SMILES: CS(=O)(=O)c1ccc(S(=O)(=O)NCC(=O)O[C@@H](Cc2c(Cl)c[n+](O)cc2Cl)c2ccc(OC(F)F)c(OCC3CC3)c2)cc1] | 255 | ¹H NMR (400 MHz, acetone) δ ppm 8.26 (s, 2 H), 8.00-8.13 (m, 4 H), 7.28 (m, 1 H), 7.15-7.21 (m, 2 H), 7.01 (dd, J = 8.38, 2.21 Hz, 1 H), 6.93 (t, J = 75.00 Hz, 1 H), 5.98-6.07 (m, 1 H), 3.89-4.10 (m, 4 H), 3.51 (dd, J = 14.11, 9.26 Hz, 1 H), 3.28 (dd, J = 14.11, 4.85 Hz, 1 H), 3.21 (s, 3 H), 1.19-1.38 (m, 1 H), 0.55-0.64 (m, 2 H), 0.32-0.42 (m, 2 H). | 695.1 | | Triturated in EtOH |
| 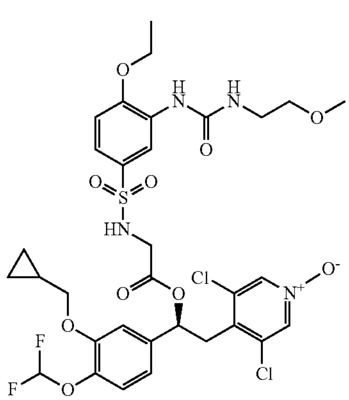 [SMILES: CCOc1ccc(S(=O)(=O)NCC(=O)O[C@@H](Cc2c(Cl)c[n+]([O-])cc2Cl)c2ccc(OC(F)F)c(OCC3CC3)c2)cc1NC(=O)NCCOC] | 256 | ¹H NMR (400 MHz, DMSO-d₆) δ ppm 8.62 (d, J = 2.65 Hz, 1 H), 8.54 (s, 2 H), 8.08 (s, 1 H), 7.97 (t, J = 6.17 Hz, 1 H), 7.19-7.30 (m, 2 H), 7.13 (d, J = 8.38 Hz, 1 H), 6.99-7.07 (m, 3 H), 6.83-6.93 (m, 1 H), 5.88 (dd, J = 8.38, 5.29 Hz, 1 H), 4.15 (q, J = 6.91 Hz, 2 H), 3.89 (d, J = 7.06 Hz, 2 H), 3.51-3.74 (m, 3 H), 3.24-3.35 (m, 5 H), 1.41 (t, J = 6.84 Hz, 3 H), 1.21 (d, J = 17.20 Hz, 1 H), 0.46-0.63 (m, 2 H), 0.28-0.43 (m, 2 H). | 777.3 | | Triturated in EtOH |

TABLE 19-continued

| Structure | Cmp | ¹H NMR | MS/ESI⁺ [MH]⁺ | Starting Material (and Conditions, if different) | Purification Method |
|---|---|---|---|---|---|
| 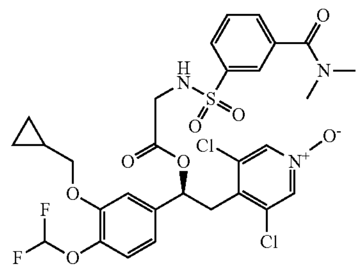 [SMILES: CN(C)C(=O)c1cccc(S(=O)(=O)NCC(=O)O[C@@H](Cc2c(Cl)c[n+]([O-])cc2Cl)c2ccc(OC(F)F)c(OCC3CC3)c2)c1] | 258 | ¹H NMR (400 MHz, acetone) δ ppm 8.53 (s, 2 H), 8.21-8.37 (m, 1 H), 7.70-7.84 (m, 2 H), 7.52-7.67 (m, 2 H), 7.11-7.21 (m, 1 H), 7.01-7.08 (m, 2 H), 6.85-6.97 (m, 1 H), 5.76-5.96 (m, 1 H), 3.87-3.95 (m, 2 H), 3.78-3.87 (m, 1 H), 3.62-3.74 (m, 1 H), 3.32-3.41 (m, 1 H), 3.12-3.23 (m, 1 H), 3.00 (s, 3 H), 2.86 (s, 3 H), 1.10-1.31 (m, 1 H), 0.51-0.61 (m, 2 H), 0.28-0.40 (m, 2 H). | 688.0 | 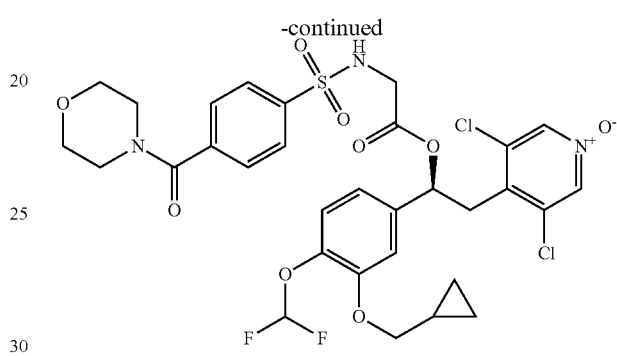 | |

Example 37

Synthesis of (S)-3,5-dichloro-4-(2-(3-(cyclopropylmethoxy)-4-(difluoromethoxy)phenyl)-2-(2-(4-(morpholine-4-carbonyl)phenylsulfonamido)-acetoxy)ethyl)pyridine 1-oxide (260)

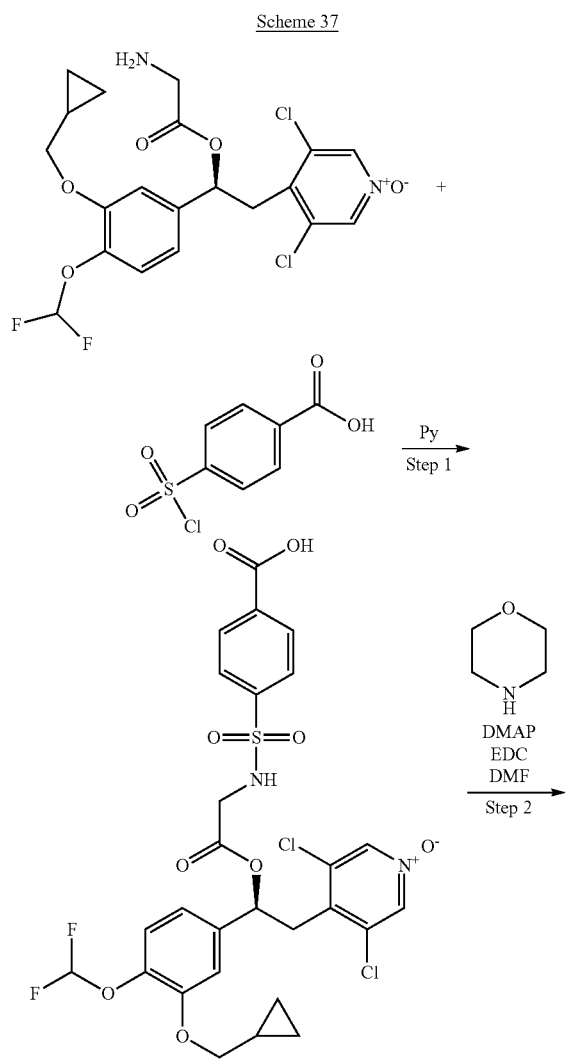

Step 1: Synthesis of (S)-4-(2-(2-(4-carboxyphenylsulfonamido)acetoxy)-2-(3-(cyclopropylmethoxy)-4-(difluoromethoxy)phenyl)ethyl)-3,5-dichloropyridine 1-oxide (259)

(S)-4-(2-(2-aminoacetoxy)-2-(3-(cyclopropylmethoxy)-4-(difluoromethoxy)-phenyl)ethyl)-3,5-dichloropyridine 1-oxide (prepared in an analogous manner as described in Scheme 1, Step 1-2) (100 mg, 0.210 mmol) was dissolved in py (2.5 ml). 4-(chlorosulfonyl)benzoic acid (60.1 mg, 0.272 mmol) was added, and the reaction was stirred at RT for 4 hours. The reaction mixture was diluted with HCl 1N and extracted with EtOAc. The organic phase was washed with HCl 1N and brine, dried over $Na_2SO_4$ and concentrated under vacuum to give (S)-4-(2-(2-(4-carboxyphenylsulfonamido)acetoxy)-2-(3-(cyclopropylmethoxy)-4-(difluoromethoxy)phenyl)ethyl)-3,5-dichloropyridine 1-oxide (120 mg, 87% yield).

Step 2: Synthesis of (S)-3,5-dichloro-4-(2-(3-(cyclopropylmethoxy)-4-(difluoromethoxy)phenyl)-2-(2-(4-(morpholine-4-carbonyl)-phenylsulfonamido)-acetoxy)ethyl)pyridine 1-oxide (260)

(S)-4-(2-(2-(4-carboxyphenylsulfonamido)acetoxy)-2-(3-(cyclopropylmethoxy)-4-(difluoromethoxy)phenyl)ethyl)-3,5-dichloropyridine 1-oxide (30 mg, 0.045 mmol), morpholine (19.76 mg, 0.227 mmol), DMAP (11.08 mg, 0.091 mmol) and EDC (43.5 mg, 0.227 mmol) were dissolved in DMF (1.5 ml). The reaction was stirred at RT overnight. The reaction mixture was diluted with water and extracted with EtOAc. The organic phase was dried over $Na_2SO_4$ and concentrated under vacuum. The crude product was purified by preparative reverse-phase HPLC to give (S)-3,5-dichloro-4-(2-(3-(cyclopropylmethoxy)-4-(difluoromethoxy)phenyl)-2-(2-(4-(morpholine-4-carbonyl)phenylsulfonamido)-acetoxy)ethyl)pyridine 1-oxide (15 mg, 0.021 mmol, 45.3% yield).

MS/ESI+ 752.3 [M+Na]+

$^1$H NMR (400 MHz, acetone) δ ppm 8.27 (s, 2 H), 7.86 (d, J=8.38 Hz, 2 H), 7.57 (d, J=7.94 Hz, 2 H), 7.18 (m, 2 H), 6.98-7.07 (m, 2 H), 6.93 (t, J=75.00 Hz, 1 H), 5.98-6.08 (m, 1 H), 3.98 (d, J=7.06 Hz, 3 H), 3.84-3.92 (m, 1 H), 3.34-3.79 (m, 9 H), 3.23-3.32 (m, 1 H), 1.21-1.39 (m, 1 H), 0.54-0.69 (m, 2 H), 0.34-0.48 (m, 2 H).

The compounds listed in Table 20 were prepared with an analogous procedure to that described in Example 37 by reacting the appropriate precursors (commercially available or synthesized by a person skilled in the art) with suitable reagents, and where purification step has been performed as indicated in Table 20.

TABLE 20

| Structure | Cmp | $^1$H NMR | MS/ESI+ [MH]+ | Starting Material(s) |
|---|---|---|---|---|
| 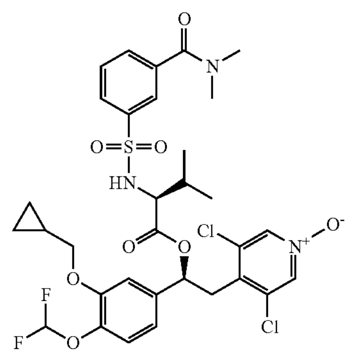 [SMILES: CC(C)[C@H](NS(=O)(=O)c1cccc(C(=O)N(C)C)c1)C(=O)O[C@@H](Cc1c(Cl)c[n+]([O-])cc1Cl)c1ccc(OC(F)F)c(OCC2CC2)c1] | 261 | $^1$H NMR (400 MHz, DMSO-d$_6$) δ ppm 8.58 (s, 2 H), 8.28-8.40 (m, 1 H), 7.72-7.77 (m, 1 H), 7.67-7.71 (m, 1 H), 7.49-7.65 (m, 2 H), 7.11-7.17 (m, 1 H), 7.02-7.09 (m, 2 H), 6.85-6.92 (m, 1 H), 5.68-5.81 (m, 1 H), 3.78-3.94 (m, 2 H), 3.49-3.59 (m, 1 H), 3.33-3.42 (m, 1 H), 3.07-3.18 (m, 1 H), 3.01 (s, 3 H), 2.87 (s, 3 H), 1.88-2.04 (m, 1 H), 1.15-1.28 (m, 1 H), 0.63-0.69 (m, 3 H), 0.52-0.61 (m, 5 H), 0.27-0.39 (m, 2 H). | 729.9 | |
| 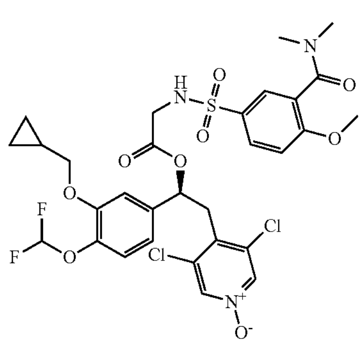 [SMILES: COc1ccc(S(=O)(=O)NCC(=O)O[C@@H](Cc2c(Cl)c[n+]([O-])cc2Cl)c2ccc(OC(F)F)c(OCC3CC3)c2)cc1C(=O)N(C)C] | 262 | $^1$H NMR (400 MHz, DMSO-d$_6$) δ ppm 8.54 (s, 2 H), 8.03-8.19 (m, 1 H), 7.65-7.78 (m, 1 H), 7.47-7.59 (m, 1 H), 7.12-7.24 (m, 2 H), 7.01-7.09 (m, 2 H), 6.80-6.97 (m, 1 H), 5.78-5.95 (m, 1 H), 3.87 (m, 5 H), 3.72-3.82 (m, 1 H), 3.57-3.69 (m, 1 H), 3.33-3.45 (m, 1 H), 3.10-3.26 (m, 1 H), 2.97 (s, 3 H), 2.71 (s, 3 H), 1.10-1.29 (m, 1 H), 0.47-0.64 (m, 2 H), 0.26-0.41 (m, 2 H). | 718.2 | |

Example 38

Synthesis of (S)-3,5-dichloro-4-(2-(3-(cyclopropyl-methoxy)-4-(difluoromethoxy)phenyl)-2-(2-((4-(me-thylsulfonamido)phenyl)-methylsulfonamido)ac-etoxy)ethyl)pyridine 1-oxide (265)

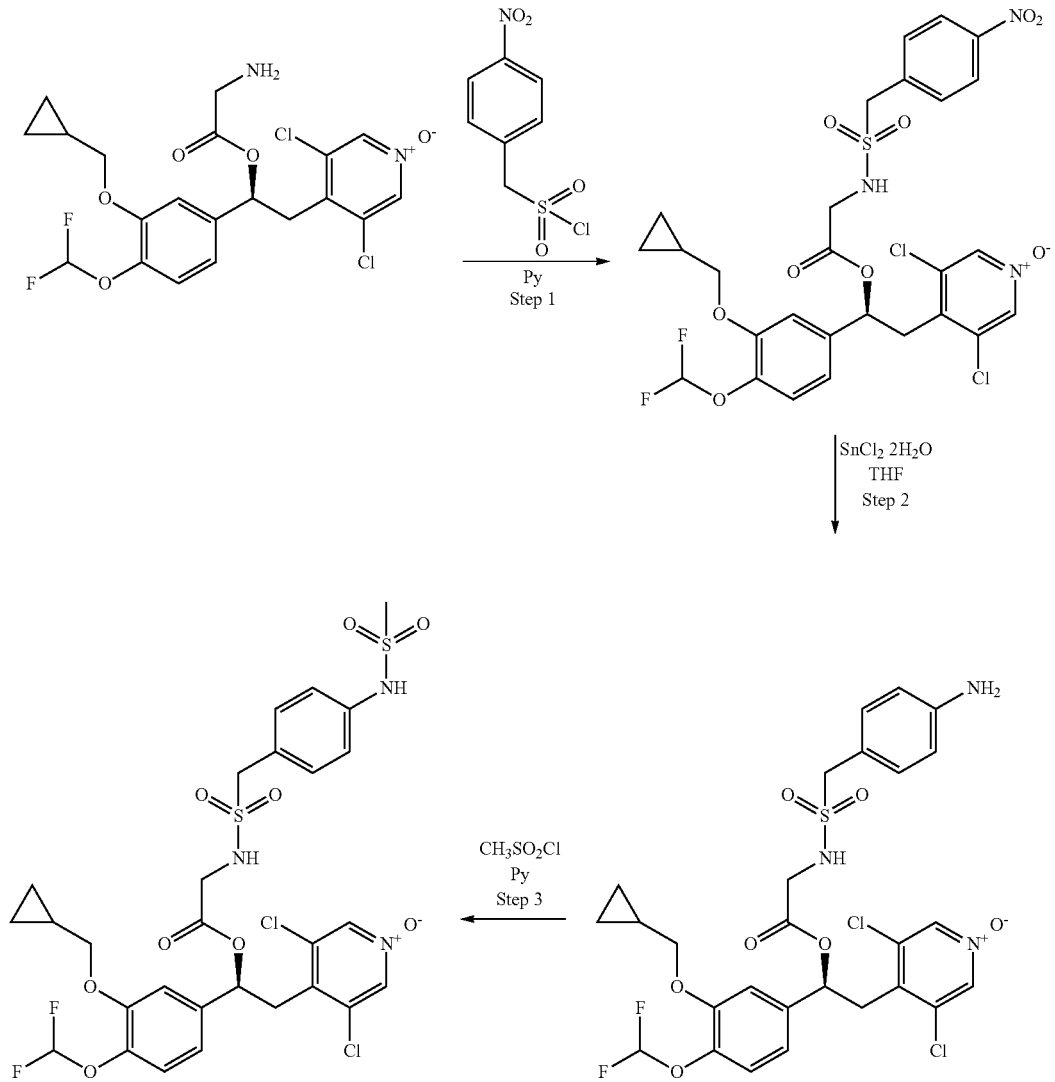

Step 1: Synthesis of (S)-3,5-dichloro-4-(2-(3-(cyclo-propylmethoxy)-4-(difluoromethoxy)phenyl)-2-(2-((4-nitrophenyl)methylsulfonamido)acetoxy)-ethyl) pyridine 1-oxide (263)

To a solution of (S)-4-(2-(2-aminoacetoxy)-2-(3-(cyclo-propylmethoxy)-4-(difluoromethoxy)phenyl)ethyl)-3,5-dichloropyridine 1-oxide (prepared in an analogous manner to that described in Scheme 1, Step 1-2) (243 mg, 0.509 mmol) dissolved in pyridine (1 mL), cooled at 0° C., (4-nitrophenyl)methanesulfonyl chloride (100 mg, 0.424 mmol) was added. The mixture was stirred at 0° C. for 2 hours. The mixture was then diluted with EtOAc and washed with HCl 0.1N, NaHCO₃ sat. sol. and brine. The organic phase was dried over Na₂SO₄ and the solvent was evaporated. (S)-3,5-dichloro-4-(2-(3-(cyclopropylmethoxy)-4-(difluo-romethoxy)phenyl)-2-(2-((4-nitrophenyl)methyl-sulfona-mido)acetoxy)ethyl)pyridine 1-oxide was obtained (287 mg, 0.42 mmol, quantitative yield).

Step 2: Synthesis of (S)-4-(2-(2-((4-aminophenyl) methylsulfonamido)-acetoxy)-2-(3-(cyclopropyl-methoxy)-4-(difluoromethoxy)phenyl)ethyl)-3,5-dichloropyridine 1-oxide (264)

To a solution of (S)-3,5-dichloro-4-(2-(3-(cyclopropyl-methoxy)-4-(difluoromethoxy)phenyl)-2-(4-nitro-2-(trifluo-romethyl)benzoyloxy)ethyl)pyridine 1-oxide (287 mg, 0.424 mmol) in THF (6 ml), tin chloride dihydrate (287 mg, 1.27 mmol) was added, and the mixture was stirred at RT for 5 hours. THF was evaporated under reduced pressure, then the crude was taken up with EtOAc and NaHCO₃ sat. sol. and filtered through a pad of Celite. The two phases were separated, then the organic phase was dried over Na₂SO₄ and the solvent was evaporated, to give 220 mg (0.340 mmol, 80% yield) of the title compound.

Step 3: Synthesis of (S)-3,5-dichloro-4-(2-(3-(cyclopropylmethoxy)-4-(difluoromethoxy)phenyl)-2-(2-((4-(methylsulfonamido)phenyl)-methylsulfonamido)acetoxy)ethyl)pyridine 1-oxide (265)

To a solution of (S)-4-(2-(2-((4-aminophenyl)methylsulfonamido)acetoxy)-2-(3-(cyclopropylmethoxy)-4-(difluoromethoxy)phenyl)ethyl)-3,5-dichloropyridine 1-oxide (220 mg, 0.340 mmol) dissolved in pyridine (1 mL), cooled at 0° C., methanesulfonyl chloride (40 µl, 0.513 mmol) was added. The mixture was stirred at 0° C. for 2 hours. The mixture was then diluted with EtOAc and washed with HCl 0.1N, NaHCO₃ sat. sol. and brine. The organic phase was dried over Na₂SO₄ and the solvent was evaporated. (S)-3,5-dichloro-4-(2-(3-(cyclopropylmethoxy)-4-(difluoromethoxy)phenyl)-2-(2-((4-(methylsulfonamido)phenyl)-methylsulfonamido)acetoxy)ethyl)pyridine 1-oxide was obtained as an orange foam which was purified by preparative HPLC to afford 47 mg (0.077 mmol, 38% yield, MS/ESI⁺ 724.2 [MH]⁺).

¹H NMR (400 MHz, acetone) δ ppm 8.61-8.81 (m, 1 H), 8.25 (s, 2 H), 7.28-7.43 (m, 4 H), 7.14-7.24 (m, 2 H), 7.02-7.07 (m, 1 H), 6.90 (t, J=75.00 Hz, 1 H), 6.42-6.50 (m, 1 H), 6.10-6.18 (m, 1 H), 4.29 (s, 2 H), 3.96 (d, J=7.06 Hz, 2 H), 3.88 (dd, J=13.23, 6.17 Hz, 1 H), 3.50-3.60 (m, 1 H), 3.29-3.36 (m, 1 H), 3.01 (s, 3 H), 1.17-1.34 (m, 1 H), 0.59 (dd, J=8.16, 1.54 Hz, 2 H), 0.31-0.42 (m, 2 H).

The compounds listed in Table 21 were prepared with an analogous procedure to that described in Example 38 by reacting the appropriate precursors (commercially available or synthesized by a person skilled in the art) with suitable reagents, and where purification step has been performed as indicated in Table 21.

TABLE 21

| Structure | Cmp | ¹H NMR | MS/ESI⁺ [MH]⁺ | Starting Material |
|---|---|---|---|---|
| (structure) | 266 | ¹H NMR (400 MHz, acetone) δ ppm 8.25 (s, 2 H), 7.99-8.12 (bs, 1 H), 7.88-7.95 (m, 1 H), 7.53-7.60 (m, 1 H), 7.13-7.20 (m, 3 H), 6.95-7.05 (m, 1 H), 6.90 (t, J = 75.00 Hz, 1 H), 5.91-6.09 (m, 1 H), 3.99 (s, 5 H), 3.83-3.91 (m, 2 H), 3.43-3.55 (m, 1 H), 3.22-3.32 (m, 1 H), 3.03 (s, 3 H), 0.79-0.97 (m, 1 H), 0.53-0.68 (m, 2 H), 0.30-0.47 (m, 2 H). | 740.3 | (structure) |
| (structure) | 267 | ¹H NMR (400 MHz, CHLOROFORM-d) δ ppm 8.21 (s, 2 H), 7.73 (d, J = 8.80 Hz, 2 H), 7.29 (d, 2 H), 7.19 (d, J = 7.94 Hz, 1 H), 6.87-6.96 (m, 2 H), 6.65 (t, J = 75.00 Hz, 1 H), 5.91 (m, 1 H), 5.05 (bs, 2 H), 3.87-3.99 (m, 2 H), 3.70-3.79 (m, 3 H), 3.47-3.57 (m, 1 H), 3.09-3.11 (s, 3 H), 1.21-1.35 (m, 1 H), 0.63-0.73 (m, 2 H), 0.32-0.47 (m, 2 H). | 732.2 [M + Na]+ | (structure) |

Example 39

Synthesis of (S)-3,5-dichloro-4-(2-(3-(cyclopropylmethoxy)-4-(difluoromethoxy)phenyl)-2-(2-(2-methoxy-4-nitrophenylamino)-2-oxoacetoxy)ethyl)pyridine 1-oxide (269)

Scheme 39

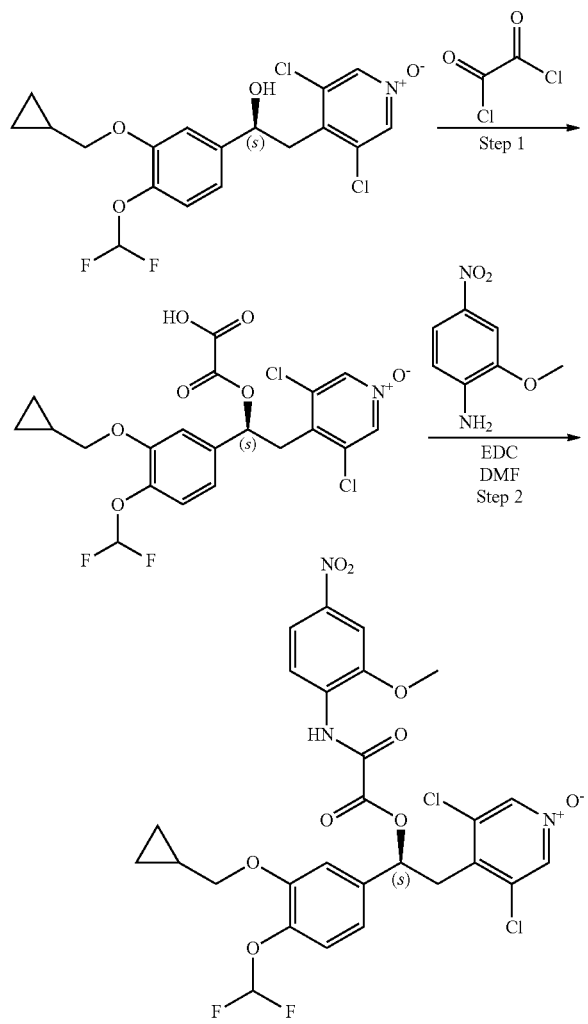

Step 1: Synthesis of (S)-4-(2-(carboxycarbonyloxy)-2-(3-(cyclopropylmethoxy)-4-(difluoromethoxy)phenyl)ethyl)-3,5-dichloropyridine 1-oxide (268)

(S)-3,5-dichloro-4-(2-(3-(cyclopropylmethoxy)-4-(difluoromethoxy)phenyl)-2-hydroxyethyl)pyridine 1-oxide (200 mg, 0.48 mmol) was dissolved in oxalyl dichloride (2 ml), and the reaction mixture was stirred at RT for 1 hour, then it was diluted with HCl 1M. The precipitate was filtered and dried in the vacuum oven to give 200 mg of the desired product (Yield: 85%).

Step 2: Synthesis of (S)-3,5-dichloro-4-(2-(3-(cyclopropylmethoxy)-4-(difluoromethoxy)phenyl)-2-(2-(2-methoxy-4-nitrophenylamino)-2-oxoacetoxy)ethyl)pyridine 1-oxide (269)

(S)-4-(2-(carboxycarbonyloxy)-2-(3-(cyclopropylmethoxy)-4-(difluoromethoxy)phenyl)ethyl)-3,5-dichloropyridine 1-oxide (50 mg, 0.10 mmol) was dissolved in DMF (5 ml), then EDC (29.2 mg, 0.15 mmol) was added. 2-methoxy-4-nitroaniline (34.2 mg, 0.2 mmol) was added at 0° C., and the mixture was stirred at 0° C. for 2 hours. The reaction was diluted with HCl 1M and extracted with EtOAc. The organic phase was dried over $Na_2SO_4$ and evaporated under vacuum. The crude product was purified by Preparative reverse-phase HPLC to give 21 mg of the title product. (Yield: 32%).

MS/ESI$^+$ 642.1 [MH]$^+$ $^1$H NMR (400 MHz, DMSO-d$_6$) δ ppm 9.71-10.03 (m, 1 H), 8.57 (s, 2 H), 8.25-8.35 (m, 1 H), 7.93-8.01 (m, 1 H), 7.86-7.92 (m, 1 H), 7.16-7.26 (m, 2 H), 7.02-7.12 (m, 2 H), 5.98-6.08 (m, 1 H), 4.02 (s, 3 H), 3.87-3.99 (m, 2 H), 3.56-3.68 (m, 1 H), 3.34-3.40 (m, 1 H), 1.16-1.28 (m, 1 H), 0.51-0.64 (m, 2 H), 0.31-0.41 (m, 2 H).

The compounds listed in Table 22 were prepared with an analogous procedure to that described in Example 39 by reacting the appropriate precursors (commercially available or synthesized by a person skilled in the art) with suitable reagents, and where purification step has been performed as indicated in Table 22.

TABLE 22

| Structure | Cmp | $^1$H NMR | MS/ESI$^+$ [MH]$^+$ | Starting Material |
|---|---|---|---|---|
| (structure shown) | 270 | $^1$H NMR (400 MHz, acetone) δ ppm 9.70-9.85 (m, 1 H), 8.27 (s, 2 H), 7.74 (d, J = 8.82 Hz, 2 H), 7.27-7.35 (m, 3 H), 7.20 (m, 1 H), 7.12 (m, 1 H), 6.93 (t, J = 75.00 Hz, 1 H), 6.15-6.24 (m, 1 H), 3.84-4.05 (m, 2 H), 3.64-3.77 (m, 1 H), 3.42-3.52 (m, 1 H), 2.49 (s, 3 H), 1.22-1.33 (m, 1 H), 0.52-0.66 (m, 2 H), 0.32-0.45 (m, 2 H). | 613.1 | (structure shown) |

217
Example 40

Synthesis of (S)-3,5-dichloro-4-(2-(3-(cyclopropyl-methoxy)-4-(difluoromethoxy)phenyl)-2-(2,2-dihy-droxy-2-(4-nitrophenyl)acetoxy)ethyl)-pyridine 1-oxide (271)

Scheme 40

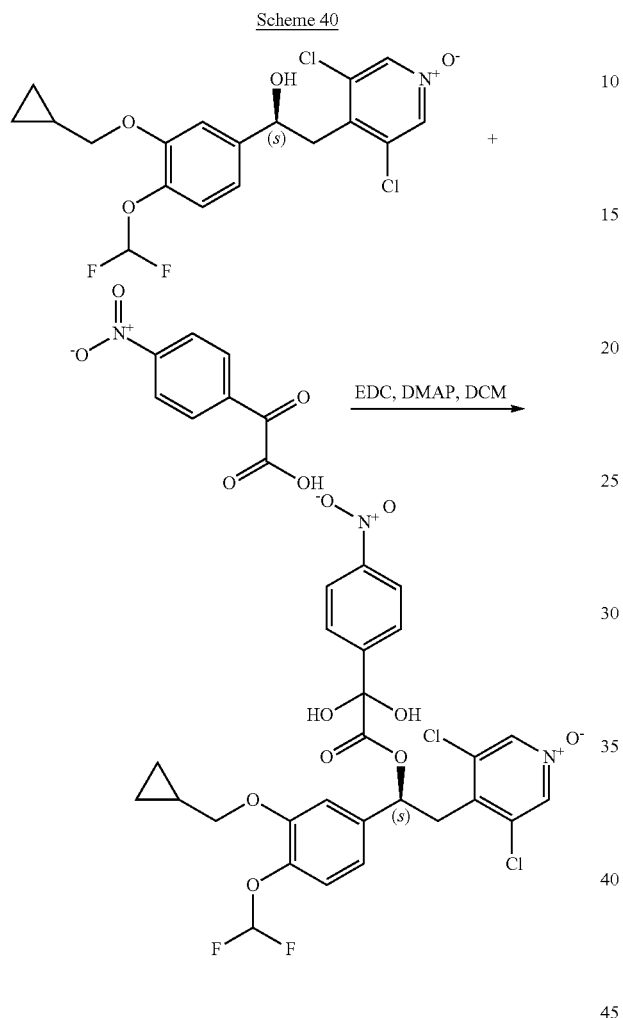

Synthesis of (S)-3,5-dichloro-4-(2-(3-(cyclopropyl-methoxy)-4-(difluoromethoxy)phenyl)-2-(2,2-dihy-droxy-2-(4-nitrophenyl)acetoxy)ethyl)-pyridine 1-oxide (271)

(S)-3,5-dichloro-4-(2-(3-(cyclopropylmethoxy)-4-(dif-luoromethoxy)phenyl)-2-hydroxyethyl)pyridine 1-oxide (300 mg, 0.71 mmol), 2-(4-nitrophenyl)-2-oxoacetic acid (300 mg, 1.54 mmol), DMAP (150 mg, 1.23 mmol) and EDC (200 mg, 1.04 mmol) were dissolved in DCM (15 ml), and the mixture was stirred at RT for 3 hours. The reaction was diluted with HCl 1M and extracted with EtOAc. The organic phase was washed with HCl 1M, $K_2CO_3$ sat. sol. and brine, dried over $Na_2SO_4$ and evaporated under vacuum. The crude product was purified by Preparative reverse-phase HPLC to give 50 mg of the final product. (Yield: 5%).

MS/ESI$^+$ 615.4 [MH]$^+$ $^1$H NMR (400 MHz, acetone) δ ppm 8.25 (s, 2 H), 8.16 (m, 2 H), 7.94 (m, 2 H), 7.10-7.15 (m, 1 H), 6.97-7.01 (m, 1 H), 6.85-6.92 (m, 2 H), 6.33 and 6.42 (2s, 2 OH), 6.04-6.13 (m, 1 H), 3.74-3.90 (m, 2 H), 3.42-3.52 (m, 1 H), 3.16-3.32 (m, 1 H), 1.12-1.32 (m, 1 H), 0.51-0.72 (m, 2 H), 0.25-0.45 (m, 2 H).

218
Example 41

Synthesis of (S)-3,5-dichloro-4-(2-(3-(cyclopropyl-methoxy)-4-(difluoromethoxy)phenyl)-2-(2-(3,4-dimethoxyphenylsulfonyloxy)acetoxy)-ethyl)pyri-dine 1-oxide (274)

Scheme 41

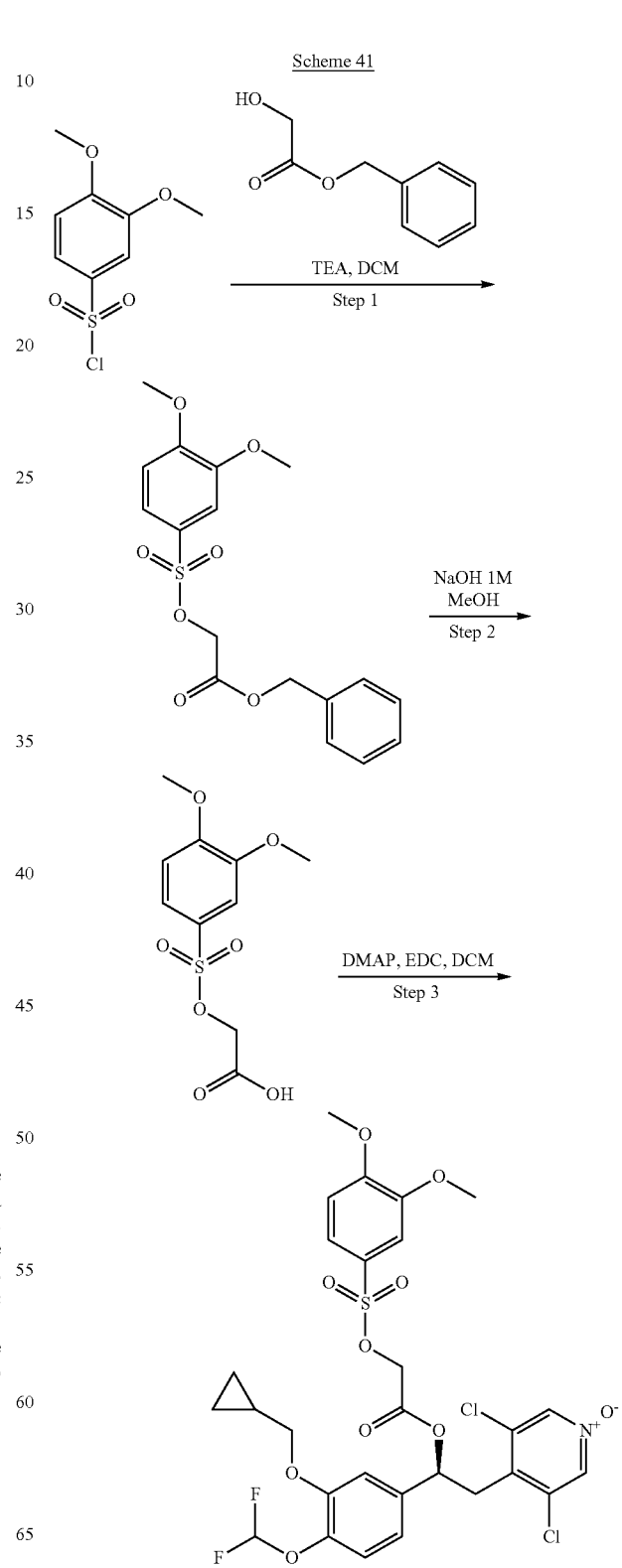

Step 1: Synthesis of benzyl 2-(3,4-dimethoxyphenylsulfonyloxy)acetate (272)

Benzyl 2-hydroxyacetate (211 mg, 1.268 mmol) was dissolved in DCM (10 ml). TEA (0.265 ml, 1.901 mmol) and 3,4-dimethoxybenzene-1-sulfonyl chloride (300 mg, 1.268 mmol) were added, and the reaction was stirred at RT for 3 hours to achieve completion. The reaction mixture was diluted with HCl 1N and extracted with DCM. The organic phase was washed with HCl 1N and $Na_2CO_3$ sat. sol., dried over $Na_2SO_4$ and concentrated under vacuum to give benzyl 2-(3,4-dimethoxyphenylsulfonyloxy)acetate (400 mg, 86% yield).

Step 2: Synthesis of 2-(3,4-dimethoxyphenylsulfonyloxy)acetic acid (273)

Benzyl 2-(3,4-dimethoxyphenylsulfonyloxy)acetate (400 mg, 1.092 mmol) was dissolved in MeOH (5 ml). NaOH 1M (2 ml) was added, and the reaction was stirred at RT for 6 hours to achieve completion. The reaction mixture was diluted with HCl 1N and extracted with EtOAc. The organic phase was washed with HCl 1N and brine, dried over $Na_2SO_4$ and concentrated under vacuum. The crude product was triturated in petroleum ether to give 2-(3,4-dimethoxyphenylsulfonyloxy)acetic acid (250 mg, 83% yield).

Step 3: Synthesis of (S)-3,5-dichloro-4-(2-(3-(cyclopropylmethoxy)-4-(difluoromethoxy)phenyl)-2-(2-(3,4-dimethoxyphenylsulfonyloxy)acetoxy)-ethyl)pyridine 1-oxide (274)

(S)-3,5-dichloro-4-(2-(3-(cyclopropylmethoxy)-4-(difluoromethoxy)phenyl)-2-hydroxyethyl)pyridine 1-oxide (30 mg, 0.071 mmol), 2-(3,4-dimethoxyphenyl-sulfonyloxy)acetic acid (39.4 mg, 0.143 mmol), DMAP (8.72 mg, 0.071 mmol), and EDC (20.53 mg, 0.107 mmol) were dissolved in DCM (2 ml). The reaction was stirred at RT for 1.5 hours. The reaction mixture was diluted with HCl 1N and extracted with DCM. The organic phase was washed with HCl 1N, $Na_2CO_3$ sat and brine, dried over $Na_2SO_4$ and concentrated under vacuum. The crude product was triturated in EtOH to give (S)-3,5-dichloro-4-(2-(3-(cyclopropylmethoxy)-4-(difluoromethoxy)phenyl)-2-(2-(3,4-dimethoxyphenylsulfonyloxy)acetoxy)-ethyl)pyridine 1-oxide (30 mg, 0.044 mmol, 61.9% yield).

MS/ESI⁺ 700.2[M+Na]⁺

¹H NMR (400 MHz, CHLOROFORM-d) δ ppm 8.15 (s, 2 H), 7.50 (dd, J=8.54, 2.16 Hz, 1 H), 7.32 (d, J=2.16 Hz, 1 H), 7.16 (d, J=8.20 Hz, 1 H), 6.87-7.00 (m, 3 H), 6.65 (t, J=75.00 Hz, 1 H), 6.08 (dd, J=9.41, 4.75 Hz, 1 H), 4.52 (d, J=3.37 Hz, 2 H), 3.84-4.00 (m, 8 H), 3.55 (m, 1 H), 3.27 (m, 1 H), 1.27 (m, 1 H), 0.67 (dd, J=8.03, 1.21 Hz, 2 H), 0.39 (d, J=5.78 Hz, 2 H).

Example 42

Synthesis of (S)-3,5-dichloro-4-(2-(3-(cyclopropylmethoxy)-4-(difluoromethoxy)phenyl)-2-(2-(3-(3,4-dimethoxyphenyl)ureido)acetoxy)-ethyl)pyridine 1-oxide (275)

Scheme 42

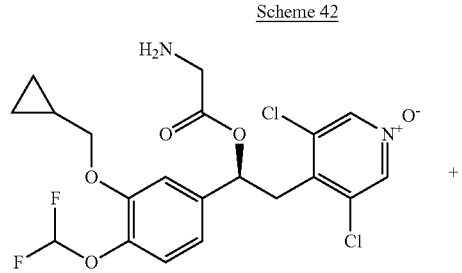

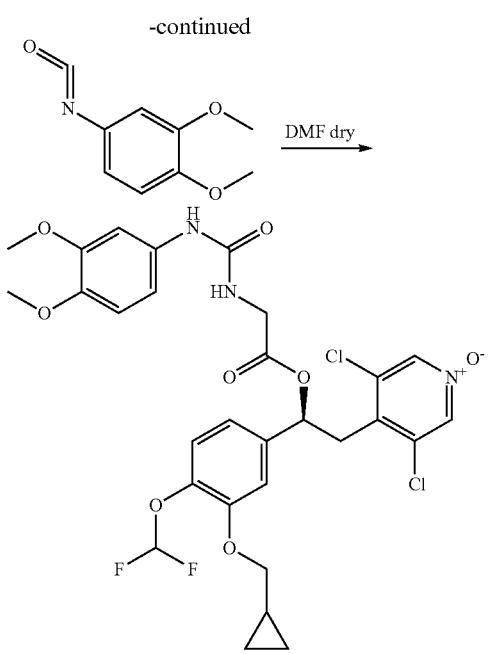

(S)-4-(2-(2-aminoacetoxy)-2-(3-(cyclopropylmethoxy)-4-(difluoromethoxy)phenyl)ethyl)-3,5-dichloropyridine 1-oxide hydrochloride (prepared in an analogous manner as described in Scheme 1, Step 1 and 2, Compound 3) (21 mg, 0.042 mmol) was dissolved in DMF dry (1 ml). 4-isocyanato-1,2-dimethoxybenzene (15.02 mg, 0.084 mmol) was added, and the reaction was stirred at RT overnight. The reaction mixture was diluted with water and extracted with EtOAc. The organic phase was washed with HCl 1N, dried over $Na_2SO_4$ and concentrated under vacuum. The crude product was purified by Preparative reverse-phase HPLC to give (S)-3,5-dichloro-4-(2-(3-(cyclopropylmethoxy)-4-(difluoromethoxy)phenyl)-2-(2-(3-(3,4-dimethoxyphenyl)ureido)acetoxy)ethyl)pyridine 1-oxide (10 mg, 36.4% yield).

MS/ESI⁺ 656.1 [MH]⁺

¹H NMR (400 MHz, DMSO-d₆) δ ppm 8.56-8.61 (m, 1 H), 8.50-8.55 (m, 2 H), 7.15-7.19 (m, 1 H), 7.08-7.12 (m, 2 H), 7.05 (t, J=75.00 Hz, 1 H), 6.95-7.01 (m, 1 H), 6.79 (m, 2 H), 6.20-6.34 (m, 1 H), 5.91-6.03 (m, 1 H), 3.81-3.99 (m, 4 H), 3.68 and 3.70 (2 s, 6 H), 3.39-3.50 (m, 1 H), 3.18-3.27 (m, 1 H), 1.16-1.32 (m, 1 H), 0.47-0.63 (m, 2 H), 0.29-0.41 (m, 2 H).

Example 43

Synthesis of (S)-3,5-dichloro-4-(2-(3-(cyclopropylmethoxy)-4-(difluoromethoxy)phenyl)-2-(3,4-dimethoxyphenylcarbamoyloxy)ethyl)pyridine 1-oxide and of (S)-3,5-dichloro-4-(2-(3-(cyclopropylmethoxy)-4-(difluoromethoxy)phenyl)-2-((3,4-dimethoxyphenyl)(methyl)-carbamoyloxy)ethyl)pyridine 1-oxide (277)

Scheme 43

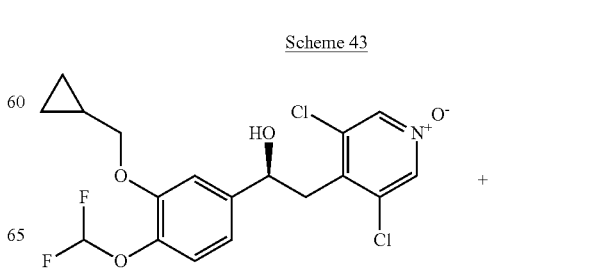

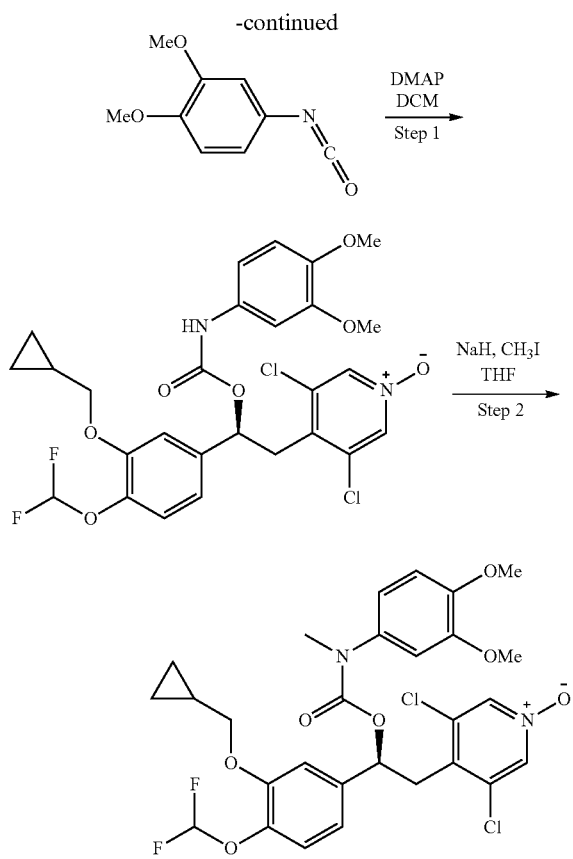

Step 1: Synthesis of (S)-3,5-dichloro-4-(2-(3-(cyclopropylmethoxy)-4-(difluoromethoxy)phenyl)-2-(3,4-dimethoxyphenylcarbamoyloxy)ethyl)pyridine 1-oxide (276)

To a stirred suspension of (S)-3,5-dichloro-4-(2-(3-(cyclopropylmethoxy)-4-(difluoromethoxy)phenyl)-2-hydroxyethyl)pyridine 1-oxide (200 mg, 0.476 mmol) in anhydrous DCM (10 ml), a solution of DMAP (87 mg, 0.714 mmol) and 4-isocyanato-1,2-dimethoxybenzene (171 mg, 0.952 mmol) in anhydrous DCM (5 ml) was added dropwise within 10 minutes. The reaction mixture was stirred at RT overnight. After 18 hours, the reaction mixture was diluted with DCM (10 ml) and washed with HCl 0.5M. The organic layer was dried over $Na_2SO_4$ and evaporated. The crude material was purified by flash chromatography on silica gel (EtOAc 100%) affording the desired product as a white solid (200 mg, 0.334 mmol, 70.1% yield, $[\alpha]_D$=−27.6, c=0.45, DCM).

MS/ESI$^+$ [MH]$^+$:598.96

$^1$H NMR (300 MHz, DMSO-d6) δ ppm 9.47 (br. s., 1 H), 8.55 (s, 2 H), 7.19 (d, 1 H), 7.09 (d, 1 H), 6.95-7.04 (m, 2 H), 6.81-6.91 (m, 2 H), 7.05 (t, 1 H), 5.98 (dd, 1 H), 3.91 (dd, 1 H), 3.87 (dd, 1 H), 3.69 (s, 3 H), 3.69 (s, 3 H), 3.48 (dd, 1 H), 3.26 (dd, 1 H), 1.08-1.36 (m, 1 H), 0.46-0.66 (m, 2 H), 0.26-0.44 (m, 2 H).

Step 2: Synthesis of (S)-3,5-dichloro-4-(2-(3-(cyclopropylmethoxy)-4-(difluoromethoxy)phenyl)-2-((3,4-dimethoxyphenyl)(methyl)carbamoyloxy)-ethyl)pyridine 1-oxide (277)

To a stirred solution of (S)-3,5-dichloro-4-(2-(3-(cyclopropylmethoxy)-4-(difluoromethoxy)phenyl)-2-(3,4-dimethoxyphenylcarbamoyloxy)ethyl)pyridine 1-oxide (127.5 mg, 0.21 mmol) in anhydrous THF (4 ml) and cooled at 0° C., sodium hydride (10.21 mg, 0.255 mmol) and iodomethane (0.016 ml, 0.255 mmol) were sequentially added. The cold bath was removed and the mixture was stirred at RT for 2 hours. Then the reaction was quenched with iced water and extracted with EtOAc. The combined organic layer were washed with brine, dried over $Na_2SO_4$ and evaporated. Purification of the resulting crude by flash chromatography on silica gel (DCM:MeOH 100:2) afforded the desired product as a white solid (95 mg, 0.155 mmol, 72.8% yield, $[\alpha]D$=+21.41, c 0.569, DCM)

MS/ESI$^+$ [MH]$^+$:613.12

$^1$H NMR (300 MHz, DMSO-d$_6$) δ ppm 8.51 (s, 2 H), 7.17 (d, 1 H), 6.92 (d, 1 H), 6.79-6.90 (m, 3 H), 7.06 (t, 1 H), 6.71 (dd, 1 H), 5.92 (dd, 1 H), 3.80-3.88 (m, 2 H), 3.78 (s, 3 H), 3.72 (s, 3 H), 3.20-3.27 (m, 1 H), 3.00-3.20 (m, 4 H), 0.87-1.45 (m, 1 H), 0.45-0.74 (m, 2 H), 0.24-0.45 (m, 2 H).

Example 44

Synthesis of (S)-3,5-dichloro-4-(2-(3-(cyclopropylmethoxy)-4-(difluoromethoxy)phenyl)-2-(3-(4-(methylsulfonamido)phenyl)propanoyloxy)-ethyl)pyridine 1-oxide (284)

Scheme 44

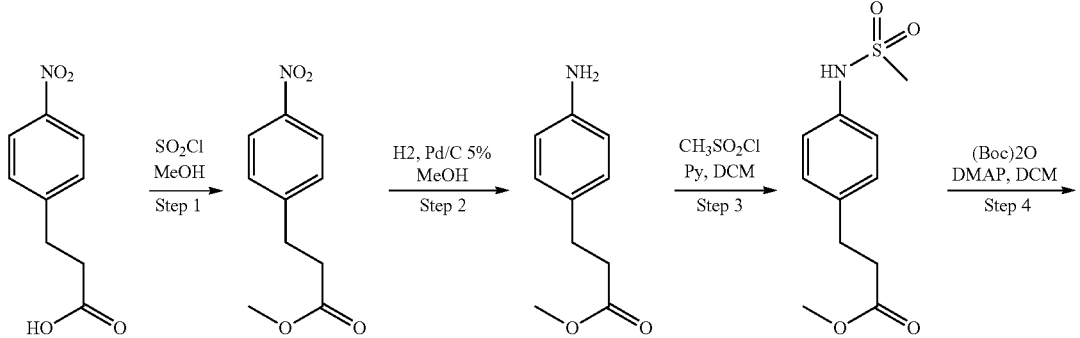

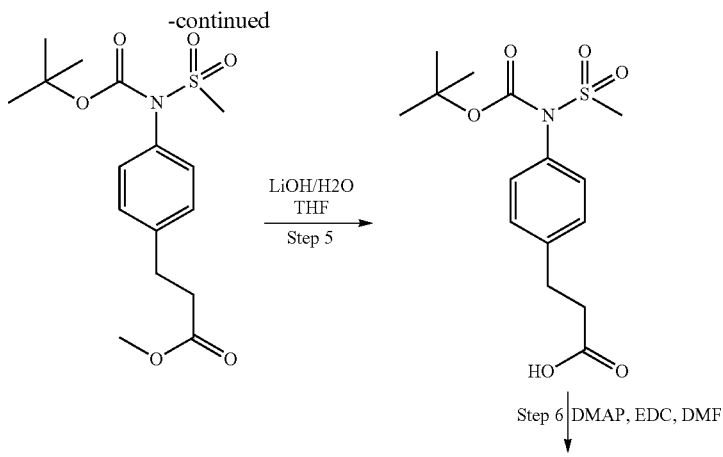

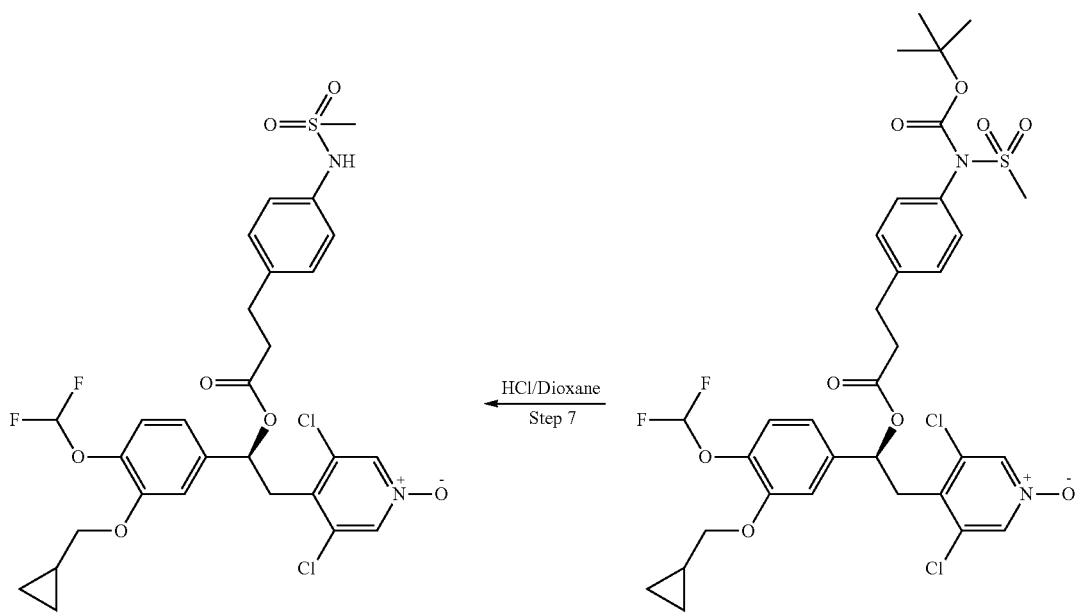

Step 1: Synthesis of methyl 3-(4-nitrophenyl)propanoate (278)

3-(4-nitrophenyl)propanoic acid (500 mg, 2.56 mmol) was dissolved in MeOH (10 ml). SOCl$_2$ (0.374 ml, 5.12 mmol) was added at 0° C., and the reaction was refluxed for 2 hours. The solvent was evaporated under vacuum, and the crude product was triturated in petroleum ether to give methyl 3-(4-nitrophenyl)propanoate (450 mg, 2.151 mmol, 84% yield).

Step 2: Synthesis of 3-(4-aminophenyl)propanoate (279)

Methyl 3-(4-nitrophenyl)propanoate (450 mg, 2.151 mmol) was dissolved in MeOH (10 ml) and then Pd/C 5% (458 mg, 0.215 mmol) was added. The solution was shaken under hydrogen atmosphere at 35 psi for 30 minutes on a Parr apparatus. The catalyst was filtered off and the solvent removed under vacuum to give methyl 3-(4-aminophenyl)propanoate (350 mg, 1.953 mmol, 91% yield).

Step 3: Synthesis of methyl 3-(4-(methylsulfonamido)phenyl)propanoate (280)

Methyl 3-(4-aminophenyl)propanoate (250 mg, 1.39 mmol) was dissolved in DCM (2 ml) and pyridine (500 μl), then methanesulfonyl chloride was added (191 mg, 1.67 mmol), and the mixture was stirred at RT for 2 hours. The reaction was diluted with DCM, and the organic phase was washed with HCl 1N (2×) and brine, dried over Na$_2$SO$_4$ and evaporated under vacuum to give 250 mg of the desired product.

Step 4: Synthesis of methyl 3-(4-(N-(tert-butoxycarbonyl)methylsulfonamido)-phenyl)propanoate (281)

Methyl 3-(4-(methylsulfonamido)phenyl)propanoate (250 mg, 0.97 mmol) was dissolved in DCM (5 ml), then DMAP (237 mg, 1.94 mmol) and di-tert-butyl dicarbonate (423 mg, 1.94 mmol) were added, and the mixture was stirred at RT for 3 hours. The reaction was diluted with DCM and washed with HCl 1N (2×), and the organic phase was dried over Na$_2$SO$_4$ and evaporated under vacuum to give 300 mg of the desired product.

Step 5: Synthesis of 3-(4-(N-(tert-butoxycarbonyl)-methylsulfonamido)phenyl)propanoic acid (282)

Methyl 3-(4-(N-(tert-butoxycarbonyl)methylsulfonamido)phenyl)propanoate (300 mg, 0.86 mmol) was dissolved in THF (3 ml), then LiOH 1N (2 ml) was added, and the mixture was stirred at RT for 6 hours. The reaction was diluted with HCl 1N, and the product was extracted with EtOAc. The organic phase was dried over $Na_2SO_4$ and evaporated under vacuum. The crude product was triturated in Petroleum Ether and filtered to give 250 mg of the desired product.

Step 6: Synthesis of (S)-4-(2-(3-(4-(N-(tert-butoxycarbonyl)-methylsulfonamido)phenyl)propanoyloxy)-2-(3-(cyclopropylmethoxy)-4-(difluoromethoxy)phenyl)ethyl)-3,5-dichloropyridine 1-oxide (283)

(S)-3,5-dichloro-4-(2-(3-(cyclopropylmethoxy)-4-(difluoromethoxy)phenyl)-2-hydroxyethyl)pyridine 1-oxide (30 mg, 0.07 mmol) and 3-(4-(N-(tert-butoxycarbonyl)methylsulfonamido)phenyl)propanoic acid (48 mg, 0.14 mmol) were dissolved in DMF (2 ml), and DMAP (17 mg, 0.14 mmol) and EDC (40 mg, 0.21 mmol) were added. The mixture was stirred at RT overnight, then was diluted with water. The precipitate was filtered, dissolved in EtOAc and washed with HCl 1N and NaHCO3 sat. sol. The organic phase was dried over $Na_2SO_4$ and evaporated under vacuum to give 40 mg of crude product, that was used for the next step without any further purification.

Step 7: Synthesis of (S)-3,5-dichloro-4-(2-(3-(cyclopropylmethoxy)-4-(difluoromethoxy)phenyl)-2-(3-(4-(methylsulfonamido)phenyl)propanoyloxy)-ethyl) pyridine 1-oxide (284)

(S)-4-(2-(3-(4-(N-(tert-butoxycarbonyl)methylsulfonamido)-phenyl)propanoyloxy)-2-(3-(cyclopropylmethoxy)-4-(difluoromethoxy)phenyl)-ethyl)-3,5-dichloropyridine 1-oxide (40 mg, 0.05 mmol) was dissolved in DCM (1.5 ml), then HCl 4M in Dioxane (1 ml, 4 mmol) was added, and the mixture was stirred at RT for 5 hours. The reaction was diluted with DCM and washed with water. The organic phase was dried over $Na_2SO_4$ and evaporated under vacuum. The crude product was purified by Preparative reverse-phase HPLC to yield 20 mg of final product (Yield: 62%).

MS/ESI$^+$:645.2; 667.2 [M+H]+; [M+Na]+

$^1$H NMR (400 MHz, acetone) δ ppm 8.45 (br. s., 1 H), 8.25 (s, 2 H), 7.09-7.29 (m, 6 H), 7.02 (dd, J=8.16, 1.98 Hz, 1 H), 6.91 (t, J=75.00 Hz, 1 H), 6.07 (dd, J=9.70, 4.41 Hz, 1 H), 3.96 (d, J=7.06 Hz, 2 H), 3.47-3.59 (m, 1 H), 3.26 (dd, J=14.11, 4.41 Hz, 1 H), 2.96 (s, 3 H), 2.74-2.89 (m, 2 H), 2.58-2.72 (m, 2 H), 1.29 (d, J=7.06 Hz, 1 H), 0.61 (dd, J=8.16, 1.54 Hz, 2 H), 0.34-0.46 (m, 2 H).

Example 45

Synthesis of (S)-3,5-dichloro-4-(2-((3-(cyclopropylmethoxy)-4-(difluoromethoxy)benzyloxy)carbonyloxy)-2-(3-(cyclopropylmethoxy)-4-(difluoromethoxy)phenyl)ethyl)pyridine 1-oxide (288)

Scheme 45

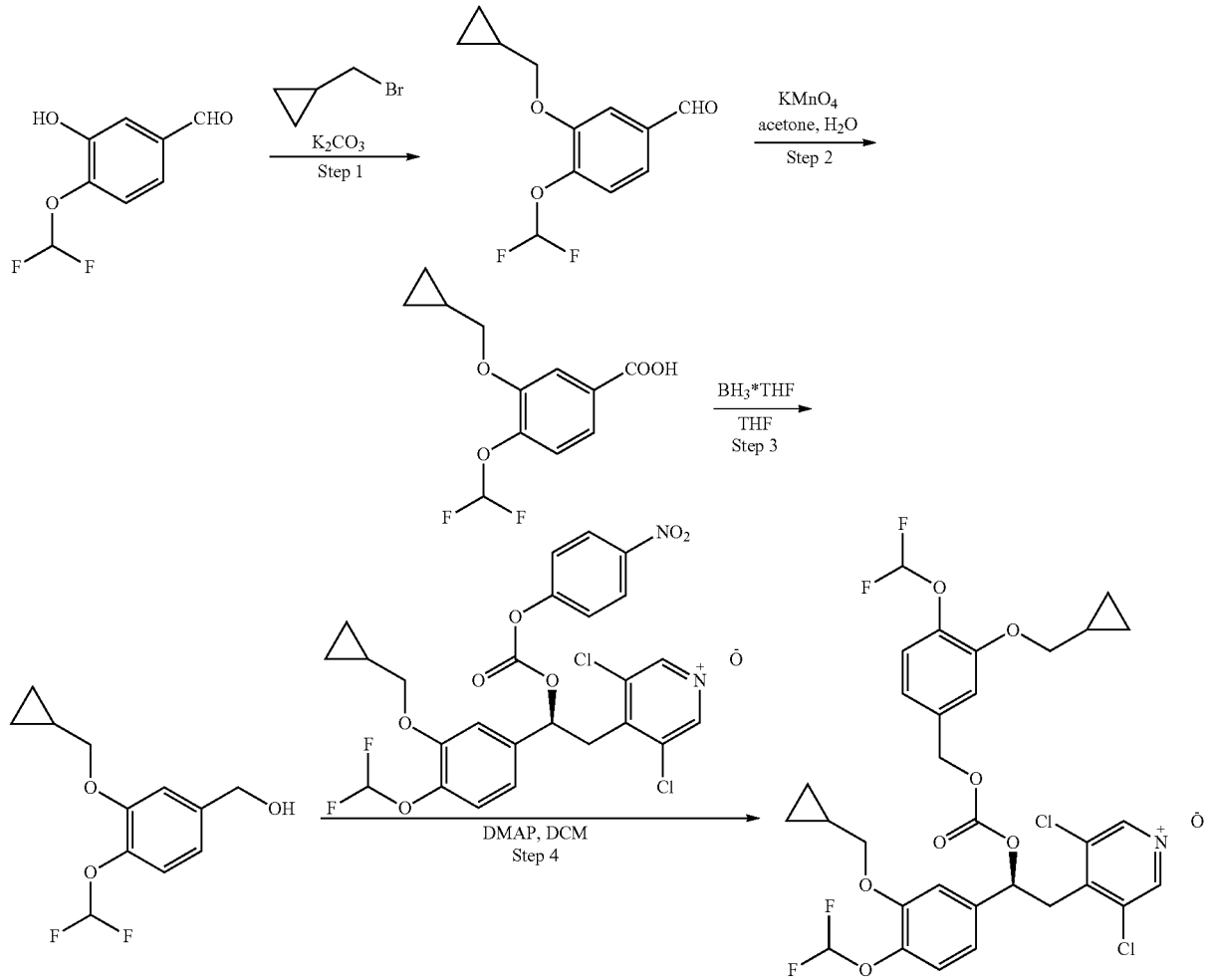

Step 1: Synthesis of 3-(cyclopropylmethoxy)-4-(difluoromethoxy)benzaldehyde (285)

To a solution of 4-(difluoromethoxy)-3-hydroxybenzaldehyde (18.4 g, 98 mmol) in DMF (200 ml), potassium carbonate (29.7 g, 215 mmol) and KI (16.3 g, 98 mmol) were added followed by (bromomethyl)cyclopropane (14.28 ml, 148 mmol), and the resulting suspension was stirred at RT for 24 hours. The mixture was poured into water (800 ml) and extracted with diethyl ether (3×300 ml); the combined organic layers were dried over $Na_2SO_4$ and the solvent was removed under vacuum affording 3-(cyclopropylmethoxy)-4-(difluoromethoxy)benzaldehyde (22.5 g, 93 mmol, 94.8% yield, MS/ESI$^+$ 243.1 [MH]$^+$). This product was used without purification.

Step 2: Synthesis of 3-(cyclopropylmethoxy)-4-(difluoromethoxy)benzoic acid (286)

To a solution of 3-(cyclopropylmethoxy)-4-(difluoromethoxy)benzaldehyde (8.6 g, 35.5 mmol) in acetone (120 ml) and water (60 ml), $KMnO_4$ (13.1 g, 70.8 mmol) was added and the reaction was heated at 60° C. for 1 h. $K_2CO_3$ (9 g, 65.2 mmol) and water (100 ml) were added, and the resulting mixture was filtered through a celite pad. The filtrate was acidified with HCl 37% (pH=1) and extracted twice with EtOAc. The organic phase was dried over $Na_2SO_4$ and the solvent was removed under vacuum affording 3-(cyclopropylmethoxy)-4-(difluoromethoxy)benzoic acid (7.6 g, 29.4 mmol, 83% yield). This product was used without any further purification.

Step 3: Synthesis of (3-(cyclopropylmethoxy)-4-(difluoromethoxy)phenyl)-methanol (287)

To a stirred solution of 3-(cyclopropylmethoxy)-4-(difluoromethoxy)benzoic acid (0.500 g, 1.936 mmol) in anhydrous THF (10 ml), $BH_3$*THF complex (1M solution in THF, 3.87 ml, 3.87 mmol) was added drop wise at RT under nitrogen atmosphere. After 3 hours, the reaction was cooled to 0° C. and quenched with aqueous $NH_4Cl$. The mixture was extracted with EtOAc and the organic phase was dried over $Na_2SO_4$ and evaporated under reduced pressure affording (3-(cyclopropylmethoxy)-4-(difluoromethoxy)phenyl) methanol (0.450 g, 1.842 mmol, 95% yield, MS/ESI$^+$ 227.1 [MH–$H_2O$]$^+$). This product was used without any further purification.

Step 4: Synthesis of (S)-3,5-dichloro-4-(2-((3-(cyclopropylmethoxy)-4-(difluoromethoxy)benzyloxy) carbonyloxy)-2-(3-(cyclopropylmethoxy)-4-(difluoromethoxy)phenyl)ethyl)pyridine 1-oxide (288)

To a stirred solution of (S)-3,5-dichloro-4-(2-(3-(cyclopropylmethoxy)-4-(difluoromethoxy)phenyl)-2-((4-nitrophenoxy)carbonyloxy)ethyl)pyridine 1-oxide (prepared in an analogous manner to that described in Scheme 3, Step 1) (0.150 g, 0.256 mmol) in DCM (10 ml), DMAP (0.016 g, 0.128 mmol) was added followed by (3-(cyclopropylmethoxy)-4-(difluoromethoxy)phenyl)methanol (0.081 g, 0.333 mmol), and the resulting mixture was stirred at RT for 4 hours. The reaction mixture was diluted with DCM (10 ml) and washed with 0.5M HCl; the organic layer was dried over $Na_2SO_4$ and evaporated to dryness. The crude was purified by flash chromatography on silica gel column (DCM:acetone=10:0.5) affording (S)-3,5-dichloro-4-(2-((3-(cyclopropylmethoxy)-4-(difluoromethoxy)benzyloxy)-carbonyloxy)-2-(3-(cyclopropylmethoxy)-4-(difluoromethoxy)phenyl)ethyl)pyridine 1-oxide as a colorless oil (0.0757 g, 0.110 mmol, 42.8% yield, MS/ESI$^+$ 689.94 [MH]$^+$, $[\alpha_D]$=–10.95, c=0.639, DCM).

$^1$H NMR (300 MHz, DMSO-$d_6$) δ ppm 8.51 (s, 2 H) 7.17 (t, J=8.5 Hz, 2 H) 7.09 (t, J=2.1 Hz, 2 H) 6.96 (dd, J=8.2, 2.1 Hz, 1 H) 6.85 (dd, J=8.2, 1.8 Hz, 1 H) 7.32 (t, 2 H) 5.85 (dd, J=8.7, 5.1 Hz, 1 H) 4.94-5.12 (m, 2 H) 3.78-3.95 (m, 4 H) 3.48 (dd, J=14.1, 8.8 Hz, 1 H) 3.25 (dd, J=14.4, 5.0 Hz, 1 H) 1.09-1.33 (m, 2 H) 0.50-0.64 (m, 4 H) 0.28-0.40 (m, 4 H).

The compounds listed in Table 23 were prepared with an analogous procedure to that described in Example 46, Step 4, by reacting the appropriate precursors (commercially available or synthesized by a person skilled in the art) with suitable reagents, and where purification step has been performed as indicated in Table 23.

TABLE 23

| Structure | Cmp | $^1$H NMR | MS/ESI$^+$ [MH]$^+$ [$\alpha_D$] | Starting Material | Purification method |
|---|---|---|---|---|---|
| 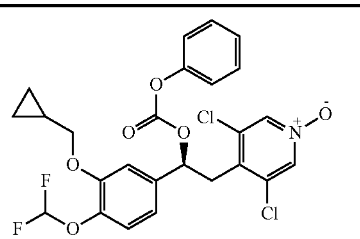 | 289 | $^1$H NMR (300 MHz, DMSO-$d_6$) δ ppm 8.59 (s, 2 H), 7.37-7.47 (m, 2 H), 7.25-7.32 (m, 1 H), 7.22 (d, 1 H), 7.10-7.17 (m, 3 H), 7.03 (dd, 1 H), 7.09 (t, 1 H), 5.91 (dd, 1 H), 3.93 (d, 2 H), 3.58 (dd, 1 H), 3.33 (dd, 1 H), 1.06-1.33 (m, 1 H), 0.49-0.69 (m, 2 H), 0.30-0.49 (m, 2 H) | 540.22 [$\alpha_D$] = +27.92 (c = 0.25 DCM) | | Preparative LC/MS |
| 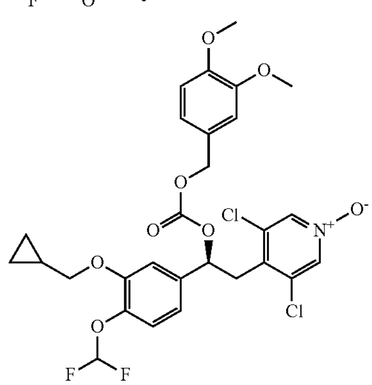 | 290 | $^1$H NMR (300 MHz, DMSO-d6) δ ppm 8.52 (s, 2 H), 7.18 (d, 1 H), 7.08 (d, 1 H), 6.96 (dd, 1 H), 6.92 (d, 1 H), 6.92 (d, 1 H), 7.06 (t, 1 H), 6.81 (dd, 1 H), 5.85 (dd, 1 H), 4.99 (s, 2 H), 3.90 (dd, 1 H), 3.85 (dd, 1 H), 3.76 (s, 3 H), 3.72 (s, 3 H), 3.48 (dd, 1 H), 3.25 (dd, 1 H), 0.98-1.33 (m, 1 H), 0.45-0.66 (m, 2 H), 0.19-0.45 (m, 2 H) | 613.91 [$\alpha_D$] = –7.407 (c = 0.54 DCM) | | Flash chromatography on silica gel (EtOAc/ petroleum ether = 4/1) |

Example 45 bis

Synthesis of (S)-4-(2-(benzyloxycarbonyloxy)-2-(3-(cyclopropylmethoxy)-4-(difluoromethoxy)phenyl)ethyl)-3,5-dichloropyridine 1-oxide (291)

Scheme 45 bis

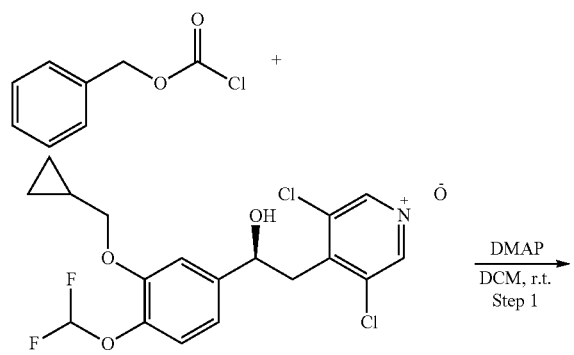

(S)-3,5-dichloro-4-(2-(3-(cyclopropylmethoxy)-4-(difluoromethoxy)phenyl)-2-hydroxyethyl)pyridine 1-oxide (160 mg, 0.381 mmol) was dissolved in DCM (20 ml), and DMAP (0.056 g, 0.539 mmol) was added followed by benzyl chloroformate (0.077 ml, 0.539 mmol). The reaction mixture was stirred at RT for 6 hours. Additional benzyl chloroformate (0.077 ml, 0.539 mmol) was added, and stirring was continued at RT overnight. The reaction mixture was diluted with DCM and washed with aqueous saturated NH$_4$Cl solution (20 mL). The organic layer was dried over sodium sulfate and evaporated to dryness. The crude was purified by chromatography on silica gel cartridge (DCM:ethyl acetate=8:2) to give 0.120 g of desired compound. A further purification by trituration with ethanol (10 mL) was required to afford (S)-4-(2-(benzyloxycarbonyloxy)-2-(3-(cyclopropylmethoxy)-4-(difluoromethoxy)phenyl)ethyl)-3,5-dichloropyridine 1-oxide as a white amorphous solid (0.101 g, 0.182 mmol, 47.9% yield, MS/ESI+554.01 [MH]+, [α$_D$]=−6.9, c=0.68, DCM).

$^1$H NMR (300 MHz, DMSO-d$_6$) δ ppm 8.53 (s, 2 H), 7.24-7.45 (m, 5 H), 7.18 (d, 1 H), 7.09 (d, 1 H), 6.96 (dd, 1 H), 7.07 (t, 1 H), 5.86 (dd, 1 H), 5.10 (d, 1 H), 5.05 (d, 1 H), 3.90 (dd, 1 H), 3.87 (dd, 1 H), 3.49 (dd, 1 H), 3.25 (dd, 1 H), 1.11-1.29 (m, 1 H), 0.49-0.61 (m, 2 H), 0.26-0.41 (m, 2 H)

The compounds listed in Table 24 were prepared with an analogous procedure to that described in Example 45 bis reacting the appropriate precursors (commercially available or synthesized by a person skilled in the art) with suitable reagents, and where purification step has been performed as indicated in Table 24.

TABLE 24

| Structure | Cmp | $^1$H NMR | MS/ESI$^+$ [MH]$^+$ [α$_D$] | Starting Material | Purification method |
|---|---|---|---|---|---|
| 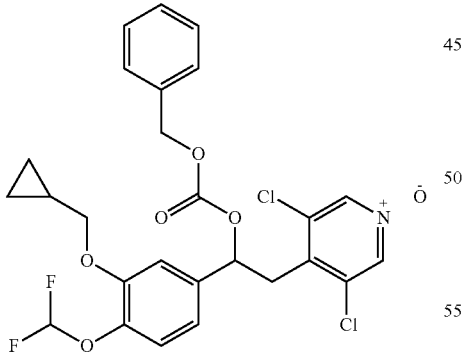 | 292 | $^1$H NMR (300 MHz, DMSO-d6) δ ppm 8.58 (s, 2 H), 7.22 (d, J = 8.22 Hz, 1 H), 7.14 (d, J = 1.76 Hz, 1 H), 7.01-7.07 (m, 2 H), 7.02 (dd, J = 8.22, 1.76 Hz, 1 H), 6.88-6.96 (m, 2 H), 7.09 (t, J = 74.83 Hz, 1 H), 5.90 (dd, J = 8.51, 4.99 Hz, 1 H), 3.92 (d, J = 6.75 Hz, 2 H), 3.74 (s, 3 H), 3.56 (dd, J = 14.23, 8.66 Hz, 1 H), 3.31 (dd, J = 14.09, 4.99 Hz, 1 H), 0.93-1.37 (m, 1 H), 0.48-0.65 (m, 2 H), 0.14-0.48 (m, 2 H) | 570.01 [α$_D$] = −37.5 (c = 0.63, DCM) | 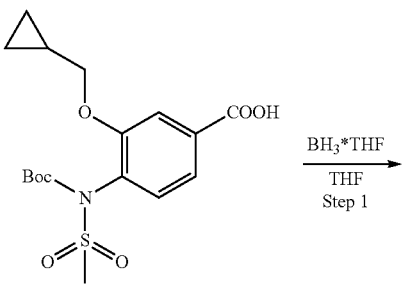 | Flash chromatography on silica gel (DCM/EtOAc = 8/2) followed by trituration with EtOH |

Example 46

Synthesis of (S)-3,5-dichloro-4-(2-(3-(cyclopropylmethoxy)-4-(difluoromethoxy)phenyl)-2-((3-(cyclopropylmethoxy)-4-(methylsulfonamido)-benzyloxy)carbonyloxy)ethyl)pyridine 1-oxide (294)

Scheme 46

-continued

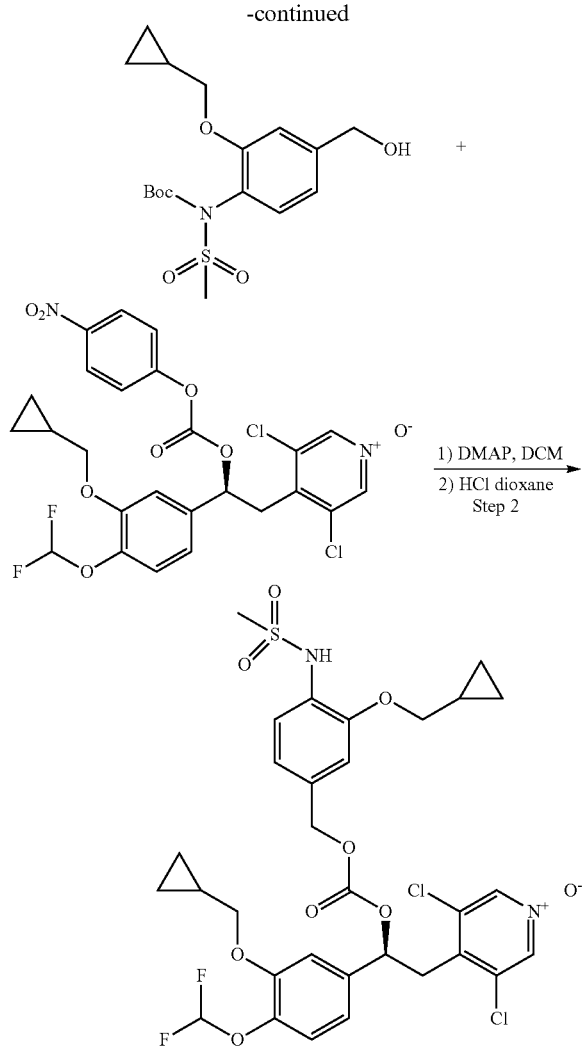

Step 1: Synthesis of 3 tert-butyl 2-(cyclopropyl-methoxy)-4-(hydroxymethyl)phenyl(methylsulfonyl) carbamate (293)

To a stirred solution of 4-(N-(tert-butoxycarbonyl)methyl-sulfonamido)-3-(cyclopropylmethoxy)benzoic acid (for reference procedure see Example 18, WO 2010/089107, which is incorporated herein by reference in its entirety) (0.500 g, 1.297 mmol) in anhydrous THF (10 ml), BH$_3$*THF complex (1M solution in THF, 2.59 ml, 2.59 mmol) was added drop wise at RT under nitrogen atmosphere. After 4 hours, the reaction was cooled to 0° C. and quenched with aqueous NH$_4$Cl. The mixture was extracted with EtOAc and the organic phase was dried over Na$_2$SO$_4$ and evaporated under reduced pressure affording tert-butyl 2-(cyclopropyl-methoxy)-4-(hydroxymethyl)phenyl(methylsulfonyl)carbamate as a colorless oil (0.430 g, 1.158 mmol, 89% yield, MS/ESI$^+$ 394.2 [MNa]$^+$). This product was used without purification.

Step 2: Synthesis of (S)-3,5-dichloro-4-(2-(3-(cyclo-propylmethoxy)-4-(difluoromethoxy)phenyl)-2-((3-(cyclopropylmethoxy)-4-(methylsulfonamido)-ben-zyloxy)carbonyloxy)ethyl)pyridine 1-oxide (294)

To a stirred solution of (S)-3,5-dichloro-4-(2-(3-(cyclopro-pylmethoxy)-4-(difluoromethoxy)phenyl)-2-((4-nitrophe-noxy)carbonyloxy)ethyl)pyridine 1-oxide (prepared in an analogous manner as described in Scheme 3, Step 1) (0.150 g, 0.256 mmol) in DCM (10 ml), DMAP (0.0156 g, 0.128 mmol) was added followed by tert-butyl 2-(cyclopropyl-methoxy)-4-(hydroxymethyl)phenyl(methylsulfonyl)car-bamate (0.124 g, 0.333 mmol), and the resulting mixture was stirred at RT for 3 hours. HCl 4M in dioxane (3 ml, 12 mmol) was added and the reaction was stirred at RT for additional 5 hours. The solvent was removed under vacuum and the residue was purified by flash chromatography on silica gel column (DCM:MeOH=10:0.15). A further purification by flash chromatography on silica gel column (DCM:acetone=10:1) was required to obtain (S)-3,5-dichloro-4-(2-(3-(cyclopropy-lmethoxy)-4-(difluoromethoxy)phenyl)-2-((3-(cyclopropyl-methoxy)-4-(methylsulfonamido)-benzyloxy)carbonyloxy) ethyl)pyridine 1-oxide as a white solid (0.073 g, 0.102 mmol, 39.7% yield, MS/ESI$^+$ 716.93 [MH]$^+$, [α$_D$]=−11.84, c=0.495, DCM).

$^1$H NMR (300 MHz, CHLOROFORM-d) δ ppm 8.11 (s, 2 H) 7.52 (d, 1 H) 7.15 (d, 1 H) 6.89-6.99 (m, 4 H) 6.82 (d, 1 H) 6.63 (t, 1 H) 5.90 (dd, 1 H) 4.93-5.08 (m, 2 H) 3.79-3.92 (m, 4 H) 3.53 (dd, 1 H) 3.25 (dd, 1 H) 3.02 (s, 3 H) 1.17-1.36 (m, 2 H) 0.60-0.75 (m, 4 H) 0.30-0.41 (m, 4 H)

Example 47

Synthesis of (S)-3,5-dichloro-4-(2-(3-(cyclopropyl-methoxy)-4-(difluoromethoxy)phenyl)-2-((4-(meth-ylsulfonamido)phenoxy)-carbonyloxy)ethyl)pyridine 1-oxide (296)

Scheme 47

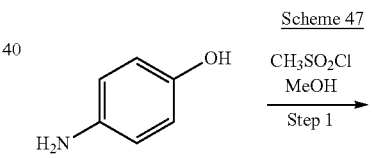

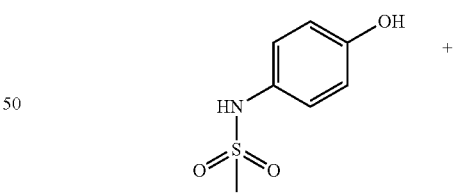

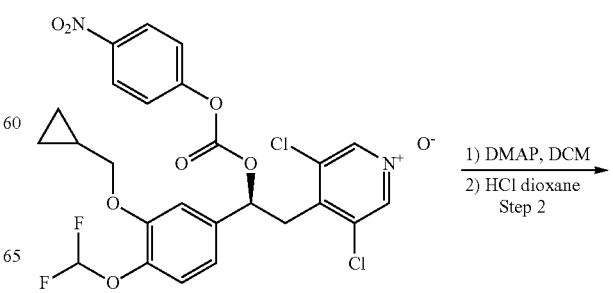

Step 1: Synthesis of N-(4-hydroxyphenyl)methanesulfonamide (295)

To a cold suspension of 4-aminophenol (5.45 g, 49.9 mmol) in MeOH (62 ml), methanesulfonyl chloride (1.95 ml, 25.2 mmol) was added under stirring maintaining the temperature between 10 and 15° C. The resulting solution was allowed to warm to RT and stirred for 2 hours. The solvent was removed under vacuum, and the residue was suspended in HCl 1N (62 ml); the insoluble was collected by filtration, washed with water, dried and purified by filtration through a silica gel pad (DCM:MeOH=100:15) affording N-(4-hydroxyphenyl)methanesulfonamide as a brown solid (1.35 g, 7.21 mmol, 28.6% yield).

Step 2: Synthesis of (S)-3,5-dichloro-4-(2-(3-(cyclopropylmethoxy)-4-(difluoromethoxy)phenyl)-2-((4-(methylsulfonamido)phenoxy)carbonyloxy)-ethyl)pyridine 1-oxide (296)

To a stirred solution of (S)-3,5-dichloro-4-(2-(3-(cyclopropylmethoxy)phenyl)-4-(difluoromethoxy)phenyl)-2-((4-nitrophenoxy)carbonyloxy)ethyl)pyridine 1-oxide (prepared in an analogous manner to that described in Example 45, Step 4) (0.140 g, 0.239 mmol) in DCM (5 ml), a solution of N-(4-hydroxyphenyl)-methanesulfonamide (0.0672 g, 0.359 mmol) and DMAP (0.0438 g, 0.359 mmol) in DCM (5 ml) was added drop wise, and the reaction was stirred at RT for 3 hours. The solvent was evaporated and the resulting crude was purified by chromatography on silica gel column (DCM: MeOH=10:0.4). A second purification by crystallization from absolute ethanol was required to obtain (S)-3,5-dichloro-4-(2-(3-(cyclopropylmethoxy)-4-(difluoromethoxy)phenyl)-2-((4-(methylsulfonamido)-phenoxy)carbonyloxy)ethyl)pyridine 1-oxide as a brown solid (0.050 g, 0.079 mmol, 33% yield, MS/ESI+ 632.74 [MH]+, [α$_D$]=−36.59, c=0.252, DCM).

$^1$H NMR (300 MHz, DMSO-d$_6$) δ ppm 9.78 (s, 1 H), 8.59 (s, 2 H), 7.17-7.25 (m, 3 H), 7.16 (d, 1 H), 7.06-7.12 (m, 2 H), 7.03 (dd, 1 H), 7.09 (t, 1 H), 5.90 (dd, 1 H), 3.93 (d, 2 H), 3.57 (dd, 1 H), 3.32 (dd, 1 H), 2.98 (s, 3 H), 1.12-1.31 (m, 1 H), 0.52-0.70 (m, 2 H), 0.28-0.46 (m, 2 H).

Example 48

Synthesis of 4-((S)-2-((R)-2-amino-3-phenylpropanoyloxy)-2-(3-(cyclopropylmethoxy)-4-(difluoromethoxy)phenyl)ethyl)-3,5-dichloropyridine 1-oxide hydrochloride (298)

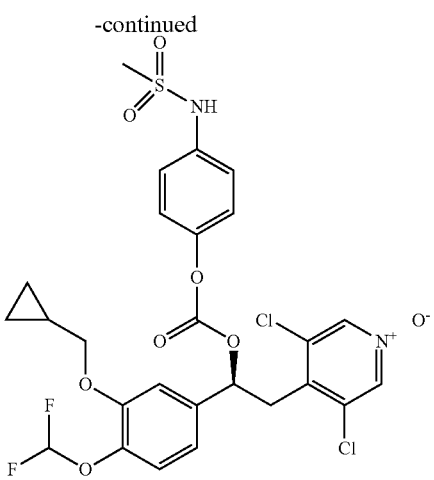

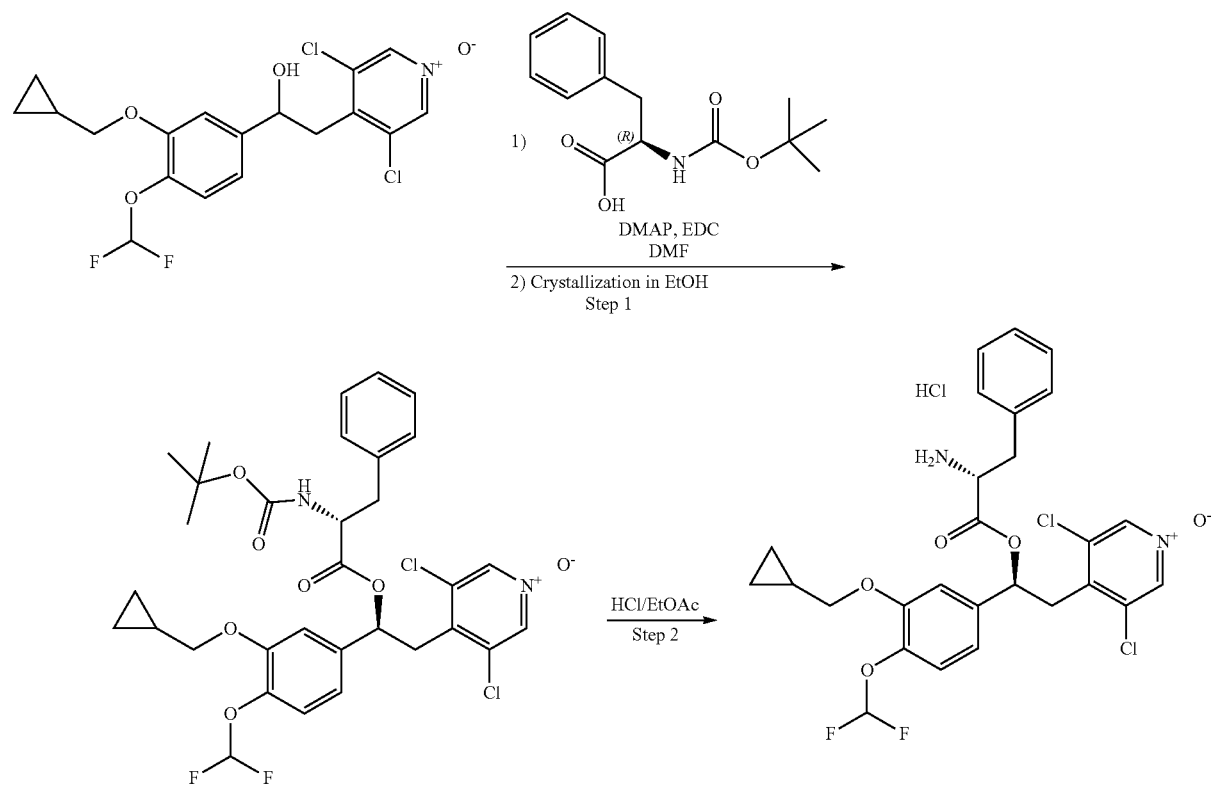

Scheme 48

235

Step 1: Synthesis of 4-((S)-2-((R)-2-(tert-butoxycarbonylamino)-3-phenylpropanoyloxy)-2-(3-(cyclopropylmethoxy)-4-(difluoromethoxy)-phenyl)ethyl)-3,5-dichloropyridine 1-oxide (297)

3,5-dichloro-4-(2-(3-(cyclopropylmethoxy)-4-(difluoromethoxy)phenyl)-2-hydroxyethyl)pyridine 1-oxide (5 g, 11.90 mmol), (R)-2-(tert-butoxycarbonylamino)-3-phenylpropanoic acid (4.73 g, 17.85 mmol), DMAP (1.599 g, 13.09 mmol), and EDC (4.56 g, 23.80 mmol) were dissolved in DMF (5 ml). The reaction was stirred at RT for 2 hours to achieve completion. The reaction mixture was diluted with water, and the precipitate was filtered, washed with water, dissolved in DCM and extracted with HCl 1N, Na$_2$CO$_3$ sat. sol. and brine. The organic phase was dried over Na$_2$SO$_4$ and concentrated under vacuum. The crude product was crystallized in EtOH to give 4-((S)-2-((R)-2-(tert-butoxycarbonylamino)-3-phenylpropanoyloxy)-2-(3-(cyclopropylmethoxy)-4-(difluoromethoxy)phenyl)ethyl)-3,5-dichloropyridine 1-oxide (3.2 g, 4.79 mmol, 40.3% yield).

Step 2: Synthesis of 4-((S)-2-((R)-2-amino-3-phenylpropanoyloxy)-2-(3-(cyclopropylmethoxy)-4-(difluoromethoxy)phenyl)ethyl)-3,5-dichloropyridine 1-oxide hydrochloride (298)

4-((S)-2-((R)-2-(tert-butoxycarbonylamino)-3-phenylpropanoyloxy)-2-(3-(cyclopropylmethoxy)-4-(difluoromethoxy)phenyl)ethyl)-3,5-dichloropyridine 1-oxide (2.9 g, 4.34 mmol) was dissolved in HCl 4M in EtOAc (15 ml). The reaction was stirred at RT for 30 minutes. A precipitate formed, and it was filtered and dried in the vacuum oven to give 4-((S)-2-((R)-2-amino-3-phenylpropanoyloxy)-2-(3-(cyclopropylmethoxy)-4-(difluoromethoxy)phenyl)ethyl)-3,5-dichloropyridine 1-oxide as an hydrochloride salt. (2 g, 3.52 mmol, 81% yield).

MS/ESI$^+$ 661.09 [MH]$^+$ $^1$H NMR (400 MHz, CHLOROFORM-d) δ ppm 8.50-9.02 (bs, 2 H), 8.19 (s, 2 H), 7.03-7.24 (m, 6 H), 6.93 (m, 1 H), 6.38-6.87 (m, 2 H), 5.76-6.10 (m, 1 H), 4.06-4.37 (m, 1 H), 3.87 (br. s., 2 H), 3.02-3.65 (m, 4 H), 1.26 (m, 1 H), 0.65 (m, 2 H), 0.38 (m, 2 H).

Example 49

Synthesis of (S,Z)-3,5-dichloro-4-(2-(3-(cyclopropylmethoxy)-4-(difluoromethoxy)phenyl)-2-(3-(phenylsulfonyl)acryloyloxy)ethyl)pyridine 1-oxide (300) and of (S,E)-3,5-dichloro-4-(2-(3-(cyclopropylmethoxy)-4-(difluoromethoxy)phenyl)-2-(3-(phenylsulfonyl)acryloyloxy)ethyl)pyridine 1-oxide (301)

Scheme 49

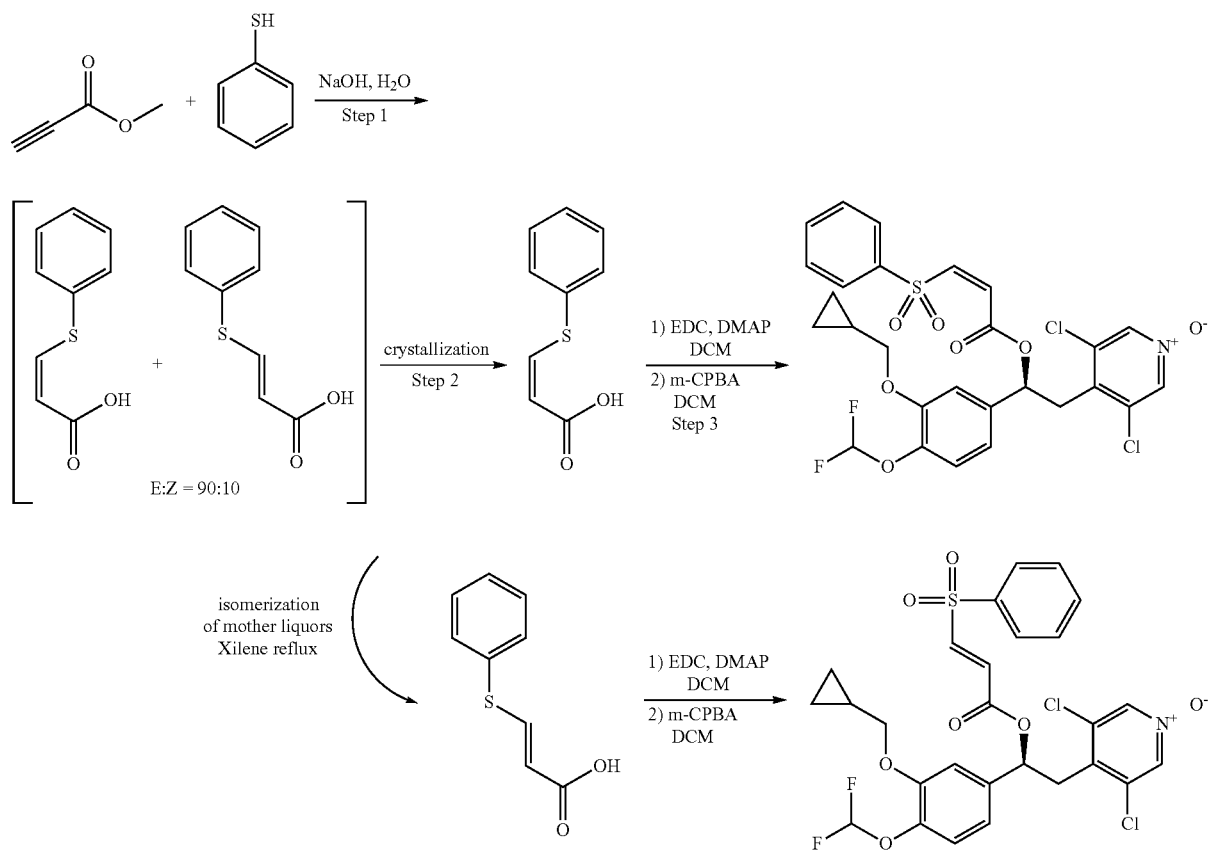

Step 1 and 2: Synthesis of (Z)-3-(phenylthio)acrylic acid (299a) and (E)-3-(phenylthio)acrylic acid (299b)

Methyl propiolate (3.37 ml, 40.0 mmol) was suspended in aqueous 2.5N NaOH (32.0 ml, 80 mmol), and the resulting mixture was cooled to 0° C. Thiophenol (4.12 ml, 40.0 mmol) was added drop wise under vigorous stirring, and the reaction was left at room temperature for 1 hour. The mixture was diluted with water (30 ml), and the pH was adjusted to 1 with aqueous 10% HCl. The aqueous solution was extracted with AcOEt (2×60 ml) and the combined organic layers were dried over $Na_2SO_4$ and evaporated to dryness (presence of two diastereoisomers, Z/E ratio about 90/10). The solid residue was suspended in $CH_3CN$ (20 ml) and heated to 40° C. to obtain complete dissolution. The solution was cooled to 0° C. and crystallization of the (Z) isomer was observed. The solid was collected by filtration and dried under vacuum affording (Z)-3-(phenylthio)acrylic acid (299a) (2.67 g, 14.81 mmol, 37% yield, MS/ESI$^+$ 181.3 [MH]$^+$).

The mother liquor solution was evaporated to dryness affording 0.890 g of mixture (Z/E ratio about 70/30). This mixture was dissolved in xylene (20 ml), heated to reflux for 10 hours (UPLC detected Z/E ratio about 40/60) and then cooled to 0° C. The white precipitate was recovered by filtration, washed with petroleum ether (2×15 ml) and dried in vacuo affording (E)-3-(phenylthio)acrylic acid (299b) (0.57 g, 3.16 mmol, 7.9% yield, MS/ESI$^+$ 181.0 [MH]$^+$).

Step 3: Synthesis of (S,Z)-3,5-dichloro-4-(2-(3-(cyclopropylmethoxy)-4-(difluoromethoxy)phenyl)-2-(3-(phenylsulfonyl)acryloyloxy)ethyl)pyridine 1-oxide (300)

A mixture of (Z)-3-(phenylthio)acrylic acid (129 mg, 0.714 mmol), (S)-3,5-dichloro-4-(2-(3-(cyclopropylmethoxy)-4-(difluoromethoxy)phenyl)-2-hydroxyethyl)pyridine 1-oxide (250 mg, 0.595 mmol), EDC (137 mg, 0.714 mmol), and DMAP (36.3 mg, 0.297 mmol) in DCM (20 ml) was stirred at room temperature for 2 hours. The reaction mixture was washed with 1N HCl (2×20 ml) and aq. sat. $NaHCO_3$ (2×20 ml). The organic phase was dried over sodium sulfate and evaporated to dryness. The crude was dissolved in DCM (30 ml), 3-chloroperbenzoic acid (75% w/w, 313 mg, 1.360 mmol) was added, and the resulting solution was stirred at room temperature for 24 hours. The reaction mixture was washed with aqueous sat. $NaHCO_3$ (2×20 ml), the organic layer was dried over $Na_2SO_4$, and the solvent was removed under vacuum. The residue was purified by flash chromatography on silica gel (DCM:AcOEt=2:1) to give (S,Z)-3,5-dichloro-4-(2-(3-(cyclopropylmethoxy)-4-(difluoromethoxy)phenyl)-2-(3-(phenylsulfonyl)-acryloyloxy)ethyl)pyridine 1-oxide (80 mg, 0.130 mmol, 21.8% yield, MS/ESI$^+$ 613.98 [MH]$^+$, [α$_D$]=+30.8, c=4.0, DCM).

$^1$H NMR (300 MHz, DMSO-d$_6$) d ppm 8.50 (s, 2 H), 7.72-7.86 (m, 3 H), 7.57-7.72 (m, 2 H), 7.21 (d, 1 H), 7.17 (d, 1 H), 7.06 (d, 1 H), 7.03 (dd, 1 H), 7.01 (d, 1 H), 7.09 (t, 1 H), 6.10 (dd, 1 H), 3.90 (d, 2 H), 3.57 (dd, 1 H), 3.30 (dd, 1 H), 1.13-1.29 (m, 1 H), 0.46-0.65 (m, 2 H), 0.19-0.46 (m, 2 H).

The synthesis of compound (S,E)-3,5-dichloro-4-(2-(3-(cyclopropylmethoxy)-4-(difluoromethoxy)phenyl)-2-(3-(phenylsulfonyl)acryloyloxy)ethyl)pyridine 1-oxide (301) was performed according to a similar procedure starting from (E)-3-(phenylthio)acrylic acid (299b).

36.5% yield, MS/ESI$^+$ 614.02 [MH]$^+$, [α$_D$]=−22.6, c=1.7 DCM.

$^1$H NMR (300 MHz, DMSO-d$_6$) δ ppm 8.49 (s, 2 H), 7.90-8.04 (m, 2 H), 7.77-7.90 (m, 1 H), 7.86 (d, 1 H), 7.57-7.77 (m, 2 H), 7.16 (d, 1 H), 7.14 (d, 1 H), 7.01 (dd, 1 H), 7.05 (t, 1 H), 6.77 (d, 1 H), 5.99 (dd, 1 H), 3.89 (d, 2 H), 3.49 (dd, 1 H), 3.26 (dd, 1 H), 1.12-1.23 (m, 1 H), 0.41-0.67 (m, 2 H), 0.13-0.41 (m, 2 H).

Example 50

Synthesis of 3,5-dichloro-4-((S)-2-(3-(cyclopropylmethoxy)-4-(difluoromethoxy)phenyl)-2-((R)-2-(N-methylphenylsulfonamido)-propanoyloxy)ethyl) pyridine 1-oxide (303)

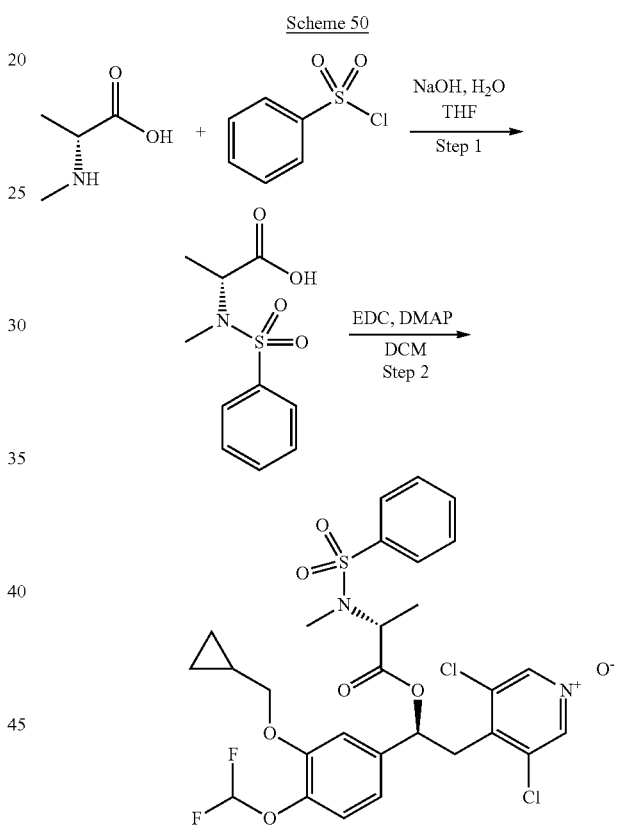

Scheme 50

Step 1: Synthesis of (R)-2-(N-methylphenylsulfonamido)propanoic acid (302)

To a mixture of D-(R)-2-(methylamino)propanoic acid (300 mg, 2.91 mmol) in 5 ml of THF and aqueous 1N NaOH (2.909 ml, 2.91 mmol) cooled in an ice bath, benzenesulfonyl chloride (334 μL, 2.62 mmol) and aqueous 1N NaOH (2.909 ml, 2.91 mmol) were simultaneously added, and the resulting mixture was stirred overnight at room temperature. The mixture was acidified with 1N HCl and extracted twice with ethyl acetate; the organic phase was dried over sodium sulfate and the solvent was removed to obtain (R)-2-(N-methylphenylsulfonamido)-propanoic acid (345 mg, 1.418 mmol, 48.7% yield, MS/ESI$^+$ 244.0 [MH]$^+$).

Step 2: Synthesis of 3,5-dichloro-4-((S)-2-(3-(cyclopropylmethoxy)-4-(difluoromethoxy)phenyl)-2-((R)-2-(N-methylphenylsulfonamido)-propanoyloxy)ethyl)pyridine 1-oxide (303)

A solution of (S)-3,5-dichloro-4-(2-(3-(cyclopropylmethoxy)-4-(difluoromethoxy)phenyl)-2-hydroxyethyl)pyridine 1-oxide (397 mg, 0.945 mmol), EDC (362 mg, 1.891 mmol), and DMAP (289 mg, 2.364 mmol) in 10 ml of dry DCM was stirred for 15 minutes at room temperature, then (R)-2-(N-methylphenyl-sulfonamido)propanoic acid (345 mg, 1.418 mmol) was added. After stirring overnight at room temperature, the reaction was complete. The mixture was washed twice with 1N HCl, then with aq. NaHCO$_3$, with brine and finally dried over sodium sulfate and evaporated to dryness. The residue was purified by flash chromatography on silica gel (AcOEt) to obtain 3,5-dichloro-4-((S)-2-(3-(cyclopropylmethoxy)-4-(difluoromethoxy)phenyl)-2-((R)-2-(N-methylphenylsulfonamido)propanoyloxy)-ethyl)pyridine 1-oxide (430 mg, 0.666 mmol, 70.5% yield, MS/ESI$^+$ 645.05 [MH]$^+$, [$\alpha_D$]=+6.6, c=0.483, DCM).

$^1$H NMR (300 MHz, DMSO-d$_6$) δ ppm 8.55 (s, 2 H), 7.69-7.80 (m, 2 H), 7.58-7.69 (m, 1 H), 7.46-7.58 (m, 2 H), 7.18 (d, 1 H), 7.05 (d, 1 H), 7.09 (t, 1 H), 6.85 (dd, 1 H), 5.90 (dd, 1 H), 4.71 (q, 1 H), 3.90 (d, 2 H), 3.40 (dd, 1 H), 3.18 (dd, 1 H), 2.62 (s, 3 H), 1.17-1.32 (m, 1 H), 1.14 (d, 3 H), 0.46-0.69 (m, 2 H), 0.21-0.45 (m, 2 H)

The compounds listed in Table 25 were prepared with an analogous procedure to that described in Example 50, by reacting the appropriate precursors (commercially available or synthesized by a person skilled in the art) with suitable reagents optionally followed by purification under appropriate conditions. Step 1 may require a further purification by preparative HPLC.

Compounds 326, 327, 329 and 328 were synthesized starting from (R)-3,5-dichloro-4-(2-(3-(cyclopropylmethoxy)-4-(difluoromethoxy)phenyl)-2-hydroxyethyl)pyridine 1-oxide (WO 2010/089107, which is incorporated herein by reference in its entirety) instead of (S)-3,5-dichloro-4-(2-(3-(cyclopropylmethoxy)-4-(difluoromethoxy)phenyl)-2-hydroxyethyl) pyridine 1-oxide.

TABLE 25

| Structure | Cmp | NMR characterization And Diastereomeric Ratio | MS/ESI$^+$ [MH]$^+$ [$\alpha_D$] | Starting Material |
|---|---|---|---|---|
| (structure) | 304 | $^1$H NMR (300 MHz, DMSO-d$_6$) δ ppm 8.58 (s, 2 H), 7.63-7.81 (m, 3 H), 7.53-7.63 (m, 2 H), 7.16 (d, 1 H), 7.04 (d, 1 H), 6.89 (dd, 1 H), 7.06 (t, 1 H), 5.88 (dd, 1 H), 4.65 (q, 1 H), 3.90 (d, 2 H), 3.38 (dd, 1 H), 3.17 (dd, 1 H), 2.71 (s, 3 H), 1.22-1.30 (m, 1 H), 1.20 (d, 3 H), 0.49-0.63 (m, 2 H), 0.28-0.42 (m, 2 H) | 645.04 +0.1, c = 0.815, DCM | (structure) |
| (structure) | 324 | 1H NMR (300 MHz, DMSO-d$_6$) δ ppm 8.55 (s, 2 H), 7.73-7.86 (m, 2 H), 7.67 (dt, 1 H), 7.56 (t, 1 H), 7.18 (d, 1 H), 7.07 (d, 1 H), 6.86 (dd, 1 H), 7.09 (t, 1 H), 5.91 (dd, 1 H), 4.75 (q, 1 H), 3.90 (d, 2 H), 3.41 (dd, 1 H), 3.18 (dd, 1 H), 2.99 (br. s., 3 H), 2.85 (br. s., 3 H), 2.63 (s, 3 H), 1.18-1.31 (m, 1 H), 1.16 (d, 3 H), 0.47-0.67 (m, 2 H), 0.21-0.44 (m, 2 H) | 716.33 −3.57 c = 0.8 DCM | (structure) |

| Structure | Cmp | NMR characterization And Diastereomeric Ratio | MS/ESI+ [MH]+ [α_D] | Starting Material |
|---|---|---|---|---|
| 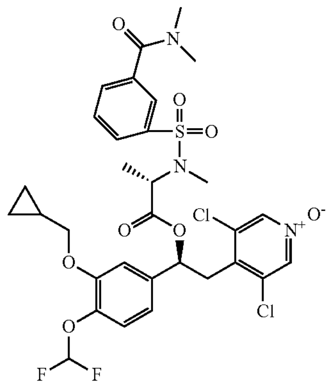 | 325 | 1H NMR (300 MHz, DMSO-d6) δ ppm 8.56 (s, 2 H), 7.78 (dt, 1 H), 7.77 (t, 1 H), 7.70 (dt, 1 H), 7.65 (t, 1 H), 7.16 (d, 1 H), 7.05 (d, 1 H), 6.89 (dd, 1 H), 7.06 (t, 1 H), 5.88 (dd, 1 H), 4.68 (q, 1 H), 3.90 (d, 2 H), 3.38 (dd, 1 H), 3.19 (dd, 1 H), 3.01 (br. s., 3 H), 2.88 (br. s., 3 H), 2.71 (s, 3 H), 1.21 (d, 3 H), 1.12-1.19 (m, 1 H), 0.46-0.67 (m, 2 H), 0.18-0.42 (m, 2 H) | 716.33 −6.38 c = 0.9 DCM | |
| 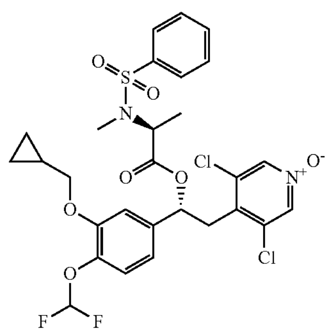 | 326 | 1H NMR (300 MHz, DMSO-d6) δ ppm 8.55 (s, 2 H), 7.70-7.79 (m, 2 H), 7.60-7.68 (m, 1 H), 7.44-7.57 (m, 2 H), 7.18 (d, 1 H), 7.05 (d, 1 H), 6.85 (dd, 1 H), 7.09 (t, 1 H), 5.90 (dd, 1 H), 4.71 (q, 1 H), 3.90 (d, 2 H), 3.40 (dd, 1 H), 3.18 (dd, 1 H), 2.62 (s, 3 H), 1.17-1.36 (m, 1 H), 1.14 (d, 3 H), 0.50-0.69 (m, 2 H), 0.26-0.44 (m, 2 H) | 645.19 −3.3 c = 0.55 DCM | |
| 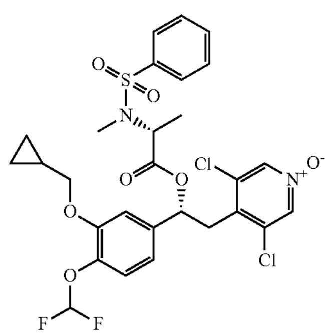 | 327 | 1H NMR (300 MHz. DMSO-d6) δ ppm 8.58 (s, 2 H), 7.63-7.80 (m, 3 H), 7.52-7.63 (m, 2 H), 7.16 (d, 1 H), 7.04 (d, 1 H), 6.89 (dd, 1 H), 7.06 (t, 1 H), 5.88 (dd, 1 H), 4.65 (g, 1 H), 3.90 (d, 2 H), 3.38 (dd, 1 H), 3.17 (dd, 1 H), 2.71 (s, 3 H), 1.21-1.30 (m, 1 H), 1.20 (d, 3 H), 0.45-0.65 (m, 2 H), 0.25-0.43 (m, 2 H) | 645.06 −3.2 c = 0.51 DCM | |
| 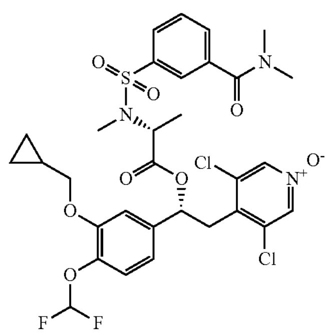 | 328 | 1H NMR (300 MHz, DMSO-d6) δ ppm 8.56 (s, 2 H), 7.58-7.82 (m, 4 H), 7.16 (d, 1 H), 7.05 (d, 1 H), 6.89 (dd, 1 H), 7.06 (t, 1 H), 5.88 (dd, 1 H), 4.68 (q, 1 H), 3.90 (d, 2 H), 3.38 (dd, 1 H), 3.19 (dd, 1 H), 3.01 (br. s., 3 H), 2.88 (br. S., 3 H), 2.71 (s, 3 H), 1.21 (d, 3 H), 1.05-1.20 (m, 1 H), 0.45-0.69 (m, 2 H), 0.19-0.43 (m, 2 H) | 716.13 +1.3 c = 0.51 DCM | |

TABLE 25-continued

| Structure | Cmp | NMR characterization And Diastereomeric Ratio | MS/ESI+ [MH]+ [α_D] | Starting Material |
|---|---|---|---|---|
| (structure shown) | 329 | 1H NMR (300 MHz, DMSO-d6) δ ppm 8.54 (s, 2 H), 7.74-7.84 (m, 2 H), 7.67 (dt, 1 H), 7.56 (t, 1 H), 7.18 (d, 1 H), 7.07 (d, 1 H), 6.86 (dd, 1 H), 7.08 (t, 1 H), 5.91 (dd, 1 H), 4.75 (q, 1 H), 3.90 (d, 2 H), 3.41 (dd, 1 H), 3.18 (dd, 1 H), 2.99 (br. s., 3 H), 2.85 (br. s., 3 H), 2.63 (s, 3 H), 1.10-1.33 (m, 1 H), 1.16 (d, 3 H), 0.45-0.75 (m, 2 H), 0.09-0.44 (m, 2 H) | 716.18 +1.92 c = 0.75 DCM | (structure shown) |

Example 52

Synthesis of (S)-3,5-dichloro-4-(2-(3-(cyclopropyl-methoxy)-4-(difluoromethoxy)phenyl)-2-(methyl(4-(methylsulfonamido)benzyl)-carbamoyloxy)ethyl) pyridine 1-oxide (305)

Scheme 52

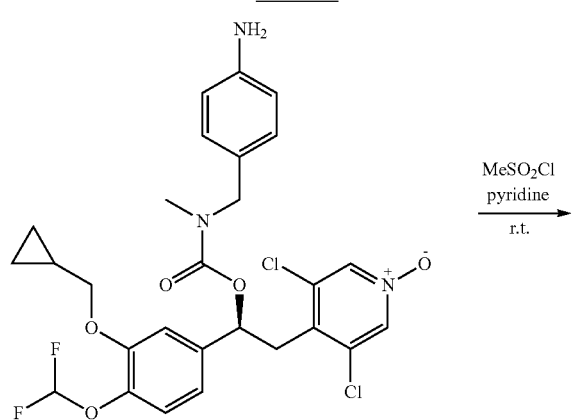

(S)-4-(2-((4-aminobenzyl)(methyl)carbamoyloxy)-2-(3-(cyclopropylmethoxy)-4-(difluoromethoxy)phenyl)ethyl)-3,5-dichloropyridine 1-oxide (for reference procedure see Example 3, Table 5) (73.2 mg, 0.126 mmol) was dissolved in pyridine (3 ml) and cooled at 0° C. Methanesulfonyl chloride (13.71 μl, 0.176 mmol) was added, and the reaction was stirred RT for 1 hour. The reaction was diluted with DCM and aqueous sat. NH4Cl. The aqueous phase was extracted twice with DCM, the combined organic layers were dried and evaporated. The residue was purified by flash chromatography on silica gel cartridge (DCM/AcOEt=80/20 to 50/50) to give (S)-3,5-dichloro-4-(2-(3-(cyclopropylmethoxy)-4-(difluoromethoxy)-phenyl)-2-(methyl(4-(methylsulfonamido)benzyl)carbamoyloxy)ethyl)pyridine 1-oxide (69 mg, 0.104 mmol, 83% yield, MS/ESI+ 660.0 [MH]+.

1H NMR (300 MHz, DMSO-d6) δ ppm 9.63 (br. s., 1 H), 8.50 and 8.56 (s, 2 H), 6.70-7.45 (m, 7 H), 5.75-6.12 (m, 1 H), 4.03-4.72 (m, 2 H), 3.71-4.01 (m, 2 H), 3.38-3.55 (m, 1 H), 3.11-3.24 (m, 1 H), 2.99 (s, 3 H), 2.68 and 2.87 (br. s., 3 H), 1.07-1.37 (m, 2 H), 0.48-0.63 (m, 2 H), 0.18-0.44 (m, 2 H)

Example 53

Synthesis of (S)-3,5-dichloro-4-(2-(3-(cyclopropyl-methoxy)-4-(difluoromethoxy)phenyl)-2-((3,4-dimethoxybenzyl)(methyl)carbamoyloxy)-ethyl) pyridine 1-oxide (306)

Scheme 53

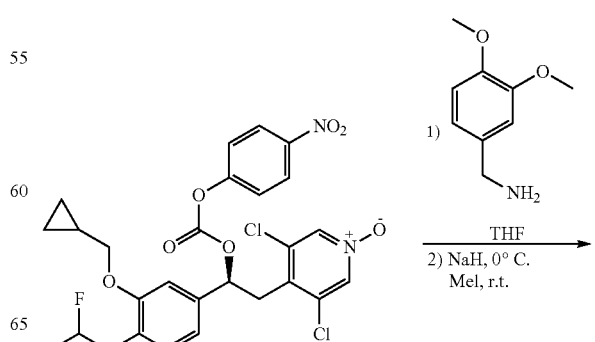

-continued

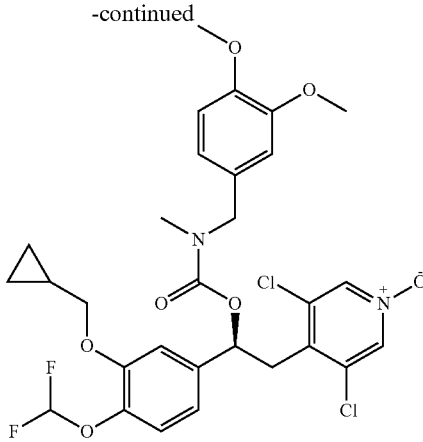

To a stirred solution of (S)-3,5-dichloro-4-(2-(3-(cyclopropylmethoxy)-4-(difluoromethoxy)phenyl)-2-((4-nitrophenoxy)carbonyloxy)ethyl)pyridine 1-oxide (for reference procedure see Example 3, Step 1) (300 mg, 0.513 mmol) in dry THF (5 ml), (3,4-dimethoxyphenyl)methanamine (0.077 ml, 0.513 mmol) was added. The mixture was stirred at RT for 2 hours and then cooled to 0° C. NaH (60% w/w dispersion in mineral oil, 61.5 mg, 1.538 mmol) was added portion wise followed by iodomethane (0.080 ml, 1.281 mmol). The cold bath was removed and the reaction was stirred at RT for 5 hours. The mixture was cooled to 0° C., quenched with water and then extracted with EtOAc. The combined organic layers were dried over $Na_2SO_4$, the solvent was evaporated, and the crude was purified by flash chromatography on silica gel column (DCM/MeOH 100/2). The desired product was obtained as a white solid (96 mg, 0.153 mmol, 29.9% yield, MS/ESI$^+$ 626.89 [MH]$^+$ [$\alpha_D$]=−12.01, c=0.616, DCM).

$^1$H NMR (300 MHz, DMSO-d$_6$) δ ppm 8.58 and 8.48 (s, 2 H), 7.13-7.25 (m, 1 H), 6.96-7.12 (m, 2 H), 6.83-6.96 (m, 1 H), 7.06 (t, 1 H), 6.69 (br. s., 1 H), 6.36-6.64 (m, 1 H), 5.85-6.15 (m, 1 H), 4.57 and 4.28 (d, 1 H), 4.36 and 4.18 (d, 1 H), 3.77-3.96 (m, 2 H), 3.74 (s, 3 H), 3.64 (s, 3 H), 3.37-3.53 (m, 1 H), 3.10-3.25 (m, 1 H), 2.85 and 2.68 (s, 3 H), 0.98-1.33 (m, 1 H), 0.48-0.68 (m, 2 H), 0.13-0.44 (m, 2 H)

Example 54

Synthesis of (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzoyloxy)-2-methylpropanoyloxy)ethyl)pyridine 1-oxide (311)

Scheme 54

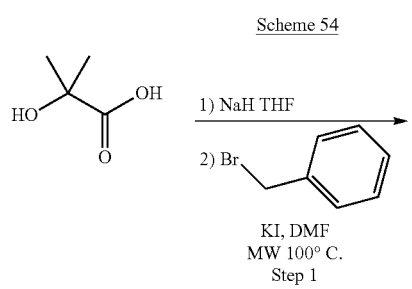

1) NaH THF

2) Br-CH₂-C₆H₅

KI, DMF
MW 100° C.
Step 1

-continued

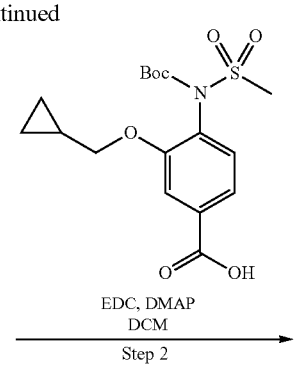

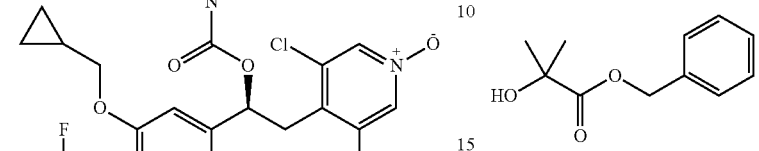

EDC, DMAP
DCM
Step 2

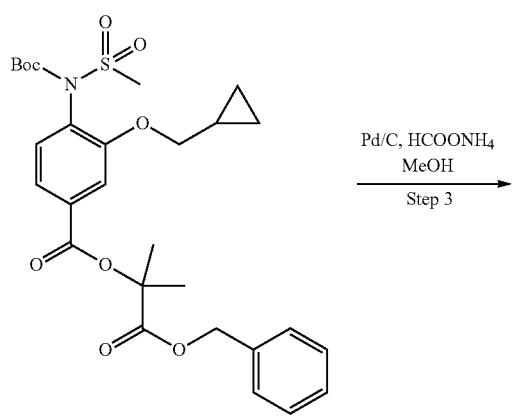

Pd/C, HCOONH$_4$
MeOH
Step 3

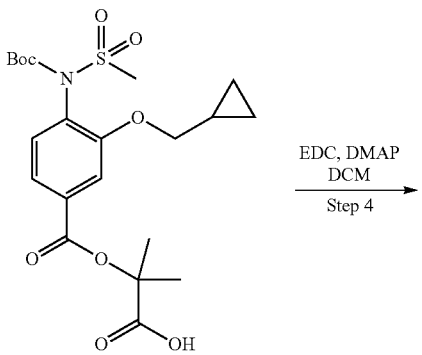

EDC, DMAP
DCM
Step 4

-continued

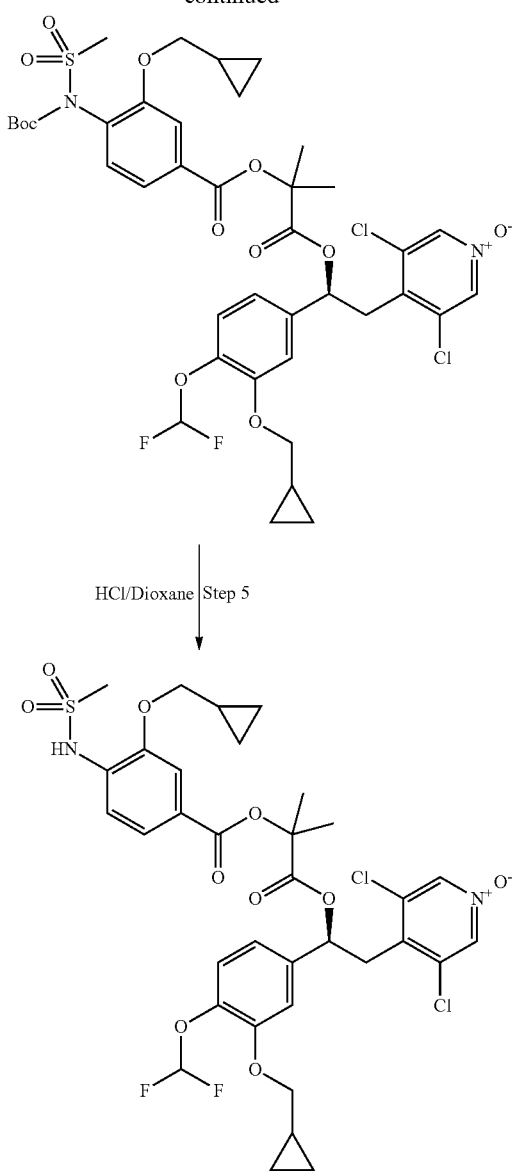

Step 1: Synthesis of benzyl 2-hydroxy-2-methylpropanoate (307)

To a solution of 2-hydroxy-2-methylpropanoic acid (500 mg, 4.80 mmol) in dry THF (10 ml), NaH (60% dispersion in mineral oil, 192 mg, 4.80 mmol) was added portionwise at 5° C. The resulting mixture was stirred 1 hour at RT. The solvent was removed, the residue was suspended in dry DMF (7 ml), and (bromomethyl)benzene (821 mg, 4.80 mmol) was added followed by a catalytic amount of KI. The reaction was heated under microwave irradiation at 100° C. for 3 hours. After cooling, the solvent was evaporated and the residue was partitioned between water and EtOAc; the organic phase was washed with brine, dried over sodium sulfate and evaporated to dryness. The residue was purified by flash chromatography on silica gel (EtOAc/petroleum ether=1/1) affording benzyl 2-hydroxy-2-methylpropanoate as a yellow liquid (773 mg, 3.98 mmol, 83% yield).

Step 2: Synthesis of 1-(benzyloxy)-2-methyl-1-oxopropan-2-yl 4-(N-(tert-butoxycarbonyl)methylsulfonamido)-3-(cyclopropylmethoxy)benzoate (308)

To a mixture of 4-(N-(tert-butoxycarbonyl)methylsulfonamido)-3-(cyclopropylmethoxy)benzoic acid (1.526 g, 3.96 mmol) and EDC (1.520 g, 7.93 mmol) in dry DCM (15 ml), benzyl 2-hydroxy-2-methylpropanoate (0.77 g, 3.96 mmol) and DMAP (0.484 g, 3.96 mmol) were added, and the resulting solution was stirred at RT for 24 hours. The solvent was evaporated and the residue was portioned between aqueous sat. NaHCO₃ and EtOAc; the organic phase was washed with 1N HCl and brine, dried over Na₂SO₄, filtered and evaporated. The crude was purified by flash chromatography on silica gel (EtOAc/petroleum ether=1/9). The residue was triturated with diisopropylether and filtered to afford 1-(benzyloxy)-2-methyl-1-oxopropan-2-yl-4-(N-(tert-butoxycarbonyl)methylsulfonamido)-3-(cyclopropylmethoxy)benzoate as a white powder (1.33 g, 2.368 mmol, 59.7% yield, MS/ESI⁺ 562.0 [MH]⁺).

Step 3: Synthesis of 2-(4-(N-(tert-butoxycarbonyl)methylsulfonamido)-3-(cyclopropylmethoxy)benzoyloxy)-2-methylpropanoic acid (309)

To a mixture of 1-(benzyloxy)-2-methyl-1-oxopropan-2-yl 4-(N-(tert-butoxycarbonyl)methylsulfonamido)-3-(cyclopropylmethoxy)benzoate (0.5 g, 0.890 mmol) and 10% Pd/C (0.100 g) in MeOH (30 ml), ammonium formate (0.337 g, 5.34 mmol) was added, and the mixture was heated to reflux for 1 hour. After cooling the catalyst was filtered off and the solvent was evaporated; the residue was dissolved in ethyl acetate and washed with 0.5N HCl and brine. The organic phase was dried over Na₂SO₄, filtered and evaporated to give 2-(4-(N-(tert-butoxycarbonyl)-methylsulfonamido)-3-(cyclopropylmethoxy)benzoyloxy)-2-methylpropanoic acid as a white powder (0.402 g, 0.853 mmol, 96% yield, MS/ESI⁺ 493.9 [MNa]⁺).

Step 4: Synthesis of (S)-4-(2-(2-(4-(N-(tert-butoxycarbonyl)-methylsulfonamido)-3-(cyclopropylmethoxy)benzoyloxy)-2-methylpropanoyloxy)-2-(3-(cyclopropylmethoxy)-4-(difluoromethoxy)phenyl)-ethyl)-3,5-dichloropyridine 1-oxide (310)

To a mixture of 2-(4-(N-(tert-butoxycarbonyl)methylsulfonamido)-3-(cyclopropylmethoxy)benzoyloxy)-2-methylpropanoic acid (300 mg, 0.636 mmol) and EDC (366 mg, 1.909 mmol) in dry DCM (10 ml), (S)-3,5-dichloro-4-(2-(3-(cyclopropylmethoxy)-4-(difluoromethoxy)phenyl)-2-hydroxyethyl)pyridine 1-oxide (267 mg, 0.636 mmol) and DMAP (78 mg, 0.636 mmol) were added, and the resulting solution was stirred at RT for 2 days. The solvent was evaporated and the residue was portioned between ethyl acetate and water; the organic phase was washed with 0.5N HCl, aqueous sat. NaHCO₃ and brine. The organic phase was dried over Na₂SO₄, filtered and evaporated. The crude was purified by flash chromatography on silica gel (DCM/MeOH/32% NH₄OH=95/5/0.5) to give (S)-4-(2-(2-(4-(N-(tert-butoxycarbonyl)methylsulfonamido)-3-(cyclopropylmethoxy)-benzoyloxy)-2-methylpropanoyloxy)-2-(3-(cyclopropylmethoxy)-4-(difluoromethoxy)phenyl)ethyl)-3,5-dichloropyridine 1-oxide as a white powder (168 mg, 0.192 mmol, 30.2% yield, MS/ESI⁺873.4 [MH]⁺).

Step 5: Synthesis of (S)-3,5-dichloro-4-(2-(3-(cyclopropylmethoxy)-4-(difluoromethoxy)phenyl)-2-(2-(3-(cyclopropylmethoxy)-4-(methylsulfonamido)-benzoyloxy)-2-methylpropanoyloxy)ethyl)pyridine 1-oxide (311)

To a solution of (S)-4-(2-(2-(4-(N-(tert-butoxycarbonyl)methylsulfonamido)-3-(cyclopropylmethoxy)benzoyloxy)-2-methylpropanoyloxy)-2-(3-(cyclopropylmethoxy)-4-(difluoromethoxy)phenyl)ethyl)-3,5-dichloropyridine 1-oxide (168 mg, 0.192 mmol) in dry DCM (2 ml), HCl 4M in dioxane (144 μl, 0.577 mmol) was added with stirring at RT for 2 days. Additional HCl 4M in dioxane (144 μl, 0.577 mmol) was freshly added and the stirring was continued for further 3 days. The volatiles were removed under vacuum, and the crude was purified by preparative HPLC. After evaporation of the solvent, the residue was triturated with iPr$_2$O and collected by filtration to give (S)-3,5-dichloro-4-(2-(3-(cyclopropylmethoxy)-4-(difluoromethoxy)phenyl)-2-(2-(3-(cyclopropylmethoxy)-4-(methylsulfonamido)benzoyloxy)-2-methylpropanoyloxy)ethyl)pyridine 1-oxide as a white solid (50 mg, 0.065 mmol, 33.6% yield, MS/ESI$^+$ 773.29 [MH]$^+$, [α$_D$]=−18.13, c=0.60, MeOH).

$^1$H NMR (300 MHz, DMSO-d$_6$) δ ppm 9.12 (s, 1 H) 8.29 (s, 2 H) 7.49 (dd, 1 H) 7.43 (d, 1 H) 7.34 (d, 1 H) 7.18 (d, 1 H) 7.07 (d, 1 H) 6.98 (dd, 1 H) 7.08 (t, 1 H) 5.97 (dd, 1 H) 3.97 (d, 2 H) 3.89 (dd, 1 H) 3.84 (dd, 1 H) 3.33-3.39 (m, 1 H) 3.16 (s, 3 H) 3.16 (dd, 1 H) 1.55 (s, 3 H) 1.49 (s, 3 H) 1.26-1.39 (m, 1 H) 1.10-1.27 (m, 1 H) 0.51-0.70 (m, 4 H) 0.38-0.48 (m, 2 H) 0.29-0.38 (m, 2 H)

The compounds listed in Table 26 were prepared with an analogous procedure to that described in Example 54, Step 2-5, by reacting the appropriate precursors (commercially available or synthesized by a person skilled in the art) with suitable reagents, and where purification step has been performed as indicated in Table 26.

TABLE 26

| Structure | Cmp | NMR characterization | MS/ESI$^+$ [MH]$^+$ [α$_D$] | Starting Material (and Conditions, if different) | Purification method |
|---|---|---|---|---|---|
| (structure) | 312 | $^1$H NMR (300 MHz, DMSO-d$_6$) δ ppm 9.29 (br. s., 1 H), 8.52 (s, 2 H), 7.54 (dd, 1 H), 7.40-7.47 (m, 2 H), 7.16 (d, 1 H), 7.03 (d, 1 H), 6.94 (dd, 1 H), 7.06 (t, 1 H), 6.05 (dd, 1 H), 5.16 (q, 1 H), 3.95 (d, 2 H), 3.84 (d, 2 H), 3.44 (dd, 1 H), 3.25 (dd, 1 H), 3.11 (s, 3 H), 1.46 (d, 3 H), 1.11-1.38 (m, 2 H), 0.49-0.70 (m, 4 H), 0.36-0.44 (m, 2 H), 0.26-0.36 (m, 2 H) | 758.83 [α$_D$] = −32.5 c = 0.72 DCM | (structure) [Step 3: THF/H$_2$O = 4/1, r.t. | Chromatography on silica gel (DCM/EtOAc = 8/2) followed by trituration with Et$_2$O |

The compounds listed in Table 27 were prepared with an analogous procedure to that described in Example 54, Step 1-4, by reacting the appropriate precursors (commercially available or synthesized by a person skilled in the art) with suitable reagents, and where purification step has been performed as indicated in Table 27.

TABLE 27

| Structure | Cmp | NMR characterization | MS/ESI$^+$ [MH]$^+$ [α$_D$] | Starting Material (and Conditions, if different) | Purification method |
|---|---|---|---|---|---|
| (structure) | 313 | $^1$H NMR (300 MHz, DMSO-d6) δ ppm 8.50 (s, 2 H), 7.61 (dd, 1 H), 7.43 (d, 1 H), 7.18 (d, 1 H), 7.11 (d, 1 H), 7.07 (d, 1 H), 6.97 (dd, 1 H), 7.07 (t, 1 H), 6.05 (dd, 1 H), 4.91 (d, 1 H), 4.84 (d, 1 H), 3.88 (d, 2 H), 3.86 (s, 3 H), 3.82 (s, 3 H), 3.45 (dd, 1 H), 3.25 (dd, 1 H), 0.84-1.36 (m, 1 H), 0.48 - 0.70 (m, 2 H), 0.21-0.44 (m, 2 H) | 642.26 [α$_D$] = −27.24, c = 0.50, DCM | Intermediate of Step 1 (structure) Intermediate of Step 2 Step 3: THF/H$_2$O = 4/1, r.t. NOTE: desired intermediate remained in aqueous phase, which was evaporated. After treatment with THF, the inorganic salts were filtered off and the filtrate evaporated to dryness | Trituration with MeOH followed by washing with MeOH/iPrOH |

Example 55

Synthesis of (S)-3,5-dichloro-4-(2-(3-(cyclopropylmethoxy)-4-(difluoromethoxy)phenyl)-2-(2-(6-(dimethylamino)nicotinoyloxy)acetoxy)ethyl)pyridine 1-oxide (331)

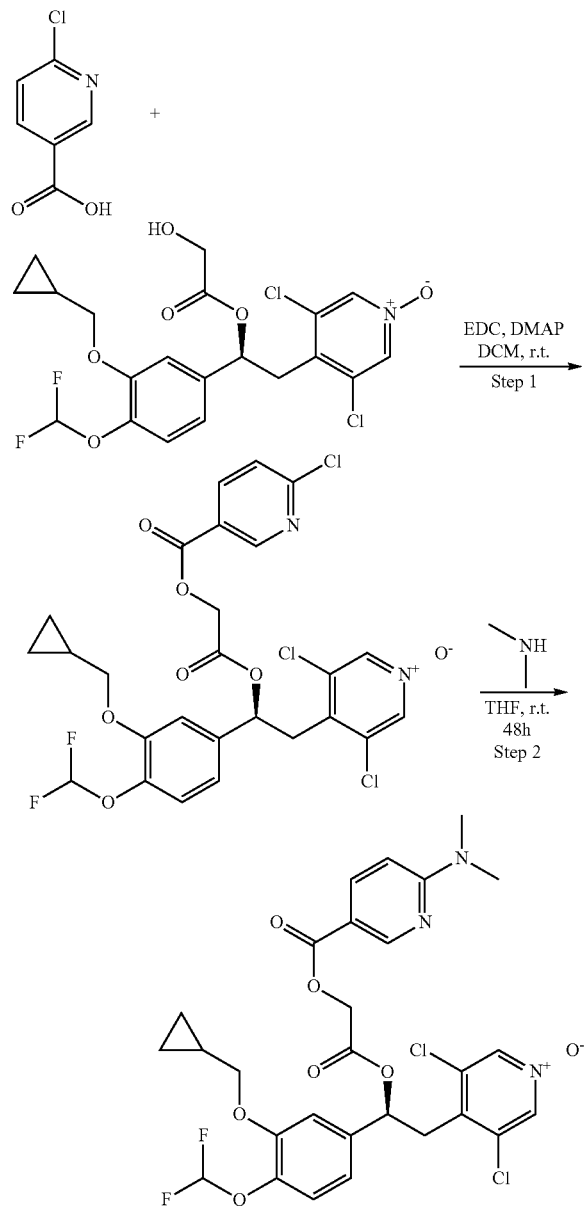

Step 1: Synthesis of (S)-3,5-dichloro-4-(2-(2-(6-chloronicotinoyloxy)acetoxy)-2-(3-(cyclopropylmethoxy)-4-(difluoromethoxy)phenyl)ethyl)pyridine 1-oxide (330)

To a mixture of (S)-3,5-dichloro-4-(2-(3-(cyclopropylmethoxy)-4-(difluoromethoxy)phenyl)-2-(2-hydroxyacetoxy)ethyl)pyridine 1-oxide (See Scheme 21, step 6-9) (200 mg, 0.418 mmol), 6-chloronicotinic acid (72.5 mg, 0.460 mmol) and EDC (240 mg, 1.255 mmol) in dry DCM (10 ml), DMAP (51.1 mg, 0.418 mmol) was added, and stirring was continued for a week-end at room temperature. The solvent was evaporated; the residue was portioned between sat. sol. NaHCO$_3$ and ethyl acetate, the organic phase was washed with brine, dried over sodium sulfate and evaporated, the residue was purified by flash chromatography on silica gel (eluent: DCM/MeOH/32% NH$_4$OH 98/2/0.2) and (S)-3,5-dichloro-4-(2-(2-(6-chloronicotinoyloxy)acetoxy)-2-(3-(cyclopropylmethoxy)-4-(difluoromethoxy)phenyl)ethyl)pyridine 1-oxide was obtained as a white solid (202 mg, 0.327 mmol, 78% yield, MS/ESI$^+$ 617.2 [MH]$^+$).

Step 2: Synthesis of (S)-3,5-dichloro-4-(2-(3-(cyclopropylmethoxy)-4-(difluoromethoxy)phenyl)-2-(2-(6-(dimethylamino)nicotinoyloxy)acetoxy)ethyl)pyridine 1-oxide (331)

A solution of (S)-3,5-dichloro-4-(2-(2-(6-chloronicotinoyloxy)acetoxy)-2-(3-(cyclopropylmethoxy)-4-(difluoromethoxy)phenyl)ethyl)pyridine 1-oxide (202 mg, 0.327 mmol) and dimethylamine (327 µl, 0.654 mmol) in dry THF (5 ml) was stirred at room temperature for 2 days. The solvent was evaporated and the residue was portioned between sat. sol. NaHCO$_3$ and ethyl acetate; the organic phase was washed with brine, dried over Na$_2$SO$_4$, filtered and evaporated and the residue was triturated with iPr$_2$O, filtered and dried under vacuum to give (S)-3,5-dichloro-4-(2-(3-(cyclopropylmethoxy)-4-(difluoromethoxy)phenyl)-2-(2-(6-(dimethylamino)nicotinoyloxy)acetoxy)-ethyl)pyridine 1-oxide as a white solid (180 mg, 0.287 mmol, 88% yield, LC-MS purity (BPI): 98%, MS/ESI$^+$ 626.24 [MH]$^+$, [α$_D$]=−37.04, c=0.50, DCM).

$^1$H NMR (300 MHz, DMSO-d$_6$) δ ppm 8.65 (d, 1 H), 8.51 (s, 2 H), 7.91 (dd, 1 H), 7.18 (d, 1 H), 7.07 (d, 1 H), 6.96 (dd, 1 H), 7.07 (t, 1 H), 6.71 (d, 1 H), 6.04 (dd, 1 H), 4.87 (d, 1 H), 4.80 (d, 1 H), 3.88 (d, 2 H), 3.44 (dd, 1 H), 3.24 (dd, 1 H), 3.13 (s, 6 H), 1.05-1.36 (m, 1 H), 0.48-0.67 (m, 2 H), 0.18-0.47 (m, 2 H)

Example 56

Synthesis of (S)-3,5-dichloro-4-(2-(3-(cyclopropylmethoxy)-4-(difluoromethoxy)phenyl)-2-(2-(2-(methylsulfonamido)pyrimidine-5-carbonyloxy)acetoxy)ethyl)pyridine 1-oxide (336)

Scheme 56

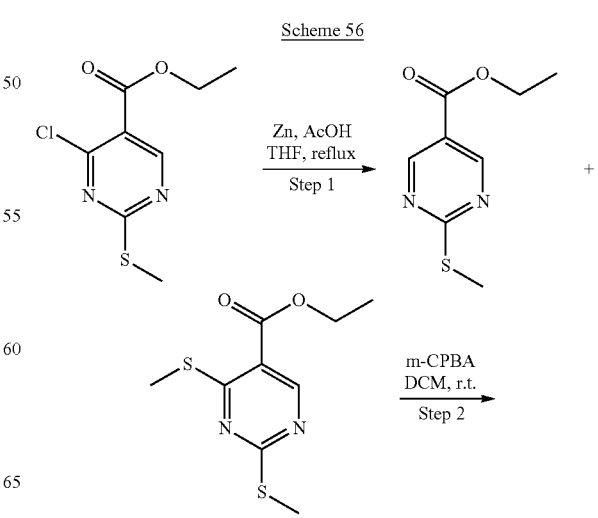

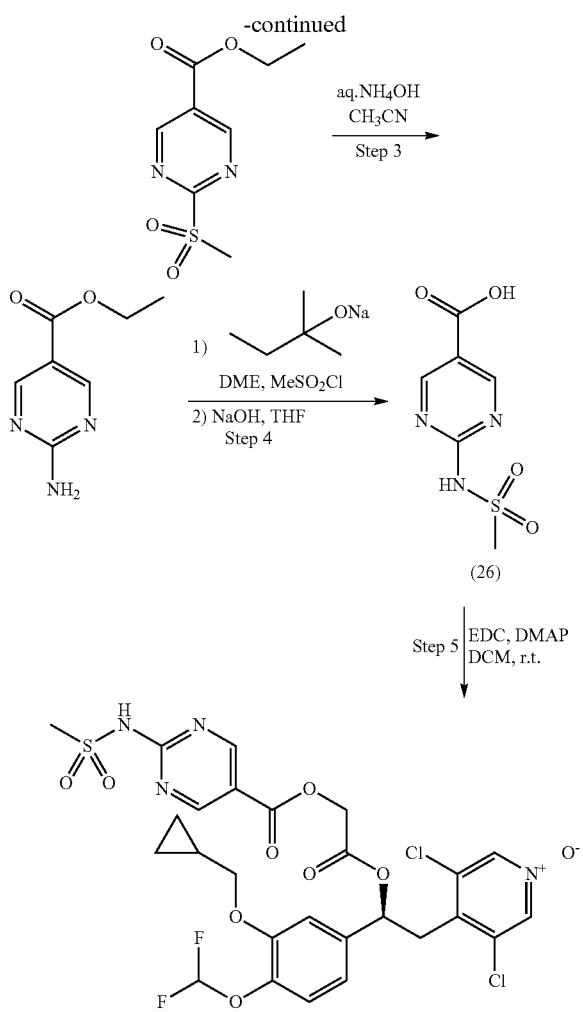

Step 1: Synthesis of ethyl 2-(methylthio)pyrimidine-5-carboxylate (332)

Ethyl 4-chloro-2-(methylthio)pyrimidine-5-carboxylate (10 g, 43.0 mmol) was suspended in dry THF (50 ml), and zinc powder (8.43 g, 129 mmol) was carefully added. The suspension was heated to reflux in a previously heated bath, and then acetic acid (2.460 ml, 43.0 mmol) was added drop wise. The mixture was reacted at the same temperature overnight. The suspension was filtered through a celite pad washing with DCM and MeOH; the filtrate was evaporated and the residue was triturated with DCM:Et$_2$O=1:1. The precipitate was discarded and the solution evaporated and purified by flash chromatography on silica gel column (petroleum ether: ethyl acetate=9:1). After solvent evaporation, the residue was treated with diethyl ether and the precipitate was filtered off. The filtrate was evaporated to dryness affording a mixture of ethyl 2-(methylthio)pyrimidine-5-carboxylate and ethyl 2,4-bis(methylthio)pyrimidine-5-carboxylate (about 1:1 ratio) as a colorless oil (3.47 g, MS/ESI$^+$ 199.1 [MH]$^+$; MS/ESI$^+$ 245.0 [MH]$^+$).

Step 2: Synthesis of ethyl 2-(methylsulfonyl)pyrimidine-5-carboxylate (333)

A mixture of ethyl 2-(methylthio)pyrimidine-5-carboxylate and ethyl 2,4-bis(methylthio)pyrimidine-5-carboxylate (about 1:1 ratio; 3.47 g) was dissolved in DCM (78 ml), and m-CPBA (77% w/w; 10.54 g, 47.0 mmol) was added portion wise stirring at room temperature. The reaction was stirred at the same temperature overnight. The obtained suspension was filtered washing with DCM and the filtrate was evaporated. The crude was dissolved in ethyl acetate (250 ml) and washed twice with a sat. NaHCO$_3$ (100 ml×2); the organic phase was dried over sodium sulfate and evaporated. The crude was purified by flash chromatography on silica gel column (DCM:iPr$_2$O=3:7) affording ethyl 2-(methylsulfonyl)pyrimidine-5-carboxylate as an off-white solid (2.154 g, 9.31 mmol, 21.7% yield over two steps, MS/ESI$^+$ 231.0 [MH]$^+$). This intermediate proved to be instable on air and it must be kept under vacuum.

Step 3: Synthesis of ethyl 2-aminopyrimidine-5-carboxylate (334)

Ethyl 2-(methylsulfonyl)pyrimidine-5-carboxylate (2.15 g, 9.34 mmol) was dissolved in acetonitrile (11.7 ml), and, with stirring at room temperature, aqueous 32% ammonium hydroxide (11.36 ml, 93 mmol) was added drop wise. A white suspension was obtained after few seconds. Acetonitrile was evaporated and the aqueous suspension was filtered on a buckner funnel. The obtained solid was washed with water (20 ml) and dried affording ethyl 2-aminopyrimidine-5-carboxylate as a white solid (1.192 g, 7.13 mmol, 76% yield, MS/ESI$^+$ 168.1 [MH]$^+$).

Step 4: Synthesis of 2-(methylsulfonamido)pyrimidine-5-carboxylic acid (335)

To a solution of ethyl 2-aminopyrimidine-5-carboxylate (0.200 g, 1.196 mmol) in DME (6 ml), a suspension of sodium 2-methylbutan-2-olate (0.527 g, 4.79 mmol) in DME (6 ml) was added drop wise stirring at room temperature under nitrogen. The resulting yellow suspension was stirred at the same temperature for 30 minutes and then cooled to −10° C. Methanesulfonyl chloride (0.278 ml, 3.59 mmol) was added drop wise maintaining the temperature below −5° C. After 1.5 hours, water (30 ml) was added, and the mixture was extracted with ethyl acetate (20 ml×3). The combined organic layers were dried over sodium sulfate and evaporated. The residue was triturated with MeOH and the mother liquors were evaporated and triturated with EtOH. The two portions collected by filtration were mixed affording 0.152 g of a mixture of ethyl 2-(methylsulfonamido)pyrimidine-5-carboxylate and methyl 2-(methylsulfonamido)-pyrimidine-5-carboxylate (about 1:1 ratio). This mixture was suspended in THF (6.380 ml) and 3N NaOH (0.425 ml, 1.276 mmol) was added. The resulting solution was heated to 50° C. for 2.5 hours. THF was evaporated and the aqueous solution was diluted with water (2 ml) and acidified with 6N HCl (pH=2) stirring at room temperature. The obtained precipitate was collected by filtration affording 2-(methylsulfonamido)-pyrimidine-5-carboxylic acid as a white solid (0.133 g, 0.612 mmol, 51.1% yield, MS/ESI$^+$ 218.0 [MH]$^+$).

Step 5: Synthesis of (S)-3,5-dichloro-4-(2-(3-(cyclopropylmethoxy)-4-(difluoromethoxy)phenyl)-2-(2-(2-(methylsulfonamido)pyrimidine-5-carbonyloxy)acetoxy)ethyl)pyridine 1-oxide (336)

To a suspension of 2-(methylsulfonamido)pyrimidine-5-carboxylic acid (0.130 g, 0.599 mmol) in dry DCM (5.44 ml), (S)-3,5-dichloro-4-(2-(3-(cyclopropylmethoxy)-4-(difluoromethoxy)phenyl)-2-(2-hydroxyacetoxy)ethyl)pyridine 1-oxide (See Scheme 21, step 6-9) (0.260 g, 0.544 mmol), EDC (0.313 g, 1.632 mmol), and DMAP (0.665 g, 0.544 mmol) were sequentially added with stirring at room temperature under nitrogen, and the mixture was stirred for 20 hours. The solvent was removed, and the crude was purified by flash chromatography on silica gel column (DCM: MeOH=97:3 to 95:5) affording (S)-3,5-dichloro-4-(2-(3-(cyclopropylmethoxy)-4-(difluoromethoxy)phenyl)-2-(2-(2-(methylsulfonamido)pyrimidine-5-carbonyloxy)acetoxy) ethyl)pyridine 1-oxide as a pale yellow spongy solid (0.168 g, 0.248 mmol, 45.6% yield, MS/ESI$^+$ 677.1 [MH]$^+$, [$\alpha_D$]=−47.48, c=0.5, MeOH).

$^1$H NMR (300 MHz, DMSO-d$_6$) δ ppm 12.01 (br. s., 1 H), 9.01 (s, 2 H), 8.52 (s, 2 H), 7.19 (d, 1 H), 7.10 (d, 1 H), 6.98 (dd, 1 H), 7.07 (t, 1 H), 6.06 (dd, 1 H), 4.97 (d, 1 H), 4.90 (d, 1 H), 3.92 (d, 2 H), 3.47 (dd, 1 H), 3.36 (s, 3 H), 3.26 (dd, 1 H), 1.08-1.38 (m, 1 H), 0.47-0.71 (m, 2 H), 0.28-0.46 (m, 2 H)

Example 57

Synthesis of (S)-3,5-dichloro-4-(2-(3-(cyclopropylmethoxy)-4-(difluoromethoxy)phenyl)-2-(2-(2-(methylsulfonamido)isonicotinoyloxy)acetoxy)ethyl) pyridine 1-oxide (341)

Step 1: Synthesis of ethyl 2-(methylsulfonamido)isonicotinate (337)

To a solution of ethyl 2-aminoisonicotinate (1 g, 6.02 mmol) in dry pyridine (20 ml), methanesulfonyl chloride (0.938 ml, 12.04 mmol) was added at room temperature, and the resulting solution was stirred for 3 hours. Pyridine was evaporated and the residue was triturated with water (20 ml). The solid was collected by filtration and dried affording ethyl 2-(methylsulfonamido)isonicotinate as a light brown powder (1.3 g, 5.32 mmol, 88% yield, MS/ESI$^+$ 245.2 [MH]$^+$).

Step 2: Synthesis of ethyl 2-(N-(tert-butoxycarbonyl)methylsulfonamido)isonicotinate (338)

To a solution of ethyl 2-(methylsulfonamido)isonicotinate (1.3 g, 5.32 mmol) and DMAP (0.780 g, 6.39 mmol) in dry DCM (40 ml), di-tert-butyl dicarbonate (1.483 ml, 6.39 mmol) was added, and the mixture was stirred at room temperature for 2 hours. The solvent was evaporated and the residue was purified by flash chromatography on silica gel column (DCM:Et$_2$O=9:1) to give ethyl 2-(N-(tert-butoxycarbonyl)methyl-sulfonamido)isonicotinate as a white solid (0.920 g, 2.67 mmol, 50.2% yield, MS/ESI$^+$ 345.2 [MH]$^+$).

Scheme 57

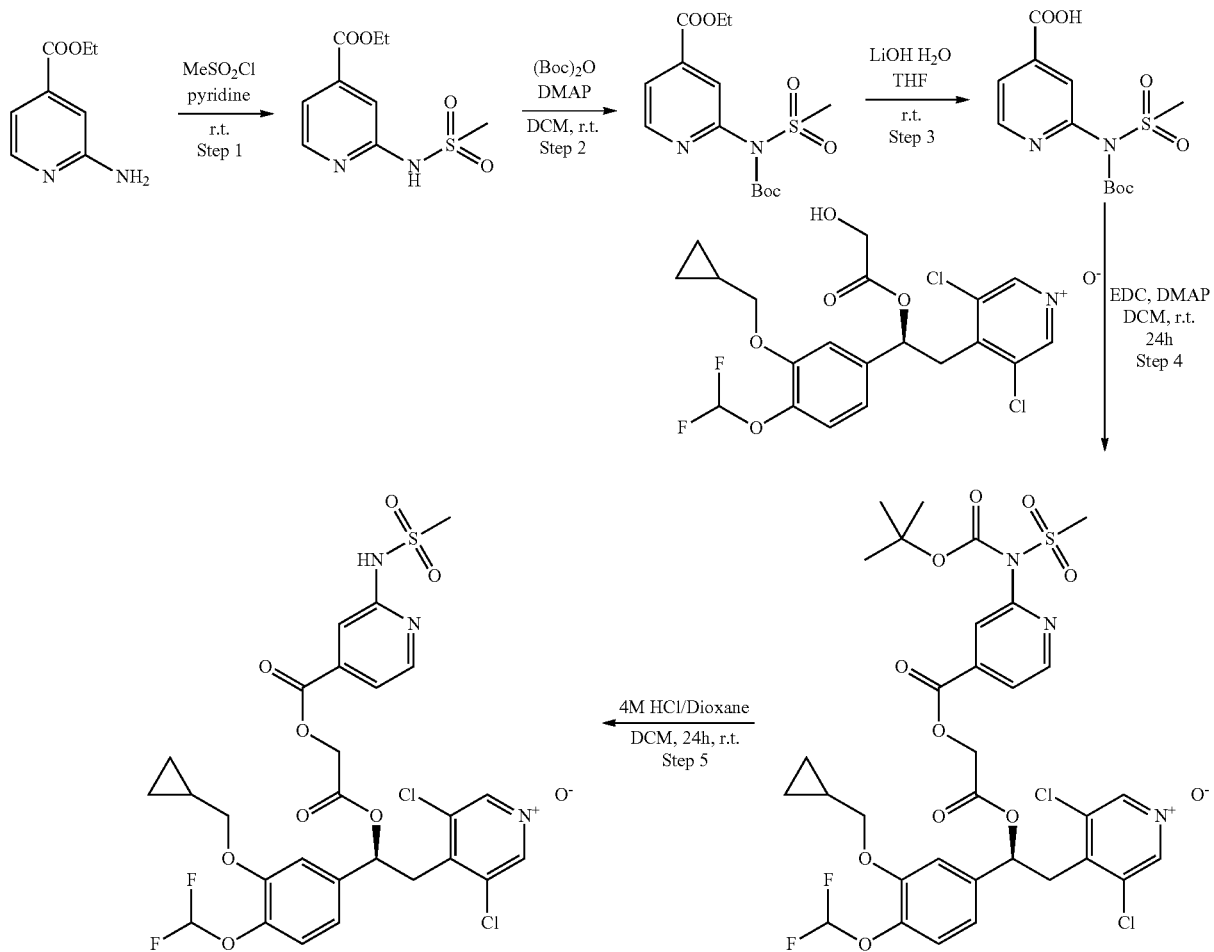

257

Step 3: Synthesis of 2-(N-(tert-butoxycarbonyl)methylsulfonamido)isonicotinic acid (339)

To a solution of ethyl 2-(N-(tert-butoxycarbonyl)methylsulfonamido)isonicotinate (0.920 g, 2.67 mmol) in THF (15 ml), aqueous 1M LiOH (2.94 ml, 2.94 mmol) was added, and the reaction was stirred at room temperature for 2 hours. The mixture was diluted with ethyl acetate and acidified with aqueous 2N HCl. The organic layer was separated, washed with brine and dried over $Na_2SO_4$. The solvent was removed under vacuum and the solid residue was purified by trituration with $iPr_2O$ affording after filtration 2-(N-(tert-butoxycarbonyl)methylsulfonamido) isonicotinic acid as a white solid (0.625 g, 1.976 mmol, 74.0% yield, MS/ESI$^+$ 339.2 [MNa]$^+$).

Step 4: Synthesis of (S)-4-(2-(2-(2-(N-(tert-butoxycarbonyl)methylsulfonamido)-isonicotinoyloxy)acetoxy)-2-(3-(cyclopropylmethoxy)-4-(difluoromethoxy)phenyl)ethyl)-3,5-dichloropyridine 1-oxide This Step was performed as Step 10, Scheme 21, starting with 2-(N-(tert-butoxycarbonyl)methylsulfonamido)isonicotinic acid and (S)-3,5-dichloro-4-(2-(3-(cyclopropylmethoxy)-4-(difluoromethoxy)phenyl)-2-(2-hydroxyacetoxy)ethyl)pyridine 1-oxide (See Scheme 21, step 6-9)

Step 5: Synthesis of (S)-3,5-dichloro-4-(2-(3-(cyclopropylmethoxy)-4-(difluoromethoxy)phenyl)-2-(2-(2-(methylsulfonamido)isonicotinoyloxy)-acetoxy)ethyl)pyridine 1-oxide This step was performed as Step 11, Scheme 21, starting with S)-4-(2-(2-(2-(N-(tert-butoxycarbonyl)methylsulfonamido)isonicotinoyloxy)acetoxy)-2-(3-(cyclopropylmethoxy)-4-(difluoromethoxy)phenyl)ethyl)-3,5-dichloropyridine 1-oxide $^1$H NMR (300 MHz, DMSO-d$_6$) δ ppm 11.01 (br. s., 1 H), 8.52 (s, 2 H), 8.48 (d, 1 H), 7.44 (s, 1 H), 7.41 (d, 1 H), 7.19 (d, 1 H), 7.09 (d, 1 H), 6.98 (dd, 1 H), 7.07 (t, 1 H), 6.05 (dd, 1 H), 5.02 (d, 1 H), 4.94 (d, 1 H), 3.90 (d, 2 H), 3.47 (dd, 1 H), 3.30 (br. s., 3 H), 3.26 (dd, 1 H), 1.13-1.33 (m, 1 H), 0.49-0.66 (m, 2 H), 0.23-0.45 (m, 2 H)

MS/ESI$^+$ 676.17 [MH]$^+$

[α$_D$]=−48.28, c=0.5, DCM)

Example 58

Synthesis of (S)-3,5-dichloro-4-(2-(3-(cyclopropylmethoxy)-4-(difluoromethoxy)phenyl)-2-(2-(thiophene-2-carbonyloxy)acetoxy)ethyl)pyridine 1-oxide (344)

Scheme 58

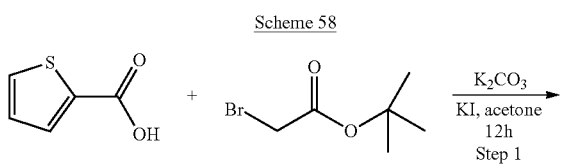

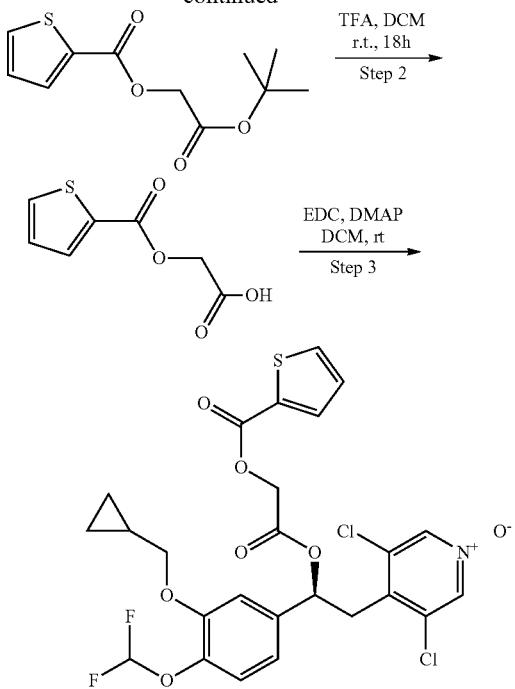

Step 1: Synthesis of 2-tert-butoxy-2-oxoethyl thiophene-2-carboxylate (342)

To a solution of thiophene-2-carboxylic acid (500 mg, 3.90 mmol) in acetone (20 ml), $K_2CO_3$ (593 mg, 4.29 mmol) was added, and mixture was stirred for 5 minutes, then KI (64.8 mg, 0.390 mmol) was added, followed by dropwise addition of tert-butyl 2-bromoacetate (0.634 ml, 4.29 mmol). The mixture was heated at 50° C. overnight. The solid residue was filtered out and washed with DCM; the solvent was evaporated and 2-tert-butoxy-2-oxoethyl thiophene-2-carboxylate was obtained as a clear oil (945 mg, 3.90 mmol, 100% yield, MS/ESI$^+$ 264.9 [MNa]$^+$) and used in the following reaction without further purification.

Step 2: Synthesis of 2-(thiophene-2-carbonyloxy)acetic acid (343)

To a solution of 2-tert-butoxy-2-oxoethyl thiophene-2-carboxylate (945 mg, 3.90 mmol) in DCM (6 ml) kept at 0° C., TFA (6.00 ml, 78 mmol) was added dropwise. The solution was stirred at room temperature overnight, then volatiles were evaporated obtaining 2-(thiophene-2-carbonyloxy)acetic acid as a white solid (710 mg, 3.81 mmol, 98% yield, MS/ESI$^+$ 186.7 [MH]$^+$) that was used in the following reaction without further purification.

Step 3: Synthesis of (S)-3,5-dichloro-4-(2-(3-(cyclopropylmethoxy)-4-(difluoromethoxy)phenyl)-2-(2-(thiophene-2-carbonyloxy)acetoxy)ethyl)pyridine 1-oxide (344)

(S)-3,5-dichloro-4-(2-(3-(cyclopropylmethoxy)-4-(difluoromethoxy)phenyl)-2-hydroxyethyl)pyridine 1-oxide (150 mg, 0.357 mmol), 2-(thiophene-2-carbonyloxy)acetic acid (80 mg, 0.428 mmol), EDC (205 mg, 1.071 mmol), and DMAP (43.6 mg, 0.357 mmol) were dissolved in DCM (15 ml), and the solution was stirred at room temperature overnight. The solution was diluted with DCM, washed with 1N HCl and 5% NaHCO$_3$, then with brine. The organic phase was dried over Na$_2$SO$_4$, and the solvent was evaporated. The crude so obtained (233 mg of a pale yellow solid) was triturated with MeOH and sonicated; the fine solid so obtained was filtered and dried in vacuum oven overnight. The desired product was obtained as a white powder (133 mg, 0.226 mmol, 63.3% yield, LC-MS/ESI$^+$ 588.04 [MH]$^+$, [α$_D$]=−24.78, c=0.51, CHCl$_3$).

1H NMR (300 MHz, DMSO-d6) δ ppm 8.51 (s, 2 H), 8.03 (dd, 1 H), 7.85 (dd, 1 H), 7.26 (dd, 1 H), 7.18 (d, 1 H), 7.07 (d, 1 H), 6.96 (dd, 1 H), 7.07 (t, 1 H), 6.04 (dd, 1 H), 4.93 (d, 1 H), 4.86 (d, 1 H), 3.89 (d, 2 H), 3.45 (dd, 1 H), 3.25 (dd, 1 H), 1.06-1.36 (m, 1 H), 0.49-0.73 (m, 2 H), 0.19-0.46 (m, 2 H)

Pharmacological Activity of the Compounds of the Invention

Example 59

In Vitro Determination of PDE4 Inhibitory Activity in the Cell Free Assay

PDE4 activity was determined in U937 human monocytic supernatants cells lysate. Cells were cultured, harvested and supernatant fraction prepared essentially as described in Torphy T J et al J. Pharmacol. Exp. Ther. 1992; 263:1195-1205, which is incorporated herein by reference in its entirety. U937 cells (Cell Bank, Interlab Cell Line Collection, ICLC HTL94002) were grown at 37° C., 5% CO$_2$ in RPMI 1640 with GlutaMAX™-I medium supplemented with 10% fetal bovine serum and 100 µg/ml Pen-strep (Gibco). Cells were harvested and washed twice by centrifugation (150×g, 8 min) in cold PBS. Washed cells were resuspended in cold Krebs-Ringer-Henseleit buffer at a final concentration 20×10$^6$ cells/ml and sonicated. After centrifugation at 15000×g for 20 min, the supernatants were pooled, divided in aliquots and stored at −80° C.

PDE4 activity was determined in cells supernatants by assaying cAMP disappearance from the incubation mixtures. The concentration of the test compounds ranged between 10$^{-12}$ M and 10$^{-6}$ M. Reactions were stopped by enzyme heat inactivation (2.5 minutes at 100° C.) and residual cAMP content was determined using the 'LANCE cAMP Assay' from PerkinElmer following the providers instructions.

The results of the tested compounds, representatives of the invention, expressed as mean±standard deviation of the nM concentration of the test compound producing 50% inhibition of cAMP disappearance (IC$_{50}$) were less than 30 nM. For a group of preferred compounds (94 out of 117 tested), the results were less than 0.5 nM. For a group of more preferred compounds (44 out of 117 tested), the results were less than 0.1 nM.

The percentage of inhibition of PDE4 activity was calculated, assuming cAMP disappearance in the absence of inhibitors as 100% and cAMP disappearance in heat inactivated samples as 0%.

Example 60

In Vitro Determination of PDE4 Inhibitory Activity in the Peripheral Blood Mononuclear Cells (PBMCs) Assay The assay, which is based on the known inhibitory activity exerted by PDE4 inhibitors on the lipopolyshaccarides (LPS)-induced tumour necrosis factor-alpha (TNF-α release in peripheral blood mononuclear cells (PBMCs), was performed according to a method previously described (Hatzelmann A et al., J. Pharmacol. Exp. Ther. 2001; 297:267-279; and Draheim R et al., J. Pharmacol. Exp. Ther. 2004; 308: 555-563, which are incorporated herein by reference in their entireties. Cryopreserved human PBMCs, (100 µl/well) were incubated in 96-well plates (10$^5$ cells/well), for 30 minutes, in the presence or absence (50 microl) of the test compounds whose concentrations ranged from 10$^{-12}$ M to 10$^{-6}$ M or from 10$^{-13}$ M to 10$^{-7}$ M. Subsequently, LPS (3 ng/ml) was added. After 18 hours of incubation at 37° C. in a humidified incubator under an atmosphere of 95% air and 5% CO$_2$, culture medium was collected and TNF-α measured by ELISA.

The results of the tested compounds, representatives of the invention, expressed as mean±95% confidence limits of the molar concentration of the test compound producing 50% inhibition of LPS-induced TNF-α release (IC$_{50}$) were less than 50 nM. For a group of preferred compounds (70 out of 95 tested), the results were less than 3 nM. For a group of further preferred compounds (24 out of 95 tested), the results were less than 0.5 nM.

The effects of the tested compounds were calculated as percentage of inhibition of TNF-α release, assuming LPS-induced TNF-α production in the absence of inhibitor compound as 100% and basal TNF-α production of PBMCs in the absence of LPS as 0%.

Example 61

In Vitro Determination of Intrinsic Clearance in Human Hepatic Microsomes

Method a.

Test compounds in duplicate at the final concentration of 1 µM are dissolved in DMSO (DMSO final concentration 0.5% v/v) and pre-incubated for 10 minutes at 37° C. in potassium phosphate buffer pH 7.4, 3 mM MgCl$_2$, with liver microsomes at the final concentration of 0.5 mg/ml. After the pre-incubation period, reactions are started by adding the cofactors mixture (NADP, Glc6P, Glc6P-DH); samples are taken at time 0, 5, 10, 15, 20 and 30 minutes, added to acetonitrile to stop reaction and centrifuged. The supernatants are analysed and quantified by LC-MS/MS.

A control sample without cofactors is always added in order to check the stability of test compounds in the matrix. 7-Ethoxycoumarin is added as reference standard. A fixed concentration of verapamil is added in every sample as internal standard for LC-MS/MS.

Zero-time incubation is used as 100% value. Percent loss of substrate in incubation is determined to estimate in-vitro half life and in-vitro intrinsic clearance of compounds. The rate constant, k (min$^{-1}$) derived for the exponential decay equation (peak area vs time) is used to calculate the rate of intrinsic clearance (CLi) of the compounds using the following equation:

$$CLi \text{ (mL/min/g liver)} = k \times V \times y$$

Where:

k is calculated from the exponential fitting decay of the area values

V=incubation volume (mL)/mg protein y=microsomal protein yield=52.5 mg/g liver

Method b.

Test compounds are incubated, in duplicate, at the concentration of 1 µM with liver microsomes (0.8 mg protein/mL) in KHB buffer (pH 7.4) at 37° C. in the presence of 1 mM NADPH. At different time points (0, 5, 10, 20, 30 and 60 minutes) 50 µL aliquots of the incubates are taken, added with 80 µL of ice-cold acetonitrile and 20 µL of 1 µM warfarin in acetonitrile (injection check) to stop the reaction and samples centrifuged. The supernatant is analysed by LC-MS/MS for unchanged compounds.

Test compounds are incubated with liver microsomes in KHB buffer in the absence of NADPH for 0 and 60 minutes, as control. Midazolam at the concentration of 1 µM, is incubated with microsomes as positive control for phase I activity of microsomes. Control samples are processed as test compounds samples.

The intrinsic clearance is determined using the half-life approach. The half-life is calculated from the relationship:

$$\text{Half-life(min)} = \frac{LN(2)}{-\text{SLOPE}} = \frac{0.693}{-\text{SLOPE}}$$

The slope refers to the curve obtained by plotting the natural logarithmic (LN) value of peak area of the compound remaining against the time and is calculated by linear regression analysis.

Results are reported as half-life in minutes and as in vitro intrinsic clearance values expressed in µL/min/mg protein (for incubation with microsomes) and scaled intrinsic clearance values as mL/min/kg.

Compounds of the invention are endowed with high or moderate intrinsic metabolic clearance. Some of the representative compounds of the invention (63 out of 70 tested), when tested according to the protocol reported, showed an intrinsic Clearance>15 mL/min/g.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

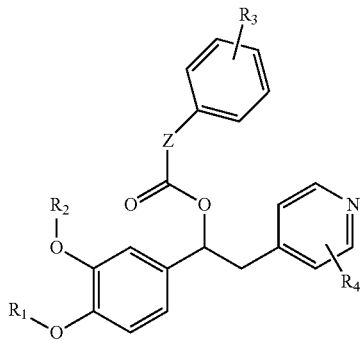

wherein:
$R_1$ and $R_2$ are different or the same and are each independently:
   ($C_1$-$C_6$) alkyl, optionally substituted by ($C_3$-$C_7$) cycloalkyl;
   ($C_1$-$C_6$) haloalkyl; or
   ($C_3$-$C_7$) cycloalkyl;

$R_4$ is one or more substituents independently selected from the group consisting of H, CN, $NO_2$, $CF_3$ and a halogen atom;

Z is
[3]-$CH_2$—X-[4];
wherein [3] indicates the point of attachment for group Z with the carboxylic group and [4] indicates the point of attachment for group Z with the phenyl group;

X is:
a group [5]-O—(CO)—$(CH_2)_n$-[4], wherein n is 0;
a group [5]-NH—(CO)-[4];
a group [5]-$NR_8$—$SO_2$—$(CH_2)_n$-[4], wherein n is 0;
a group [5]-S—(CO)-[4]; or
a group [5]-$NR_9$—$(CH_2)_n$-[4], wherein n is 1;
wherein [5] indicates the point of attachment for group X with the methylene group and [4] indicates the point of attachment for group X with the phenyl group;

$R_8$ is hydrogen, ($C_1$-$C_4$) alkyl, or ($C_3$-$C_8$)heterocycloalkyl ($C_1$-$C_4$) alkyl;

$R_9$ is hydrogen, ($C_1$-$C_4$) alkyl, or a group —$SO2(C_1$-$C_4$) alkyl;

$R_3$ are one or more optional substituents which may be the same or different, and are independently selected from the group consisting of:
($C_1$-$C_6$) alkyl optionally substituted by one or more ($C_3$-$C_7$)cycloalkyl;
($C_1$-$C_6$) haloalkyl;
($C_3$-$C_7$) heterocycloalkyl;
($C_3$-$C_7$) heterocycloalkyl($C_1$-$C_4$) alkyl;
a group —$OR_{11}$ wherein $R_{11}$ is selected from the group consisting of:
   H;
   ($C_1$-$C_6$) haloalkyl;
   a group —$SO_2R_{12}$, wherein $R_{12}$ is ($C_1$-$C_6$) alkyl;
   a group —$C(O)R_{12}$ wherein $R_{12}$ is as above defined;
   ($C_1$-$C_{10}$) alkyl optionally substituted by one or more ($C_3$-$C_7$) cycloalkyl or by a group —$NR_{13}R_{14}$ as below defined; and
   ($C_3$-$C_7$) cycloalkyl;
a group —$SR_{25}$ wherein $R_{25}$ is selected from the group consisting of:
   H;
   ($C_1$-$C_6$) haloalkyl;
   a group —$C(O)R_{12}$;
   ($C_1$-$C_{10}$) alkyl optionally substituted by one or more ($C_3$-$C_7$) cycloalkyl or by a group —$NR_{13}R_{14}$; and
   ($C_3$-$C_7$) cycloalkyl;
halogen atoms;
CN;
$NO_2$;
$NR_{13}R_{14}$ wherein $R_{13}$ and $R_{14}$ are different or the same and are independently selected from the group consisting of:
   H;
   ($C_1$-$C_4$) alkyl-$NR_{15}R_{16}$ wherein $R_{15}$ and $R_{16}$ are different or the same and are independently selected from the group consisting of: H and ($C_1$-$C_6$) alkyl, which is optionally substituted with ($C_3$-$C_7$) cycloalkyl or ($C_3$-$C_7$) heterocycloalkyl; or they form with the nitrogen atom to which they are linked a ($C_3$-$C_y$)heterocycloalkyl which is optionally substituted by ($C_1$-$C_6$) alkyl;
linear or branched ($C_1$-$C_6$) alkyl, optionally substituted with ($C_3$-$C_7$) cycloalkyl, ($C_3$-$C_7$) heterocycloalkyl, a group —OH, ($C_1$-$C_6$) alkoxyl or by an amino carbonyl group;

a group —SO$_2$R$_{17}$, wherein R$_{17}$ is selected in the group consisting of: (C$_1$-C$_6$) alkyl optionally substituted by (C$_3$-C$_7$) cycloalkyl or (C$_3$-C$_7$)heterocycloalkyl; (C$_3$-C$_7$) heterocycloalkyl; and phenyl optionally substituted by one or more (C$_1$-C$_6$) alkyl, halogen or —OH;

a group —C(O)R$_{18}$, wherein R$_{18}$ is selected in the group consisting of: (C$_1$-C$_6$) alkyl optionally substituted by (C$_3$-C$_7$) cycloalkyl; (C$_1$-C$_6$) alkylcarboxyl; and phenyl optionally substituted by one or more (C$_1$-C$_6$) alkyl, halogen or hydroxyl; and a group —NR$_{20}$R$_{21}$; wherein R$_{20}$ and R$_{21}$ are different or the same and are independently selected from the group consisting of: H and (C$_1$-C$_6$) alkyl, which is optionally substituted with (C$_1$-C$_6$)alkoxy;

a group —C(O)OR$_{19}$, wherein R$_{19}$ is selected in the group consisting of: (C$_1$-C$_6$) alkyl optionally substituted by (C$_3$-C$_7$) cycloalkyl; and phenyl optionally substituted by one or more (C$_1$-C$_6$) alkyl, halogen or —OH;

or they form with the nitrogen atom to which they are linked a saturated or partially saturated heterocyclic ring, which is optionally substituted by (C$_1$-C$_6$) alkyl; (C$_1$-C$_4$) alkyl-NR$_{13}$R$_{14}$;

COR$_{22}$ wherein R$_{22}$ is phenyl, heterocycloalkyl or (C$_1$-C$_6$) alkyl;

—SO$_2$R$_{23}$ wherein R$_{23}$ is (C$_1$-C$_4$) alkyl, —OH or NR$_{28}$R$_{29}$ wherein R$_{28}$ and R$_{29}$ are each independently H or (C$_1$-C$_4$) alkyl;

—COOR$_{24}$ wherein R$_{24}$ is H or (C$_1$-C$_4$) alkyl or (C$_1$-C$_4$) alkyl-NR$_{13}$R$_{14}$; and —CONR$_{13}$R$_{14}$ wherein R$_{13}$ and R$_{14}$ are as defined above;

wherein groups R$_3$, R$_4$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{28}$ and R$_{29}$ may have the same or different meanings at each occurrence, if present in more than one group;

or an N-oxide on the pyridine ring, or a pharmaceutically acceptable salts thereof.

2. A compound, N-oxide, or a pharmaceutically acceptable salt according to claim 1, having a formula (IC):

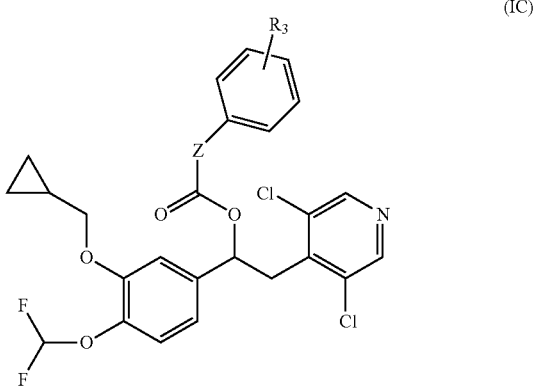

wherein Z and R$_3$ are as defined above.

3. A compound, N-oxide, or a pharmaceutically acceptable salt according to claim 1, wherein Z is:

[3]-CH$_2$—X-[4] wherein X is a group [5]-O—(CO)—(CH$_2$)$_n$-[4], wherein n is 0;

[3]-CH$_2$—X-[4] wherein X is a group [5]-S—(CO)-[4];

[3]-CH$_2$—X-[4] wherein X is a group [5]-NR$_9$—(CH$_2$)$_n$-[4], wherein n is 1; or

[3]-CH$_2$—X-[4] wherein X is a group [5]-NR$_8$—SO$_2$—(CH$_2$)$_n$-[4], wherein n is 0.

4. A compound, N-oxide, or a pharmaceutically acceptable salt according to claim 1, which is an N-oxide on the pyridine ring.

5. A compound, N-oxide, or a pharmaceutically acceptable salt according to claim 1, which is represented by formula (I)':

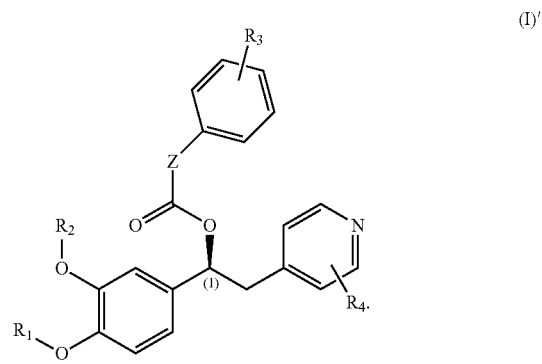

6. A compound, N-oxide, or a pharmaceutically acceptable salt according to claim 1, which is a compound selected from the group consisting of:

(S)-3,5-dichloro-4-(2-(3-(cyclopropylmethoxy)-4-(difluoromethoxy)phenyl)-2-2-((3,4-dimethoxybenzyl)(methyl)amino)acetoxy)ethyl)pyridine 1-oxide;

(S)-3,5-dichloro-4-(2-(3-(cyclopropylmethoxy)-4-(difluoromethoxy)phenyl)-2-(2-(3,4-dimahoxybenzylamino)acetoxy)ethyl)pyridine 1-oxide;

(S)-3,5-dichloro-4-(2-(3-(cyclopropylmethoxy)-4-(difluoromethoxy)phenyl)-2-(2-(3-(cyclopropylmethoxy)-4-(methylsulfonamido)benzoyloxy)acetoxy)-ethyl)pyridine 1-oxide;

(S)-3,5-dichloro-4(2-(3-(cyclopropylmethoxy)-4-(difluoromethoxy)phenyl)-2-(2-(3-(cyclopropylmethoxy)-4-(methylsulfonamido)benzamido)acetoxy)-ethyl)pyridine 1-oxide;

(S)-3,5-dichloro-4-(2-(3-(cyclopropylmethoxy)-4-(difluoromethoxy)phenyl)-2-(2-(methyl(4-(methylsulfonamido)benzyl)amino)acetoxy)ethyl)pyridine 1-oxide;

(S)-3,5-dichloro-4-(2-(3-(cyclopropylmethoxy)-4-(difluoromethoxy)phenyl)-2-(2-(2-(methoxycarbonyl)phenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(2-(methylsulfonyl)benzamido)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(N-(2-morpholinoethyl)methylsulfonamido)benzoyloxy)-acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(methylsulfonyloxy)benzamido)acetoxy)ethyl)pyridine 1-oxide;

(S)-3,5-dichloro-4-(2-(3-(cyclopropylmethoxy)-4-(difluoromethoxy)phenyl)-2-(2-(4-(methylsulfonyloxy)benzamido)acetoxy)ethyl)pyridine 1-oxide;

(S)-4-(2-(2-benzamidoacetoxy)-2-(3-(cyclopropylmethoxy)-4-(difluoromethoxy)phenyl)ethyl)-3,5-dichloropyridine 1-oxide;

(S)-4-(2-(2-(4-carbamoylbenzamido)acetoxy)-2-(3-(cyclopropylmethoxy)-4-(difluoromethoxy)phenyl)ethyl)-3,5-dichloropyridine 1-oxide;

(S)-3,5-dichloro-4-(2-(3-(cyclopropylmethoxy)-4-(difluoromethoxy)phenyl)-2-(2-(4-methoxy-3-(N-(2-morpholinoethyl)methylsulfonamido)benzamido)acetoxy)ethyl)pyridine 1-oxide;
(S)-4-(2-(2-(3-acetamido-4-methoxyphenylsulfonamido)acetoxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)phenyl)-2-(2-(3,4-dimethoxybenzoyloxy)acetoxy)ethyl)pyridine 1-oxide;
(S)-3,5-dichloro-4-(2-(3-(cyclopropylmethoxy)-4-(difluoromethoxy)phenyl)-2-(2-(4-(N-methylsulfamoyl)benzoyloxy)acetoxy)ethyl)pyridine 1-oxide;
(S)-4-(2-(2-(3-(N-(2-amino-2-oxoethyl)methylsulfonamido)-4-methoxybenzamido)acetoxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)phenyl)-2-(2-(3,4-dimethoxybenzamido)acetoxy)ethyl)pyridine 1-oxide;
(S)-3,5-dichloro-4-(2-(3-(cyclopropylmethoxy)-4-(difluoromethoxy)phenyl)-2-(2-(2-methoxy-4-(methylsulfonyloxy)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(4-(methylsulfonamidomethyl)benzoyloxy)acetoxy)ethyl)pyridine 1-oxide;
(S)-4-(2-(2-(3-(N-(2-amino-2-oxoethyl)methylsulfonamido)-4-methoxybenzoyloxy)acetoxy)-2-(3-(cyclopropylmethoxy)-4-(difluoromethoxy)phenypethyl)-3,5-dichloropyridine 1-oxide;
(S)-3,5-dichloro-4-(2-(3-(cyclopropylmethoxy)-4-(difluoromethoxy)phenyl)-2-(2-(4-methoxy-3-(methylsulfonyloxy)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(4-methoxy-3-(methylsulfonyloxy)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(4-methoxy-3-(methylsulfonamido)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(3,4-dimethoxyphenylsulfonamido)acetoxy)ethyl)pyridine 1-oxide;
(S)-3,5-dichloro-4-(2-(2-(4-(cyclopropylmethoxy)-3-(methylsulfonyloxy)-benzoyloxy)acetoxy)-2-(3-(cyclopropylmethoxy)-4-difluoromethoxy)phenyl)ethyl)pyridine 1-oxide;
(S)-3,5-dichloro-4-(2-(3-(cyclopropylmethoxy)-4-(difluoromethoxy)phenyl)-2-(2-(5-(N-(cyclopropylmethyl)methylsulfonamido)-2-hydroxybenzoyloxy)acetoxy)-ethyl)pyridine 1-oxide;
(S)-3,5-dichloro-4-(2-(3-(cyclopropylmethoxy)-4-(difluoromethoxy)phenyl)-2-(2-(3,4-dimethoxy-N-methylphenylsulfonamido)acetoxy)ethyl)pyridine 1-oxide;
(S)-3,5-dichloro-4-(2-(3-(cyclopropylmethoxy)-4-(difluoromethoxy)phenyl)-2-(2-(N-(4-(methylthio)phenyl)methylsulfonamido)acetoxy)ethyl)pyridine 1-oxide;
(S)-3,5-dichloro-4-(2-(3-(cyclopropylmethoxy)-4-(difluoromethoxy)phenyl)-2-(2-(N-(3,4-dimethoxyphenyl)methylsulfonamido)acetoxy)ethyl)pyridine 1-oxide;
(S)-3,5-dichloro-4(2(3-(cyclopropylmethoxy)-4-(difluoromethoxy)phenyl)-2-(2-(4-(morpholine-4-carbonyl)phenylsulfonamido)acetoxy)ethyl)pyridine 1-oxide;
(S)-3,5-dichloro-4-(2-(3-(cyclopropylmethoxy)-4-(difluoromethoxy)phenyl)-2-(2-(3,4-dimethoxy-N-(2-morpholinoethyl)phenylsulfonamido)acetoxy)ethyl)-pyridine 1-oxide;
(S)-3,5-dichloro-4-(2-(2-(3-(cyclopropylmethoxy)-4-(N-(2-(4-methylpiperazin-1-yl) ethyl)methylsulfonamido)benzoyloxy)acetoxy)-2-(3-(cyclopropylmethoxy)-4-(difluoromethoxy)phenyl)ethyl)pyridine 1-oxide;
(S)-3,5-dichloro-4-(2-(3-(cyclopropylmethoxy)-4-(difluoromethoxy)phenyl)-2-(2-(4-(methylsulfonamido)phenylsulfonamido)acetoxy)ethyl)pyridine 1-oxide;
(S)-3,5-dichloro-4-(2-(3-(cyclopropylmethoxy)-4-(difluoromethoxy)phenyl)-2-(2-(4-(N-methylsulfamoyl)phenylsulfonamido)acetoxy)ethyl)pyridine 1-oxide;
(S)-3,5-dichloro-4-(2-(3-(cyclopropylmethoxy)-4-(difluoromethoxy)phenyl)-2-(2-(2,5-dimethoxyphenylsulfonamido)acetoxy)ethyl)pyridine 1-oxide;
(S)-3,5-dichloro-4-(2-(3-(cyclopropylmethoxy)-4-(difluoromethoxy)phenyl)-2-(2-(4-(methylsulfonyl)phenylsulfonamido)acetoxy)ethyl)pyridine 1-oxide;
(S)-3,5-dichloro-4-(2-(3-(cyclopropylmethoxy)-4-(difluoromethoxy)phenyl)-2-(2-(4-ethoxy-3-(3-(2-methoxyethyl)ureido)phenylsulfonamido)acetoxy)-ethyl)pyridine 1-oxide;
(S)-3,5-dichloro-4-(2-(3-(cyclopropylmethoxy)-4-(difluoromethoxy)phenyl)-2-(2-((4-(methylsulfonamido)phenyl)methylsulfonamido)acetoxy)ethyl)pyridine 1-oxide;
(S)-4-(2-(2-(2-(benzoyloxy)acetoxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)phenyl)-2-(2-(3-(methylsulfonamido)benzoyloxy)acetoxy)ethyl)pyridine 1-oxide;
(S)-4-(2-(2-(2-(benzoyloxy)acetoxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)phenyl)-2-(2-(3-(methylsulfonamido)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(3-(cyclopropylmethoxy)-4-(methylsulfonamido)benzoylthio)acetoxy)ethyl)-pyridine 1-oxide;
(S)-3,5-dichloro-4-(2-(3-(cyclopropylmethoxy)-4-(difluoromethoxy)phenyl)-2-(2-(4-methoxy-3-(methylsulfonamido)benzoylthio)acetoxy)ethyl)pyridine 1-oxide;
(S)-3,5-dichloro-4-(2(3-(cyclopropylmethoxy)-4-(difluoromethoxy)phenyl)-2-(2-(4-(methylsulfonamido)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(3-(N-methylsulfamoyl)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(4-methoxy-3-(methylsulfonamido)phenylsulfonamido)acetoxy)ethyl)pyridine 1-oxide;
(S)-3,5-dichloro-4-(2-(3-(cyclopropylmethoxy)-4-(difluoromethoxy)phenyl)-2-(2-(2-(methylsulfonamido)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(3-methoxy-5-(methylsulfonamido)benzoyloxy)acetoxy)ethyl)pyridine 1-oxide;
(S)-3,5-dichloro-4-(2-(3-(cyclopropylmethoxy)-4-(difluoromethoxy)phenyl)-2-(2-(4-methoxy-3-(methylsulfonyloxy)benzoylthio)acetoxy)ethyl)pyridine 1-oxide;
(S)-3,5-dichloro-4-(2-(3-(cyclopropylmethoxy)-4-(difluoromethoxy)phenyl)-2-(2-(3-(methylsulfonamido)-5-(trifluoromethyl)benzoyloxy)acetoxy)ethyl)pyridine 1-oxide;

(S)-3,5-dichloro-4-(2-(3-(cyclopropylmethoxy)-4-(difluoromethoxy)phenyl)-2-(2-(4-methoxy-3-(N-(2-morpholinoethyl)methylsulfonamido)benzoylthio)acetoxy)ethyl)pyridine 1-oxide;

(S)-3,5-dichloro-4-(2-(2-(4-(cyclopropylmethoxy)-3-(morpholinomethyl)-benzoyloxy)acetoxy)-2-(3-(cyclopropylmethoxy)-4-(difluoromethoxy)phenyl)ethyl) pyridine 1-oxide;

(S)-3,5-dichloro-4-(2-(3-(cyclopropylmethoxy)-4-(difluoromethoxy)phenyl)-2-(2-(3-(dimethylcarbamoyl) phenylsulfonamido)acetoxy)ethyl)pyridine 1-oxide;

(S)-3,5-dichloro-4-(2-(3-(cyclopropylmethoxy)-4-(difluoromethoxy)phenyl)-2-(2-(3-(dimethylcarbamoyl)-4-methoxyphenylsulfonamido)acetoxy)ethyl)pyridine 1-oxide;

or a pharmaceutically acceptable salt of said compound.

7. A combination, comprising a compound, N-oxide on the pyridine ring, or pharmaceutically acceptable salt according to claim 1 and a second pharmaceutically active component selected from the group consisting of a beta2-agonist, a corticosteroid, and an antimuscarinic agent.

8. A pharmaceutical composition, comprising a compound, N-oxide on the pyridine ring, or pharmaceutically acceptable salt according to claim 1 and one or more pharmaceutically acceptable carriers and/or excipients.

9. A kit, comprising a pharmaceutical compositions according to claim 8 and a device which is a single- or multi-dose dry powder inhaler, a metered dose inhaler or a soft mist nebulizer.

* * * * *